(12) United States Patent
Takahashi et al.

(10) Patent No.: US 9,783,522 B2
(45) Date of Patent: Oct. 10, 2017

(54) 2-AMINO-PYRIDINE AND 2-AMINO-PYRIMIDINE DERIVATIVES AND MEDICINAL USE THEREOF

(71) Applicant: MITSUBISHI TANABE PHARMA CORPORATION, Osaka-shi (JP)

(72) Inventors: Taichi Takahashi, Osaka (JP); Akinori Umino, Osaka (JP); Daisuke Iijima, Osaka (JP); Hisayuki Takamatsu, Osaka (JP)

(73) Assignee: MITSUBISHI TANABE PHARMA CORPORATION, Osaka-shi (JP)

( * ) Notice: Subject to any disclaimer, the term of this patent is extended or adjusted under 35 U.S.C. 154(b) by 0 days.

(21) Appl. No.: 15/306,312

(22) PCT Filed: Apr. 24, 2015

(86) PCT No.: PCT/JP2015/062467
§ 371 (c)(1),
(2) Date: Oct. 24, 2016

(87) PCT Pub. No.: WO2015/163435
PCT Pub. Date: Oct. 29, 2015

(65) Prior Publication Data
US 2017/0044133 A1 Feb. 16, 2017

(30) Foreign Application Priority Data

Apr. 24, 2014 (JP) ................................ 2014-090759

(51) Int. Cl.
| | |
|---|---|
| *C07D 401/04* | (2006.01) |
| *C07D 401/10* | (2006.01) |
| *C07D 401/12* | (2006.01) |
| *C07D 403/12* | (2006.01) |
| *C07D 405/04* | (2006.01) |
| *C07D 405/10* | (2006.01) |
| *C07D 405/14* | (2006.01) |
| *C07D 417/04* | (2006.01) |
| *C07D 471/04* | (2006.01) |
| *C07D 239/42* | (2006.01) |
| *C07D 213/74* | (2006.01) |
| *A61K 31/4418* | (2006.01) |
| *A61K 31/443* | (2006.01) |
| *A61K 31/4439* | (2006.01) |
| *A61K 31/444* | (2006.01) |
| *A61K 31/4545* | (2006.01) |
| *A61K 31/505* | (2006.01) |
| *A61K 31/506* | (2006.01) |
| *C07D 213/80* | (2006.01) |
| *C07D 405/12* | (2006.01) |

(Continued)

(52) U.S. Cl.
CPC .......... *C07D 401/04* (2013.01); *A61K 31/443* (2013.01); *A61K 31/444* (2013.01); *A61K 31/4418* (2013.01); *A61K 31/4439* (2013.01); *A61K 31/4545* (2013.01); *A61K 31/505* (2013.01); *A61K 31/506* (2013.01); *C07D 213/74* (2013.01); *C07D 213/80* (2013.01); *C07D 239/42* (2013.01); *C07D 401/10* (2013.01); *C07D 401/12* (2013.01); *C07D 403/12* (2013.01); *C07D 405/04* (2013.01); *C07D 405/10* (2013.01); *C07D 405/12* (2013.01); *C07D 405/14* (2013.01); *C07D 411/04* (2013.01); *C07D 413/04* (2013.01); *C07D 417/04* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 8,754,097 | B2 | 6/2014 | Schiemann et al. |
| 8,791,111 | B2 | 7/2014 | Schiemann et al. |
| 9,006,246 | B2 | 4/2015 | Ohata et al. |

(Continued)

FOREIGN PATENT DOCUMENTS

| | | |
|---|---|---|
| JP | 2006-522118 A | 9/2006 |
| JP | 2007-246474 A | 9/2007 |

(Continued)

OTHER PUBLICATIONS

International Search Report issued Jun. 9, 2015 in PCT/JP2015/062467 filed Apr. 24, 2015.
Ji Woong Choi, et al., "LPA Receptors: Subtypes and Biological Actions" Annual Review of Pharmacology and Toxicology, vol. 50, 2010, pp. 157-186 and cover pages.
Anna J. S. Houben, et al., "Autotaxin and LPA Receptor Signaling in Cancer" Cancer Metastasis Rev., 2011, pp. 557-565.
Matthew G. K. Benesch, et al., "Autotaxin in the Crosshairs: Taking Aim at Cancer and Other Inflammatory Conditions" FEBS Letters, 2014, pp. 2712-2727.
Andrew M. Tager, et al., "The Lysophosphatidic Acid Receptor LPA, Links Pulmonary Fibrosis to Lung Injury by Mediating Fibroblast Recruitment and Vascular Leak" Nature Medicine, vol. 14, No. 1, 2008, pp. 45-54.
Nikos Oikonomou, et al., "Pulmonary Autotaxin Expression Contributes to the Pathogenesis of Pulmonary Fibrosis" American Journal of Respiratory Cell and Molecular Biology, vol. 47, 2012, pp. 566-574.

(Continued)

*Primary Examiner* — Timothy R Rozof
(74) *Attorney, Agent, or Firm* — Oblon, McClelland, Maier & Neustadt, L.L.P.

(57) ABSTRACT

Provided is a compound superior in an autotaxin inhibitory action and the like, effective as a prophylactic or therapeutic drug for diseases involving ATX. The present invention relates to a compound represented by the following formula (I):

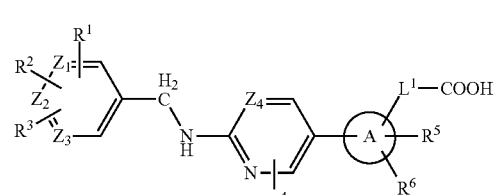

[wherein each symbol is as described in the DESCRIPTION], which has a superior autotaxin inhibitory action and is useful as a prophylactic or therapeutic drug for diseases involving ATX.

19 Claims, No Drawings

(51) Int. Cl.
    *C07D 411/04*    (2006.01)
    *C07D 413/04*    (2006.01)

(56) References Cited

U.S. PATENT DOCUMENTS

| | | |
|---|---|---|
| 2006/0264435 A1 | 11/2006 | Bonnert et al. |
| 2010/0222341 A1 | 9/2010 | Schiemann et al. |
| 2011/0166117 A1 | 7/2011 | Bonnert et al. |
| 2012/0316162 A1 | 12/2012 | Schiemann et al. |
| 2013/0012505 A1 | 1/2013 | Staehle et al. |
| 2013/0109699 A1 | 5/2013 | Ohata et al. |
| 2013/0150326 A1 | 6/2013 | Roppe et al. |
| 2015/0231118 A1 | 8/2015 | Ohata et al. |

FOREIGN PATENT DOCUMENTS

| | | |
|---|---|---|
| JP | 2013-523607 A | 6/2013 |
| JP | 2013-129632 A | 7/2013 |
| JP | 2013-536200 A | 9/2013 |
| WO | 03/062234 A1 | 7/2003 |
| WO | WO 2007/089335 A2 | 8/2007 |
| WO | WO 2009/046841 A2 | 4/2009 |
| WO | WO 2009/151800 A1 | 12/2009 |
| WO | 2011/047481 A1 | 4/2011 |
| WO | WO 2011/133888 A1 | 10/2011 |
| WO | WO 2011/133920 A1 | 10/2011 |
| WO | WO 2012/005227 A1 | 1/2012 |
| WO | WO 2012/024620 A2 | 2/2012 |
| WO | WO 2013/061297 A1 | 5/2013 |

OTHER PUBLICATIONS

Hitoshi Ikeda, et al., "Effects of Lysophosphatidic Acid on Proliferation of Stellate Cells and Hepatocytes in Culture" Biochemical and Biophysical Research Communnications, vol. 248, No. 2, Jul. 20, 1998, pp. 436-440.
Mikio Yanase, et al., "Lysophosphatidic Acid Enhances Collagen Gel Contraction by Hepatic Stellate Cells: Association with Rho-Kinase" Biochemical and Biophysical Research Communications, vol. 277, No. 1, Oct. 14, 2000, pp. 72-78.
Hitoshi Ikeda, et al., "Involvement of Rho/Rho Kinase Pathway in Regulation of Apoptosis in Rat Hepatic Stellate Cells" Am J Physiol Gastrointest Liver Physiol. vol. 285, Nov. 2003, pp. G880-G886.
Jean-Philippe Pradere, et al., "LPA, Receptor Activation Promotes Renal Interstitial Fibrosis" Journal of the American Society of Nephrology, 2007, pp. 3110-3118.
Makoto Inoue, et al., "Initiation of Neuropathic Pain Requires Lysophosphatidic Acid Receptor Signaling" Nature Medicine, vol. 10, No. 7, 2004, pp. 712-718.
Makoto Inoue, et al., "Autotaxin, a Synthetic Enzyme of Lysophosphatidic Acid (LPA), Mediates the Induction of Nerve-Injured Neuropathic Pain" Molecular Pain, Feb. 8, 2008, pp. 1-5.
Ioanna Nikitopoulou, et al., "Autotaxin Expression from Synovial Fibroblasts is Essential for the Pathogenesis of Modeled Arthritis" J. Exp. Med., vol. 209, No. 5, 2012, pp. 925-933.
Wolfgang Siess, et al., "Lysophosphatidic Acid Mediates the Rapid Activation of Platelets and Endothelial Cells by Mildly Oxidized Low Density Lipoprotein and Accumulates in Human Atherosclerotic Lesions" Proc. Natl. Acad. Sci. USA, vol. 96, 1999, pp. 6931-6936.
Zhe Zhou, et al., "Lipoprotein-Derived Lysophosphatidic Acid Promotes Atherosclerosis by Releasing CXCL1 from the Endothelium" Cell Metabolism, vol. 13, May 4, 2011, pp. 592-600.
Peng Cui, et al., "Synthesis and Biological Evaluation of Phosphonate Derivatives as Autotaxin (ATX) Inhibitors" Bioorganic & Medicinal Chemistry Letters, vol. 17, 2007, pp. 1634-1640.

2-AMINO-PYRIDINE AND 2-AMINO-PYRIMIDINE DERIVATIVES AND MEDICINAL USE THEREOF

TECHNICAL FIELD

The present invention relates to a novel autotaxin inhibitor and use thereof. More particularly, it relates to a prophylactic or therapeutic drug for a disease caused by autotoxin, comprising a compound represented by the formula (1) or a pharmacologically acceptable salt thereof as an active ingredient.

BACKGROUND ART

Autotaxin (ATX) was isolated from a culture supernatant of human malignant melanoma cell line A2058 and identified as a cell migration stimulating factor. ATX is also called secreted lysophospholipase D (lysophopholipase D; lysoPLD) and ENPP2 (Ectonucleotide Pyrophosphatase/Phosphodiesterase 2), and mainly affords lysoPLD activity. It hydrolyzes lysophosphatidylcholine (LPC) and produces lysophosphatidic acid (LPA) which is a lipid mediator having various physiological activities.

LPA produced by ATX binds to a G-protein-coupled receptor and intracellularly transmits signals, whereby various physiological actions are shown. As LPA receptor, 6 kinds of subtypes of from LPA1 to LPA6 are known. LPA receptor subtypes are distributed everywhere in the body, at different tissues to be localized in depending on the subtypes, and various receptor subtypes are involved in respective biological functions depending on the tissue. LPA receptor is classified into two subfamilies. LPA1 to LPA3 are classified into the endothelial differentiation gene (Edg) family. LPA4 to LPA6 are non-Edg family LPA receptors, and are receptors similar to the purinergic receptor family (non-patent documents 1 and 2). LPA is physiologically (both homeostasis maintenance and pathology) involved in a wide variety of life phenomena via these LPA receptors. As the actions of LPA via LPA receptors, various functions such as cell proliferation, anti-apoptotic action, cell migration, cancer cell infiltration, wound therapy, development and differentiation of brain nerve system, angiogenesis in fetus, lymphocyte trafficking via high expression of ATX in high endothelial venules (HEVs) and secondary lymphoid tissues, hair follicle formation, bone calcification and the like are known.

On the other hand, firstly in relation to diseases, various studies have revealed that the intracellular signal pathway via ATX and LPA receptor is deeply involved in cancer (non-patent document 3).

In addition, it has been clarified that the intracellular signal pathway via ATX and LPA receptors is involved in various carcinomas and various inflammatory diseases. Specifically, it is related to various diseases including cancer, tumor, neoplasm, various carcinomas such as malignant melanoma, brain tumor, neuroblastoma, glioblastoma multiforme, EBV positive Hodgkin lymphoma, glioblastoma, non-small cell lung cancer, lung tumor, breast tumor, ovary tumor, pancreas tumor, prostatic intraepithelial neoplasia, prostate tumor, thyroid tumor, follicular lymphoma, liver tumor, renal cell carcinoma and the like, asthma, pulmonary fibrosis including idiopathic pulmonary fibrosis, rheumatoid arthritis, type II diabetes-related obesity, atherosclerosis, acute coronary syndrome, hepatic fibrosis, cholestatic pruritus, inflammatory bowel disease, Crohn's disease, ulcerative colitis, neuropathic pain and the like (non-patent document 4).

Furthermore, it has been clarified that intracellular signal pathway via ATX and LPA receptor is involved in various fibrosis diseases.

To be more specific in relation to the involvement in the above-mentioned diseases, for example, it is shown as regards pulmonary fibrosis that LPA concentration increases in alveolar lavage fluid of idiopathic pulmonary fibrosis patients and ATX concentration increases in lung tissue of bleomycin-induced pulmonary fibrosis model. Furthermore, it is shown that progression of bleomycin-induced pulmonary fibrosis and death were markedly suppressed in LPA1 deficient mouse (non-patent documents 5 and 6).

In hepatic fibrosis, it is shown that LPA promotes contraction and growth of hepatic stellate cells that play a key role in hepatic fibrosis, thus suppressing apoptosis, and serum autotaxin activity and plasma LPA level are promoted along with the progression of hepatic fibrosis in chronic hepatitis C patients (non-patent documents 7-9).

In renal fibrosis, it is shown that production of LPA and expression of LPA1 are promoted in a lateral ureteral ligation model, LPA1 deficient mouse shows resistance to fibrosis, and LPA receptor antagonists suppress progression of fibrosis (non-patent document 10).

In neuropathic pain, it has been clarified that LPA produced by ATX contributes to the expression of neuropathic pain, and LPA1 deficient mouse shows resistance to neuropathic pain (non-patent documents 11 and 12).

In rheumatoid arthritis, it has been clarified that the amount of ATX in the synovial tissues and synovial fluids increases in rheumatoid arthritis patients, and ATX conditional knockout mouse shows resistance to the onset of arthritis (non-patent document 13).

In atherosclerosis, LPA accumulates in arteriosclerosis lesions and promotes activation of platelets and endothelial cells by oxidation of low density lipoprotein (non-patent document 14). LPA and ATX accelerate Chemokine (C—X—C motif) ligand 1 production of vascular endothelial cells and promote migration of monocytes (non-patent document 15). Therefore, LPA and ATX are considered to be involved in cardiovascular diseases.

As ATX inhibitors, non-patent document 16 describes a particular lipid analog, patent document 1 describes a tetrahydrocarboline derivative, patent document 2 describes a 1H-indole compound, patent document 3 describes a piperidine or piperazine derivative, and patent document 4 describes a pyridazine derivative.

However, the compound of the present invention is not structurally similar to the compounds described in these patents.

On the other hand, as a compound similar to the compound of the present invention, patent document 5 describes a certain kind of amino-pyrimidine compound, patent document 6 describes a particular aminopyridazine compound, patent document 7 describes a certain kind of amino-pyridine or amino-triazine compound, and patent document 8 describes a certain kind of aminopyridine compound.

However, none of the above-mentioned patent documents describe that the compounds described therein have an inhibitory action on autotaxin and the like.

DOCUMENT LIST

Patent Documents patent document 1: WO 2012/005227
patent document 2: WO 2012/024620
patent document 3: WO 2009/046841
patent document 4: WO 2013/061297
patent document 5: WO 2011/133888
patent document 6: WO 2011/133920
patent document 7: WO 2007/089335
patent document 8: WO 2009/151800

Non-Patent Documents non-patent document 1: Choi et al., Annu Rev Pharmacol Toxicol. 2010, 50: 157-186
non-patent document 2: Houben et al., Cancer Metastasis Rev. 2011, 30(3-4): 557-65
non-patent document 3: Houben et al., Cancer Metastasis Rev. 2011; 30(3-4): 557-65
non-patent document 4: Benesch et al., FEBS Lett. 2014
non-patent document 5: Tager et al., Nat Med. 2008; 14(1): 45-54
non-patent document 6: Oikonomou et al., Am J Respir Cell Mol Biol. 2012; 47(5): 566-74
non-patent document 7: Ikeda et al., Biochem Biophys Res Commun. 1998 Jul. 20; 248(2): 436-40
non-patent document 8: Yanase et al., Biochem Biophys Res Commun. 2000 Oct. 14; 277(1): 72-8
non-patent document 9: Ikeda et al., Am J Physiol Gastrointest Liver Physiol. 2003 November; 285(5): G880-6
non-patent document 10: Pradere et al., J Am Soc Nephrol. 2007; 18(12): 3110-8
non-patent document 11: Inoue et al., Nat Med. 2004; 10(7): 712-8
non-patent document 12: Inoue et al., Mol Pain. 2008 Feb. 8; 4:6
non-patent document 13: Nikitopoulou et al., J Exp Med. 2012; 209(5): 925-33
non-patent document 14: Siess et al., Proc Natl Acad Sci USA. 1999; 96(12): 6931-6
non-patent document 15: Zhou et al., Cell Metab. 2011 May 4; 13(5): 592-600
non-patent document 16: Peng et al., Bioorganic & Medicinal Chemistry Letters 2007, 17: 1634-1640

SUMMARY OF THE INVENTION

Problems to be Solved by the Invention

The present invention aims to provide a compound superior in an autotaxin inhibitory action and the like, and useful for the prophylaxis or treatment of a disease involving ATX.

Means of Solving the Problems

The present inventors have conducted intensive studies in an attempt to solve the aforementioned problems and found a particular compound that inhibits ATX and found that a prophylactic or therapeutic drug for a disease involving ATX can be provided, which resulted in the completion of the present invention. That is, the gist of the present invention is as described below.

[1] A compound represented by the following formula (1) or a pharmacologically acceptable salt thereof:

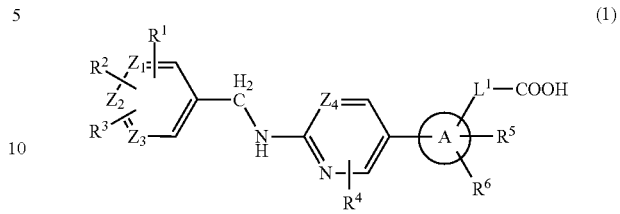

{wherein,
A is cycloalkyl, a heterocyclic group, aryl or heteroaryl;
$Z_1$, $Z_2$ and $Z_3$ are any of the following A)-D):
A) all of $Z_1$, $Z_2$ and $Z_3$ are carbons;
B) $Z_1$ is nitrogen, and $Z_2$ and $Z_3$ are carbons;
C) $Z_2$ is nitrogen, and $Z_1$ and $Z_3$ are carbons;
D) $Z_1$ and $Z_2$ are nitrogens, and $Z_3$ is carbon;
$Z_4$ is either carbon or nitrogen;
$R^1$ is halogen, alkyl, haloalkyl, alkoxy, haloalkoxy, cyano, a heterocyclic group, aryl or heteroaryl (wherein the heteroaryl optionally further has substituent(s) selected from alkyl);
$R^2$ and $R^3$ are the same or different and each is hydrogen, halogen, alkyl, haloalkyl, alkoxy, haloalkoxy or aryl;
$R^4$ is hydrogen, alkyl or halogen;
$R^5$ and $R^6$ are the same or different and each is —$X^1$—$R^{7a}$ (wherein
$X^1$ is a single bond, linear alkylene, cyclic alkylene, —O—, —O-alkylene- or —CO— (wherein linear alkylene, cyclic alkylene or —O-alkylene- for $X^1$ optionally further has substituent(s) selected from hydroxy, halogen, alkyl, hydroxyalkyl and alkoxy);
$R^{7a}$ is hydrogen, hydroxy, halogen, alkyl, haloalkyl, hydroxyalkyl, alkoxy, carboxyl, —$NR^{7b}R^{7c}$ (wherein $R^{7b}$ and $R^{7c}$ are the same or different and each is hydrogen, hydroxy, halogen, alkyl, haloalkyl, hydroxyalkyl, alkoxyalkyl or aminoalkyl), alkyleneoxide, cyano, dialkylcarbamoyl, alkylsulfonyl, a heterocyclic group or heteroaryl (wherein heterocyclic group or heteroaryl for $R^{7a}$ optionally further has substituent(s) selected from hydroxy, halogen, alkyl, haloalkyl, hydroxyalkyl, alkoxyalkyl and aminoalkyl.)); and
$L^1$ is a group selected from the following 1)-6):
1) —$X^2$—,
2) —$X^2$—$(CH_2)_n$—,
3) —O—$X^3$—,
4) —O—$(CH_2)_n$—$X^3$—,
5) —CO—$X^3$—,
6) —CO—NH—$X^3$—
(wherein
$X^2$ is a single bond, linear alkylene, cyclic alkylene, alkenylene, alkynylene, heterocycloalkylene or heteroarylene;
$X^3$ is linear alkylene, cyclic alkylene, alkenylene, alkynylene, heterocycloalkylene or heteroarylene; (wherein linear alkylene, cyclic alkylene, alkenylene or alkynylene for $X^2$ or $X^3$ optionally further has substituent(s) selected from alkyl (wherein the alkyl optionally has substituent(s) selected from aryl and heteroaryl), cycloalkyl, hydroxyalkyl, haloalkyl and alkyleneoxide); and
n is an integer of 1-3)}.

[2] The compound of [1], wherein A is aryl or heteroaryl, or a pharmacologically acceptable salt thereof.

[3] The compound of [1], wherein A is a heterocyclic group, or a pharmacologically acceptable salt thereof.

[4] The compound of any one of [1]-[3], wherein all of $Z_1$, $Z_2$ and $Z_3$ are carbons, or a pharmacologically acceptable salt thereof.

[5] The compound of any one of [1]-[4], wherein $R^1$ is halogen, haloalkyl or haloalkoxy, or a pharmacologically acceptable salt thereof.

[6] The compound of [5], wherein $R^1$ is haloalkoxy, or a pharmacologically acceptable salt thereof.

[7] The compound of any one of [1]-[6], wherein $R^1$ is substituted at the 3-position of the 6-membered ring, or a pharmacologically acceptable salt thereof.

[8] The compound of any one of [1]-[7], wherein $R^5$ and $R^6$ are the same or different and each is any of
1) —$X^1$—$R^{7a}$ ($X^1$ is —O—, and $R^{7a}$ is alkyl),
2) —$X^1$—$R^{7a}$ ($X^1$ is linear alkylene or cyclic alkylene, and $R^{7a}$ is hydrogen), and
3) —$X^1$—$R^{7a}$ ($X^1$ is a single bond, and $R^{7a}$ is halogen or cyano), or a pharmacologically acceptable salt thereof.

[9] The compound of any one of [1]-[8], wherein $L^1$ is 1) —$X^2$—($X^2$ is straight chain alkylene or cyclic alkylene), or a pharmacologically acceptable salt thereof.

[10] The compound of [9], wherein $L^1$ is 1) —$X^2$—($X^2$ is C1-2 straight chain alkylene or C3-6 cyclic alkylene), or a pharmacologically acceptable salt thereof.

[11] The compound of any one of [1] and [4]-[10], wherein cycloalkyl for A is a group selected from the following:

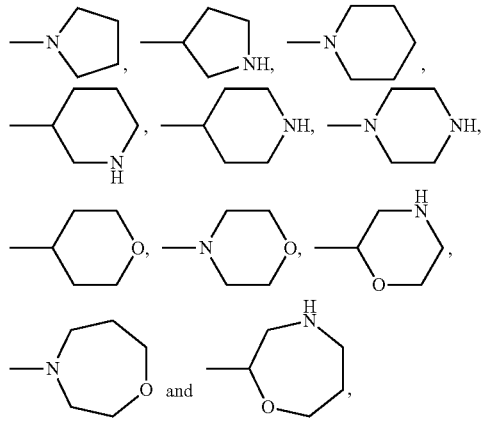

the heterocyclic group for A is a group selected from the following:

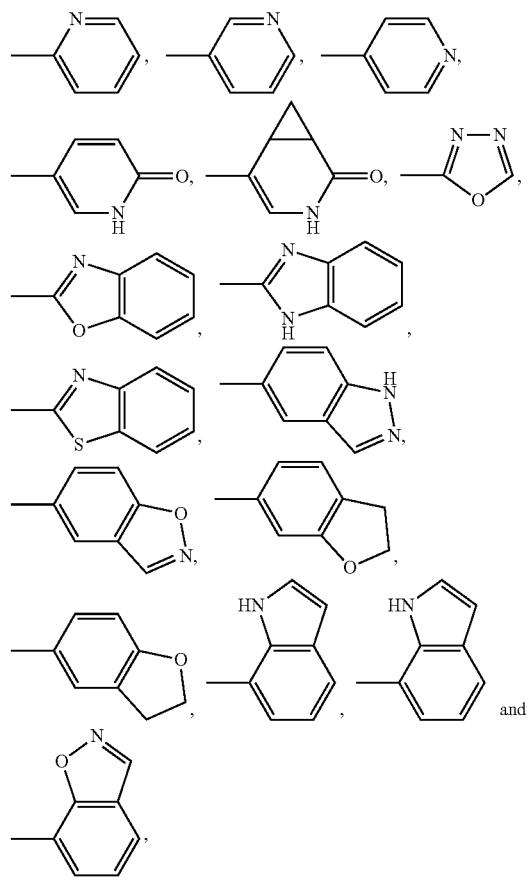

aryl for A is the following group:

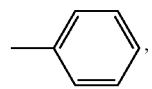

and heteroaryl for A is a group selected from the following:

or a pharmacologically acceptable salt thereof.

[12] The compound of any one of [2] and [11], wherein A is

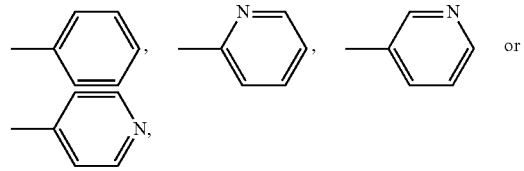

or a pharmacologically acceptable salt thereof.

[13] The compound of any one of [3] and [11], wherein A is

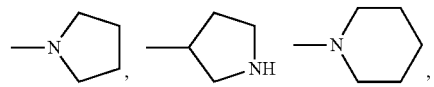

-continued

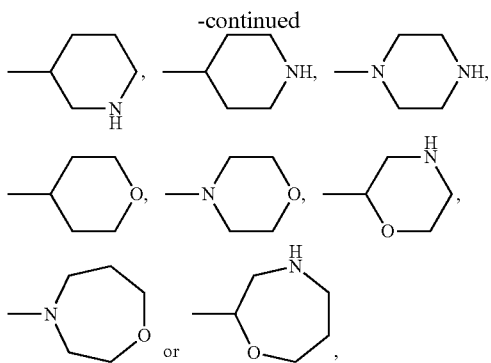

or a pharmacologically acceptable salt thereof.

[14] The compound of [1], wherein the compound represented by the formula (1) is any of the following, or a pharmacologically acceptable salt thereof:

2-[6-(3-trifluoromethoxy-benzylamino)-pyridin-3-yl]-3H-benzimidazole-4-carboxylic acid,
2-[6-(3-trifluoromethoxy-benzylamino)-pyridin-3-yl]-benzoxazole-6-carboxylic acid,
1-methyl-5-[6-(3-trifluoromethoxy-benzylamino)-pyridin-3-yl]-1H-indazole-3-carboxylic acid,
5-[6-(3-trifluoromethoxy-benzylamino)-pyridin-3-yl]-1H-indazole-3-carboxylic acid,
3-{3-cyano-2-methoxy-5-[6-(3-trifluoromethoxy-benzylamino)-pyridin-3-yl]-phenyl}-propionic acid,
3-{2-chloro-5-[2-(3-trifluoromethoxy-benzylamino)-pyrimidin-5-yl]-phenyl}-propionic acid,
3-{3-cyano-2-methoxy-5-[6-(3-trifluoromethoxy-benzylamino)-pyridin-3-yl]-phenyl}-2-methyl-propionic acid,
2-{2-methoxy-5-[6-(3-trifluoromethoxy-benzylamino)-pyridin-3-yl]-phenyl}-cyclopropanecarboxylic acid,
(1S,2S)-2-{2-methoxy-5-[6-(3-trifluoromethoxy-benzylamino)-pyridin-3-yl]-phenyl}-cyclopropanecarboxylic acid,
2-[5-methoxy-6'-(3-trifluoromethoxy-benzylamino)-[2,3']bipyridinyl-6-yl]-cyclopropanecarboxylic acid,
(1S,2S)-2-[5-methoxy-6'-(3-trifluoromethoxy-benzylamino)-[2,3']bipyridinyl-6-yl]-cyclopropanecarboxylic acid,
(1S,2S)-2-{3-methoxy-6-[2-(3-trifluoromethoxy-benzylamino)-pyrimidin-5-yl]-pyridin-2-yl}-cyclopropanecarboxylic acid,
(1S,2S)-2-[5-chloro-6'-(3-trifluoromethoxy-benzylamino)-[2,3']bipyridinyl-6-yl]-cyclopropanecarboxylic acid,
(1S,2S)-2-[5-ethoxy-6'-(3-trifluoromethoxy-benzylamino)-[2,3']bipyridinyl-6-yl]-cyclopropanecarboxylic acid,
(1S,2S)-2-[5-methyl-6'-(3-trifluoromethoxy-benzylamino)-[2,3']bipyridinyl-6-yl]-cyclopropanecarboxylic acid,
3-{2-methoxy-5-[2-(3-trifluoromethoxy-benzylamino)-pyrimidin-5-yl]-phenyl}-propionic acid,
3-{2-methoxy-5-[6-(3-trifluoromethoxy-benzylamino)-pyridin-3-yl]-phenyl}-propionic acid,
2-{2-methoxy-5-[6-(3-trifluoromethoxy-benzylamino)-pyridin-3-yl]-phenyl}-2-methyl-propionic acid,
2-{3-cyano-2-methoxy-5-[6-(3-trifluoromethoxy-benzylamino)-pyridin-3-yl]-phenyl}-2-methyl-propionic acid,
2-chloro-3-(1-methyl-pyrrolidin-3-yloxy)-5-[2-(3-trifluoromethoxy-benzylamino)-pyrimidin-5-yl]-benzoic acid,
2-chloro-3-(pyrrolidin-3-yloxy)-5-[2-(3-trifluoromethoxy benzylamino)-pyrimidin-5-yl]-benzoic acid,
3-(azetidin-3-yloxy)-2-chloro-5-[2-(3-trifluoromethoxy-benzylamino)-pyrimidin-5-yl]-benzoic acid,
2-chloro-3-(1-methyl-azetidin-3-yloxy)-5-[2-(3-trifluoromethoxy-benzylamino)-pyrimidin-5-yl]-benzoic acid,
2-methoxy-3-pyridin-4-yl-5-[2-(3-trifluoromethoxy-benzylamino)-pyrimidin-5-yl]-benzoic acid,
2-methoxy-5-[6-(3-trifluoromethoxy-benzylamino)-pyridin-3-yl]-benzoic acid,
3-fluoro-2-methoxy-5-[6-(3-trifluoromethoxy-benzylamino) pyridin-3-yl]-benzoic acid,
2,3-dimethoxy-5-[6-(3-trifluoromethoxy-benzylamino)-pyridin-3-yl]-benzoic acid,
2-chloro-3-methoxy-5-[6-(3-trifluoromethoxy-benzylamino) pyridin-3-yl]-benzoic acid,
3-cyano-2-methoxy-5-[6-(3-trifluoromethoxy-benzylamino)-pyridin-3-yl]-benzoic acid,
7-[6-(3-trifluoromethoxy-benzylamino)-pyridin-3-yl]-1H-indazole-3-carboxylic acid,
4-methoxy-7-[6-(3-trifluoromethoxy-benzylamino)-pyridin-3-yl]-1H-indazole-3-carboxylic acid,
1-(2-methoxy-ethyl)-5-[6-(3-trifluoromethoxy-benzylamino)-pyridin-3-yl]-1H-indazole-3-carboxylic acid,
1-methyl-5-[2-(3-trifluoromethoxy-benzylamino)-pyrimidin-5-yl]-1H-indazole-3-carboxylic acid,
1-(3-methanesulfonyl-propyl)-5-[6-(3-trifluoromethoxy-benzylamino)-pyridin-3-yl]-1H-indazole-3-carboxylic acid,
1-(3-cyano-propyl)-5-[6-(3-trifluoromethoxy-benzylamino)-pyridin-3-yl]-1H-indazole-3-carboxylic acid,
(E)-3-{3-methyl-2-oxo-5-[6-(3-trifluoromethoxy-benzylamino)-pyridin-3-yl]-3-aza-bicyclo[4.1.0]hept-4-en-1-yl}-acrylic acid,
(E)-3-[1-methyl-6-oxo-6'-(3-trifluoromethoxy-benzylamino)-1,6-dihydro-[3,3']bipyridinyl-5-yl]-acrylic acid,
(1S,2S)-2-[5-isopropoxy-6'-(3-trifluoromethoxy-benzylamino)-[2,3']bipyridinyl-6-yl]-cyclopropanecarboxylic acid,
3-{3-cyano-2-methoxy-5-[2-(3-trifluoromethoxy-benzylamino)-pyrimidin-5-yl]-phenyl}-propionic acid,
(E)-3-{2-methoxy-5-[6-(3-trifluoromethoxy-benzylamino)-pyridin-3-yl]-phenyl}-acrylic acid,
3-{2-methoxy-4-[6-(3-trifluoromethoxy-benzylamino)-pyridin-3-yl]-phenyl}-propionic acid,
(trans)-2-{2-methoxy-4-[6-(3-trifluoromethoxy-benzylamino)-pyridin-3-yl]-phenyl}-cyclopropanecarboxylic acid,
(trans)-2-{2-methoxy-5-[2-(3-trifluoromethoxy-benzylamino)-pyrimidin-5-yl]-phenyl}-cyclopropanecarboxylic acid,
3-{2-methoxy-3-oxetan-3-yl-5-[6-(3-trifluoromethoxy-benzylamino)-pyridin-3-yl]-phenyl}-propionic acid,
3-{3-cyano-2-methoxy-5-[6-(3-trifluoromethoxy-benzylamino)-pyridin-3-yl]-phenyl}-3-methyl-butyric acid,
3-{3-cyano-2-methoxy-5-[2-(3-trifluoromethoxy-benzylamino)-pyrimidin-5-yl]-phenyl}-3-methyl-butyric acid,
(3-{2-methoxy-5-[6-(3-trifluoromethoxy-benzylamino)-pyridin-3-yl]-phenyl}-oxetan-3-yl)-acetic acid,
3-{2-methoxy-5-[6-(3-trifluoromethoxy-benzylamino)-pyridin-3-yl]-phenyl}-3-methyl-butyric acid,
3-{2,6-dimethoxy-4-[6-(3-trifluoromethoxy-benzylamino)-pyridin-3-yl]-phenyl}-propionic acid,
3-{2,6-dimethoxy-4-[6-(3-trifluoromethoxy-benzylamino)-pyridin-3-yl]-phenyl}-2-methyl-propionic acid,
1-[1-methyl-6-oxo-6'-(3-trifluoromethoxy-benzylamino)-1,6-dihydro-[3,3']bipyridinyl-5-yl]-cyclopropanecarboxylic acid,
2-{3-imidazol-1-ylmethyl-2-methoxy-5-[6-(3-trifluoromethoxy-benzylamino)-pyridin-3-yl]-phenyl}-2-methyl-propionic acid, {2-methoxy-5-[6-(3-trifluoromethoxy-benzylamino)-pyridin-3-yl]-phenyl}-acetic acid,
1-{2-methoxy-5-[6-(3-trifluoromethoxy-benzylamino)-pyridin-3-yl]-phenyl}-cyclopropanecarboxylic acid,
2-{2-methoxy-5-[2-(3-trifluoromethoxy-benzylamino)-pyrimidin-5-yl]-phenyl}-2-methyl-propionic acid,
2-[6-methoxy-6'-(3-trifluoromethoxy-benzylamino)-[3,3']bipyridinyl-5-yl]-2-methyl-propionic acid,
2-[5-methoxy-6'-(3-trifluoromethoxy-benzylamino)-[2,3']bipyridinyl-6-yl]-2-methyl-propionic acid,
2-{3-hydroxymethyl-2-methoxy-5-[6-(3-trifluoromethoxy-benzylamino)-pyridin-3-yl]-phenyl}-2-methyl-propionic acid,
2-{2-methoxy-3-methoxymethyl-5-[6-(3-trifluoromethoxy-benzylamino)-pyridin-3-yl]-phenyl}-2-methyl-propionic acid,
2-{2-methoxy-3-[(2,2,2-trifluoro-ethylamino)-methyl]-5-[6-(3-trifluoromethoxy-benzylamino)-pyridin-3-yl]-phenyl}-2-methyl-propionic acid,
2-{3-fluoromethyl-2-methoxy-5-[6-(3-trifluoromethoxy-benzylamino)-pyridin-3-yl]-phenyl}-2-methyl-propionic acid,
{2-methoxy-5-[6-(3-trifluoromethoxy-benzylamino)-pyridin-3-yl]-phenoxy}-acetic acid,
2-{2-methoxy-5-[6-(3-trifluoromethoxy-benzylamino)-pyridin-3-yl]-phenoxy}-propionic acid,
2-chloro-3-(2-methoxy-ethoxy)-5-[2-(3-trifluoromethoxy-benzylamino)-pyrimidin-5-yl]-benzoic acid,
2-chloro-3-(tetrahydro-pyran-4-yloxy)-5-[2-(3-trifluoromethoxy-benzylamino)-pyrimidin-5-yl]-benzoic acid,
2-chloro-3-[2-(2-oxo-pyrrolidin-1-yl)-ethoxy]-5-[2-(3-trifluoromethoxy-benzylamino)-pyrimidin-5-yl]-benzoic acid,
2-chloro-3-(2-oxo-pyrrolidin-3-yloxy)-5-[2-(3-trifluoromethoxy-benzylamino)-pyrimidin-5-yl]-benzoic acid,
2-chloro-3-(oxetan-3-yloxy)-5-[2-(3-trifluoromethoxy-benzylamino)-pyrimidin-5-yl]-benzoic acid,
2-chloro-3-dimethylcarbamoylmethoxy-5-[2-(3-trifluoromethoxy-benzylamino)-pyrimidin-5-yl]-benzoic acid,
2-chloro-3-(2-dimethylamino-ethoxy)-5-[2-(3-trifluoromethoxy-benzylamino)-pyrimidin-5-yl]-benzoic acid,
2-chloro-3-(2-morpholin-4-yl-ethoxy)-5-[2-(3-trifluoromethoxy-benzylamino)-pyrimidin-5-yl]-benzoic acid,
3-furan-3-yl-2-methoxy-5-[2-(3-trifluoromethoxy-benzylamino)-pyrimidin-5-yl]-benzoic acid,
2-methoxy-5-[2-(3-trifluoromethoxy-benzylamino)-pyrimidin-5-yl]-benzoic acid, and
5-[6-(3-isopropyl-benzylamino)-pyridin-3-yl]-2-methoxy-benzoic acid.

[15] A pharmaceutical composition comprising the compound of any one of [1]-[14], or a pharmacologically acceptable salt thereof, and a pharmaceutically acceptable carrier.

[16] The pharmaceutical composition of [15], which is used as an ATX inhibitor.

[17] The pharmaceutical composition of [15], which is used for the treatment or prophylaxis of a disease involving ATX.

[18] The pharmaceutical composition of [17], wherein the disease involving ATX is cancer or tumor such as malignant melanoma, brain tumor, neuroblastoma, glioblastoma multiforme, EBV positive Hodgkin lymphoma, glioblastoma, non-small cell lung cancer, lung tumor, breast tumor, ovary tumor, pancreas tumor, prostatic intraepithelial neoplasia, prostate tumor, thyroid tumor, follicular lymphoma, liver tumor, renal cell carcinoma and the like, fibrosis such as pulmonary fibrosis, hepatic fibrosis, renal fibrosis, atherosclerosis and the like, asthma, rheumatoid arthritis, type II diabetes-related obesity, acute coronary syndrome, cholestatic pruritus, or an inflammatory disease such as inflammatory bowel disease, Crohn's disease, ulcerative colitis, neuropathic pain and the like.

Effect of the Invention

The present invention can provide a compound superior in an autotaxin inhibitory action and the like, and effective for the prophylaxis or treatment of a disease involving ATX, for example, as a prophylactic or therapeutic drug for various diseases such as cancer or tumor such as malignant melanoma, brain tumor, neuroblastoma, glioblastoma multiforme, EBV positive Hodgkin lymphoma, glioblastoma, non-small cell lung cancer, lung tumor, breast tumor, ovary tumor, pancreas tumor, prostatic intraepithelial neoplasia, prostate tumor, thyroid tumor, follicular lymphoma, liver tumor, renal cell carcinoma and the like, fibrosis such as pulmonary fibrosis, hepatic fibrosis, renal fibrosis, atherosclerosis and the like, asthma, rheumatoid arthritis, type II diabetes-related obesity, acute coronary syndrome, cholestatic pruritus, or an inflammatory disease such as inflammatory bowel disease, Crohn's disease, ulcerative colitis, neuropathic pain and the like.

DESCRIPTION OF EMBODIMENTS

The compound of the present invention is a novel compound having an autotaxin inhibitory action, which is represented by the following formula (1):

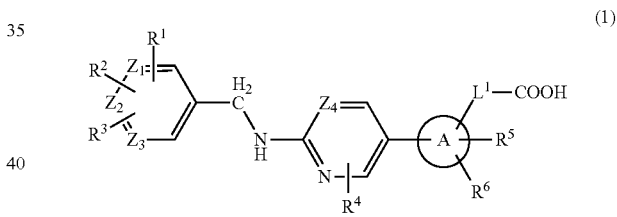

(1)

{wherein,
A is cycloalkyl, a heterocyclic group, aryl or heteroaryl;
$Z_1$, $Z_2$ and $Z_3$ are any of the following A)-D):
A) all of $Z_1$, $Z_2$ and $Z_3$ are carbons;
B) $Z_1$ is nitrogen, and $Z_2$ and $Z_3$ are carbons;
C) $Z_2$ is nitrogen, and $Z_1$ and $Z_3$ are carbons;
D) $Z_1$ and $Z_2$ are nitrogens, and $Z_3$ is carbon;
$Z_4$ is either carbon or nitrogen;
$R^1$ is halogen, alkyl, haloalkyl, alkoxy, haloalkoxy, cyano, a heterocyclic group, aryl or heteroaryl (wherein the heteroaryl optionally further has substituent(s) selected from alkyl);
$R^2$ and $R^3$ are the same or different and each is hydrogen, halogen, alkyl, haloalkyl, alkoxy, haloalkoxy or aryl;
$R^4$ is hydrogen, alkyl or halogen;
$R^5$ and $R^6$ are the same or different and each is —$X^1$—$R^{7a}$ (wherein
$X^1$ is a single bond, linear alkylene, cyclic alkylene, —O—, —O-alkylene- or —CO— (wherein linear alkylene, cyclic alkylene or —O-alkylene- for $X^1$ optionally further has substituent(s) selected from hydroxy, halogen, alkyl, hydroxyalkyl and alkoxy);
$R^{7a}$ is hydrogen, hydroxy, halogen, alkyl, haloalkyl, hydroxyalkyl, alkoxy, carboxyl, —$NR^{7b}R^{7c}$ (wherein $R^{7b}$ and $R^{7c}$ are the same or different and each is hydrogen, hydroxy, halogen, alkyl, haloalkyl, hydroxyalkyl, alkoxyalkyl or aminoalkyl), alkyleneoxide, cyano, dialkylcarbamoyl, alkylsulfonyl, a heterocyclic group or heteroaryl (wherein heterocyclic group or heteroaryl for $R^{7a}$ optionally further has substituent(s) selected from hydroxy, halogen, alkyl, haloalkyl, hydroxyalkyl, alkoxyalkyl and aminoalkyl.)); and $L^1$ is a group selected from the following 1)-6):
1) —$X^2$—,
2) —$X^2$—(CH$_2$)$_n$—,
3) —O—$X^3$—,
4) —O—(CH$_2$)$_n$—$X_3$—,
5) —CO—$X^3$—,
6) —CO—NH—$X^3$—

(wherein
$X^2$ is a single bond, linear alkylene, cyclic alkylene, alkenylene, alkynylene, heterocycloalkylene or heteroarylene;
$X^3$ is linear alkylene, cyclic alkylene, alkenylene, alkynylene, heterocycloalkylene or heteroarylene;
(wherein linear alkylene, cyclic alkylene, alkenylene or alkynylene for $X^2$ or $X^3$ optionally further has substituent(s) selected from alkyl (wherein the alkyl optionally has substituent(s) selected from aryl and heteroaryl), cycloalkyl, hydroxyalkyl, haloalkyl and alkyleneoxide); and
n is an integer of 1-3)}
(sometimes to be abbreviated as "compound (1)" in the present specification), or a pharmaceutically acceptable salt thereof.

In the present specification, the substituent for each symbol is as described below.

As the "halogen" for $R^1$, $R^2$, $R^3$, $R^4$, $R^{7a}$, $R^{7b}$, $R^{7c}$, a fluorine atom, a chlorine atom, a bromine atom, and an iodine atom can be mentioned.

The "alkyl" for $R^1$, $R^2$, $R^3$, $R^4$, $R^{7a}$, $R^{7b}$, $R^{7c}$ is C1-6 alkyl such as methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like can be mentioned.

The "alkoxy" for $R^1$, $R^2$, $R^3$, $R^{7a}$ is C1-6 alkoxy such as methoxy, ethoxy, propoxy, isopropyloxy, butoxy, isobutyloxy, sec-butyloxy, tert-butyloxy, pentyloxy, isopentyloxy, neopentyloxy, 1-ethylpropyloxy, hexyloxy, isohexyloxy, 1,1-dimethylbutyloxy, 2,2-dimethylbutyloxy, 3,3-dimethylbutyloxy, 2-ethylbutyloxy and the like can be mentioned.

The "haloalkyl" for $R^1$, $R^2$, $R^3$, $R^{7a}$, $R^{7b}$, $R^{7c}$ is C1-6 haloalkyl such as fluoromethyl, difluoromethyl, trifluoromethyl, 2,2,2-trifluoroethyl, 2,2,3,3,3-pentafluoropropyl and the like can be mentioned.

The "haloalkoxy" for $R^1$, $R^2$, $R^3$ is C1-6 haloalkoxy such as fluoromethyloxy, difluoromethyloxy, trifluoromethyloxy, 2,2,2-trifluoroethyloxy, 2,2,3,3,3-pentafluoropropyloxy and the like can be mentioned.

The "aryl" for $R^1$, $R^2$, $R^3$ is C6-10 aryl such as phenyl, 1-naphthyl, 2-naphthyl and the like can be mentioned.

The "hydroxyalkyl" for $R^{7a}$, $R^{7b}$, $R^{7c}$ is C1-6 hydroxyalkyl such as hydroxymethyl, 1-hydroxyethyl, 2-hydroxyethyl, 1-hydroxypropyl, 2-hydroxypropyl, 3-hydroxypropyl, 1-hydroxybutyl, 2-hydroxybutyl, 3-hydroxybutyl, 4-hydroxybutyl, 1-hydroxypentyl, 2-hydroxypentyl, 3-hydroxypentyl, 4-hydroxypentyl, 5-hydroxypentyl, 1-hydroxyhexyl, 2-hydroxyhexyl, 3-hydroxyhexyl, 4-hydroxyhexyl, 5-hydroxyhexyl, 6-hydroxyhexyl and the like can be mentioned.

The "alkyleneoxide" for $R^{7a}$ is C2-4 alkyleneoxide such as ethyleneoxide, trimethyleneoxide, tetramethyleneoxide and the like can be mentioned.

The "alkylsulfonyl" for $R^{7a}$ is C1-6 alkylsulfonyl such as methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, neopentylsulfonyl, 1-ethylpropylsulfonyl, hexylsulfonyl, isohexylsulfonyl, 1,1-dimethylbutylsulfonyl, 2,2-dimethylbutylsulfonyl, 3,3-dimethylbutylsulfonyl, 2-ethylbutylsulfonyl and the like can be mentioned.

The "dialkylcarbamoyl" for $R^{7a}$ is dialkylcarbamoyl wherein the alkyl moiety is the same or different and C1-6 alkyl such as dimethylcarbamoyl, diethylcarbamoyl, dipropylcarbamoyl, dibutylcarbamoyl, dipentylcarbamoyl, dihexylcarbamoyl, ethylmethylcarbamoyl and the like can be mentioned.

The "alkoxyalkyl" for $R^{7b}$, $R^{7c}$ is one wherein the C1-4 alkyl moiety has a C1-4 alkoxy moiety such as methoxymethyl, methoxyethyl, methoxypropyl, methoxybutyl, ethoxymethyl, ethoxyethyl, ethoxypropyl, ethoxybutyl, propoxymethyl, propoxyethyl, propoxypropyl, propoxybutyl, butoxymethyl, butoxyethyl, butoxypropyl, butoxybutyl and the like can be mentioned.

The "aminoalkyl" for $R^{7b}$, $R^{7c}$ is C1-6 aminoalkyl such as aminomethyl, 1-aminoethyl, 2-aminoethyl, 1-aminopropyl, 2-aminopropyl, 3-aminopropyl, 1-aminobutyl, 2-aminobutyl, 3-aminobutyl, 4-aminobutyl, 1-aminopentyl, 2-aminopentyl, 3-aminopentyl, 4-aminopentyl, 5-aminopentyl, 1-aminohexyl, 2-aminohexyl, 3-aminohexyl, 4-aminohexyl, 5-aminohexyl, 6-aminohexyl and the like can be mentioned.

The "linear alkylene" for $X^1$, $X^2$, $X^3$ is C1-6 straight chain alkylene such as methylene, ethylene, trimethylene, tetramethylene, pentamethylene, hexamethylene can be mentioned.

The "cyclic alkylene" for $X^1$, $X^2$, $X^3$ is C3-7 cycloalkylene such as cyclopropylene, cyclobutylene, cyclopentylene, cyclohexylene, cycloheptylene and the like can be mentioned.

The "alkenylene" for $X^2$, $X^3$ is C2-6 alkenylene such as ethene-1,2-diyl, propene-diyl such as propene-1,3-diyl and the like, butene-diyl such as butene-1,4-diyl and the like, pentene-diyl such as pentene-1,5-diyl and the like, hexene-diyl such as hexene-1,6-diyl and the like, and the like can be mentioned.

The "alkynylene" for $X^2$, $X^3$ is C2-6 alkynylene such as ethyne-1,2-diyl, propyne-1,3-diyl, butyne-diyl such as butyne-1,4-diyl and the like, pentyne-diyl such as pentyne-1,5-diyl and the like, hexyne-diyl such as hexyne-1,6-diyl and the like, and the like can be mentioned.

The "—O-alkylene-" for $X^1$ is —O— straight chain C1-6 alkylene- such as oxymethylene, oxyethylene, oxytrimethylene, oxytetramethylene, oxypentamethylene, oxyhexamethylene and the like can be mentioned.

The cycloalkyl for A is C3-7 cycloalkyl optionally further having a double bond, and cyclopropyl, cyclobutyl, cyclopentyl, cyclohexyl, cycloheptyl and the like can be mentioned. Preferred is the following cycloalkyl.

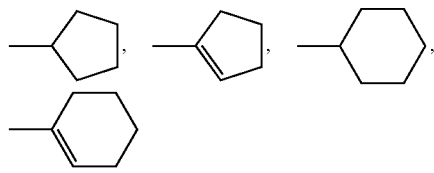

The heterocyclic group for A is a C3-7 heterocyclic group optionally having 1-4 nitrogen atoms; or 1-2 sulfur atoms, or oxygen atoms; further, an optionally oxo-substituted heterocyclic group and, for example, the following heterocyclic groups can be mentioned.

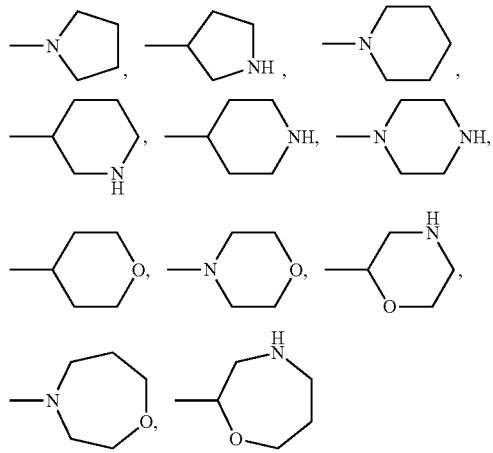

The aryl for A is C6-10 aryl such as phenyl, 1-naphthyl, 2-naphthyl and the like can be mentioned. Preferred is phenyl.

The heteroaryl for A is C5-10 heteroaryl optionally having 1-4 nitrogen atoms; or 1-2 oxygen atoms, or nitrogen atoms; which is optionally further oxo-substituted, further optionally partially saturated and, for example, the following groups can be mentioned.

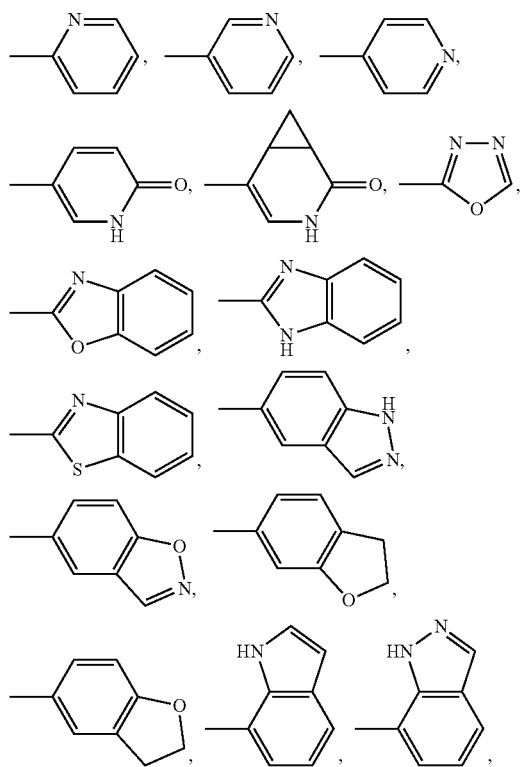

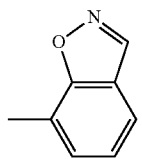

The "heterocycloalkylene" for $X^2$, X is C3-6 heterocycloalkylene optionally containing 1-4 nitrogen atoms, which is optionally oxo-substituted and, for example, the following groups can be mentioned.

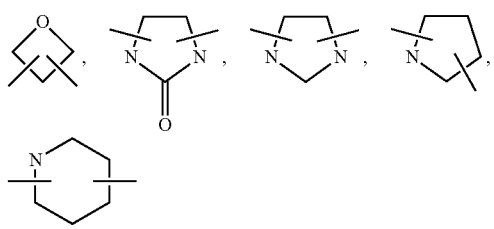

The "heteroarylene" for $X^2$, $X^3$ is C5-6 heteroarylene optionally containing 1-4 nitrogen atoms or 1-2 oxygen atoms and, for example, the following groups can be mentioned.

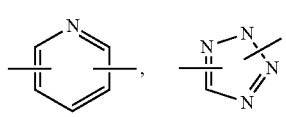

The "heterocyclic group" for $R^1$, $R^{7a}$ is a C3-7 heterocyclic group optionally containing 1-4 nitrogen atoms, or 1-2 sulfur atoms, oxygen atoms, which is optionally further oxo-substituted. For example, the following groups can be mentioned.

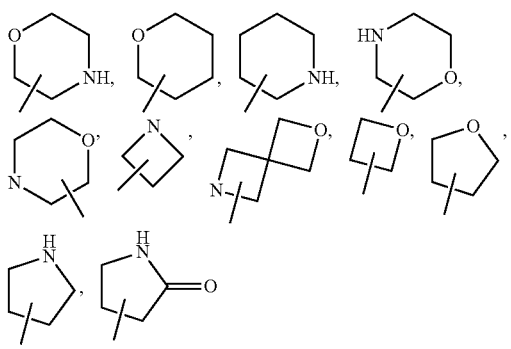

The "heteroaryl" for $R^1$, $R^{7a}$ is C5-6 heteroaryl optionally containing 1-4 nitrogen atoms, or 1-2 oxygen atoms. For example, the following groups can be mentioned.

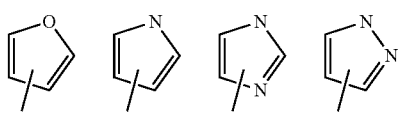

The linear alkylene, cyclic alkylene or —O-alkylene- for $X^1$ optionally further has (preferably 1-3, more preferably, 1-2) substituent(s) selected from hydroxy, halogen, alkyl, hydroxyalkyl and alkoxy at substitutable position(s). When a plurality of substituents are present, the respective substituents may be the same or different.

As the "halogen" optionally used to substitute linear alkylene, cyclic alkylene, —O-alkylene- for $X^1$, a fluorine atom, a chlorine atom, a bromine atom, and an iodine atom can be mentioned.

As the "alkyl" optionally used to substitute linear alkylene, cyclic alkylene, —O-alkylene- for $X^1$, C1-4 alkyl such as methyl, ethyl, propyl, isopropyl, butyl, isobutyl, sec-butyl, tert-butyl and the like can be mentioned.

As the "hydroxyalkyl" optionally used to substitute linear alkylene, cyclic alkylene, —O-alkylene- for $X^1$, C1-4 hydroxyalkyl such as hydroxymethyl, 1-hydroxyethyl, 2-hydroxyethyl, 1-hydroxypropyl, 2-hydroxypropyl, 3-hydroxypropyl, 1-hydroxybutyl, 2-hydroxybutyl, 3-hydroxybutyl, 4-hydroxybutyl and the like can be mentioned.

As the "alkoxy" optionally used to substitute linear alkylene, cyclic alkylene, —O-alkylene- for $X^1$, C1-4 alkoxy such as methoxy, ethoxy, propoxy, isopropoxy, butoxy, isobutoxy, sec-butoxy, tert-butoxy and the like can be mentioned.

The linear alkylene, cyclic alkylene, alkenylene and alkynylene for $X^2$ or $X^3$ optionally further has (preferably 1-3, more preferably, 1-2) substituent(s) selected from alkyl, cycloalkyl, hydroxyalkyl, haloalkyl and alkyleneoxide at substitutable position(s). When a plurality of substituents are present, the respective substituents may be the same or different.

As the "alkyl" optionally used to substitute linear alkylene, cyclic alkylene, alkenylene, alkynylene for $X^2$ or $X^3$ is C1-4 alkyl such as methyl, ethyl, propyl, isopropyl, butyl, isobutyl, sec-butyl, tert-butyl and the like can be mentioned.

The "alkyl" optionally used to substitute linear alkylene, cyclic alkylene, alkenylene and alkynylene for $X^2$ or $X^3$ optionally has (preferably 1-3, more preferably, 1-2) substituent(s) selected from aryl and heteroaryl at substitutable position(s). When a plurality of substituents are present, the respective substituents may be the same or different. As the "aryl" optionally used to substitute the "alkyl", C6-10 aryl such as phenyl and the like can be mentioned; and as the "heteroaryl" optionally used to substitute the "alkyl", C5-6 heteroaryl optionally containing 1-4 nitrogen atoms, or 1-2 oxygen atoms such as pyridyl and the like can be mentioned.

As the "cycloalkyl" optionally used to substitute linear alkylene, cyclic alkylene, alkenylene, alkynylene for $X^2$ or $X^3$, C3-7 cycloalkyl such as cyclopropyl, cyclobutyl, cyclopentyl, cyclohexyl, cycloheptyl and the like can be mentioned.

As the "hydroxyalkyl" optionally used to substitute linear alkylene, cyclic alkylene, alkenylene and alkynylene for $X^2$ or $X^3$, C1-4 hydroxyalkyl such as hydroxymethyl, 1-hydroxyethyl, 2-hydroxyethyl, 1-hydroxypropyl, 2-hydroxypropyl, 3-hydroxypropyl, 1-hydroxybutyl, 2-hydroxybutyl, 3-hydroxybutyl, 4-hydroxybutyl and the like can be mentioned.

As the "haloalkyl" optionally used to substitute linear alkylene, cyclic alkylene, alkenylene and alkynylene for $X^2$ or $X^3$, C1-4 haloalkyl such as fluoromethyl, difluoromethyl, trifluoromethyl, 2,2,2-trifluoroethyl, 2,2,3,3,3-pentafluoropropyl and the like can be mentioned.

As the "alkyleneoxide" optionally used to substitute linear alkylene, cyclic alkylene, alkenylene and alkynylene for $X^2$ or $X^3$, C2-4 alkyleneoxide such as ethyleneoxide, trimethyleneoxide, tetramethyleneoxide and the like can be mentioned.

The heteroaryl for $R^1$ optionally further has substituent(s) (preferably 1-3, more preferably, 1-2) selected from alkyl at substitutable position(s). When a plurality of substituents are present, the respective substituents may be the same or different.

As the "alkyl" optionally used to substitute heteroaryl for $R^1$, C1-4 alkyl such as methyl, ethyl, propyl, isopropyl, butyl, isobutyl, sec-butyl, tert-butyl and the like can be mentioned.

The heterocyclic group and heteroaryl for $R^{7a}$ optionally further have substituent(s) (preferably 1-3, more preferably, 1-2) selected from hydroxy, halogen, alkyl, haloalkyl, hydroxyalkyl, alkoxyalkyl and aminoalkyl at substitutable position(s). When a plurality of substituents are present, the respective substituents may be the same or different.

As the "halogen" optionally used to substitute heterocyclic group and heteroaryl for $R^{7a}$, a fluorine atom, a chlorine atom, a bromine atom and an iodine atom can be mentioned.

As the "alkyl" optionally used to substitute a heterocyclic group and heteroaryl for $R^{7a}$, C1-4 alkyl such as methyl, ethyl, propyl, isopropyl, butyl, isobutyl, sec-butyl, tert-butyl and the like can be mentioned.

The "haloalkyl" optionally used to substitute a heterocyclic group and heteroaryl for $R^{7a}$, C1-4 haloalkyl such as fluoromethyl, difluoromethyl, trifluoromethyl, 2,2,2-trifluoroethyl, 2,2,3,3,3-pentafluoropropyl and the like can be mentioned.

The "hydroxyalkyl" optionally used to substitute a heterocyclic group and heteroaryl for $R^{7a}$, C1-4 hydroxyalkyl such as hydroxymethyl, 1-hydroxyethyl, 2-hydroxyethyl, 1-hydroxypropyl, 2-hydroxypropyl, 3-hydroxypropyl, 1-hydroxybutyl, 2-hydroxybutyl, 3-hydroxybutyl, 4-hydroxybutyl and the like can be mentioned.

The "alkoxyalkyl" optionally used to substitute a heterocyclic group and heteroaryl for $R^{7a}$, one wherein the C1-4 alkoxy moiety has a C1-4 alkyl moiety, such as methoxymethyl, methoxyethyl, methoxypropyl, methoxybutyl, ethoxymethyl, ethoxyethyl, ethoxypropyl, ethoxybutyl, propoxymethyl, propoxyethyl, propoxypropyl, propoxybutyl, butoxymethyl, butoxyethyl, butoxypropyl, butoxybutyl and the like can be mentioned.

As the "aminoalkyl" optionally used to substitute a heterocyclic group and heteroaryl for $R^{7a}$, C1-6 aminoalkyl such as aminomethyl, 1-aminoethyl, 2-aminoethyl, 1-aminopropyl, 2-aminopropyl, 3-aminopropyl, 1-aminobutyl, 2-aminobutyl, 3-aminobutyl, 4-aminobutyl, 1-aminopentyl, 2-aminopentyl, 3-aminopentyl, 4-aminopentyl, 5-aminopentyl, 1-aminohexyl, 2-aminohexyl, 3-aminohexyl, 4-aminohexyl, 5-aminohexyl, 6-aminohexyl and the like can be mentioned.

A is preferably cycloalkyl (e.g., cyclohexenyl); a heterocyclic group (e.g., piperidinyl); aryl (e.g., phenyl); or heteroaryl (e.g., dihydrobenzofuranyl, oxodihydropyridinyl, oxoazabicycloheptenyl, oxadiazolyl, pyridyl, benzimidazolyl, benzoxazolyl, benzisoxazolyl, benzthiazolyl, indolyl, indazolyl, imidazopyridyl), more preferably, cyclohexenyl, piperidinyl, dihydrobenzofuranyl (e.g., 2,3-dihydro-1-benzofuranyl), oxodihydropyridinyl (e.g., 2-oxo-1,2-dihydropyridyl), oxoazabicycloheptenyl (e.g., 2-oxo-3-azabicyclo[4.1.0]hept-4-enyl), phenyl, oxadiazolyl (e.g., 1,3,4-oxadiazolyl), pyridyl, benzimidazolyl, benzoxazolyl, benzisoxazolyl, benzthiazolyl, indolyl (e.g., 1H-indolyl),- indazolyl (e.g., 1H-indazolyl) or imidazopyridyl (e.g., imidazo[1,2-a]pyridyl).

$Z_1$, $Z_2$ and $Z_3$ are preferably that
A) all of $Z_1$, $Z_2$ and $Z_3$ are carbons,
B) $Z_1$ is nitrogen, and $Z_2$ and $Z_3$ are carbons, or
C) $Z_2$ is nitrogen, and $Z_1$ and $Z_3$ are carbons.

$Z_4$ is either carbon or nitrogen.

$R^1$ is preferably halogen (e.g., a fluorine atom, a chlorine atom); alkyl (e.g., methyl, isopropyl); haloalkyl (e.g., trifluoromethyl); alkoxy (e.g., isopropoxy); haloalkoxy (e.g., trifluoromethoxy); cyano; a heterocyclic group (e.g., pyrrolidinyl); aryl (e.g., phenyl); or heteroaryl (e.g., pyrazolyl) optionally having 1 to 3 substituent(s) selected from alkyl (e.g., methyl), more preferably, a fluorine atom, a chlorine atom, methyl, isopropyl, trifluoromethyl, isopropoxy, trifluoromethoxy, cyano, pyrrolidinyl, phenyl, or pyrazolyl optionally having 1 to 3 methyl.

$R^2$ and $R^3$ are preferably the same or different and each is hydrogen; halogen (e.g., a fluorine atom, a chlorine atom); or alkyl (e.g., methyl), more preferably, hydrogen, a fluorine atom, a chlorine atom or methyl.

$R^4$ is preferably hydrogen; alkyl (e.g., methyl); or halogen (e.g., a fluorine atom, a chlorine atom), more preferably, hydrogen, methyl, a fluorine atom or a chlorine atom.

$R^5$ and $R^6$ are preferably the same or different and each is —$X^1$—$R^{7a}$ wherein $X^1$ is a single bond; linear alkylene (e.g., methylene, ethylene, trimethylene); —O—; —O-alkylene- (e.g., —O-methylene-, —O-ethylene-) optionally having 1 to 3 substituent(s) selected from alkyl (e.g., methyl); or —CO—, and $R^{7a}$ is hydrogen; hydroxy; halogen (e.g., a fluorine atom, a chlorine atom); alkyl (e.g., methyl, ethyl, isopropyl); haloalkyl (e.g., fluoromethyl, trifluoromethyl, trifluoroethyl); hydroxyalkyl (e.g., hydroxymethyl); alkoxy (e.g., methoxy, ethoxy, isopropoxy); carboxyl; —$NR^{7b}R^{7c}$ ($R^{7b}$ and $R^{7c}$ are the same or different and each is, hydrogen; alkyl (e.g., methyl); or haloalkyl (e.g., trifluoroethyl)); cyano; dialkylcarbamoyl (e.g., dimethylcarbamoyl); alkylsulfonyl (e.g., methylsulfonyl); a heterocyclic group (e.g., oxetanyl, azetidinyl, pyrrolidinyl, oxopyrrolidinyl, tetrahydropyranyl, morpholinyl) optionally having 1 to 3 substituent(s) selected from alkyl (e.g., methyl); or heteroaryl (e.g., pyrazolyl, imidazolyl, furyl, pyridyl), more preferably, (1) —$X^1$—$R^{7a}$ wherein $X^1$ is a single bond, and $R^{7a}$ is hydrogen; halogen (e.g., a fluorine atom, a chlorine atom); alkyl (e.g., methyl); haloalkyl (e.g., fluoromethyl); hydroxyalkyl (e.g., hydroxymethyl); alkoxy (e.g., methoxy, ethoxy, isopropoxy); carboxyl; —$NR^{7b}R^{7c}$ (wherein $R^{7b}$ and $R^{7c}$ are hydrogen; cyano; a heterocyclic group (e.g., oxetanyl); or heteroaryl (e.g., furyl, pyridyl), (2) —$X^1$—$R^{7a}$ wherein $X^1$ is linear alkylene (e.g., methylene, ethylene, trimethylene), and $R^{7a}$ is hydrogen; hydroxy; halogen (e.g., a fluorine atom); alkoxy (e.g., methoxy); —$NR^{7b}R^{7c}$ (wherein $R^{7b}$ and $R^{7c}$ are the same or different and each is hydrogen or haloalkyl (e.g., trifluoroethyl)); cyano; alkylsulfonyl (e.g., methylsulfonyl); or heteroaryl (e.g., pyrazolyl, imidazolyl), (3) —$X^1$—$R^{7a}$ wherein $X^1$ is —O—, and $R^{7a}$ is alkyl (e.g., methyl, ethyl, isopropyl); haloalkyl (e.g., trifluoromethyl, trifluoroethyl); or a heterocyclic group (e.g., oxetanyl, azetidinyl, pyrrolidinyl, oxopyrrolidinyl, tetrahydropyranyl) optionally having 1 to 3 substituent(s) selected from alkyl (e.g., methyl), (4) —$X^1$—$R^{7a}$ wherein $X^1$ is —O-alkylene- (e.g., —O-methylene-, —O-ethylene-) optionally having 1 to 3 substituent(s) selected from alkyl (e.g., methyl), and $R^{7a}$ is hydrogen; alkyl (e.g., methyl); haloalkyl (e.g., trifluoroethyl); alkoxy (e.g., methoxy); —$NR^{7b}R^{7c}$ (wherein $R^{7b}$ and $R^{7c}$ are the same or different and each is alkyl (e.g., methyl)); dialkylcarbamoyl (e.g., dimethylcarbamoyl); or a heterocyclic group (e.g., oxopyrrolidinyl, morpholinyl), or (5) —$X^1$—$R^{7a}$ wherein $X^1$ is —CO—, and $R^{7a}$ is —$NR^{7b}R^{7c}$ (wherein $R^{7b}$ and $R^{7c}$ are the same or different and each is hydrogen or alkyl (e.g., methyl)).

$L^1$ is preferably
1) —$X^2$— wherein $X^2$ is a single bond; linear alkylene (e.g., methylene, ethylene) optionally having 1 to 3 substituent(s) selected from alkyl (e.g., methyl); cyclic alkylene (e.g., cyclopropylene); alkenylene (e.g., ethene-1,2-diyl); or heterocycloalkylene (e.g., piperidinediyl),
2) —$X^2$—$(CH_2)_n$— wherein $X^2$ is a single bond; linear alkylene (e.g., methylene) optionally having 1 to 3 substituent(s) selected from alkyl (e.g., methyl); cyclic alkylene (e.g., cyclohexylene); heterocycloalkylene (e.g., oxetanediyl, oxoimidazolidinediyl); or heteroarylene (e.g., tetrazolediyl), and n is 1-3,
3) —O—$X^3$— wherein $X^3$ is linear alkylene (e.g., methylene, ethylene) optionally having 1 to 3 substituent(s) selected from alkyl (e.g., methyl),
4) —O—$(CH_2)_n$—$X^3$— wherein $X^3$ is cyclic alkylene (e.g., cyclohexylene), and n is 1-3,
5) —CO—$X^3$— wherein $X^3$ is linear alkylene (e.g., ethylene) optionally having 1 to 3 substituent(s) selected from alkyl (e.g., methyl); or heterocycloalkylene (e.g., pyrrolidinediyl, piperidinediyl), or
6) —CO—NH—$X^3$— wherein $X^3$ is (a) alkyl (e.g., methyl, isopropyl) optionally having 1 to 3 substituent(s) selected from aryl (e.g., phenyl) and heteroaryl (e.g., pyridyl) and (b) linear alkylene (e.g., methylene, ethylene) optionally having 1 to 3 substituent(s) selected from hydroxyalkyl (e.g., hydroxymethyl); cyclic alkylene (e.g., cyclopentylene); or heteroarylene (e.g., pyridinediyl), more preferably,
1) —$X^2$— wherein $X^2$ is a single bond; methylene or ethylene optionally having 1 to 3 methyl; cyclopropylene (e.g., 1,1-cyclopropylene, 1,2-cyclopropylene); ethene-1,2-diyl; or piperidinediyl (e.g., piperidine-1,4-diyl),
2) —$X^2$—$(CH_2)_n$— wherein $X^2$ is a single bond; methylene optionally having 1 to 3 methyl; cyclohexylene (e.g., 1,4-cyclohexylene); oxetanediyl (e.g., oxetane-3,3-diyl); oxoimidazolidinediyl (e.g., 2-oxoimidazolidine-1,3-diyl); or tetrazolediyl (e.g., tetrazole-1,3-diyl), and n is 1 or 2,
3) —O—$X^3$— wherein $X^3$ is methylene or ethylene optionally having 1 to 3 methyl,
4) —O—$(CH_2)_n$—$X^3$— wherein $X^3$ is cyclohexylene (e.g., 1,4-cyclohexylene), and n is 1,
5) —CO—$X^3$— wherein $X^3$ is ethylene optionally having 1 to 3 methyl; pyrrolidinediyl (e.g., pyrrolidine-1,2-diyl); or piperidinediyl (e.g., piperidine-1,4-diyl), or
6) —CO—NH—$X^3$— wherein $X^3$ is methylene or ethylene optionally having 1 to 3 substituent(s) selected from (a) methyl and isopropyl optionally having 1 to 3 substituent(s) selected from phenyl and pyridyl, and (b) hydroxymethyl; cyclopentylene (e.g., 1,2-cyclopentylene); or pyridinediyl (e.g., pyridine-2,5-diyl).

In one embodiment, A is preferably aryl (e.g., phenyl) or heteroaryl (e.g., dihydrobenzofuranyl, oxodihydropyridinyl, oxoazabicycloheptenyl, oxadiazolyl, pyridyl, benzimidazolyl, benzoxazolyl, benzisoxazolyl, benzthiazolyl, indolyl, indazolyl, imidazopyridyl). In another embodiment, A is preferably a heterocyclic group (e.g., piperidinyl, tetrahydropyranyl).

In one embodiment, all of $Z_1$, $Z_2$ and $Z_3$ are preferably carbons.

In one embodiment, $R^1$ is preferably halogen (e.g., a fluorine atom, a chlorine atom), haloalkyl (e.g., trifluoromethyl) or haloalkoxy (e.g., trifluoromethoxy), more preferably, haloalkoxy (e.g., trifluoromethoxy).

In one embodiment, $R^1$ is at any substitutable position of a 6-membered ring substituted by $R^1$, preferably, at the 3-position of the 6-membered ring.

In one embodiment, $R^5$ and $R^6$ are preferably the same or different, and any of
1) —$X^1$—$R^{7a}$ ($X^1$ is —O—, and $R^{7a}$ is alkyl (e.g., methyl, ethyl, isopropyl)),
2) —$X^1$—$R^{7a}$ ($X^1$ is linear alkylene (e.g., methylene, ethylene, trimethylene) or cyclic alkylene, and $R^{7a}$ is hydrogen), and
3) —$X^1$—$R^{7a}$ ($X^1$ is a single bond, and $R^{7a}$ is halogen (e.g., a fluorine atom, a chlorine atom) or cyano).

In one embodiment, $L^1$ is preferably 1) —$X^2$— ($X^2$ is straight chain alkylene (e.g., methylene, ethylene) or cyclic alkylene (e.g., cyclopropylene)), more preferably, 1) —$X^2$— ($X^2$ is C1-2 straight chain alkylene (e.g., methylene, ethylene) or C3-6 cyclic alkylene (e.g., cyclopropylene)).

In one embodiment, cycloalkyl for A is preferably a group selected from the following:

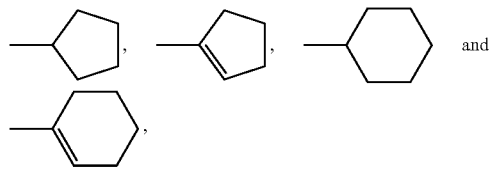

a heterocyclic group for A is preferably a group selected from the following:

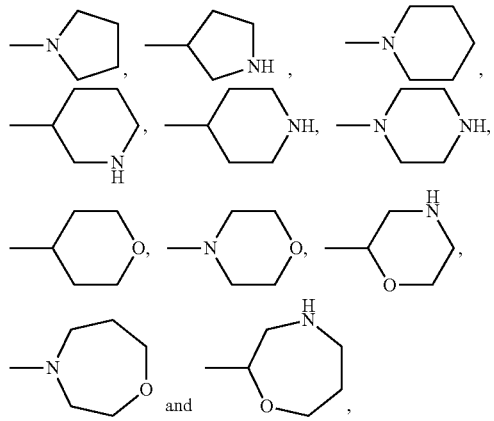

aryl for A is preferably the following group:

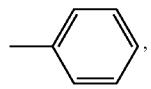

heteroaryl for A is preferably a group selected from the following:

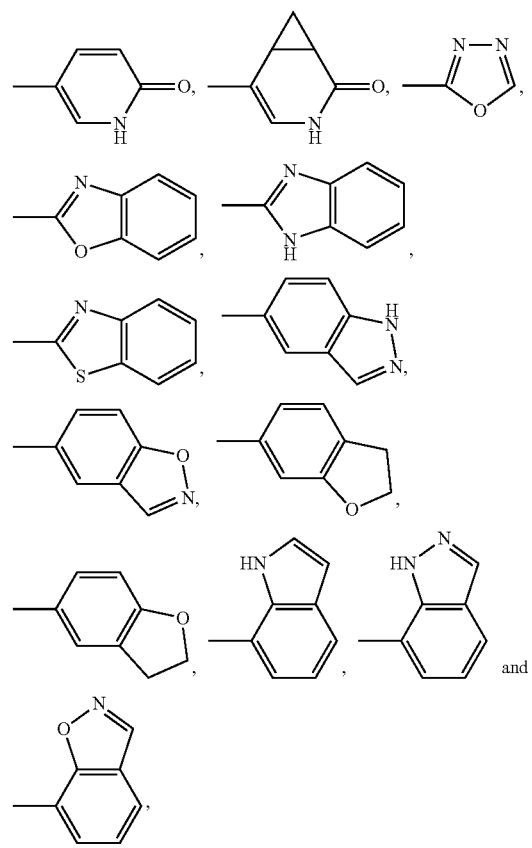

more preferably, A is

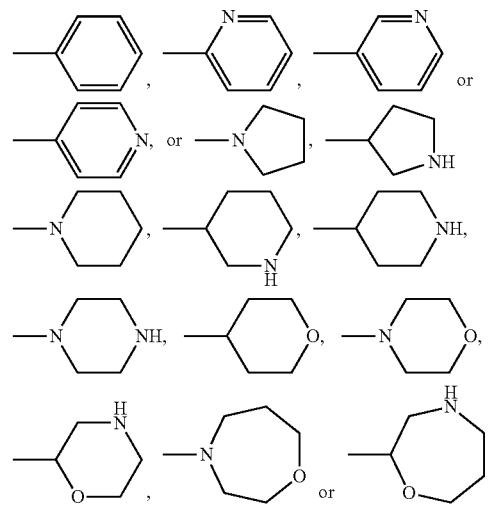

Preferable examples of compound (1) include the following compounds.

[Compound 1-A]

Compound (1) wherein

A is cycloalkyl (e.g., cyclohexenyl); a heterocyclic group (e.g., piperidinyl, tetrahydropyranyl); aryl (e.g., phenyl); or heteroaryl (e.g., dihydrobenzofuranyl, oxodihydropyridinyl, oxoazabicycloheptenyl, oxadiazolyl, pyridyl, benzimidazolyl, benzoxazolyl, benzisoxazolyl, benzthiazolyl, indolyl, indazolyl, imidazopyridyl);

$Z_1$, $Z_2$ and $Z_3$ are that

A) all of $Z_1$, $Z_2$ and $Z_3$ are carbons,

B) $Z_1$ is nitrogen, and $Z_2$ and $Z_3$ are carbons, or

C) $Z_2$ is nitrogen, and $Z_1$ and $Z_3$ are carbons;

$Z_4$ is carbon or nitrogen;

$R^1$ is halogen (e.g., a fluorine atom, a chlorine atom); alkyl (e.g., methyl, isopropyl); haloalkyl (e.g., trifluoromethyl); alkoxy (e.g., isopropoxy); haloalkoxy (e.g., trifluoromethoxy); cyano; a heterocyclic group (e.g., pyrrolidinyl); aryl (e.g., phenyl); or heteroaryl (e.g., pyrazolyl) optionally having 1 to 3 substituent(s) selected from alkyl (e.g., methyl);

$R^2$ and $R^3$ are the same or different and each is hydrogen; halogen (e.g., a fluorine atom, a chlorine atom); or alkyl (e.g., methyl);

$R^4$ is hydrogen; alkyl (e.g., methyl); or halogen (e.g., a fluorine atom, a chlorine atom);

$R^5$ and $R^6$ are the same or different and each is —$X^1$—$R^{7a}$ wherein $X^1$ is a single bond; linear alkylene (e.g., methylene, ethylene, trimethylene); —O—; —O-alkylene- (e.g., —O-methylene-, —O-ethylene-) optionally having 1 to 3 substituent(s) selected from alkyl (e.g., methyl); or —CO—, and $R^{7a}$ is hydrogen; hydroxy; halogen (e.g., a fluorine atom, a chlorine atom); alkyl (e.g., methyl, ethyl, isopropyl); haloalkyl (e.g., fluoromethyl, trifluoromethyl, trifluoroethyl); hydroxyalkyl (e.g., hydroxymethyl); alkoxy (e.g., methoxy, ethoxy, isopropoxy); carboxyl; —$NR^{7b}R^{7c}$ (wherein $R^{7b}$ and $R^{7c}$ are the same or different and each is hydrogen; alkyl (e.g., methyl); or haloalkyl (e.g., trifluoroethyl)); cyano; dialkylcarbamoyl (e.g., dimethylcarbamoyl); alkylsulfonyl (e.g., methylsulfonyl); a heterocyclic group (e.g., oxetanyl, azetidinyl, pyrrolidinyl, oxopyrrolidinyl, tetrahydropyranyl, morpholinyl) optionally having 1 to 3 substituent(s) selected from alkyl (e.g., methyl); or heteroaryl (e.g., pyrazolyl, imidazolyl, furyl, pyridyl); and $L^1$ is 1) —$X^2$— wherein $X^2$ is a single bond; linear alkylene (e.g., methylene, ethylene) optionally having 1 to 3 qjsubstituent(s) selected from alkyl (e.g., methyl); cyclic alkylene (e.g., cyclopropylene); alkenylene (e.g., ethene-1,2-diyl); or heterocycloalkylene (e.g., piperidinediyl), 2) —$X^2$—$(CH_2)_n$— wherein $X^2$ is a single bond; linear alkylene (e.g., methylene) optionally having 1 to 3 substituent(s) selected from alkyl (e.g., methyl); cyclic alkylene (e.g., cyclohexylene); heterocycloalkylene (e.g., oxetanediyl, oxoimidazolidinediyl); or heteroarylene (e.g., tetrazolediyl), and n is 1-3, 3) —O—$X^3$— wherein $X^3$ is linear alkylene (e.g., methylene, ethylene) optionally having 1 to 3 substituent(s) selected from alkyl (e.g., methyl), 4) —O—$(CH_2)_n$—$X^3$— wherein $X^3$ is cyclic alkylene (e.g., cyclohexylene), and n is 1-3, 5) —CO—$X^3$— wherein $X^3$ is linear alkylene (e.g., ethylene) optionally having 1 to 3 substituent(s) selected from alkyl (e.g., methyl); or heterocycloalkylene (e.g., pyrrolidinediyl, piperidinediyl), or 6) —CO—NH—$X^3$— wherein $X^3$ is linear alkylene (e.g., methylene, ethylene) optionally having 1 to 3 substituent(s) selected from (a) alkyl (e.g., methyl, isopropyl) optionally having 1 to 3 substituent(s) selected from aryl (e.g., phenyl) and heteroaryl (e.g., pyridyl), and (b) hydroxyalkyl (e.g., hydroxymethyl); cyclic alkylene (e.g., cyclopentylene); or heteroarylene (e.g., pyridinediyl).

[Compound 1-B]

Compound (1) wherein

A is cyclohexenyl, piperidinyl, tetrahydropyranyl, dihydrobenzofuranyl (e.g., 2,3-dihydro-1-benzofuranyl), oxodihydropyridinyl (e.g., 2-oxo-1,2-dihydropyridyl), oxoazabicycloheptenyl (e.g., 2-oxo-3-azabicyclo[4.1.0]hept-4-enyl), phenyl, oxadiazolyl (e.g., 1,3,4-oxadiazolyl), pyridyl, benzimidazolyl, benzoxazolyl, benzisoxazolyl, benzthiazolyl, indolyl (e.g., 1H-indolyl), indazolyl (e.g., 1H-indazolyl) or imidazopyridyl (e.g., imidazo[1,2-a]pyridyl);

$Z_1$, $Z_2$ and $Z_3$ are that

A) all of $Z_1$, $Z_2$ and $Z_3$ are carbons,

B) $Z_1$ is nitrogen, and $Z_2$ and $Z_3$ are carbons, or

C) $Z_2$ is nitrogen, and $Z_1$ and $Z_3$ are carbons;

$Z_4$ is carbon or nitrogen;

$R^1$ is a fluorine atom, a chlorine atom, methyl, isopropyl, trifluoromethyl, isopropoxy, trifluoromethoxy, cyano, pyrrolidinyl, phenyl, or pyrazolyl optionally having 1 to 3 methyl;

$R^2$ and $R^3$ are the same or different and each is hydrogen, a fluorine atom, a chlorine atom or methyl;

$R^4$ is hydrogen, methyl, a fluorine atom or a chlorine atom;

$R^5$ and $R^6$ are the same or different and each is (1) —$X^1$—$R^{7a}$ wherein $X^1$ is a single bond, and $R^{7a}$ is hydrogen; halogen (e.g., a fluorine atom, a chlorine atom); alkyl (e.g., methyl); haloalkyl (e.g., fluoromethyl); hydroxyalkyl (e.g., hydroxymethyl); alkoxy (e.g., methoxy, ethoxy, isopropoxy); carboxyl; —$NR^{7b}R^{7c}$ (wherein $R^{7b}$ and $R^{7c}$ are hydrogens); cyano; a heterocyclic group (e.g., oxetanyl); or heteroaryl (e.g., furyl, pyridyl), (2) —X—$R^{7a}$ wherein $X^1$ is linear alkylene (e.g., methylene, ethylene, trimethylene), and $R^{7a}$ is hydrogen; hydroxy; halogen (e.g., a fluorine atom); alkoxy (e.g., methoxy); —$NR^{7b}R^{7c}$ (wherein $R^{7b}$ and $R^{7c}$ are the same or different and each is hydrogen or haloalkyl (e.g., trifluoroethyl)); cyano; alkylsulfonyl (e.g., methylsulfonyl); or heteroaryl (e.g., pyrazolyl, imidazolyl), (3) —$X^1$—$R^{7a}$ wherein $X^1$ is —O—, and $R^{7a}$ is alkyl (e.g., methyl, ethyl, isopropyl); haloalkyl (e.g., trifluoromethyl, trifluoroethyl); or heterocyclic group (e.g., oxetanyl, azetidinyl, pyrrolidinyl, oxopyrrolidinyl, tetrahydropyranyl) optionally having 1 to 3 substituent(s) selected from alkyl (e.g., methyl), (4) —$X^1$—$R^{7a}$ wherein $X^1$ is —O-alkylene- (e.g., —O-methylene-, —O-ethylene-) optionally having 1 to 3 substituent(s) selected from alkyl (e.g., methyl), and $R^{7a}$ is hydrogen; alkyl (e.g., methyl); haloalkyl (e.g., trifluoromethyl); alkoxy (e.g., methoxy); —$NR^{7b}R^{7c}$ (wherein $R^{7b}$ and $R^{7c}$ are the same or different and each is alkyl (e.g., methyl)); dialkylcarbamoyl (e.g., dimethylcarbamoyl); or a heterocyclic group (e.g., oxopyrrolidinyl, morpholinyl), or (5) —$X^1$—$R^{7a}$ wherein $X^1$ is —CO—, $R^{7a}$ is —$NR^{7b}R^{7c}$ (wherein $R^{7b}$ and $R^{7c}$ are the same or different and each is hydrogen or alkyl (e.g., methyl)); and $L^1$ is 1) —$X^2$— wherein $X^2$ is a single bond; methylene or ethylene optionally having 1 to 3 methyl; cyclopropylene (e.g., 1,1-cyclopropylene, 1,2-cyclopropylene); ethene-1,2-diyl; or piperidinediyl (e.g., piperidine-1,4-diyl), 2) —$X^2$—$(CH_2)_n$— wherein $X^2$ is a single bond; methylene optionally having 1 to 3 methyl; cyclohexylene (e.g., 1,4-cyclohexylene); oxetanediyl (e.g., oxetane-3,3-diyl); oxoimidazolidinediyl (e.g., 2-oxoimidazolidine-1,3-diyl); or tetrazolediyl (e.g., tetrazole-1,3-diyl), and n is 1-3, 3) —O—$X^3$— wherein $X^3$ is methylene or ethylene optionally having 1 to 3 methyl, 4) —O—(CH$_2$)$_n$—X$^3$— wherein X$^3$ is cyclohexylene (e.g., 1,4-cyclohexylene), and n is 1-3,
5) —CO—X$^3$— wherein X$^3$ is ethylene optionally having 1 to 3 methyl; pyrrolidinediyl (e.g., pyrrolidine-1,2-diyl); or piperidinediyl (e.g., piperidine-1,4-diyl), or
6) —CO—NH—X$^3$— wherein X$^3$ is methylene or ethylene optionally having 1 to 3 substituent(s) selected from (a) methyl and isopropyl optionally having 1 to 3 substituent(s) selected from phenyl and pyridyl, and (b) hydroxymethyl; cyclopentylene (e.g., 1,2-cyclopentylene); or pyridinediyl (e.g., pyridine-2,5-diyl).

[Compound 1-C]
Compound (1) wherein
A is aryl (e.g., phenyl) or heteroaryl (e.g., oxodihydropyridinyl, oxoazabicycloheptenyl, pyridyl, benzimidazolyl, benzoxazolyl, indazolyl);
Z$_1$, Z$_2$ and Z$_3$ are that
A) all of Z$_1$, Z$_2$ and Z$_3$ are carbons;
Z$_4$ is carbon or nitrogen;
R$^1$ is alkyl (e.g., isopropyl) or haloalkoxy (e.g., trifluoromethoxy);
R$^2$ and R$^3$ are hydrogen;
R$^4$ is hydrogen;
R$^5$ and R$^6$ are the same or different and each is —X—R$^{7a}$ wherein X$^1$ is a single bond; linear alkylene (e.g., methylene, ethylene, trimethylene); —O—; —O-alkylene- (e.g., —O-methylene-, —O-ethylene-) optionally having 1 to 3 substituent(s) selected from alkyl (e.g., methyl); or —CO—, and R$^{7a}$ is hydrogen; hydroxy; halogen (e.g., a fluorine atom, a chlorine atom); alkyl (e.g., methyl, ethyl, isopropyl); haloalkyl (e.g., fluoromethyl); hydroxyalkyl (e.g., hydroxymethyl); alkoxy (e.g., methoxy, ethoxy, isopropoxy); —NR$^{7b}$R$^{7c}$ (wherein R$^{7b}$ and R$^{7c}$ are the same or different and each is hydrogen; alkyl (e.g., methyl); or haloalkyl (e.g., trifluoroethyl)); cyano; dialkylcarbamoyl (e.g., dimethylcarbamoyl); alkylsulfonyl (e.g., methylsulfonyl); a heterocyclic group (e.g., oxetanyl, azetidinyl, pyrrolidinyl, oxopyrrolidinyl, tetrahydropyranyl, morpholinyl) optionally having 1 to 3 substituent(s) selected from alkyl (e.g., methyl); or heteroaryl (e.g., imidazolyl, furyl, pyridyl); and
L$^1$ is
1) —X$^2$— wherein X$^2$ is a single bond; linear alkylene (e.g., methylene, ethylene) optionally having 1 to 3 substituent(s) selected from alkyl (e.g., methyl); cyclic alkylene (e.g., cyclopropylene); or alkenylene (e.g., ethene-1,2-diyl),
2) —X$^2$—(CH$_2$)$_n$— wherein X$^2$ is a single bond; linear alkylene (e.g., methylene) optionally having 1 to 3 substituent(s) selected from alkyl (e.g., methyl); or heterocycloalkylene (e.g., oxetanediyl), and n is 1-3, or
3) —O—X$^3$— wherein X$^3$ is linear alkylene (e.g., methylene) optionally having 1 to 3 substituent(s) selected from alkyl (e.g., methyl).

[Compound 1-D]
Compound (1) wherein
A is oxodihydropyridinyl (e.g., 2-oxo-1,2-dihydropyridyl), oxoazabicycloheptenyl (e.g., 2-oxo-3-azabicyclo[4.1.0]hept-4-enyl), phenyl, pyridyl, benzimidazolyl, benzoxazolyl or indazolyl (e.g., 1H-indazolyl);
Z$_1$, Z$_2$ and Z$_3$ are that
A) all of Z$_1$, Z$_2$ and Z$_3$ are carbons;
Z$_4$ is carbon or nitrogen;
R$^1$ is isopropyl or trifluoromethoxy;
R$^2$ and R$^3$ are hydrogen;
R$^4$ is hydrogen;
R$^5$ and R$^6$ are the same or different and each is (1) —X$^1$—R$^{7a}$ wherein X$^1$ is a single bond, and R$^{7a}$ is hydrogen; halogen (e.g., a fluorine atom, a chlorine atom); alkyl (e.g., methyl); haloalkyl (e.g., fluoromethyl); hydroxyalkyl (e.g., hydroxymethyl); alkoxy (e.g., methoxy, ethoxy, isopropoxy); cyano; a heterocyclic group (e.g., oxetanyl); or heteroaryl (e.g., furyl, pyridyl),
(2) —X$^1$—R$^{7a}$ wherein X$^1$ is linear alkylene (e.g., methylene, ethylene, trimethylene), and R$^{7a}$ is hydrogen; hydroxy; halogen (e.g., a fluorine atom); alkoxy (e.g., methoxy); —NR$^{7b}$R$^{7c}$ (wherein R$^{7b}$ and R$^{7c}$ are the same or different and each is hydrogen or haloalkyl (e.g., trifluoroethyl)); cyano; alkylsulfonyl (e.g., methylsulfonyl); or heteroaryl (e.g., imidazolyl),
(3) —X—R$^{7a}$ wherein X$^1$ is —O—, and R$^{7a}$ is alkyl (e.g., methyl, ethyl, isopropyl); or a heterocyclic group (e.g., oxetanyl, azetidinyl, pyrrolidinyl, oxopyrrolidinyl, tetrahydropyranyl) optionally having 1 to 3 substituent(s) selected from alkyl (e.g., methyl), or
(4) —X$^1$—R$^{7a}$ wherein X$^1$ is —O-alkylene- (e.g., —O-methylene-, —O-ethylene-) optionally having 1 to 3 substituent(s) selected from alkyl (e.g., methyl), and R$^{7a}$ is hydrogen; alkyl (e.g., methyl); alkoxy (e.g., methoxy); —NR$^{7b}$R$^{7c}$ (wherein R$^{7b}$ and R$^{7c}$ are the same or different and each is alkyl (e.g., methyl)); dialkylcarbamoyl (e.g., dimethylcarbamoyl); or a heterocyclic group (e.g., oxopyrrolidinyl, morpholinyl); and
L$^1$ is
1) —X$^2$— wherein X$^2$ is a single bond; methylene or ethylene optionally having 1 to 3 methyl; cyclopropylene (e.g., 1,1-cyclopropylene, 1,2-cyclopropylene); or ethene-1,2-diyl,
2) —X$^2$—(CH$_2$)$_n$— wherein X$^2$ is a single bond; methylene optionally having 1 to 3 methyl; or oxetanediyl (e.g., oxetane-3,3-diyl), and n is 1-3,
3) —O—X$^3$— wherein X$^3$ is methylene optionally having 1 to 3 methyl.

[Compound 1-E]
Compound (1) wherein
A is aryl (e.g., phenyl) or heteroaryl (e.g., pyridyl, benzimidazolyl, benzoxazolyl, indazolyl);
Z$_1$, Z$_2$ and Z$_3$ are that
A) all of Z$_1$, Z$_2$ and Z$_3$ are carbons;
Z$_4$ is carbon or nitrogen;
R$^1$ is alkyl (e.g., isopropyl) or haloalkoxy (e.g., trifluoromethoxy);
R$^2$ and R$^3$ are hydrogen;
R$^4$ is hydrogen;
R$^5$ and R$^6$ are the same or different and each is —X$^1$—R$^{7a}$ wherein X$^1$ is a single bond; linear alkylene (e.g., methylene, ethylene, trimethylene); —O—; or —O-alkylene- (e.g., —O-methylene-, —O-ethylene-), and R$^{7a}$ is hydrogen; halogen (e.g., a fluorine atom, a chlorine atom); alkyl (e.g., methyl); alkoxy (e.g., methoxy); cyano; alkylsulfonyl (e.g., methylsulfonyl); a heterocyclic group (e.g., oxetanyl, azetidinyl, tetrahydropyranyl); or heteroaryl (e.g., imidazolyl, furyl, pyridyl); and
L$^1$ is
1) —X$^2$— wherein X$^2$ is a single bond; linear alkylene (e.g., methylene, ethylene) optionally having 1 to 3 substituent(s) selected from alkyl (e.g., methyl); or cyclic alkylene (e.g., cyclopropylene),
2) —X$^2$—(CH$_2$)$_n$— wherein X$^2$ is a single bond; linear alkylene (e.g., methylene); or heterocycloalkylene (e.g., oxoimidazolidinediyl), and n is 1-3,
3) —O—X$^3$— wherein X$^3$ is linear alkylene (e.g., methylene), or 4) —O—(CH$_2$)$_n$—X$^3$— wherein X$^3$ is cyclic alkylene (e.g., cyclohexylene), and n is 1-3.

[Compound 1-F]
Compound (1) wherein
A is phenyl, pyridyl, benzimidazolyl, benzoxazolyl or indazolyl (e.g., 1H-indazolyl);
Z$_1$, Z$_2$ and Z$_3$ are that
A) all of Z$_1$, Z$_2$ and Z$_3$ are carbons;
Z$_4$ is carbon or nitrogen;
R$^1$ is isopropyl or trifluoromethoxy;
R$^2$ and R$^3$ are hydrogen;
R$^4$ is hydrogen;
R$^5$ and R$^6$ are the same or different and each is
(1) —X$^1$—R$^{7a}$ wherein X$^1$ is a single bond, and R$^{7a}$ is hydrogen; halogen (e.g., a fluorine atom, a chlorine atom); alkyl (e.g., methyl); alkoxy (e.g., methoxy); cyano; a heterocyclic group (e.g., oxetanyl); or heteroaryl (e.g., furyl, pyridyl),
(2) —X$^1$—R$^{7a}$ wherein X$^1$ is linear alkylene (e.g., methylene, ethylene, trimethylene), and R$^{7a}$ is hydrogen; alkoxy (e.g., methoxy); alkylsulfonyl (e.g., methylsulfonyl); or heteroaryl (e.g., imidazolyl),
(3) —X$^1$—R$^{7a}$ wherein X$^1$ is —O—, and R$^{7a}$ is a heterocyclic group (e.g., oxetanyl, azetidinyl, tetrahydropyranyl), or
(4) —X$^1$—R$^{7a}$ wherein X$^1$ is —O-alkylene- (e.g., —O-methylene-, —O-ethylene-), and R$^{7a}$ is hydrogen; or alkoxy (e.g., methoxy); and
L$^1$ is
1) —X$^2$— wherein X$^2$ is a single bond; methylene or ethylene optionally having 1 to 3 methyl; or cyclopropylene (e.g., 1,2-cyclopropylene),
2) —X$^2$—(CH$_2$)$_n$— wherein X$^2$ is a single bond; methylene; or oxoimidazolidinediyl (e.g., 2-oxoimidazolidine-1,3-diyl), and n is 1-3,
3) —O—X$^3$— wherein X$^3$ is methylene, or
4) —O—(CH$_2$)$_n$—X$^3$— wherein X$^3$ is cyclohexylene, and n is 1-3.

[Compound 1-G]
Compound (1) wherein
A is aryl (e.g., phenyl) or heteroaryl (e.g., pyridyl);
Z$_1$, Z$_2$ and Z$_3$ are that
A) all of Z$_1$, Z$_2$ and Z$_3$ are carbons;
Z$_4$ is carbon or nitrogen;
R$^1$ is haloalkoxy (e.g., trifluoromethoxy);
R$^2$ and R$^3$ are hydrogen;
R$^4$ is hydrogen;
R$^5$ and R$^6$ are the same or different and each is —X$^1$—R$^{7a}$ wherein X$^1$ is a single bond; linear alkylene (e.g., methylene); —O—; or —O-alkylene- (e.g., —O-methylene-, —O-ethylene-) optionally having 1 to 3 substituent(s) selected from alkyl (e.g., methyl), and R$^{7a}$ is hydrogen; halogen (e.g., a chlorine atom); alkyl (e.g., methyl, ethyl, isopropyl); alkoxy (e.g., methoxy, ethoxy, isopropoxy); or cyano; and
L$^1$ is
1) —X$^2$— wherein X$^2$ is linear alkylene (e.g., ethylene); or cyclic alkylene (e.g., cyclopropylene).

[Compound 1-H]
Compound (1) wherein
A is phenyl or pyridyl;
Z$_1$, Z$_2$ and Z$_3$ are that
A) all of Z$_1$, Z$_2$ and Z$_3$ are carbons;
Z$_4$ is carbon or nitrogen;
R$^1$ is trifluoromethoxy;
R$^2$ and R$^3$ is hydrogen;
R$^4$ is hydrogen;
R$^5$ and R$^6$ are the same or different and each is
(1) —X$^1$—R$^{7a}$ wherein X$^1$ is a single bond, and R$^{7a}$ is hydrogen; halogen (e.g., a chlorine atom); alkyl (e.g., methyl); alkoxy (e.g., methoxy, ethoxy, isopropoxy); or cyano,
(2) —X$^1$—R$^{7a}$ wherein X$^1$ is linear alkylene (e.g., methylene), and R$^{7a}$ is hydrogen,
(3) —X$^1$—R$^{7a}$ wherein X$^1$ is —O—, and R$^{7a}$ is alkyl (e.g., methyl, ethyl, propyl), or
(4) —X$^1$—R$^{7a}$ wherein X$^1$ is —O-alkylene- (e.g., —O-methylene-, —O-ethylene-) optionally having 1 to 3 substituent(s) selected from alkyl (e.g., methyl), and R$^{7a}$ is hydrogen; or alkyl (e.g., methyl); and
L$^1$ is
1) —X$^2$— wherein X$^2$ is ethylene or cyclopropylene.

Specific examples of compound (1) include the compounds of Examples 1-39 and 41-176; of these
2-[6-(3-trifluoromethoxy-benzylamino)-pyridin-3-yl]-3H-benzimidazole-4-carboxylic acid,
2-[6-(3-trifluoromethoxy-benzylamino)-pyridin-3-yl]-benzoxazole-6-carboxylic acid,
1-methyl-5-[6-(3-trifluoromethoxy-benzylamino)-pyridin-3-yl]-1H-indazole-3-carboxylic acid,
5-[6-(3-trifluoromethoxy-benzylamino)-pyridin-3-yl]-1H-indazole-3-carboxylic acid,
3-{3-cyano-2-methoxy-5-[6-(3-trifluoromethoxy-benzylamino)-pyridin-3-yl]-phenyl}-propionic acid,
3-{2-chloro-5-[2-(3-trifluoromethoxy-benzylamino)-pyrimidin-5-yl]-phenyl}-propionic acid,
3-{3-cyano-2-methoxy-5-[6-(3-trifluoromethoxy-benzylamino)-pyridin-3-yl]-phenyl}-2-methyl-propionic acid,
2-{2-methoxy-5-[6-(3-trifluoromethoxy-benzylamino)-pyridin-3-yl]-phenyl}-cyclopropanecarboxylic acid,
(1S,2S)-2-{2-methoxy-5-[6-(3-trifluoromethoxy-benzylamino)-pyridin-3-yl]-phenyl}-cyclopropanecarboxylic acid,
2-[5-methoxy-6'-(3-trifluoromethoxy-benzylamino)-[2,3']bipyridinyl-6-yl]-cyclopropanecarboxylic acid,
(1S,2S)-2-[5-methoxy-6'-(3-trifluoromethoxy-benzylamino)-[2,3']bipyridinyl-6-yl]-cyclopropanecarboxylic acid,
(1S,2S)-2-{3-methoxy-6-[2-(3-trifluoromethoxy-benzylamino)-pyrimidin-5-yl]-pyridin-2-yl}-cyclopropanecarboxylic acid,
(1S,2S)-2-[5-chloro-6'-(3-trifluoromethoxy-benzylamino)-[2,3']bipyridinyl-6-yl]-cyclopropanecarboxylic acid,
(1S,2S)-2-[5-ethoxy-6'-(3-trifluoromethoxy-benzylamino)-[2,3']bipyridinyl-6-yl]-cyclopropanecarboxylic acid,
(1S,2S)-2-[5-methyl-6'-(3-trifluoromethoxy-benzylamino)-[2,3']bipyridinyl-6-yl]-cyclopropanecarboxylic acid,
3-{2-methoxy-5-[2-(3-trifluoromethoxy-benzylamino)-pyrimidin-5-yl]-phenyl}-propionic acid,
3-{2-methoxy-5-[6-(3-trifluoromethoxy-benzylamino)-pyridin-3-yl]-phenyl}-propionic acid,
2-{2-methoxy-5-[6-(3-trifluoromethoxy-benzylamino)-pyridin-3-yl]-phenyl}-2-methyl-propionic acid,
2-{3-cyano-2-methoxy-5-[6-(3-trifluoromethoxy-benzylamino)-pyridin-3-yl]-phenyl}-2-methyl-propionic acid,
2-chloro-3-(1-methyl-pyrrolidin-3-yloxy)-5-[2-(3-trifluoromethoxy-benzylamino)-pyrimidin-5-yl]-benzoic acid,
2-chloro-3-(pyrrolidin-3-yloxy)-5-[2-(3-trifluoromethoxy-benzylamino)-pyrimidin-5-yl]-benzoic acid,
3-(azetidin-3-yloxy)-2-chloro-5-[2-(3-trifluoromethoxy-benzylamino)-pyrimidin-5-yl]-benzoic acid,
2-chloro-3-(1-methyl-azetidin-3-yloxy)-5-[2-(3-trifluoromethoxy-benzylamino)-pyrimidin-5-yl]-benzoic acid,
2-methoxy-3-pyridin-4-yl-5-[2-(3-trifluoromethoxy-benzylamino)-pyrimidin-5-yl]-benzoic acid, 2-methoxy-5-[6-(3-trifluoromethoxy-benzylamino)-pyridin-3-yl]-benzoic acid,
3-fluoro-2-methoxy-5-[6-(3-trifluoromethoxy-benzylamino)-pyridin-3-yl]-benzoic acid,
2,3-dimethoxy-5-[6-(3-trifluoromethoxy-benzylamino)-pyridin-3-yl]-benzoic acid,
2-chloro-3-methoxy-5-[6-(3-trifluoromethoxy-benzylamino)-pyridin-3-yl]-benzoic acid,
3-cyano-2-methoxy-5-[6-(3-trifluoromethoxy-benzylamino)-pyridin-3-yl]-benzoic acid,
7-[6-(3-trifluoromethoxy-benzylamino)-pyridin-3-yl]-1H-indazole-3-carboxylic acid,
4-methoxy-7-[6-(3-trifluoromethoxy-benzylamino)-pyridin-3-yl]-1H-indazole-3-carboxylic acid,
1-(2-methoxy-ethyl)-5-[6-(3-trifluoromethoxy-benzylamino)-pyridin-3-yl]-1H-indazole-3-carboxylic acid,
1-methyl-5-[2-(3-trifluoromethoxy-benzylamino)-pyrimidin-5-yl]-1H-indazole-3-carboxylic acid,
1-(3-methanesulfonyl-propyl)-5-[6-(3-trifluoromethoxy-benzylamino)-pyridin-3-yl]-1H-indazole-3-carboxylic acid,
1-(3-cyano-propyl)-5-[6-(3-trifluoromethoxy-benzylamino)-pyridin-3-yl]-1H-indazole-3-carboxylic acid,
(E)-3-{3-methyl-2-oxo-5-[6-(3-trifluoromethoxy-benzylamino)-pyridin-3-yl]-3-aza-bicyclo[4.1.0]hept-4-en-1-yl}-acrylic acid,
(E)-3-[1-methyl-6-oxo-6'-(3-trifluoromethoxy-benzylamino)-1,6-dihydro-[3,3']bipyridinyl-5-yl]-acrylic acid,
(1S,2S)-2-[5-isopropoxy-6'-(3-trifluoromethoxy-benzylamino)-[2,3']bipyridinyl-6-yl]-cyclopropanecarboxylic acid,
3-{3-cyano-2-methoxy-5-[2-(3-trifluoromethoxy-benzylamino)-pyrimidin-5-yl]-phenyl}-propionic acid,
(E)-3-{2-methoxy-5-[6-(3-trifluoromethoxy-benzylamino)-pyridin-3-yl]-phenyl}-acrylic acid,
3-{2-methoxy-4-[6-(3-trifluoromethoxy-benzylamino)-pyridin-3-yl]-phenyl}-propionic acid,
(trans)-2-{2-methoxy-4-[6-(3-trifluoromethoxy-benzylamino)-pyridin-3-yl]-phenyl}-cyclopropanecarboxylic acid,
(trans)-2-{2-methoxy-5-[2-(3-trifluoromethoxy-benzylamino)-pyrimidin-5-yl]-phenyl}-cyclopropanecarboxylic acid,
3-{2-methoxy-3-oxetan-3-yl-5-[6-(3-trifluoromethoxy-benzylamino)-pyridin-3-yl]-phenyl}-propionic acid,
3-{3-cyano-2-methoxy-5-[6-(3-trifluoromethoxy-benzylamino)-pyridin-3-yl]-phenyl}-3-methyl-butyric acid,
3-{3-cyano-2-methoxy-5-[2-(3-trifluoromethoxy-benzylamino)-pyrimidin-5-yl]-phenyl}-3-methyl-butyric acid,
(3-{2-methoxy-5-[6-(3-trifluoromethoxy-benzylamino)-pyridin-3-yl]-phenyl}-oxetan-3-yl)-acetic acid,
3-{2-methoxy-5-[6-(3-trifluoromethoxy-benzylamino)-pyridin-3-yl]-phenyl}-3-methyl-butyric acid,
3-{2,6-dimethoxy-4-[6-(3-trifluoromethoxy-benzylamino)-pyridin-3-yl]-phenyl}-propionic acid,
3-{2,6-dimethoxy-4-[6-(3-trifluoromethoxy-benzylamino)-pyridin-3-yl]-phenyl}-2-methyl-propionic acid,
1-[1-methyl-6-oxo-6'-(3-trifluoromethoxy-benzylamino)-1,6-dihydro-[3,3']bipyridinyl-5-yl]-cyclopropanecarboxylic acid,
2-{3-imidazol-1-ylmethyl-2-methoxy-5-[6-(3-trifluoromethoxy-benzylamino)-pyridin-3-yl]-phenyl}-2-methyl-propionic acid,
{2-methoxy-5-[6-(3-trifluoromethoxy-benzylamino)-pyridin-3-yl]-phenyl}-acetic acid,
1-{2-methoxy-5-[6-(3-trifluoromethoxy-benzylamino)-pyridin-3-yl]-phenyl}-cyclopropanecarboxylic acid,
2-{2-methoxy-5-[2-(3-trifluoromethoxy-benzylamino)-pyrimidin-5-yl]-phenyl}-2-methyl-propionic acid,
2-[6-methoxy-6'-(3-trifluoromethoxy-benzylamino)-[3,3']bipyridinyl-5-yl]-2-methyl-propionic acid,
2-[5-methoxy-6'-(3-trifluoromethoxy-benzylamino)-[2,3']bipyridinyl-6-yl]-2-methyl-propionic acid,
2-{3-hydroxymethyl-2-methoxy-5-[6-(3-trifluoromethoxy-benzylamino)-pyridin-3-yl]-phenyl}-2-methyl-propionic acid,
2-{2-methoxy-3-methoxymethyl-5-[6-(3-trifluoromethoxy-benzylamino)-pyridin-3-yl]-phenyl}-2-methyl-propionic acid,
2-{2-methoxy-3-[(2,2,2-trifluoro-ethylamino)-methyl]-5-[6-(3-trifluoromethoxy-benzylamino)-pyridin-3-yl]-phenyl}-2-methyl-propionic acid,
2-{3-fluoromethyl-2-methoxy-5-[6-(3-trifluoromethoxy-benzylamino)-pyridin-3-yl]-phenyl}-2-methyl-propionic acid,
{2-methoxy-5-[6-(3-trifluoromethoxy-benzylamino)-pyridin-3-yl]-phenoxy}-acetic acid,
2-{2-methoxy-5-[6-(3-trifluoromethoxy-benzylamino)-pyridin-3-yl]-phenoxy}-propionic acid,
2-chloro-3-(2-methoxy-ethoxy)-5-[2-(3-trifluoromethoxy-benzylamino)-pyrimidin-5-yl]-benzoic acid,
2-chloro-3-(tetrahydro-pyran-4-yloxy)-5-[2-(3-trifluoromethoxy-benzylamino)-pyrimidin-5-yl]-benzoic acid,
2-chloro-3-[2-(2-oxo-pyrrolidin-1-yl)-ethoxy]-5-[2-(3-trifluoromethoxy-benzylamino)-pyrimidin-5-yl]-benzoic acid,
2-chloro-3-(2-oxo-pyrrolidin-3-yloxy)-5-[2-(3-trifluoromethoxy-benzylamino)-pyrimidin-5-yl]-benzoic acid,
2-chloro-3-(oxetan-3-yloxy)-5-[2-(3-trifluoromethoxy-benzylamino)-pyrimidin-5-yl]-benzoic acid,
2-chloro-3-dimethylcarbamoylmethoxy-5-[2-(3-trifluoromethoxy-benzylamino)-pyrimidin-5-yl]-benzoic acid,
2-chloro-3-(2-dimethylamino-ethoxy)-5-[2-(3-trifluoromethoxy-benzylamino)-pyrimidin-5-yl]-benzoic acid,
2-chloro-3-(2-morpholin-4-yl-ethoxy)-5-[2-(3-trifluoromethoxy-benzylamino)-pyrimidin-5-yl]-benzoic acid,
3-furan-3-yl-2-methoxy-5-[2-(3-trifluoromethoxy-benzylamino)-pyrimidin-5-yl]-benzoic acid,
2-methoxy-5-[2-(3-trifluoromethoxy-benzylamino)-pyrimidin-5-yl]-benzoic acid, and
5-[6-(3-isopropyl-benzylamino)-pyridin-3-yl]-2-methoxy-benzoic acid are preferable.

Since the compound of the present invention has a basic group and an acidic group in a molecule, examples of a pharmacologically acceptable salt thereof include metal salt, ammonium salt, salt with organic base, salt with inorganic acid, salt with organic acid, salt with basic amino acid, salt with acidic amino acid and the like.

Preferable examples of the metal salt include alkali metal salts such as sodium salt, potassium salt and the like; alkaline earth metal salts such as calcium salt, magnesium salt, barium salt and the like; aluminum salt and the like.

Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Of these, a pharmaceutically acceptable salt is preferable.

The compound of the present invention encompasses the above-mentioned compound (1) and a pharmaceutically acceptable salt thereof, as well as hydrate and solvate thereof.

The compound of the present invention (1) can be produced according to, for example, the following production methods 1-28.

Production Method 1

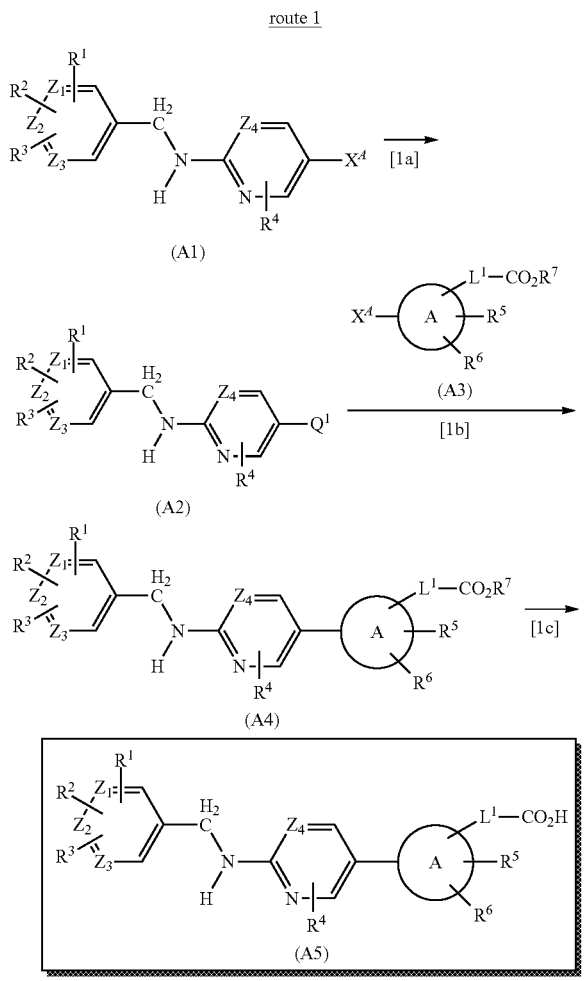

[in the above-mentioned scheme, $R^7$ is alkyl, $X^A$ is halogen, $Q^1$ is borate, and other symbols are as defined above].

[Step 1a]

In the above-mentioned scheme, compound (A2) can be produced by reacting compound (A1) with bis(pinacol) diborane in a solvent in the presence of a transition metal complex and a base. The solvent is not particularly limited as long as it does not adversely influence the reaction and, for example, toluene, benzene, xylene, dichloromethane, dichloroethane, chloroform, tetrahydrofuran (THF), dimethoxyethane (DME), dioxane, diethyl ether, acetonitrile, ethyl acetate, N,N-dimethylformamide (DMF), dimethyl sulfoxide (DMSO), N-methylpyrrolidone (NMP), methyl alcohol, ethyl alcohol, i-propyl alcohol, n-butyl alcohol, water or a mixed solvent can be used as appropriate. Examples of the transition metal complex to be used include 0 valent palladium complexes such as tetrakis(triphenylphosphine)palladium(0), tris(dibenzylideneacetone)dipalladium(0), bis(dibenzylideneacetone)palladium(0), bis(tri-tert-butylphosphine)palladium(0), and bis(tricyclohexylphosphine)palladium(0), and divalent palladium complexes such as palladium(II) acetate, palladium(II) trifluoroacetate, bis(triphenylphosphine)palladium (II) dichloride, bis(tri-O-tolylphosphine)palladium(II) dichloride, bis(tricyclohexylphosphine)palladium(II) dichloride, bis(benzonitrile)palladium(II) dichloride, bis(acetonitrile)palladium(II) dichloride, bis(acetylacetone)palladium(II), [1,1'-bis(diphenylphosphino)ferrocene]palladium (II) dichloride, bis(di-tert-butyl(4-dimethylaminophenyl) phosphine)dichloropalladium(II)(A-$^{ta}$Phos), and bis (dicyclohexyl(4-dimethylaminophenyl)phosphine) dichloropalladium(II)(A-$^{CA}$Phos). In addition, a suitable ligand may be added and, for example, tri-tert-butylphosphine, tri-cyclohexylphosphine, 1,1'-bis(diphenylphosphino)ferrocene (DPPF), 1-[2-[bis(tert-butyl)phosphino] phenyl]-3,5-diphenyl-1H-pyrazole (TrippyPhos), (±)-2,2'-bis(diphenylphosphino)-1,1'-binaphthyl (BINAP), 2-dicyclohexylphosphino-2'-(N,N-dimethylamino)biphenyl, tri(ortho-tolyl)phosphine, 1,3-bis(diphenylphosphino)propane, 1,2,3,4,5-pentaphenyl-1-(di-tert-butylphosphino)ferrocene (Q-Phos), 4,5-bis(diphenylphosphino)-9,9-dimethylxanthene (Xantphos), di(1-adamantyl)-n-butylphosphine (CataCXium A), (2-biphenyl)di-tert-butylphosphine (JohnPhos), (S)-1-[(1R)-2-(diphenylphosphino)ferrocenyl]ethyldicyclohexylphosphine (CyPFtBu JosiPhos), 2-dicyclohexylphosphino-2',6'-diisopropoxybiphenyl (RuPhos), 2-dicyclohexylphosphino-2',6'-dimethoxybiphenyl (SPhos), 2-dicyclohexylphosphino-2'-(N,N-dimethylamino)biphenyl (DavePhos), 2-dicyclohexylphosphino-2',4',6'-triisopropylbiphenyl (XPhos), 2-di-tert-butylphosphino-2',4',6'-triisopropyl-1,1'-biphenyl (tert-butyl-X-Phos), 2-(dicyclohexylphosphino)-3,6-dimethoxy-2',4',6'-triisopropyl-1,1'-biphenyl (BrettPhos) and the like can be mentioned. Examples of the base include sodium hydrogen carbonate, sodium carbonate, potassium carbonate, cesium carbonate, sodium acetate, potassium acetate, lithium tert-butoxide, sodium tert-butoxide, potassium tert-butoxide, tripotassium phosphate, dipotassium hydrogen phosphate, potassium dihydrogen phosphate, triethylamine, diisopropylethylamine, 1,8-diazabicyclo[5.4.0]undecene (DBU), diazabicyclononene (DBN), 1,4-diazabicyclo[2.2.2]octane (DABCO) and the like can be mentioned. The amount of the transition metal complex to be used is 0.01-0.3 equivalents, preferably 0.03-0.1 equivalents, relative to compound (A1). The amount of the base to be used is 1-10 equivalents, preferably 2-7 equivalents, relative to compound (A1). Particularly, it can be preferably produced by a method using reaction conditions such as those described in J. Org. Chem., 1995, 60, 7508-7510.

[Step 1b]

In the above-mentioned scheme, compound (A4) can be produced by reacting compound (A2) with compound (A3) in a solvent in the presence of a transition metal complex and a base. The solvent is not particularly limited as long as it does not adversely influence the reaction and, for example, toluene, benzene, xylene, dichloromethane, dichloroethane, chloroform, tetrahydrofuran (THF), dimethoxyethane (DME), dioxane, diethyl ether, acetonitrile, ethyl acetate, N,N-dimethylformamide (DMF), dimethyl sulfoxide (DMSO), N-methylpyrrolidone (NMP), methyl alcohol, ethyl alcohol, i-propyl alcohol, n-butyl alcohol, water or a mixed solvent can be used as appropriate. Examples of the transition metal complex to be used include 0 valent palladium complexes such as tetrakis(triphenylphosphine)palladium(0), tris(dibenzylideneacetone)dipalladium(0), bis(dibenzylideneacetone)palladium(0), bis(tri-tert-butylphosphine)palladium(0), and bis(tricyclohexylphosphine)palladium(0), and divalent palladium complexes such as palladium(II) acetate, palladium(II) trifluoroacetate, bis(triphenylphosphine)palladium(II) dichloride, bis(tri-O-tolylphosphine)palladium(II) dichloride, bis(tricyclohexylphosphine)palladium(II) dichloride, bis(benzonitrile)palladium(II) dichloride, bis(acetonitrile)palladium(II) dichloride, bis(acetylacetone)palladium(II), [1,1'-bis(diphenylphosphino)ferrocene]palladium(II) dichloride, bis(di-tert-butyl(4-dimethylaminophenyl)phosphine)dichloropalladium(II)(A-$^{ta}$Phos), and bis(dicyclohexyl(4-dimethylaminophenyl)phosphine)dichloropalladium(II)(A-$^{CA}$Phos). In addition, a suitable ligand may be added and, for example, tri-tert-butylphosphine, tri-cyclohexylphosphine, 1,1'-bis(diphenylphosphino)ferrocene (DPPF), 1-[2-[bis(tert-butyl)phosphino]phenyl]-3,5-diphenyl-1H-pyrazole (TrippyPhos), (±)-2,2'-bis(diphenylphosphino)-1,1'-binaphthyl (BINAP), 2-dicyclohexylphosphino-2-(N,N-dimethylamino)biphenyl, tri(ortho-tolyl)phosphine, 1,3-bis(diphenylphosphino)propane, 1,2,3,4,5-pentaphenyl-1-(di-tert-butylphosphino)ferrocene (Q-Phos), 4,5-bis(diphenylphosphino)-9,9-dimethylxanthene (Xantphos), di(1-adamantyl)-n-butylphosphine (CataCXium A), (2-biphenyl)di-tert-butylphosphine (JohnPhos), (S)-1-[(1R)-2-(diphenylphosphino)ferrocenyl]ethyl-dicyclohexylphosphine (CyPFtBu JosiPhos), 2-dicyclohexylphosphino-2',6'-diisopropoxybiphenyl (RuPhos), 2-dicyclohexylphosphino-2',6'-dimethoxybiphenyl (SPhos), 2-dicyclohexylphosphino-2'-(N,N-dimethylamino)biphenyl (DavePhos), 2-dicyclohexylphosphino-2',4',6'-triisopropylbiphenyl (XPhos), 2-di-tert-butylphosphino-2',4',6'-triisopropyl-1,1'-biphenyl (tert-butyl-X-Phos), 2-(dicyclohexylphosphino)-3,6-dimethoxy-2',4',6'-triisopropyl-1,1'-biphenyl (BrettPhos) and the like can be mentioned. Examples of the base include sodium hydrogen carbonate, sodium carbonate, potassium carbonate, cesium carbonate, sodium acetate, potassium acetate, lithium tert-butoxide, sodium tert-butoxide, potassium tert-butoxide, tripotassium phosphate, dipotassium hydrogen phosphate, potassium dihydrogen phosphate, triethylamine, diisopropylethylamine, 1,8-diazabicyclo[5.4.0]undecene (DBU), diazabicyclononene (DBN), 1,4-diazabicyclo[2.2.2]octane (DABCO) and the like can be mentioned. The amount of the transition metal complex to be used is 0.01-0.3 equivalents, preferably 0.03-0.1 equivalents, relative to compound (A2). The amount of the base to be used is 1-10 equivalents, preferably 2-7 equivalents, relative to compound (A2). Particularly, it can be preferably produced by a method using reaction conditions such as those described in Organic Letters, 2006, 8, 1787-1789.

[Step 1c]

In the above-mentioned scheme, compound (A5) can be produced by hydrolyzing compound (A4) according to a generally-used method, and can be produced by hydrolyzing in a suitable mixed aqueous solution, in the presence of a base. As a solvent, for example, a mixed aqueous solution of methyl alcohol, ethyl alcohol, THF and the like can be preferably used. As the base, for example, lithium hydroxide, sodium hydroxide and potassium hydroxide can be preferably used.

Production Method 2

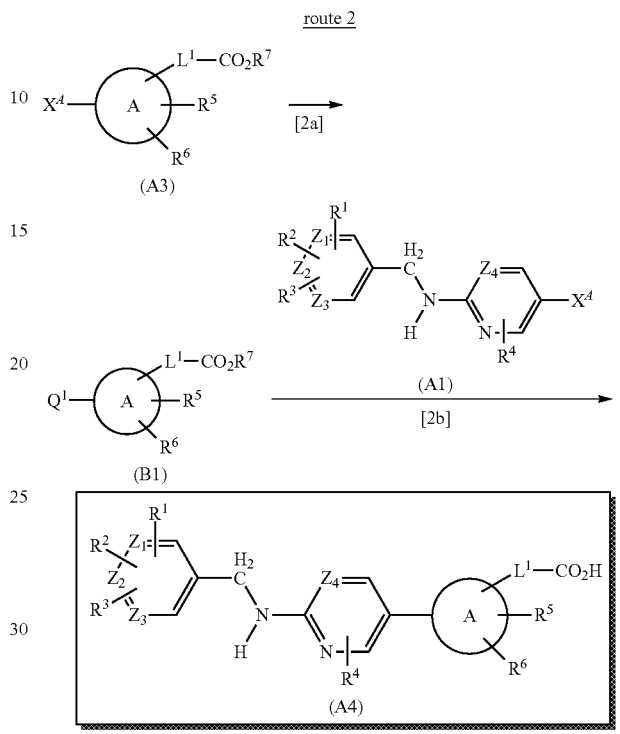

[in the above-mentioned scheme, $R^7$ is alkyl, $X^A$ is halogen, $Q^1$ is borate, and other symbols are as defined above].

[Step 2a]

In the above-mentioned scheme, compound (B1) can be produced by reacting compound (A1) with bis(pinacol)diborane by a method similar to that in [Step 1a]. Particularly, it can be preferably produced by a method using reaction conditions such as those described in J. Org. Chem., 1995, 60, 7508-7510.

[Step 2b]

In the above-mentioned scheme, compound (A4) can be produced by reacting compound (B1) with compound (A1) by a method similar to that in [Step 1b]. Particularly, it can be preferably produced by a method using reaction conditions such as those described in Organic Letters, 2006, 8, 1787-1789.

Production Method 3

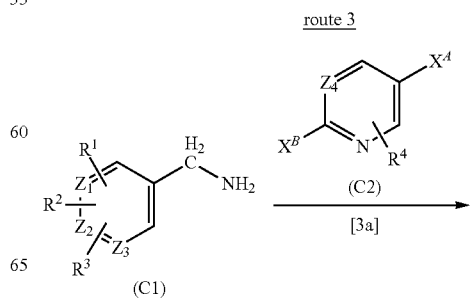

-continued

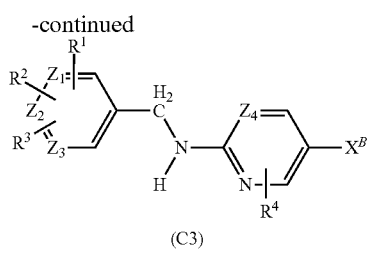

(C3)

[in the above-mentioned scheme, $X^A$ and $X^B$ are halogens, and other symbols are as defined above].

[Step 3a]

In the above-mentioned scheme, compound (C3) can be produced by reacting compound (C1) with compound (C2) in a solvent in the presence or absence of a base. As the solvent, for example, polar solvents such as N,N-dimethylformamide (DMF), N-methylpyrrolidone (NMP), dimethyl sulfoxide (DMSO), acetonitrile, ethyl alcohol (EtOH), n-butyl alcohol (n-BuOH) and the like can be appropriately used. As the base, for example, organic bases such as triethylamine, diisopropylethylamine and the like or inorganic salts such as potassium carbonate, sodium carbonate, sodium hydrogen carbonate, cesium carbonate, tripotassium phosphate and the like can be appropriately used. This reaction preferably proceeds at room temperature-200° C., preferably room temperature-150° C. In addition, it can be preferably produced by a method using a microwave reactor, as described in Tetrahedron Letters 2002, 43, 5739-5742, or by a method using reaction conditions such as those described in Bioorg. Med. Chem. Lett., 2006, 16, 4048-4052.

Production Method 4

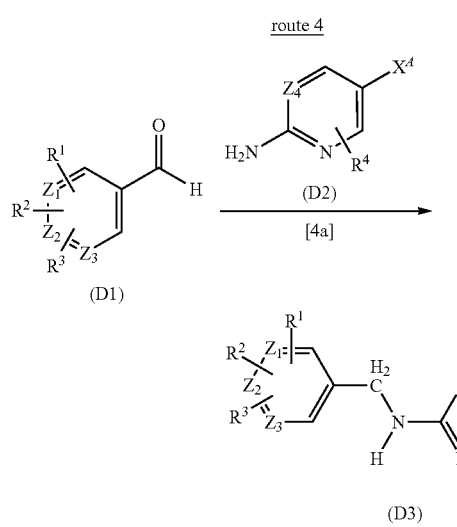

[in the above-mentioned scheme, $X^A$ is halogen, and other symbols are as defined above].

[Step 4a]

In the above-mentioned scheme, (D3) can be produced by treating compound (D1) and compound (D2) with a reducing agent in a solvent with an acid catalyst or without a catalyst. As a solvent inert to the reaction (amide solvents such as N,N-dimethylformamide, N-methylpyrrolidone, halogenated solvents such as dichloromethane and the like, ether solvents such as tetrahydrofuran) can be appropriately used. As the acid catalyst, Lewis acids such as tetraisopropoxytitanium and the like, acetic acid, trifluoroacetic acid and the like are used. As the reducing agent, sodium borohydride, sodium cyanoborohydride, sodium triacetoxyborohydride, decaborane and the like are used. This reaction preferably proceeds at −78° C.-40° C., preferably −10° C.-room temperature.

Production Method 5

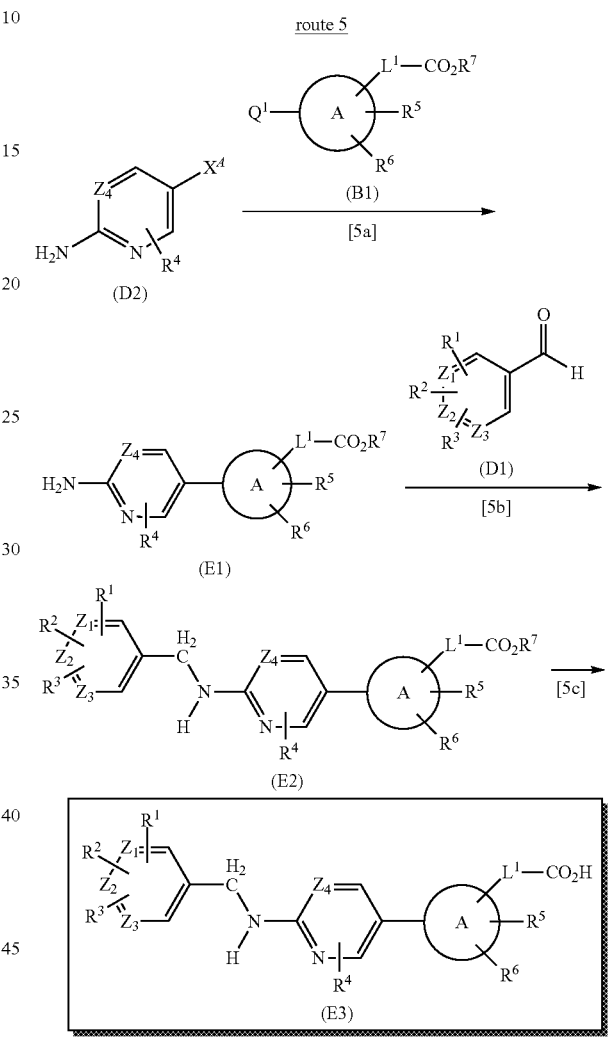

[in the above-mentioned scheme, $X^A$ is halogen, $R^7$ is alkyl, $Q^1$ is borate, and other symbols are as defined above].

[Step 5a]

In the above-mentioned scheme, compound (E1) can be produced by reacting compound (D2) with compound (B1) by a method similar to that in [Step 1b]. Particularly, it can be preferably produced by a method using reaction conditions such as those described in Organic Letters, 2006, 8, 1787-1789.

[Step 5b]

In the above-mentioned scheme, (E2) can be produced by treating compound (E1) and compound (D1) with a reducing agent in a solvent with an acid catalyst or without a catalyst. As the solvent, a solvent inert to the reaction (amide solvents such as N,N-dimethylformamide, N-methylpyrrolidone, halogenated solvents such as dichloromethane and the like, ether solvents such as tetrahydrofuran) can be appropriately used. As the acid catalyst, Lewis acids such as tetraisopropoxytitanium and the like, acetic acid, trifluoroacetic acid and the like are used. As the reducing agent, sodium borohydride, sodium cyanoborohydride, sodium triacetoxyborohydride, decaborane and the like are used. This reaction preferably proceeds at −78° C.-40° C., preferably −10° C.-room temperature.

[Step 5c]

In the above-mentioned scheme, compound (E3) can be produced by hydrolyzing compound (E2) according to a generally-used method, by hydrolyzing in a suitable mixed aqueous solution in the presence of a base. As the solvent, for example, a mixed aqueous solution of methyl alcohol, ethyl alcohol, THF and the like can be preferably used. As the base, for example, lithium hydroxide, sodium hydroxide, potassium hydroxide and the like can be preferably used.

Production Method 6 (when $Z_4$ is Carbon)

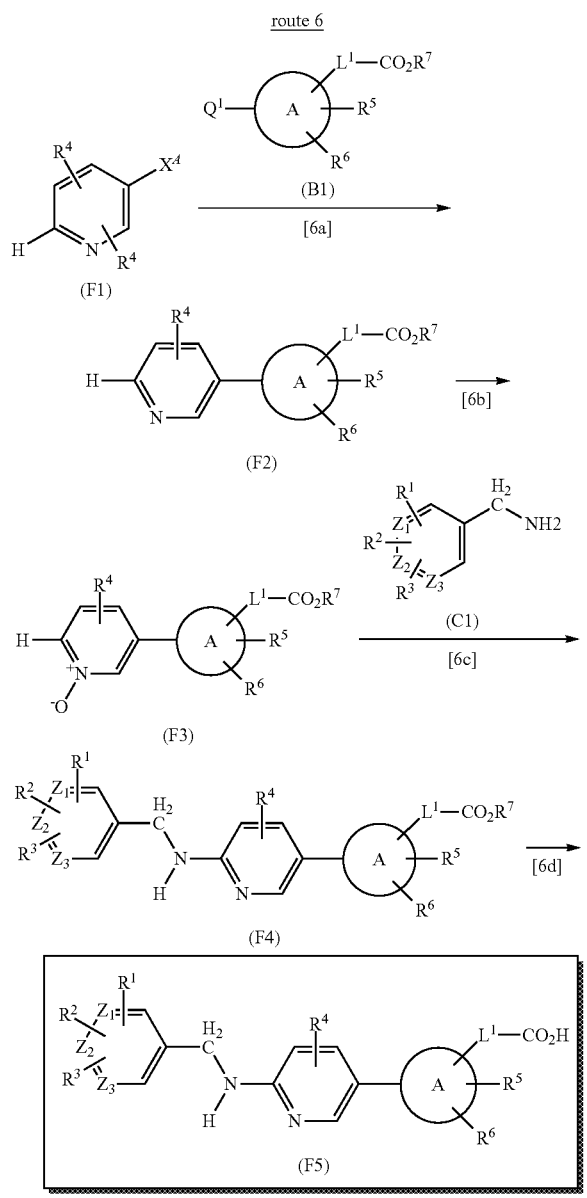

[in the above-mentioned scheme, $X^A$ is halogen, $R^7$ is alkyl, $Q^1$ is borate, and other symbols are as defined above].

[Step 6a]

In the above-mentioned scheme, compound (F2) can be produced by reacting compound (F1) with compound (B1) by a method similar to that in Step [1b].

[Step 6b]

In the above-mentioned scheme, compound (F3) can be produced by reacting compound (F2) in a solvent in the presence of an oxidant. The solvent is not particularly limited as long as it does not adversely influence the reaction and, for example, dichloromethane, chloroethane, chloroform, ethyl acetate, acetonitrile, acetic acid, acetone, tetrahydrofuran, water can be mentioned. The solvent may be a mixed solvent thereof. Examples of the oxidant include 3-chloroperbenzoic acid, methyltrioxorhenium(VII)/hydrogen peroxide, dimethyldioxirane and the like. Particularly, it can be preferably produced by a method using reaction conditions such as those described in Euro. J. Med. Chem., 2013, 62, 649-660.

[Step 6c]

In the above-mentioned scheme, compound (F4) can be produced by reacting compound (F3) with compound (C1) in a solvent in the presence of an activator and a base. The solvent is not particularly limited as long as it does not adversely influence the reaction and, for example, dichloromethane, dichloroethane, chloroform, tetrahydrofuran (THF), dimethoxyethane (DME), dioxane, diethyl ether, acetonitrile, ethyl acetate, toluene and the like can be mentioned. As the activator, paratoluenesulfonyl chloride, (benzothiazol-1-yloxy)tris(dimethylamino)phosphonium hexafluorophosphate (BOP), (benzothiazol-1-yloxy) tripyrrolidinophosphonium hexafluorophosphate (PyBOP) and the like can be mentioned. The reaction particularly preferably proceeds under conditions using (benzothiazol-1-yloxy)tripyrrolidinophosphonium hexafluorophosphate (PyBOP) and the like. As the base, triethylamine, diisopropylethylamine, N-methylmorpholine, dimethylaniline, diethylaniline, pyridine, 2,6-lutidine, 2,4,6-collidine, N,N-dimethyl-4-aminopyridine (DMAP), 1,8-diazabicyclo[5.4.0]undecene (DBU), diazabicyclononene (DBN), 1,4-diazabicyclo[2.2.2]octane (DABCO) and the like can be mentioned. This reaction preferably proceeds at 0° C.-100° C., preferably room temperature-70° C.

[Step 6d]

In the above-mentioned scheme, compound (F5) can be produced from compound (F4) by a reaction according to a method similar to that in [Step 1c].

Production Method 7

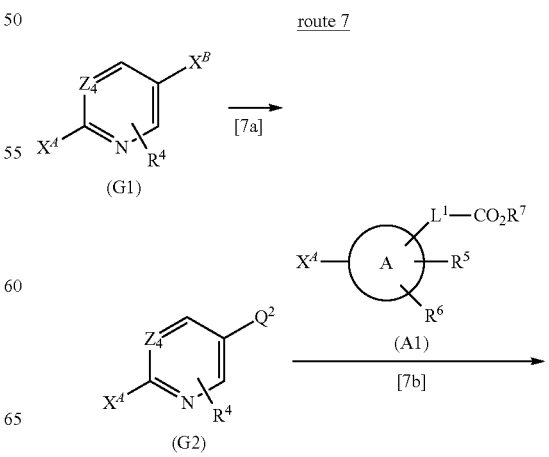

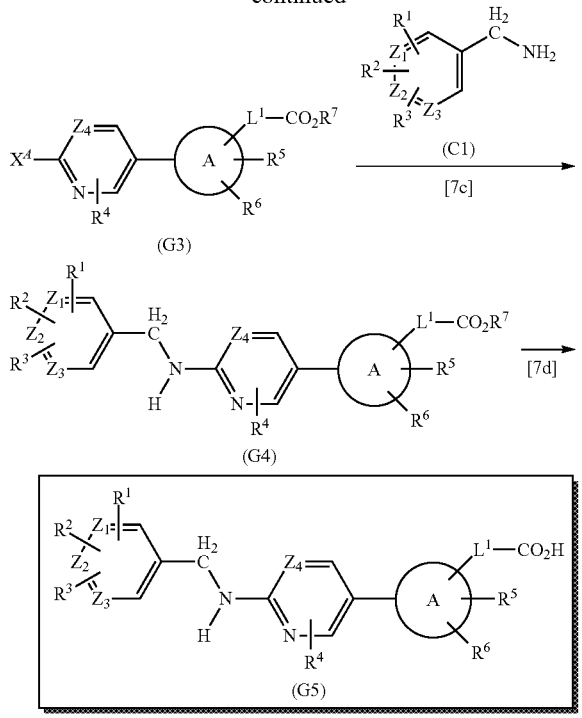

[in the above-mentioned scheme, $X^A$ and $X^B$ are halogens, $R^7$ is alkyl, $Q^2$ is borate, and other symbols are as defined above].

[Step 7a]

In the above-mentioned scheme, compound (G2) can be produced by reacting compound (G1) with bis(pinacol) diborane by a method similar to that in [Step 1a]. Particularly, it can be preferably produced by a method using reaction conditions such as those described in J. Org. Chem., 1995, 60, 7508-7510.

[Step 7b]

In the above-mentioned scheme, compound (G3) can be produced by reacting compound (G2) with compound (A1) by a method similar to that in [Step 1b]. Particularly, it can be preferably produced by a method using reaction conditions such as those described in Organic Letters, 2006, 8, 1787-1789.

[Step 7c]

In the above-mentioned scheme, compound (G4) can be produced by reacting compound (G3) with (C1) in a suitable solvent in the presence of a transition metal complex and a base. The solvent is not particularly limited as long as it does not adversely influence the reaction and, for example, toluene, benzene, xylene, dichloromethane, dichloroethane, chloroform, tetrahydrofuran (THF), dimethoxyethane (DME), dioxane, diethyl ether, acetonitrile, ethyl acetate, N,N-dimethylformamide (DMF), dimethyl sulfoxide (DMSO), N-methylpyrrolidone (NMP), methyl alcohol, ethyl alcohol, i-propyl alcohol, n-butyl alcohol, water or a mixed solvent can be used as appropriate. Examples of the transition metal complex to be used include 0 valent palladium complexes such as tetrakis(triphenylphosphine)palladium(0), tris(dibenzylideneacetone)dipalladium(0), bis(dibenzylideneacetone)palladium(0), bis(tri-tert-butylphosphine)palladium(0), bis(tricyclohexylphosphine) palladium(0), and divalent palladium complexes such as palladium(II) acetate, palladium(II) trifluoroacetate, bis(triphenylphosphine)palladium(II) dichloride, bis(tri-O-tolylphosphine)palladium(II) dichloride, bis(tricyclohexylphosphine)palladium(II) dichloride, bis(benzonitrile)palladium (II) dichloride, bis(acetonitrile)palladium(II) dichloride, bis (acetylacetone)palladium(II), [1,1'-bis(diphenylphosphino) ferrocene]palladium(II) dichloride, bis(di-tert-butyl(4-dimethylaminophenyl)phosphine)dichloropalladium(II) (A-$^{ta}$Phos), bis(dicyclohexyl(4-dimethylaminophenyl)phosphine)dichloropalladium(II)(A-$^{CA}$Phos) and the like. In addition, a suitable ligand may be added and, for example, tri-tert-butylphosphine, tri-cyclohexylphosphine, 1,1'-bis (diphenylphosphino)ferrocene (DPPF), 1-[2-[bis(tert-butyl) phosphino]phenyl]-3,5-diphenyl-1H-pyrazole (Trippy-Phos), (±)-2,2'-bis(diphenylphosphino)-1,1'-binaphthyl (BINAP), 2-dicyclohexylphosphino-2-(N,N-dimethylamino)biphenyl, tri(ortho-tolyl)phosphine, 1,3-bis(diphenylphosphino)propane, 1,2,3,4,5-pentaphenyl-1-(di-tert-butylphosphino)ferrocene (Q-Phos), 4,5-bis (diphenylphosphino)-9,9-dimethylxanthene (Xantphos), di(1-adamantyl)-n-butylphosphine (CataCXium A), (2-biphenyl)di-tert-butylphosphine (JohnPhos), (S)-1-[(1R)-2-(diphenylphosphino)ferrocenyl]ethyldicyclohexylphosphine (CyPFtBu JosiPhos), 2-dicyclohexylphosphino-2',6'-diisopropoxybiphenyl (RuPhos), 2-dicyclohexylphosphino-2',6'-dimethoxybiphenyl (SPhos), 2-dicyclohexylphosphino-2'-(N,N-dimethylamino)biphenyl (DavePhos), 2-dicyclohexylphosphino-2',4',6'-triisopropylbiphenyl (XPhos), 2-di-tert-butylphosphino-2',4',6'-triisopropyl-1,1'-biphenyl (tert-butyl-X-Phos), 2-(dicyclohexylphosphino)-3,6-dimethoxy-2',4',6'-triisopropyl-1,1'-biphenyl (BrettPhos) and the like can be mentioned. Examples of the base include sodium hydrogen carbonate, sodium carbonate, potassium carbonate, cesium carbonate, sodium acetate, potassium acetate, lithium tert-butoxide, sodium tert-butoxide, potassium tert-butoxide, tripotassium phosphate, dipotassium hydrogen phosphate, potassium dihydrogen phosphate, triethylamine, diisopropylethylamine, 1,8-diazabicyclo[5.4.0]undecene (DBU), diazabicyclononene (DBN), 1,4-diazabicyclo[2.2.2]octane (DABCO) and the like. The amount of the transition metal complex to be used may be 0.01-0.5 equivalents, preferably 0.03-0.1 equivalents, relative to compound (G3). The amount of the base to be used may be 1-10 equivalents, preferably 2-5 equivalents, relative to compound (G3). Particularly, it can be preferably produced under reaction conditions as those described in Journal of Organic Chemistry, 1996, 61, 7240-7241.

[Step 7d]

In the above-mentioned scheme, compound (G5) can be produced by hydrolyzing compound (G4) according to a generally-used method, by hydrolyzing in a suitable mixed aqueous solution in the presence of a base. As the solvent, for example, a mixed aqueous solution of methyl alcohol, ethyl alcohol, THF and the like can be preferably used. As the base, for example, lithium hydroxide, sodium hydroxide, potassium hydroxide and the like can be preferably used. Production Method 8 (when a is Heterocyclic Group Such as Pyrrolidinyl, Piperidinyl, Piperazinyl, Morpholinyl, 1,4-Oxazepanyl and the Like)

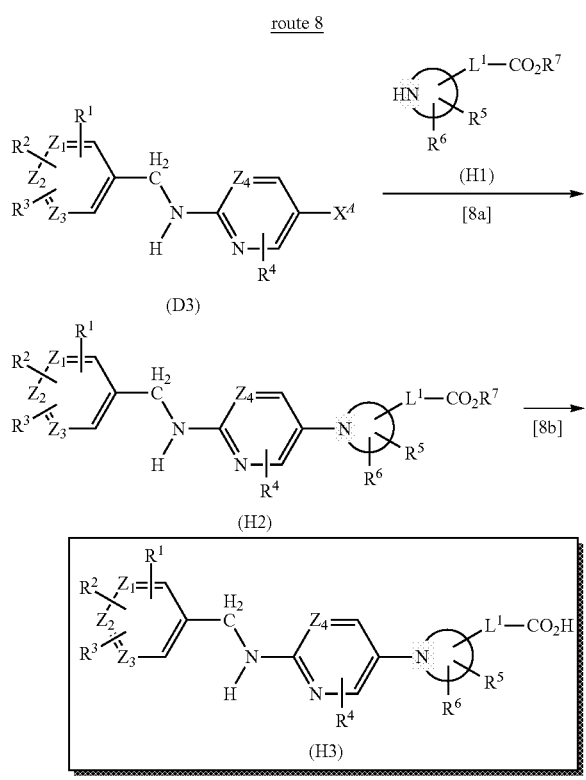

route 8

(D3)

(H2)

(H3)

[in the above-mentioned scheme, $X^A$ is halogen, $R^7$ is alkyl, and other symbols are as defined above].

[Step 8a]

In the above-mentioned scheme, compound (H2) can be produced by reacting compound (D3) with (H1) in a suitable solvent in the presence of a transition metal complex and a base. The solvent is not particularly limited as long as it does not adversely influence the reaction and, for example, toluene, benzene, xylene, dichloromethane, dichloroethane, chloroform, tetrahydrofuran (THF), dimethoxyethane (DME), dioxane, diethyl ether, acetonitrile, ethyl acetate, N,N-dimethylformamide (DMF), dimethyl sulfoxide (DMSO), N-methylpyrrolidone (NMP), methyl alcohol, ethyl alcohol, i-propyl alcohol, n-butyl alcohol, water or a mixed solvent can be used as appropriate. Examples of the transition metal complex to be used include 0 valent palladium complexes such as tetrakis(triphenylphosphine)palladium(0), tris(dibenzylideneacetone)dipalladium(0), bis(dibenzylideneacetone)palladium(0), bis(tri-tert-butylphosphine)palladium(0), bis(tricyclohexylphosphine)palladium(0), and divalent palladium complexes such as palladium(II) acetate, palladium(II) trifluoroacetate, bis(triphenylphosphine)palladium(II) dichloride, bis(tri-O-tolylphosphine)palladium(II) dichloride, bis(tricyclohexylphosphine)palladium(II) dichloride, bis(benzonitrile)palladium(II) dichloride, bis(acetonitrile)palladium(II) dichloride, bis(acetylacetone)palladium(II), [1,1'-bis(diphenylphosphino)ferrocene]palladium(II) dichloride, bis(di-tert-butyl(4-dimethylaminophenyl) phosphine) dichloropalladium(II) (A-$^{ta}$Phos), bis(dicyclohexyl(4-dimethylaminophenyl)phosphine)dichloropalladium(II)(A-$^{CA}$Phos) and the like. In addition, a suitable ligand may be added and, for example, tri-tert-butylphosphine, tri-cyclohexylphosphine, 1,1'-bis(diphenylphosphino)ferrocene (DPPF), 1-[2-[bis(tert-butyl)phosphino]phenyl]-3,5-diphenyl-1H-pyrazole (TrippyPhos), (±)-2,2'-bis(diphenylphosphino)-1,1'-binaphthyl (BINAP), 2-dicyclohexylphosphino-2'-(N,N-dimethylamino)biphenyl, tri(ortho-tolyl)phosphine, 1,3-bis(diphenylphosphino)propane, 1,2,3,4,5-pentaphenyl-1-(di-tert-butylphosphino)ferrocene (Q-Phos), 4,5-bis(diphenylphosphino)-9,9-dimethylxanthene (Xantphos), di(1-adamantyl)-n-butylphosphine (CataCXium A), (2-biphenyl)di-tert-butylphosphine (JohnPhos), (S)-1-[(1R)-2-(diphenylphosphino)ferrocenyl]ethyldicyclohexylphosphine (CyPFtBu JosiPhos), 2-dicyclohexylphosphino-2',6'-diisopropoxybiphenyl (RuPhos), 2-dicyclohexylphosphino-2',6'-dimethoxybiphenyl (SPhos), 2-dicyclohexylphosphino-2'-(N,N-dimethylamino)biphenyl (DavePhos), 2-dicyclohexylphosphino-2',4',6'-triisopropylbiphenyl (XPhos), 2-di-tert-butylphosphino-2',4',6'-triisopropyl-1,1'-biphenyl (tert-butyl-X-Phos), 2-(dicyclohexylphosphino)-3,6-dimethoxy-2',4',6'-triisopropyl-1,1'-biphenyl (BrettPhos) and the like can be mentioned. Examples of the base include sodium hydrogen carbonate, sodium carbonate, potassium carbonate, cesium carbonate, sodium acetate, potassium acetate, lithium tert-butoxide, sodium tert-butoxide, potassium tert-butoxide, tripotassium phosphate, dipotassium hydrogen phosphate, potassium dihydrogen phosphate, triethylamine, diisopropylethylamine, 1,8-diazabicyclo[5.4.0]undecene (DBU), diazabicyclononene (DBN), 1,4-diazabicyclo[2.2.2]octane (DABCO) and the like. The amount of the transition metal complex to be used may be 0.01-0.5 equivalents, preferably 0.03-0.1 equivalents, relative to compound (D3). The amount of the base to be used may be 1-10 equivalents, preferably 2-5 equivalents, relative to compound (D3). Particularly, it can be preferably produced under reaction conditions as those described in Chemical Science, 2011, 2, 27-50.

[Step 8b]

In the above-mentioned scheme, compound (H3) can be produced by hydrolyzing compound (H2) according to a generally-used method, by hydrolyzing in a suitable mixed aqueous solution in the presence of a base. As the solvent, for example, a mixed aqueous solution of methyl alcohol, ethyl alcohol, THF and the like can be preferably used. As the base, for example, lithium hydroxide, sodium hydroxide, potassium hydroxide and the like can be preferably used.

Production Method 9 (when A is Benzimidazolyl, Benzoxazolyl or Benzthiazolyl)

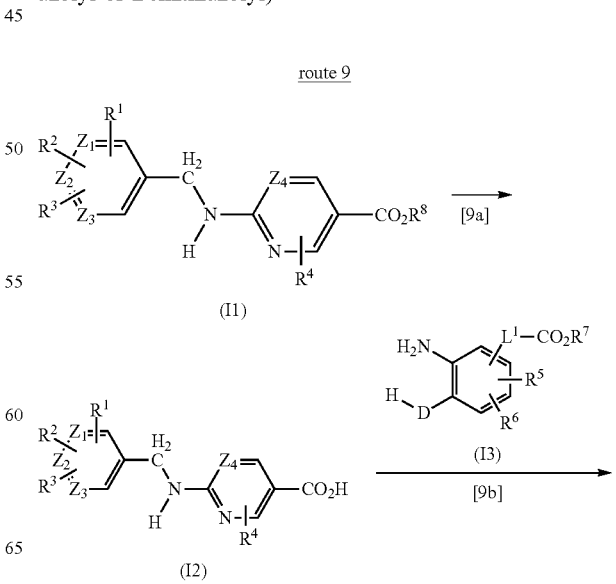

route 9

(I1)

(I2)

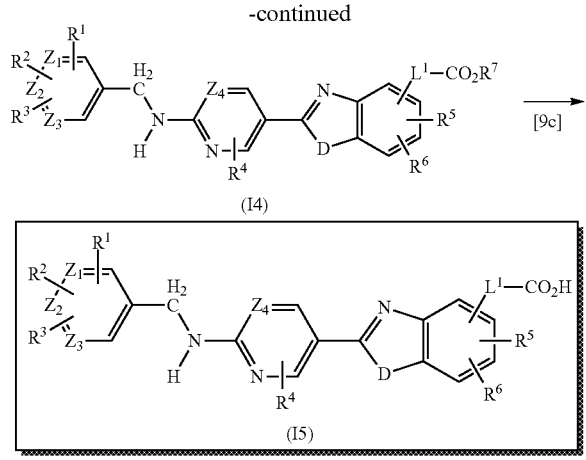

for example, a mixed aqueous solution of methyl alcohol, ethyl alcohol, THF and the like can be preferably used. As the base, for example, lithium hydroxide, sodium hydroxide, potassium hydroxide and the like can be preferably used.

Production Method 10 (when A is Oxadiazolyl)

route 10

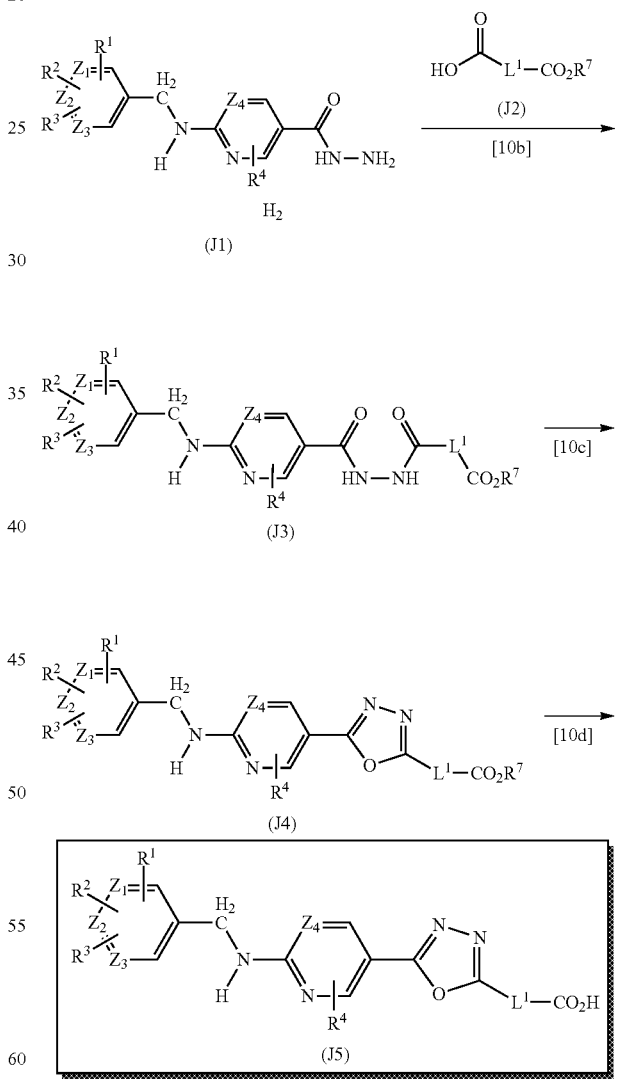

[in the above-mentioned scheme, R⁷ and R⁸ are alkyl, D is NH, O or S, and other symbols are as defined above]

[Step 9a]

In the above-mentioned scheme, compound (I2) can be produced by hydrolyzing compound (I1) according to a generally-used method, by hydrolyzing in a suitable mixed aqueous solution in the presence of a base. As the solvent, for example, a mixed aqueous solution of methyl alcohol, ethyl alcohol, THF and the like can be preferably used. As the base, for example, lithium hydroxide, sodium hydroxide and potassium hydroxide can be preferably used.

[Step 9b]

In the above-mentioned scheme, compound (I4) can be produced by reacting compound (I2) with compound (I3) in the presence of a condensing agent, in the presence or absence of a base, in the presence or absence of an activator, in a solvent or without solvent. As the condensing agent, 1-ethyl-3-(3-dimethylaminopropyl)carbodiimide hydrochloride (WSC.HCl), N,N'-dicyclohexylcarbodiimide (DCC), diethyl cyanophosphonate, O-(7-azabenzotriazol-1-yl)-N,N,N',N'-tetramethyluronium hexafluorophosphate (HATU), 1,1-carbonylimidazole (CDI), (benzothiazol-1-yloxy)tris(dimethylamino)phosphonium hexafluorophosphate (BOP), (benzothiazol-1-yloxy)tripyrrolidinophosphonium hexafluorophosphate (PyBOP), polyphosphoric acid (PPA), anhydrous propylphosphonic acid (T3P (registered trade mark)), methyl N-(triethylammoniumsulfonyl)carbamate (Burgess reagent) and the like can be mentioned. Examples of the base include triethylamine, diisopropylethylamine, pyridine, lutidine and the like. As the activator, 1-hydroxy-7-azabenzotriazole (HOAt), 1-hydroxybenzotriazole (HOBt) and the like can be mentioned. As the solvent, a solvent inert to the reaction can be used and, for example, toluene, benzene, xylene, dichloromethane, dichloroethane, chloroform, tetrahydrofuran (THF), dimethoxyethane (DME), dioxane, diethyl ether, acetonitrile, ethyl acetate, N,N-dimethylformamide (DMF), dimethyl sulfoxide (DMSO), N-methylpyrrolidone (NMP), acetone and the like can be mentioned. This reaction preferably proceeds at 0° C.-250° C., preferably room temperature-150° C. Particularly, it can be preferably produced by a method using reaction conditions such as those described in Tetrahedron Letters, 2012. 53. 2440-2443.

[Step 9c]

In the above-mentioned scheme, compound (I5) can be produced by hydrolyzing compound (I4) according to a generally-used method, by hydrolyzing in a suitable mixed aqueous solution in the presence of a base. As the solvent,

[in the above-mentioned scheme, R⁷ and R⁸ are alkyl, and other symbols are as defined above]

[Step 10a]

In the above-mentioned scheme, compound (J1) can be produced by reacting compound (I1) with hydrazine.monohydrate in a solvent or without solvent. As the solvent, for example, alcohol solvents such as methyl alcohol, ethyl alcohol, i-propyl alcohol, n-butyl alcohol and the like, ether solvents such as tetrahydrofuran (THF), dimethoxyethane (DME), dioxane, diethyl ether and the like, highly-polar solvents such as dimethyl sulfoxide (DMSO), N,N-dimethylformamide (DMF), N-methylpyrrolidone (NMP) and the like can be mentioned. This reaction preferably proceeds at room temperature-150° C., preferably room temperature-100° C.

[Step 10b]

In the above-mentioned scheme, compound (J3) can be produced by reacting compound (J1) with compound (J2) in a solvent, in the presence of a condensing agent, in the presence or absence of an activator, in the presence or absence of a base. As the solvent, for example, toluene, benzene, xylene, dichloromethane, dichloroethane, chloroform, tetrahydrofuran (THF), dimethoxyethane (DME), dioxane, diethyl ether, acetonitrile, ethyl acetate, N,N-dimethylformamide (DMF), dimethyl sulfoxide (DMSO), N-methylpyrrolidone (NMP), acetone and the like can be mentioned. As the base, triethylamine, diisopropylethylamine, pyridine, lutidine and the like can be mentioned. As the condensing agent, 1-ethyl-3-(3-dimethylaminopropyl)carbodiimide hydrochloride (WSC.HCl), N,N'-dicyclohexylcarbodiimide (DCC), diethyl cyanophosphonate, O-(7-azabenzotriazol-1-yl)-N,N,N',N'-tetramethyluronium hexafluorophosphate (HATU), 1,1-carbonylimidazole (CDI), (benzothiazol-1-yloxy)tris(dimethylamino)phosphonium hexafluorophosphate (BOP), (benzothiazol-1-yloxy)tripyrrolidinophosphonium hexafluorophosphate (PyBOP), polyphosphoric acid (PPA), anhydrous propylphosphonic acid (T3P (registered trade mark)), methyl N-(triethylammoniumsulfonyl)carbamate (Burgess reagent) and the like can be mentioned. As the activator, 1-hydroxy-7-azabenzotriazole (HOAt), 1-hydroxybenzotriazole (HOBt) and the like can be mentioned. This reaction preferably proceeds at 0° C.-100° C., preferably room temperature-40° C.

[Step 10c]

In the above-mentioned scheme, compound (J4) can be produced by reacting compound (J3) in a solvent, in the presence of a condensing agent, in the presence or absence of an activator, in the presence or absence of a base. As the solvent, for example, toluene, benzene, xylene, dichloromethane, dichloroethane, chloroform, tetrahydrofuran (THF), dimethoxyethane (DME), dioxane, diethyl ether, acetonitrile, ethyl acetate, N,N-dimethylformamide (DMF), dimethyl sulfoxide (DMSO), N-methylpyrrolidone (NMP), acetone and the like can be mentioned. As the base, triethylamine, diisopropylethylamine, pyridine, lutidine and the like can be mentioned. As the condensing agent, 1-ethyl-3-(3-dimethylaminopropyl)carbodiimide hydrochloride (WSC.HCl), N,N'-dicyclohexylcarbodiimide (DCC), diethyl cyanophosphonate, O-(7-azabenzotriazol-1-yl)-N,N,N',N'-tetramethyluronium hexafluorophosphate (HATU), 1,1-carbonylimidazole (CDI), (benzothiazol-1-yloxy) tris(dimethylamino)phosphonium hexafluorophosphate (BOP), (benzothiazol-1-yloxy)tripyrrolidinophosphonium hexafluorophosphate (PyBOP), polyphosphoric acid (PPA), anhydrous propylphosphonic acid (T3P (registered trade mark)), methyl N-(triethylammoniumsulfonyl)carbamate (Burgess reagent) and the like can be mentioned. As the activator, 1-hydroxy-7-azabenzotriazole (HOAt), 1-hydroxybenzotriazole (HOBt) and the like can be mentioned. This reaction preferably proceeds at 0° C.-150° C., preferably room temperature-120° C. In addition, it can be preferably produced in One-Pot from compound (J1) by using the reaction conditions described in, for example, Tetrahedron, 2009, 65, 9989-9996 or Tetrahedron Letters, 2009, 50, 6435-6439.

[Step 10d]

In the above-mentioned scheme, compound (J5) can be produced by hydrolyzing compound (J4) according to a generally-used method, by hydrolyzing in a suitable mixed aqueous solution in the presence of a base. As the solvent, for example, a mixed aqueous solution of methyl alcohol, ethyl alcohol, THF and the like can be preferably used. As the base, for example, lithium hydroxide, sodium hydroxide, potassium hydroxide and the like can be preferably used.

Production Method 11

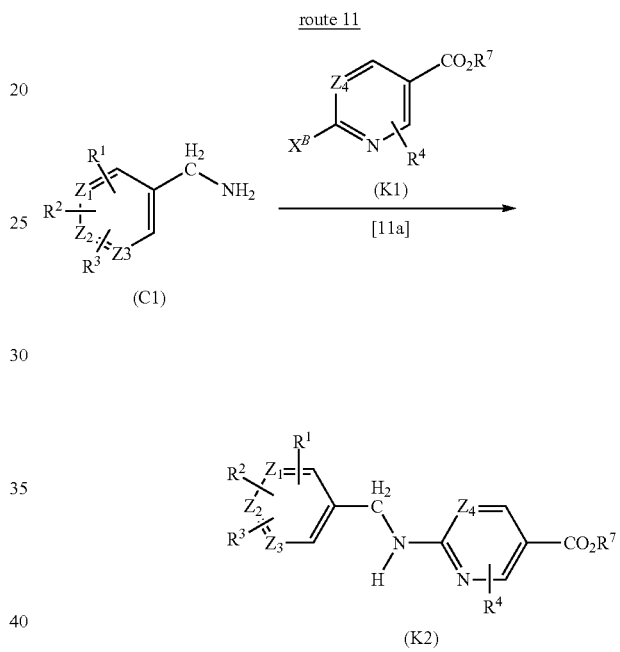

[in the above-mentioned scheme, $X^B$ is halogen, $R^7$ is alkyl, and other symbols are as defined above].

[Step 11a]

In the above-mentioned scheme, compound (K2) can be produced by reacting compound (C1) with compound (K1) in a solvent in the presence or absence of a base. As the solvent, for example, polar solvents such as N,N-dimethylformamide (DMF), N-methylpyrrolidone (NMP), dimethyl sulfoxide (DMSO), ethyl alcohol (EtOH), i-propyl alcohol (i-PrOH), n-butyl alcohol (n-BuOH) and the like can be appropriately used. As the base, for example, organic bases such as triethylamine, diisopropylethylamine and the like or inorganic salts such as potassium carbonate, sodium carbonate, sodium hydrogen carbonate, cesium carbonate, tripotassium phosphate and the like can be used as appropriate. This reaction preferably proceeds at room temperature-200° C., preferably room temperature-150° C. In addition, it can be preferably produced by a method using a microwave reactor, as described in Tetrahedron Letters, 2002, 43, 5739-5742. Also, it can be produced by, for example, a reaction using a transition metal complex as described in Tetrahedron, 2008, 64, 5604-5619, Tetrahedron Letters, 2007, 48, 2519-2525 or Chemical Science., 2011, 2, 27-50.

Production Method 12

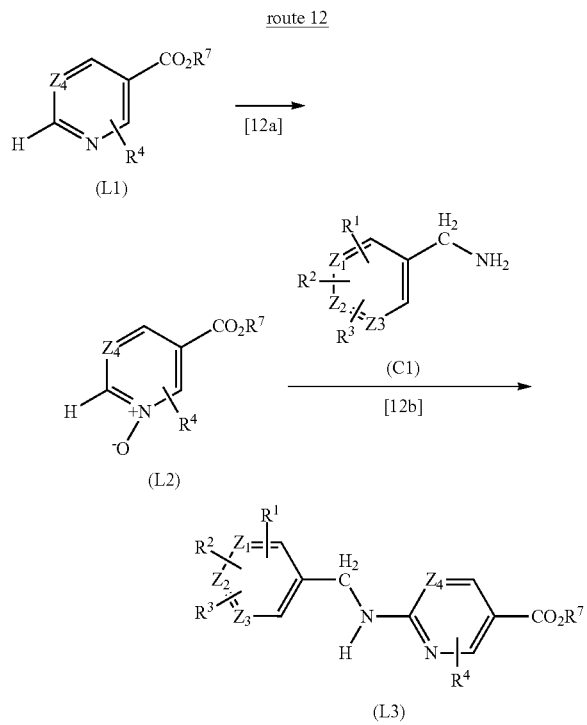

[in the above-mentioned scheme, $R^7$ is alkyl, and other symbols are as defined above].

[Step 12a]

In the above-mentioned scheme, compound (L2) can be produced from compound (L1) by a reaction according to a method similar to that in [Step 6b].

[Step 12b]

In the above-mentioned scheme, compound (L3) can be produced by reacting compound (L2) with compound (C1) by a method similar to that in [Step 6c].

Production Method 13

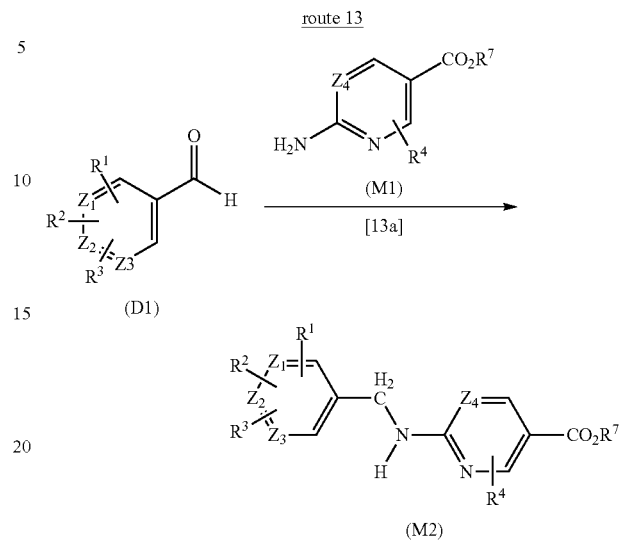

[in the above-mentioned scheme, $R^7$ is alkyl, and other symbols are as defined above].

[Step 13a]

In the above-mentioned scheme, (M2) can be produced by treating compound (D1) and compound (M1) with a reducing agent in a solvent with an acid catalyst or without a catalyst. As the solvent, a solvent inert to the reaction (amide solvents such as N,N-dimethylformamide, N-methylpyrrolidone, halogenated solvents such as dichloromethane and the like, ether solvents such as tetrahydrofuran) can be appropriately used. As the acid catalyst, Lewis acids such as tetraisopropoxytitanium and the like, acetic acid, trifluoroacetic acid and the like are used. As the reducing agent, sodium borohydride, sodium cyanoborohydride, sodium triacetoxyborohydride, decaborane and the like are used. This reaction preferably proceeds at −78° C.-40° C., preferably −10° C.-room temperature.

Production Method 14 (when $L^1$ is —O—$X^3$— or —O—$(CH_2)_n$—$X^3$—)

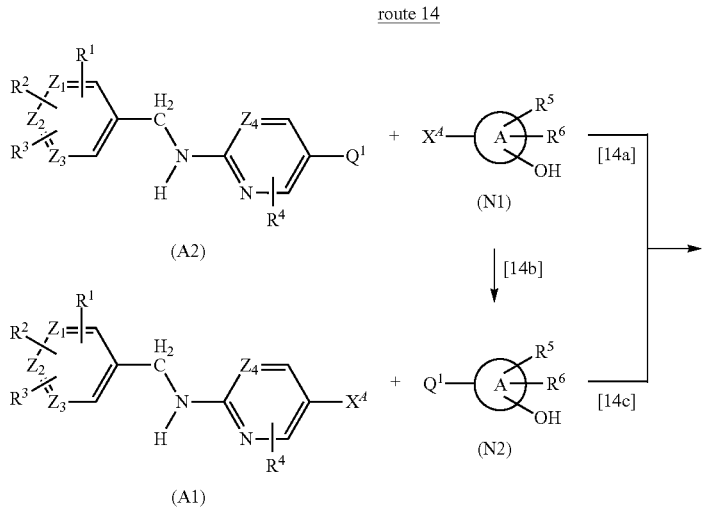

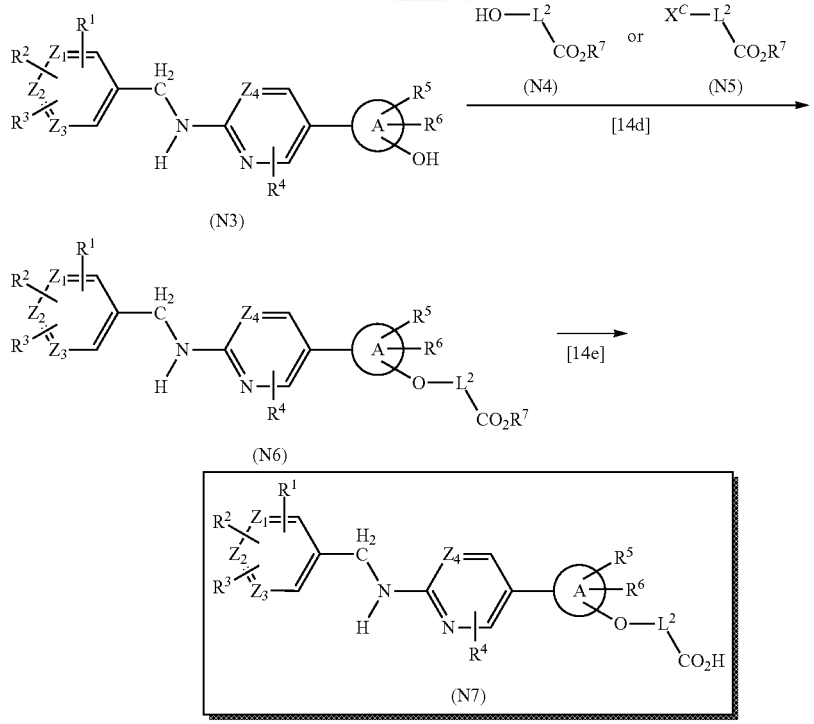

[in the above-mentioned scheme, $R^7$ is alkyl, $X^A$ and $X^C$ are halogens, $Q^1$ is borate, $L^2$ is —$X^3$— or —$(CH_2)_n$—$X^3$—, and other symbols are as defined above].

[Step 14a]

In the above-mentioned scheme, compound (N3) can be produced from compound (A2) and compound (N1) by a method similar to that in [Step 1b].

[Step 14b]

In the above-mentioned scheme, compound (N2) can be produced from compound (N1) by a method similar to that in [Step 2a].

[Step 14c]

In the above-mentioned scheme, compound (N3) can be is produced from compound (A1) and compound (N2) by a method similar to that in [Step 1b].

[Step 14d]

In the above-mentioned scheme, compound (N6) can be produced by reacting compound (N3) with compound (N4) in a solvent in the presence of a Mitsunobu reagent and a phosphine reagent. As the Mitsunobu reagent, for example, diethyl azodicarboxylate (DEAD), diisopropyl azodicarboxylate (DIAD), di-tert-butyl azodicarboxylate (DBAD), 1,1'-(azodicarbonyl)dipiperidine (ADPP), di-p-nitrobenzyl azodicarboxylate (DNAD), 1,1'-azobis(N,N'-bisdiisopropyl formamide) (TIPA), 1,6-dimethyl-1,5,7-hexahydro-1,4,6,7-tetrazocine-2,5-dione (DHTD), N,N,N',N'-tetramethylazodicarboxamide (TMAD), di-p-chlorobenzyl azodicarboxylate (DCAD), di-2-methoxyethyl azodicarboxylate (DMEAD) and the like can be mentioned. As the phosphine reagent, for example, triphenylphosphine, tri-n-butylphosphine, tri-n-octylphosphine, tricyclohexylphosphine, diphenyl-2-pyridylphosphine and the like can be mentioned. This reaction preferably proceeds even in the absence of a phosphine reagent when a Tsunoda reagent such as cyanomethylenetributylphosphorane, cyanomethylenetrimethylphosphorane and the like is used. The solvent is not particularly limited as long as it does not adversely influence the reaction, toluene, benzene, xylene, dichloromethane, dichloroethane, chloroform, tetrahydrofuran (THF), dimethoxyethane (DME), dioxane, diethyl ether, acetonitrile, ethyl acetate, N,N-dimethylformamide (DMF), dimethyl sulfoxide (DMSO), N-methylpyrrolidone (NMP) and the like can be mentioned. This reaction preferably proceeds at −40° C.-100° C., preferably 0° C.-70° C.

Compound (N6) can be produced by reacting compound (N3) with compound (N5) in a solvent in the presence of a base, in the presence or absence of a phase-transfer catalyst. The is solvent is not particularly limited as long as it does not adversely influence the reaction, toluene, benzene, xylene, dichloromethane, dichloroethane, chloroform, tetrahydrofuran (THF), dimethoxyethane (DME), dioxane, diethyl ether, acetone, acetonitrile, ethyl acetate, N,N-dimethylformamide (DMF), dimethyl sulfoxide (DMSO), N-methylpyrrolidone (NMP) and the like can be mentioned. As the base, sodium hydrogen carbonate, sodium carbonate, potassium carbonate, cesium carbonate, sodium hydride, sodium tert-butoxide, potassium tert-butoxide, lithium hexamethyl disilazide (LiHMDS), sodium hexamethyl disilazide (NaHMDS), potassium hexamethyl disilazide (KHMDS), lithium diisopropylamide (LDA), iso-propylmagnesium chloride, iso-propylmagnesium bromide, i-propylmagnesium chloride lithium chloride salt and the like can be mentioned. This reaction particularly preferably proceeds using sodium hydride, potassium tert-butoxide. As the phase-transfer catalyst, halogenated quaternary ammonium salt, crown ether and the like can be mentioned. This reaction preferably proceeds at −78° C.-100° C., particularly 0° C.-70° C.

[Step 14e]

In the above-mentioned scheme, compound (N7) can be produced by hydrolyzing compound (N6) according to a generally-used method, by hydrolyzing in a suitable mixed aqueous solution in the presence of a base. As the solvent, for example, a mixed aqueous solution of methyl alcohol, ethyl alcohol, THF and the like can be preferably used. As the base, for example, lithium hydroxide, sodium hydroxide and potassium hydroxide can be preferably used.

Production Method 15 (when $X^1$ of —$X^1$—$R^{7a}$ for $R^6$ is —O— or —O-alkylene-)

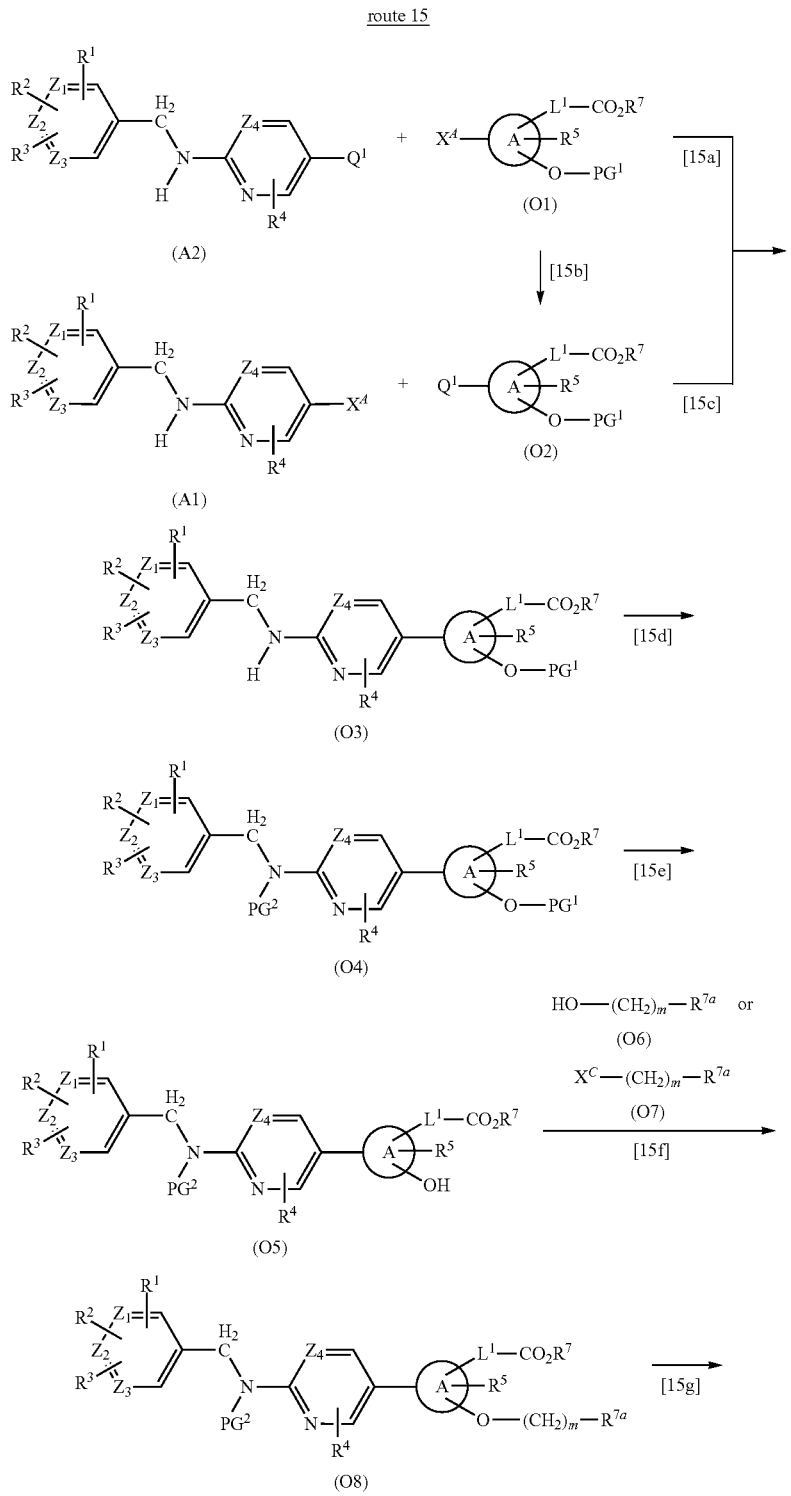

route 15

-continued

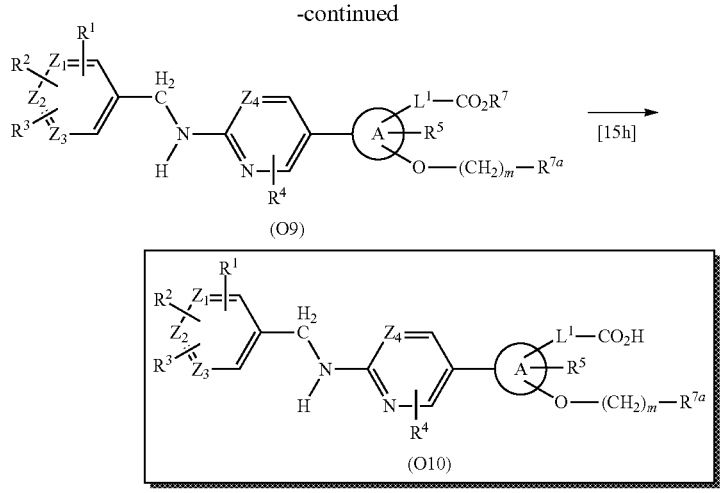

[in the above-mentioned scheme, $R^7$ is alkyl, $X^A$ and $X^C$ are halogens, $Q^1$ is borate, $PG^1$ is a hydroxyl-protecting group, $PG^2$ is an amino-protecting group, m is an integer of 0-6, and other symbols are as defined above].

[Step 15a]
In the above-mentioned scheme, compound (O3) can be produced from compound (A2) and compound (O1) by a method similar to that in [Step 1b].

[Step 15b]
In the above-mentioned scheme, compound (02) can be produced from compound (01) by a method similar to that in [Step 2a].

[Step 15c]
In the above-mentioned scheme, compound (O3) can be produced from compound (A1) and compound (O2) by a method similar to that in [Step 1b].

[Step 15d]
In the above-mentioned scheme, compound (O4) can be produced by protecting compound (O3) with $PG^2$ by a general method.

[Step 15e]
In the above-mentioned scheme, compound (O5) can be produced by removing $PG^1$ of compound (O4) by a general method.

[Step 15f]
In the above-mentioned scheme, compound (O8) can be produced from compound (O5) by a reaction with compound (O6) or compound (O7) by a method similar to that in [Step 14d].

[Step 15g]
In the above-mentioned scheme, compound (O9) can be produced by removing $PG^2$ of compound (O8) by a general method.

[Step 15h]
In the above-mentioned scheme, compound (O10) can be produced by hydrolyzing compound (O9) by a general method. Production method 16 (when $X^1$ of —$X^1$—$R^{7a}$ for $R^5$ is —O—, $R^6$ is heteroaryl (that is, $X^1$ of —$X^1$—$R^{7a}$ for $R^6$ is a single bond, and $R^{7a}$ is heteroaryl))

route 16

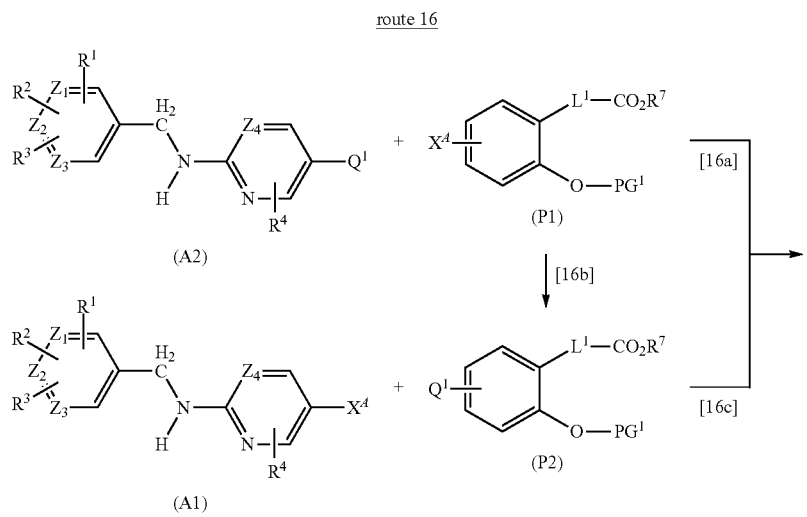

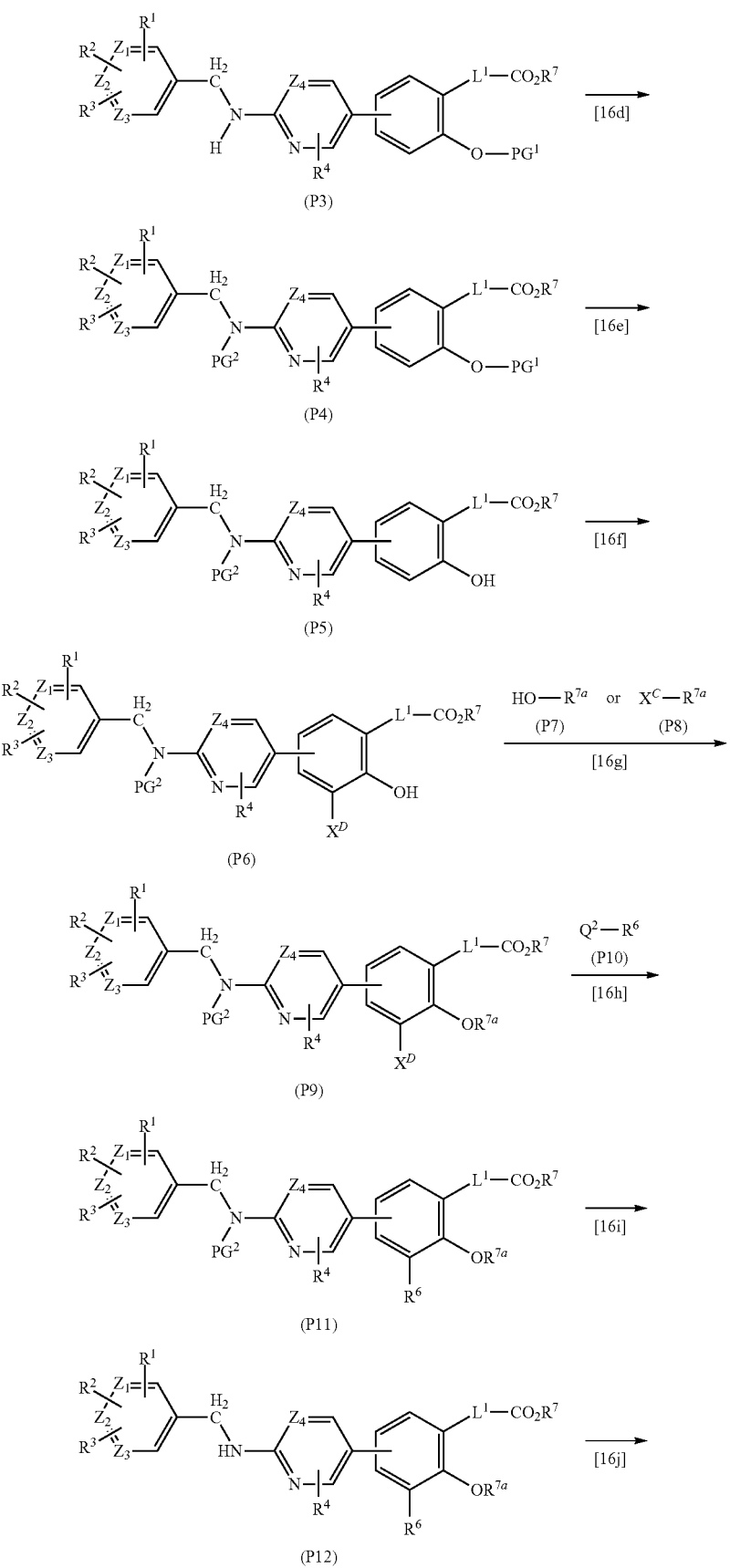

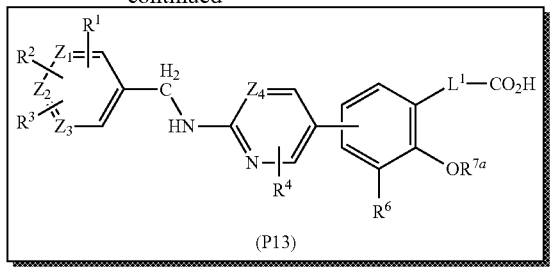

(P13)

[in the above-mentioned scheme, $R^7$ is alkyl, $X^A$, $X^C$ and $X^D$ are halogens, $Q^1$ and $Q^2$ are borate, $PG^1$ is a hydroxyl-protecting group, $PG^2$ is an amino-protecting group, and other symbols are as defined above].

[Step 16a]

In the above-mentioned scheme, compound (P3) can be produced from compound (A2) and compound (P1) by a method similar to that in [Step 1b].

[Step 16b]

In the above-mentioned scheme, compound (P2) can be produced from compound (P1) by a method similar to that in [Step 2a].

[Step 16c]

In the above-mentioned scheme, compound (P3) can be produced from compound (A1) and compound (P2) by a method similar to that in [Step 1b].

[Step 16d]

In the above-mentioned scheme, compound (P4) can be produced by protecting compound (P3) with $PG^2$ by a general method.

[Step 16e]

In the above-mentioned scheme, compound (P5) can be produced by removing $PG^1$ of compound (P4) by a general method.

[Step 16f]

In the above-mentioned scheme, compound (P6) can be produced by reacting compound (P5) in a solvent, in the presence of a halogenating reagent in the presence or absence of a base. As the halogenating reagent, for example, bromine, iodine, chlorine, iodine monochloride, N-bromosuccinimide (NBS), N-chlorosuccinimide (NCS), N-iodosuccinimide (NIS), dibromoisocyanuric acid (DBI), chloramine-T, 1,3-dibromo-5,5'-dimethylhydantoin, 1,3-iodo-5,5'-dimethylhydantoin, pyridinium bromoperbromide and the like can be mentioned. As the base, triethylamine, diisopropylethylamine, pyridine and the like can be mentioned. The solvent is not particularly limited as long as it does not adversely influence the reaction, tetrahydrofuran, dichloromethane, dichloroethane, chloroform, diethyl ether, dioxane, dimethoxyethane, acetonitrile, methyl alcohol, ethyl alcohol, water and the like can be mentioned. This reaction preferably proceeds at −78° C.-80° C., preferably 0° C.-70° C. Particularly, it proceeds under the reaction conditions described in Bull. Chem. Soc. Jpn., 1993, 66, 1576-1579.

[Step 16g]

In the above-mentioned scheme, compound (P9) can be produced from compound (P6) by using compound (P7) or compound (P8) according to a method similar to that in [Step 14d].

[Step 16h]

In the above-mentioned scheme, compound (P11) can be produced by reacting compound (P9) with compound (P10) in a solvent in the presence of a transition metal complex and a base. The solvent is not particularly limited as long as it does not adversely influence the reaction and, for example, toluene, benzene, xylene, dichloromethane, dichloroethane, chloroform, tetrahydrofuran (THF), dimethoxyethane (DME), dioxane, diethyl ether, acetonitrile, ethyl acetate, N,N-dimethylformamide (DMF), dimethyl sulfoxide (DMSO), N-methylpyrrolidone (NMP), methyl alcohol, ethyl alcohol, i-propyl alcohol, n-butyl alcohol, water or a mixed solvent and the like can be appropriately used. Examples of the transition metal complex to be used include 0 valent palladium complexes such as tetrakis(triphenylphosphine)palladium(0), tris(dibenzylideneacetone)dipalladium(0), bis(dibenzylideneacetone)palladium(0), bis(tri-tert-butylphosphine)palladium(0), and bis(tricyclohexylphosphine)palladium(0), and divalent palladium complexes such as palladium(II) acetate, palladium(II) trifluoroacetate, bis(triphenylphosphine)palladium (II) dichloride, bis(tri-O-tolylphosphine)palladium(II) dichloride, bis(tricyclohexylphosphine)palladium(II) dichloride, bis(benzonitrile)palladium(II) dichloride, bis(acetonitrile)palladium(II) dichloride, bis(acetylacetone)palladium(II), [1,1'-bis(diphenylphosphino)ferrocene]palladium (II) dichloride, bis(di-tert-butyl(4-dimethylaminophenyl)phosphine) dichloropalladium (II) (A-$^{ta}$Phos), bis (dicyclohexyl (4-dimethylaminophenyl)phosphine) dichloropalladium(II)(A-$^{CA}$Phos) and the like. In addition, a suitable ligand may be added and, for example, tri-tert-butylphosphine, tri-cyclohexylphosphine, 1,1'-bis(diphenylphosphino)ferrocene (DPPF), 1-[2-[bis(tert-butyl)phosphino]phenyl]-3,5-diphenyl-1H-pyrazole (TrippyPhos), (±)-2,2'-bis(diphenylphosphino)-1,1'-binaphthyl (BINAP), 2-dicyclohexylphosphino-2-(N,N-dimethylamino)biphenyl, tri(ortho-tolyl)phosphine, 1,3-bis(diphenylphosphino)propane, 1,2,3,4,5-pentaphenyl-1-(di-tert-butylphosphino)ferrocene (Q-Phos), 4,5-bis(diphenylphosphino)-9,9-dimethylxanthene (Xantphos), di(1-adamantyl)-n-butylphosphine (CataCXium A), (2-biphenyl)di-tert-butylphosphine (JohnPhos), (S)-1-[(1R)-2-(diphenylphosphino)ferrocenyl]ethyldicyclohexylphosphine (CyPFtBu JosiPhos), 2-dicyclohexylphosphino-2',6'-diisopropoxybiphenyl (RuPhos), 2-dicyclohexylphosphino-2',6'-dimethoxybiphenyl (SPhos), 2-dicyclohexylphosphino-2'-(N,N-dimethylamino)biphenyl (DavePhos), 2-dicyclohexylphosphino-2',4',6'-triisopropylbiphenyl (XPhos), 2-di-tert-butylphosphino-2',4',6'-triisopropyl-1,1'-biphenyl (tert-butyl-X-Phos), 2-(dicyclohexylphosphino)-3,6-dimethoxy-2',4',6'-triisopropyl-1,1'-biphenyl (BrettPhos) and the like. Examples of the base include sodium hydrogen carbonate, sodium carbonate, potassium carbonate, cesium carbonate, sodium acetate, potassium acetate, lithium tert-butoxide, sodium tert-butoxide, potassium tert-butoxide, tripotassium phosphate, dipotassium hydrogen phosphate, potassium dihydrogen phosphate, triethylamine, diisopropylethylamine, 1,8-diazabicyclo[5.4.0]undecene (DBU), diazabicyclononene (DBN), 1,4-diazabicyclo[2.2.2]octane (DABCO) and the like. The amount of the transition metal complex to be used may be 0.01-0.3 equivalents, preferably 0.03-0.1 equivalents, relative to compound (P9). The amount of the base to be used may be 1-10 equivalents, preferably 2-7 equivalents, relative to compound (P9). Particularly, it can be preferably produced by a method using reaction conditions such as those described in Organic Letters, 2006, 8, 1787-1789.

[Step 16i]

In the above-mentioned scheme, compound (P12) can be is produced by removing $PG^2$ of compound (P11) by a general method.

[Step 16j]

In the above-mentioned scheme, compound (P13) can be produced from compound (P12) by a method similar to Step [1c]. Production method 17 (when $L^1$ is —CO—NH—$X^3$—)

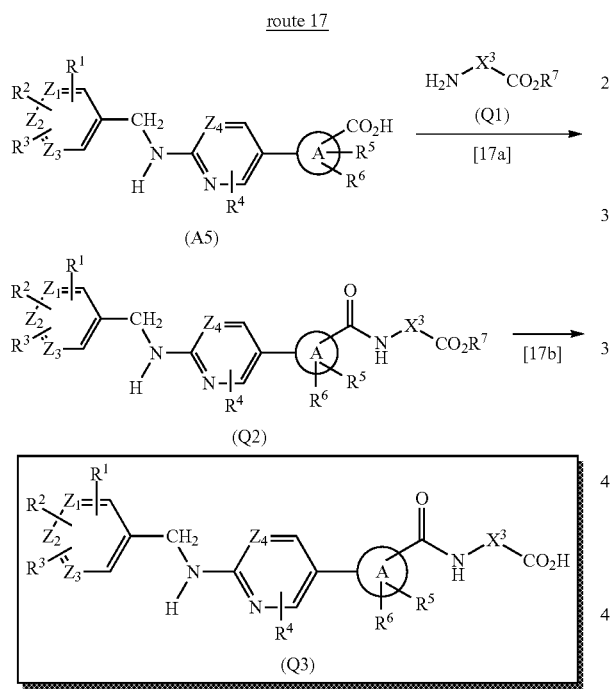

[in the above-mentioned scheme, $R^7$ is alkyl, and other symbols are as defined above].

[Step 17a]

In the above-mentioned scheme, compound (Q2) can be produced by reacting compound (A5) with compound (Q1) in a solvent, in the presence of a condensing agent, in the presence or absence of an activator, in the presence or absence of a base. As the solvent, for example, toluene, benzene, xylene, dichloromethane, dichloroethane, chloroform, tetrahydrofuran (THF), dimethoxyethane (DME), dioxane, diethyl ether, acetonitrile, ethyl acetate, N,N-dimethylformamide (DMF), dimethyl sulfoxide (DMSO), N-methylpyrrolidone (NMP), acetone and the like can be mentioned. As the base, triethylamine, diisopropylethylamine, pyridine, lutidine and the like can be mentioned. As the condensing agent, 1-ethyl-3-(3-dimethylaminopropyl)carbodiimide hydrochloride (WSC.HCl), N,N'-dicyclohexylcarbodiimide (DCC), diethyl cyanophosphonate, O-(7-azabenzotriazol-1-yl)-N,N,N',N'-tetramethyluronium hexafluorophosphate (HATU), 1,1-carbonylimidazole (CDI), (benzothiazol-1-yloxy)tris(dimethylamino)phosphonium hexafluorophosphate (BOP), (benzothiazol-1-yloxy)tripyrrolidinophosphonium hexafluorophosphate (PyBOP) and the like can be mentioned. As the activator, 1-hydroxy-7-azabenzotriazole (HOAt), 1-hydroxybenzotriazole (HOBt) and the like can be mentioned. This reaction preferably proceeds at 0° C.-100° C., preferably room temperature-40° C.

[Step 17b]

In the above-mentioned scheme, compound (Q3) can be produced from compound (Q2) by a method similar to Step [1c].

Production Method 18

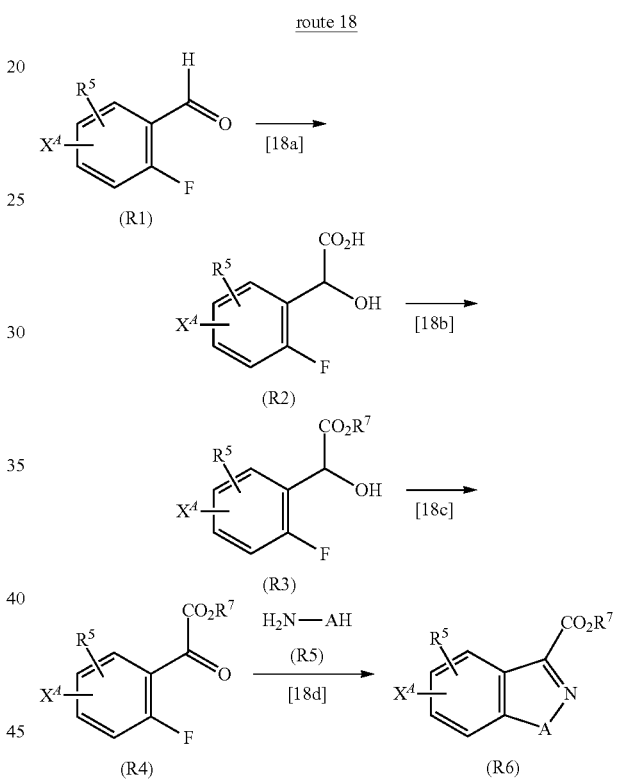

[in the above-mentioned scheme, $R^7$ is alkyl, $X^4$ is halogen, A is NH or O, and other symbols are as defined above].

[Step 18a]

In the above-mentioned scheme, compound (R2) can be produced by reacting compound (R1) with trimethylsilyl cyanide in a solvent, in the presence of a base or a Lewis acid. As the base, N,N-dimethyl-4-aminopyridine, 1,4-diazabicyclo[2.2.2]octane and the like can be mentioned. As the Lewis acid, zinc iodide, iron(III) chloride, titanium(IV) tetraisopropoxide and the like can be mentioned. As the solvent, dichloromethane, dichloroethane, chloroform, tetrahydrofuran (THF), dimethoxyethane (DME), dioxane, diethyl ether, acetonitrile, ethyl acetate, nitromethane and the like can be mentioned.

[Step 18b]

In the above-mentioned scheme, compound (R3) can be produced by reacting compound (R2) in an alcohol solvent, in the presence of an acid catalyst. As the alcohol solvent, for example, ethyl alcohol, methyl alcohol and the like can be mentioned. Examples of the acid catalyst include hydrochloric acid, sulfuric acid and the like. As the reaction temperature, the reaction preferably proceeds at room temperature-150° C., particularly 50° C.-100° C.

[Step 18c]

In the above-mentioned scheme, compound (R4) can be produced by reacting compound (R3) in a DMSO solvent, in the presence of acetic anhydride. This reaction preferably proceeds at room temperature-150° C., particularly 50° C.-100° C. In addition, it can be produced by a method using a general oxidant.

[Step 18d]

In the above-mentioned scheme, compound (R6) can be produced by reacting compound (R4) with compound (R5) in a solvent in the presence or absence of a base. The solvent is not particularly limited as long as it does not adversely influence the reaction and, for example, methyl alcohol, ethyl alcohol, i-propyl alcohol, n-butyl alcohol, N,N-dimethylformamide (DMF), dimethyl sulfoxide (DMSO), N-methylpyrrolidone (NMP), acetic acid, dichloromethane, dichloroethane, chloroform, tetrahydrofuran (THF), dimethoxyethane (DME), dioxane, diethyl ether and the like can be mentioned. The reaction preferably proceeds particularly in an alcohol solvent. As the base, triethylamine, diisopropylethylamine, N-methylmorpholine, sodium acetate, sodium hydrogen carbonate, sodium carbonate, potassium carbonate, cesium carbonate, sodium acetate, potassium acetate and the like can be mentioned. As the reaction temperature, the reaction preferably proceeds at room temperature-150° C., particularly 50° C.-100° C.

Production Method 19

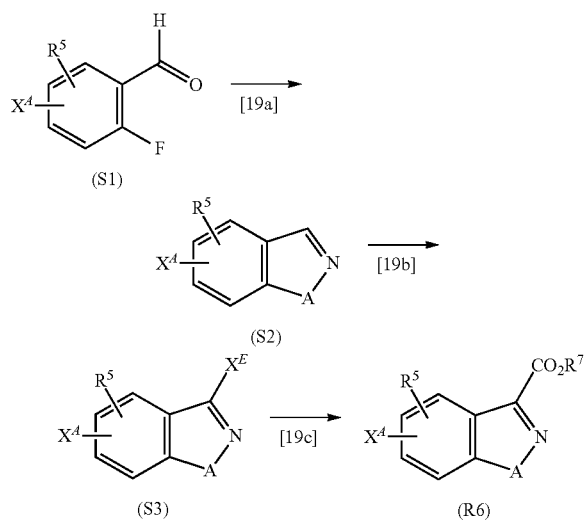

route 19

(S1)

(S2)

(S3)

(R6)

[in the above-mentioned scheme, $R^7$ is alkyl, $X^A$ and $X^E$ are halogens, A is NH or O, and other symbols are as defined above].

[Step 19a]

In the above-mentioned scheme, compound (S2) can be produced by reacting compound (S1) with hydrazine monohydrate in a solvent in the presence or absence of a base. The solvent is not particularly limited as long as it does not adversely influence the reaction and, for example, tetrahydrofuran (THF), dimethoxyethane (DME), dioxane, diethyl ether, acetonitrile, ethyl acetate, acetic acid, N,N-dimethylformamide (DMF), dimethyl sulfoxide (DMSO), N-methylpyrrolidone (NMP), methyl alcohol, ethyl alcohol, i-propyl alcohol, n-butyl alcohol, water and the like can be mentioned. As the base, triethylamine, diisopropylethylamine, N-methylmorpholine, pyridine, 2,6-lutidine, 2,4,6-collidine, N,N-dimethyl-4-aminopyridine (DMAP), 1,8-diazabicyclo[5.4.0]undecene (DBU), diazabicyclononene (DBN), 1,4-diazabicyclo[2.2.2]octane (DABCO), sodium hydrogen carbonate, sodium carbonate, potassium carbonate, cesium carbonate, sodium acetate, potassium acetate and the like can be mentioned. As the reaction temperature, the reaction preferably proceeds at room temperature-150° C., particularly 50° C.-100° C.

[Step 19b]

In the above-mentioned scheme, compound (S3) can be produced by treating compound (S2) with a halogenating reagent in a solvent in the presence or absence of a base. The solvent is not particularly limited as long as it does not adversely influence the reaction and, for example, toluene, benzene, xylene, dichloromethane, dichloroethane, chloroform, tetrahydrofuran (THF), dimethoxyethane (DME), dioxane, diethyl ether, acetonitrile, ethyl acetate, acetic acid, N,N-dimethylformamide (DMF), dimethyl sulfoxide (DMSO), N-methylpyrrolidone (NMP), methyl alcohol, ethyl alcohol, i-propyl alcohol, n-butyl alcohol, acetone, water and the like can be mentioned. Examples of the halogenating reagent include iodine, bromine, N-iodosuccinimide, N-bromosuccinimide and the like can be mentioned. As the base, sodium hydrogen carbonate, sodium carbonate, potassium carbonate, cesium carbonate, sodium acetate, potassium acetate, lithium tert-butoxide, sodium tert-butoxide, potassium tert-butoxide, tripotassium phosphate, dipotassium hydrogen phosphate, potassium dihydrogen phosphate, lithium hydroxide, sodium hydroxide, potassium hydroxide, triethylamine, diisopropylethylamine, N-methylmorpholine and the like can be mentioned. This reaction preferably proceeds at −20° C.- 80° C., particularly 0° C.-room temperature.

[Step 19c]

In the above-mentioned scheme, compound (R6) can be produced by reacting compound (S3) in a solvent in the presence of a transition metal complex and a base under a carbon monoxide atmosphere. The solvent is not particularly limited as long as it does not adversely influence the reaction and, for example, alcohol solvents such as methyl alcohol, ethyl alcohol, i-propyl alcohol, n-butyl alcohol and the like can be mentioned, and it may be a mixed solvent with toluene, benzene, xylene, dichloromethane, dichloroethane, chloroform, tetrahydrofuran (THF), dimethoxyethane (DME), dioxane, diethyl ether, acetonitrile, ethyl acetate, N,N-dimethylformamide (DMF), dimethyl sulfoxide (DMSO), N-methylpyrrolidone (NMP). Examples of the transition metal complex to be used include 0 valent palladium complexes such as tetrakis(triphenylphosphine)palladium(0), tris(dibenzylideneacetone)dipalladium(0), bis(dibenzylideneacetone)palladium(0), bis(tri-tert-butylphosphine)palladium(0), bis(tricyclohexylphosphine)palladium(0), and divalent palladium complexes such as palladium(II) acetate, palladium(II) trifluoroacetate, bis(triphenylphosphine)palladium(II) dichloride, bis(tri-O-tolylphosphine)palladium(II) dichloride, bis(tricyclohexylphosphine)palladium(II) dichloride, bis(benzonitrile)palladium (II) dichloride, bis(acetonitrile)palladium(II) dichloride, bis(acetylacetone)palladium(II), [1,1'-bis(diphenylphosphino)ferrocene]palladium(II) dichloride, bis(di-tert-butyl(4-dimethylaminophenyl)phosphine) dichloropalladium(II) (A-$^{ta}$Phos), bis(dicyclohexyl(4-dimethylaminophenyl)phosphine)dichloropalladium(II)(A-$^{CA}$Phos). In addition, a suitable ligand may be added and, for example, tri-tert-butylphosphine, tri-cyclohexylphosphine, 1,1'-bis(diphenylphosphino)ferrocene (DPPF), 1-[2-[bis(tert-butyl)phosphino]phenyl]-3,5-diphenyl-1H-pyrazole (TrippyPhos), (±)-2,2'-bis(diphenylphosphino)-1,1'-binaphthyl (BINAP), 2-dicyclohexylphosphino-2-(N,N-dimethylamino)biphenyl, tri(ortho-tolyl)phosphine, 1,3-bis(diphenylphosphino)propane, 1,2,3,4,5-pentaphenyl-1-(di-tert-butylphosphino)ferrocene (Q-Phos), 4,5-bis(diphenylphosphino)-9,9-dimethylxanthene (Xantphos), di(1-adamantyl)-n-butylphosphine (CataCXium A), (2-biphenyl)di-tert-butylphosphine (JohnPhos), (S)-1-[(1R)-2-(diphenylphosphino)ferrocenyl]ethyldicyclohexylphosphine (CyPFtBu JosiPhos), 2-dicyclohexylphosphino-2',6'-diisopropoxybiphenyl (RuPhos), 2-dicyclohexylphosphino-2',6'-dimethoxybiphenyl (SPhos), 2-dicyclohexylphosphino-2'-(N,N-dimethylamino)biphenyl (DavePhos), 2-dicyclohexylphosphino-2',4',6'-triisopropylbiphenyl (XPhos), 2-di-tert-butylphosphino-2',4',6'-triisopropyl-1,1'-biphenyl (tert-butyl-X-Phos), 2-(dicyclohexylphosphino)-3,6-dimethoxy-2',4',6'-triisopropyl-1,1'-biphenyl (BrettPhos) can be mentioned. Examples of the base include sodium hydrogen carbonate, sodium carbonate, potassium carbonate, cesium carbonate, sodium acetate, potassium acetate, lithium tert-butoxide, sodium tert-butoxide, potassium tert-butoxide, tripotassium phosphate, dipotassium hydrogen phosphate, potassium dihydrogen phosphate, triethylamine, diisopropylethylamine, 1,8-diazabicyclo[5.4.0]undecene (DBU), diazabicyclononene (DBN), 1,4-diazabicyclo[2.2.2]octane (DABCO) and the like. The amount of the transition metal complex to be used may be 0.01-0.3 equivalents, preferably 0.03-0.1 equivalents, relative to compound (S3). The amount of the base to be used may be 1-10 equivalents, preferably 2-7 equivalents, relative to compound (S3). Particularly, it can be preferably produced by a method using reaction conditions such as those described in Organometallics, 2008, 27, 5402-5422.

Production Method 20 route 20

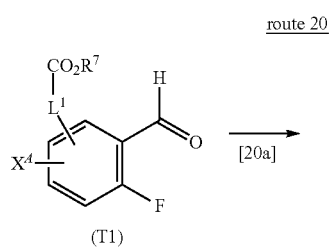

(T1)

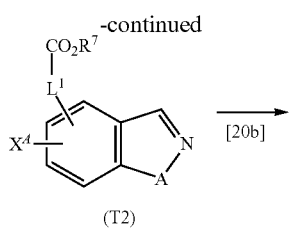

(T2)

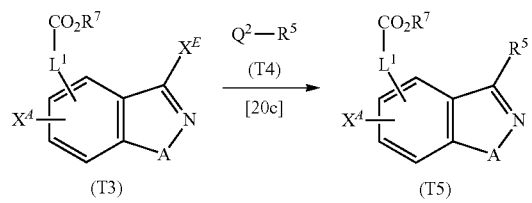

[in the above-mentioned scheme, $R^7$ is alkyl, $X^A$ and $X^E$ are halogens, $Q^2$ is borate, A is NH or O, and other symbols are as defined above].

[Step 20a]

In the above-mentioned scheme, compound (T2) can be produced from compound (T1) by a method similar to Step [18d].

[Step 20b]

In the above-mentioned scheme, compound (T3) can be produced from compound (T2) by a method similar to Step [19b].

[Step 20c]

In the above-mentioned scheme, compound (T5) can be produced from compound (T3) and compound (T4) by a method similar to Step [16h].

Production Method 21 route 21

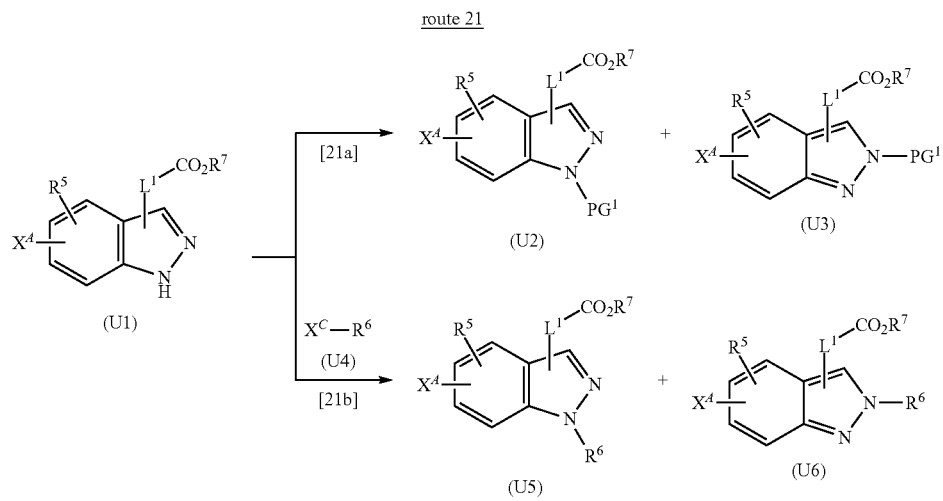

(A = NH)

[in the above-mentioned scheme, $R^7$ is alkyl, $X^A$ and Xc are halogens, $PG^1$ is an amino-protecting group, and other symbols are as defined above].

[Step 21a]

In the above-mentioned scheme, compound (U2) and (U3) can be produced by protecting compound (U1) with $PG^1$ by a general method.

[Step 21b]

In the above-mentioned scheme, compound (U5) and (U6) can be produced by reacting compound (U1) with compound (U4) in a solvent in the presence of a base, in the presence or absence of a phase-transfer catalyst. The solvent is not particularly limited as long as it does not adversely influence the reaction, toluene, benzene, xylene, dichloromethane, dichloroethane, chloroform, tetrahydrofuran (THF), dimethoxyethane (DME), dioxane, diethyl ether, acetone, acetonitrile, ethyl acetate, N,N-dimethylformamide (DMF), dimethyl sulfoxide (DMSO), N-methylpyrrolidone (NMP) and the like can be mentioned. As the base, sodium hydrogen carbonate, sodium carbonate, potassium carbonate, cesium carbonate, sodium hydride, sodium tert-butoxide, potassium tert-butoxide, lithium hexamethyl disilazide (LiHMDS), sodium hexamethyl disilazide (NaHMDS), potassium hexamethyl disilazide (KHMDS), lithium diisopropylamide (LDA), iso-propylmagnesium chloride, iso-propylmagnesium bromide, i-propylmagnesium chloride lithium chloride salt and the like can be mentioned. This reaction particularly preferably proceeds using sodium hydride, potassium tert-butoxide and the like. As the phase-transfer catalyst, halogenated quaternary ammonium salt, crown ether and the like can be mentioned. This reaction preferably proceeds at −78° C.-100° C., particularly 0° C.-70° C.

Production Method 22

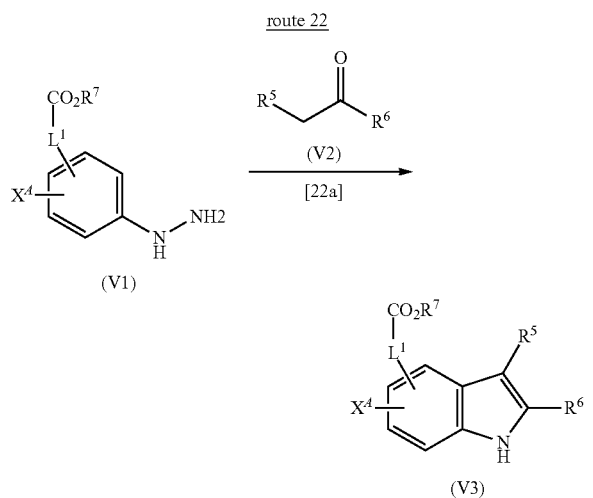

[in the above-mentioned scheme, $R^7$ is alkyl, $X^A$ is halogen, and other symbols are as defined above].

[Step 22a]

In the above-mentioned scheme, compound (V3) can be produced by reacting compound (V1) with compound (V2) in a solvent, in the presence of an acid or a Lewis acid. The solvent is not particularly limited as long as it does not adversely influence the reaction and, for example, toluene, benzene, dichloromethane, dichloroethane, chloroform, methyl alcohol, ethyl alcohol, acetic acid and the like can be mentioned. As the acid or Lewis acid, for example, hydrochloric acid, sulfuric acid, p-toluenesulfonic acid, trifluoromethanesulfonic acid, methanesulfonic acid, pyridinium p-toluenesulfonate, polyphosphoric acid, trifluoroacetic acid, zinc chloride, trifluoroborane.ether complex and the like can be mentioned. This reaction preferably proceeds at 50° C.-150° C., particularly 70° C.-120° C. In addition, it can be preferably produced by a method using a microwave reactor, as described in Tetrahedron, 2012, 68, 10049-10058.

Production Method 23

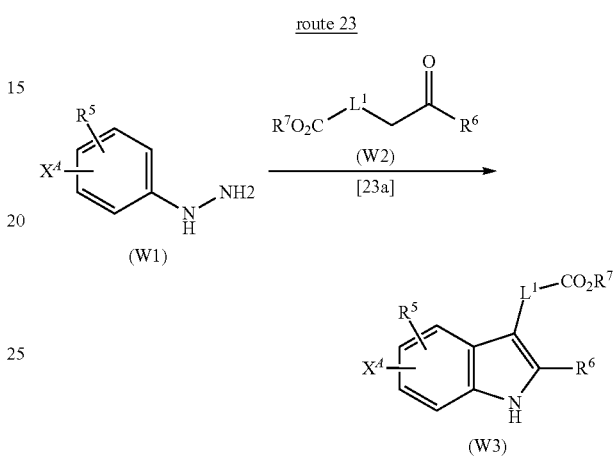

[in the above-mentioned scheme, $R^7$ is alkyl, $X^A$ is halogen, and other symbols are as defined above].

In the above-mentioned scheme, compound (W3) can be produced from compound (W1) and compound (W2) by a method similar to Step [22a].

Production Method 24

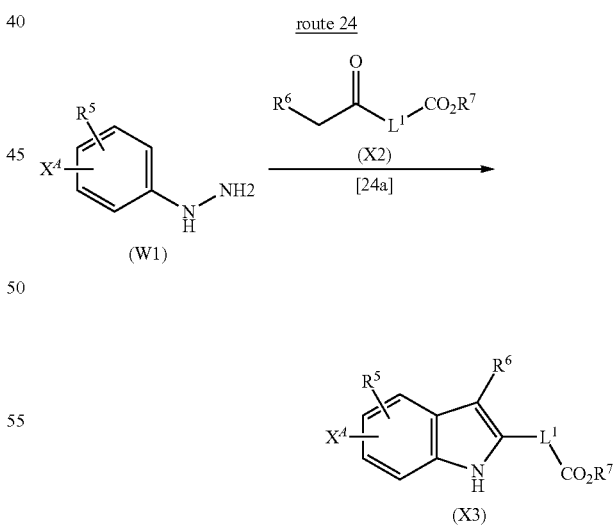

[in the above-mentioned scheme, $R^7$ is alkyl, $X^A$ is halogen, and other symbols are as defined above].

[Step 24a]

In the above-mentioned scheme, compound (X3) can be produced from compound (X1) and compound (X2) by a method similar to Step [22a].

Production Method 25

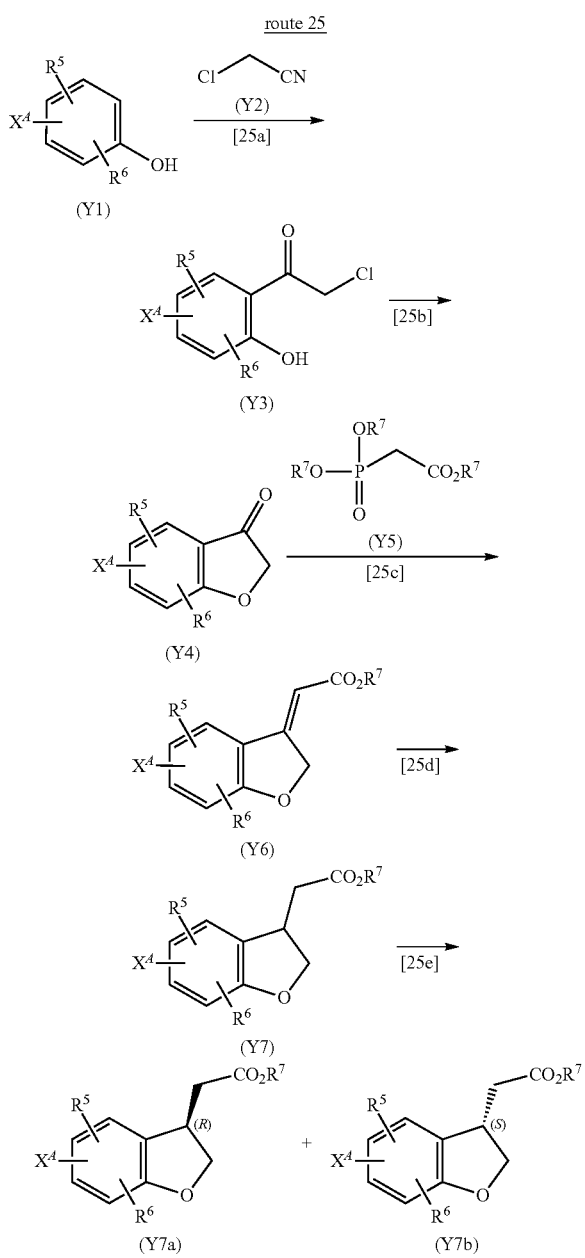

[in the above-mentioned scheme, $R^7$ is alkyl, $X^A$ is halogen, and other symbols are as defined above].

[Step 25a]

In the above-mentioned scheme, compound (Y3) can be produced by reacting compound (Y1) with compound (Y2) in a solvent, in the presence of aluminum trichloride and boron trichloride. The solvent is not particularly limited as long as it does not adversely influence the reaction and, for example, dichloromethane, dichloroethane, chloroform and the like can be mentioned. Particularly, it can be preferably produced by a method using reaction conditions such as those described in J. Org. Chem., 1981, 46, 189-191.

[Step 25b]

In the above-mentioned scheme, compound (Y4) can be produced by treating compound (Y3) with a base in a solvent. The solvent is not particularly limited as long as it does not adversely influence the reaction and, for example, toluene, benzene, xylene, dichloromethane, dichloroethane, chloroform, tetrahydrofuran (THF), dimethoxyethane (DME), dioxane, diethyl ether, acetonitrile, ethyl acetate, N,N-dimethylformamide (DMF), dimethyl sulfoxide (DMSO), N-methylpyrrolidone (NMP), methyl alcohol, ethyl alcohol, i-propyl alcohol, n-butyl alcohol and the like can be mentioned. As the base, sodium hydrogen carbonate, sodium carbonate, potassium carbonate, cesium carbonate, sodium acetate, potassium acetate, lithium tert-butoxide, sodium tert-butoxide, potassium tert-butoxide, tripotassium phosphate, dipotassium hydrogen phosphate, potassium dihydrogen phosphate and the like can be mentioned. Particularly, it can be preferably produced by a method using reaction conditions such as those described in J. Fluoresc, 2011, 21, 2173-2184.

[Step 25c]

In the above-mentioned scheme, compound (Y6) can be produced by reacting compound (Y4) with a Wittg-Horner reagent (Y5) in a solvent in the presence of a base. The solvent is not particularly limited as long as it does not adversely influence the reaction and, for example, toluene, benzene, xylene, dichloromethane, dichloroethane, chloroform, tetrahydrofuran (THF), dimethoxyethane (DME), dioxane, diethyl ether, acetonitrile, ethyl acetate, N,N-dimethylformamide (DMF), dimethyl sulfoxide (DMSO), N-methylpyrrolidone (NMP), methyl alcohol, ethyl alcohol, i-propyl alcohol, n-butyl alcohol and the like can be mentioned. As the base, sodium hydride, sodium tert-butoxide, potassium tert-butoxide and the like can be mentioned. This reaction preferably proceeds at −20° C.-80° C., particularly 0° C.-60° C.

[Step 25d]

In the above-mentioned scheme, compound (Y7) can be produced by catalytic hydrogenation reaction of compound (Y6) in a solvent in the presence of palladium carbon (Pd/C), under a hydrogen atmosphere. The solvent is not particularly limited as long as it does not adversely influence the reaction and, for example, methyl alcohol, ethyl alcohol, ethyl acetate and the like can be mentioned.

[Step 25e]

In the above-mentioned scheme, compound (Y7a) and (Y7b) can be preferably produced by optical resolution of compound (Y7) by using a reversed-phase HPLC apparatus mounting a chiral column.

Production Method 26

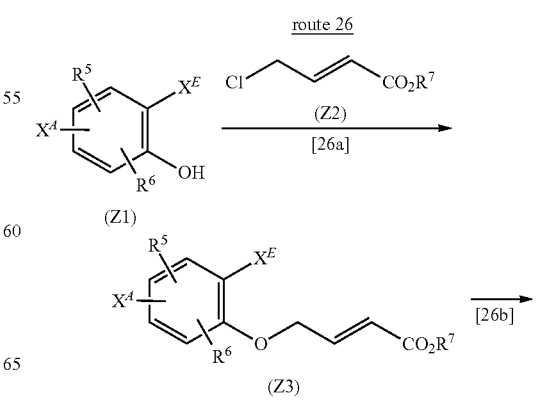

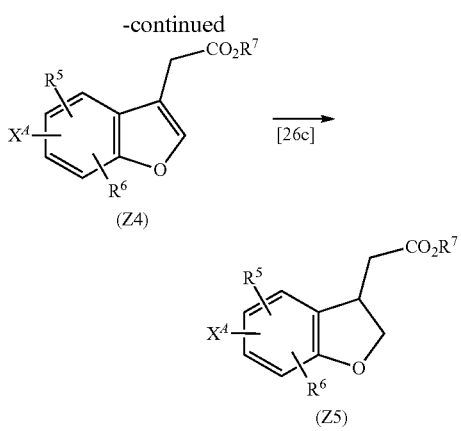

[in the above-mentioned scheme, $R^7$ is alkyl, $X^A$ and $X^E$ are halogens, and other symbols are as defined above].

[Step 26a]

In the above-mentioned scheme, compound (Z3) can be produced by reacting compound (Z1) with compound (Z2) in a solvent in the presence of a base, in the presence or absence of a phase-transfer catalyst. The solvent is not particularly limited as long as it does not adversely influence the reaction, toluene, benzene, xylene, dichloromethane, dichloroethane, chloroform, tetrahydrofuran (THF), dimethoxyethane (DME), dioxane, diethyl ether, acetone, acetonitrile, ethyl acetate, N,N-dimethylformamide (DMF), dimethyl sulfoxide (DMSO), N-methylpyrrolidone (NMP) can be mentioned. As the base, sodium hydrogen carbonate, sodium carbonate, potassium carbonate, cesium carbonate, sodium hydride, sodium tert-butoxide, potassium tert-butoxide, lithium hexamethyl disilazide (LiHMDS), sodium hexamethyl disilazide (NaHMDS), potassium hexamethyl disilazide (KHMDS), lithium diisopropylamide (LDA), iso-propylmagnesium chloride, iso-propylmagnesium bromide, i-propylmagnesium chloride lithium chloride salt and the like can be mentioned. This reaction particularly preferably proceeds using sodium hydride, potassium tert-butoxide. As the phase-transfer catalyst, halogenated quaternary ammonium salt, crown ether and the like can be mentioned. This reaction preferably proceeds at 0° C.-120° C., particularly room temperature-80° C.

[Step 26b]

In the above-mentioned scheme, compound (Z4) can be produced from compound (Z3) by an intramolecular Heck reaction in a solvent in the presence of a transition metal complex and a base. The solvent is not particularly limited as long as it does not adversely influence the reaction and, for example, toluene, benzene, xylene, dichloromethane, dichloroethane, chloroform, tetrahydrofuran (THF), dimethoxyethane (DME), dioxane, diethyl ether, acetonitrile, ethyl acetate, N,N-dimethylformamide (DMF), dimethyl sulfoxide (DMSO), N-methylpyrrolidone (NMP), methyl alcohol, ethyl alcohol, i-propyl alcohol, n-butyl alcohol, water or a mixed solvent and the like can be appropriately used. Examples of the transition metal complex to be used include 0 valent palladium complexes such as tetrakis(triphenylphosphine)palladium(0), tris(dibenzylideneacetone)dipalladium(0), bis(dibenzylideneacetone)palladium(0), bis(tri-tert-butylphosphine)palladium(0), bis(tricyclohexylphosphine)palladium(0), and divalent palladium complexes such as palladium(II) acetate, palladium(II) trifluoroacetate, bis(triphenylphosphine)palladium (II) dichloride, bis(tri-O-tolylphosphine)palladium(II) dichloride, bis(tricyclohexylphosphine)palladium(II) dichloride, bis(benzonitrile)palladium(II) dichloride, bis(acetonitrile)palladium(II) dichloride, bis(acetylacetone)palladium(II), [1,1'-bis(diphenylphosphino)ferrocene]palladium (II) dichloride, bis(di-tert-butyl (4-dimethylaminophenyl) phosphine) dichloropalladium (II) (A-$^{ta}$Phos), bis(dicyclohexyl(4-dimethylaminophenyl) phosphine) dichloropalladium (II) (A-$^{CA}$Phos) and the like. In addition, a suitable ligand may be added and, for example, tri-tert-butylphosphine, tri-cyclohexylphosphine, 1,1'-bis(diphenylphosphino)ferrocene (DPPF), 1-[2-[bis(tert-butyl)phosphino]phenyl]-3,5-diphenyl-1H-pyrazole (TrippyPhos), (±)-2,2'-bis(diphenylphosphino)-1,1'-binaphthyl (BINAP), 2-dicyclohexylphosphino-2-(N,N-dimethylamino)biphenyl, tri(ortho-tolyl)phosphine, 1,3-bis(diphenylphosphino)propane, 1,2,3,4,5-pentaphenyl-1-(di-tert-butylphosphino)ferrocene (Q-Phos), 4,5-bis(diphenylphosphino)-9,9-dimethylxanthene (Xantphos), di(1-adamantyl)-n-butylphosphine (CataCXium A), (2-biphenyl)di-tert-butylphosphine (JohnPhos), (S)-1-[(1R)-2-(diphenylphosphino)ferrocenyl]ethyldicyclohexylphosphine (CyPFtBu JosiPhos), 2-dicyclohexylphosphino-2',6'-diisopropoxybiphenyl (RuPhos), 2-dicyclohexylphosphino-2',6'-dimethoxybiphenyl (SPhos), 2-dicyclohexylphosphino-2'-(N,N-dimethylamino)biphenyl (DavePhos), 2-dicyclohexylphosphino-2',4',6'-triisopropylbiphenyl (XPhos), 2-di-tert-butylphosphino-2',4',6'-triisopropyl-1,1'-biphenyl (tert-butyl-X-Phos), 2-(dicyclohexylphosphino)-3,6-dimethoxy-2',4',6'-triisopropyl-1,1'-biphenyl (BrettPhos) and the like can be mentioned. Examples of the base include sodium hydrogen carbonate, sodium carbonate, potassium carbonate, cesium carbonate, sodium acetate, potassium acetate, lithium tert-butoxide, sodium tert-butoxide, potassium tert-butoxide, tripotassium phosphate, dipotassium hydrogen phosphate, potassium dihydrogen phosphate, triethylamine, diisopropylethylamine, 1,8-diazabicyclo[5.4.0]undecene (DBU), diazabicyclononene (DBN), 1,4-diazabicyclo[2.2.2]octane (DABCO) and the like can be mentioned. The amount of the transition metal complex to be used may be 0.01-0.3 equivalents, preferably 0.03-0.1 equivalents, relative to compound (Z3). The amount of the base to be used may be 1-10 equivalents, preferably 2-7 equivalents, relative to compound (Z3). It can be particularly preferably produced by a method using reaction conditions such as those described in Heterocycles, 1989, 28, 55-58.

[Step 25c]

In the above-mentioned scheme, compound (Z5) can be produced from compound (Z4) by a method similar to Step [24d].

Production Method 27 route 27

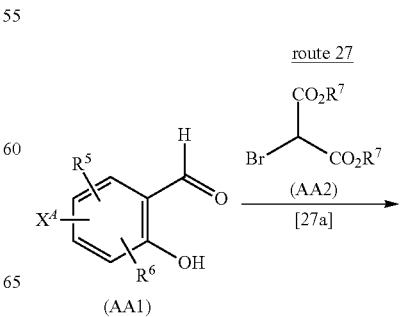

-continued

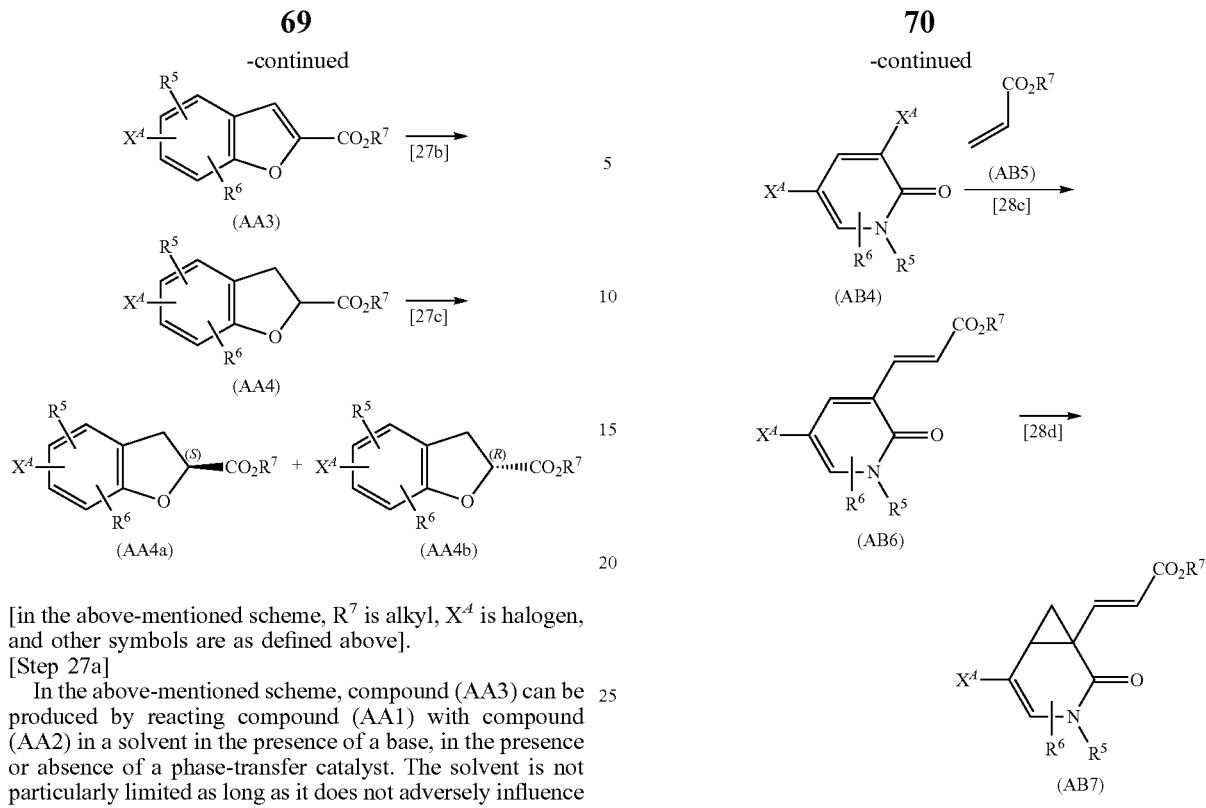

[in the above-mentioned scheme, $R^7$ is alkyl, $X^A$ is halogen, and other symbols are as defined above].

[Step 27a]

In the above-mentioned scheme, compound (AA3) can be produced by reacting compound (AA1) with compound (AA2) in a solvent in the presence of a base, in the presence or absence of a phase-transfer catalyst. The solvent is not particularly limited as long as it does not adversely influence the reaction, toluene, benzene, xylene, dichloromethane, dichloroethane, chloroform, tetrahydrofuran (THF), dimethoxyethane (DME), dioxane, diethyl ether, acetone, acetonitrile, ethyl acetate, N,N-dimethylformamide (DMF), dimethyl sulfoxide (DMSO), N-methylpyrrolidone (NMP) and the like can be mentioned. As the base, sodium hydrogen carbonate, sodium carbonate, potassium carbonate, cesium carbonate, sodium hydride, sodium tert-butoxide, potassium tert-butoxide, lithium hexamethyl disilazide (LiHMDS), sodium hexamethyl disilazide (NaHMDS), potassium hexamethyl disilazide (KHMDS), lithium diisopropylamide (LDA), iso-propylmagnesium chloride, iso-propylmagnesium bromide, i-propylmagnesium chloride lithium chloride salt and the like can be mentioned. This reaction particularly preferably proceeds using potassium carbonate, cesium carbonate, sodium hydride and the like. As the phase-transfer catalyst, halogenated quaternary ammonium salt, crown ether and the like can be mentioned. This reaction preferably proceeds at room temperature-150° C., particularly 80° C.-120° C.

[Step 27b]

In the above-mentioned scheme, compound (AA4) can be produced from compound (AA3) by a method similar to Step [25d].

[Step 27c]

In the above-mentioned scheme, compound (AA4a) and (AA4b) can be produced by optical resolution of compound (AA4) by a method similar to that in Step [25e].

Production Method 28 route 28

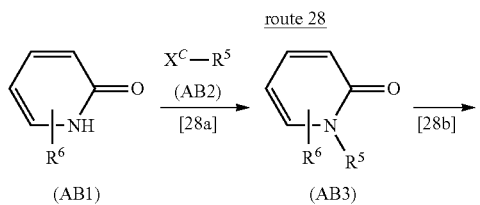

[in the above-mentioned scheme, $R^7$ is alkyl, $X^A$ and $X^C$ are halogens, and other symbols are as defined above].

[Step 28a]

In the above-mentioned scheme, compound (AB3) can be produced by reacting compound (AB1) with compound (AB2) in a solvent in the presence of a base, in the presence or absence of a phase-transfer catalyst. The solvent is not particularly limited as long as it does not adversely influence the reaction, toluene, benzene, xylene, dichloromethane, dichloroethane, chloroform, tetrahydrofuran (THF), dimethoxyethane (DME), dioxane, diethyl ether, acetone, acetonitrile, ethyl acetate, N,N-dimethylformamide (DMF), dimethyl sulfoxide (DMSO), N-methylpyrrolidone (NMP) and the like can be mentioned. As the base, sodium hydrogen carbonate, sodium carbonate, potassium carbonate, cesium carbonate, sodium hydride, sodium tert-butoxide, potassium tert-butoxide, lithium hexamethyl disilazide (LiHMDS), sodium hexamethyl disilazide (NaHMDS), potassium hexamethyl disilazide (KHMDS), lithium diisopropylamide (LDA), iso-propylmagnesium chloride, iso-propylmagnesium bromide, i-propylmagnesium chloride lithium chloride salt and the like can be mentioned. This reaction particularly preferably proceeds using sodium hydride, potassium tert-butoxide and the like. As the phase-transfer catalyst, halogenated quaternary ammonium salt, crown ether and the like can be mentioned. This reaction preferably proceeds at −78° C.-100° C., particularly 0° C.-70° C. Particularly, it can be preferably produced by a method using reaction conditions such as those described in J. Am. Chem. Soc., 2010, 132, 15380-15389.

[Step 28b]

In the above-mentioned scheme, compound (AB4) can be produced by reacting compound (AB3) in a solvent, in the presence of a halogenating reagent, and in the presence or absence of a base. As the halogenating reagent, for example, bromine, iodine, chlorine, iodine monochloride, N-bromosuccinimide (NBS), N-chlorosuccinimide (NCS), N-iodosuccinimide (NIS), dibromoisocyanuric acid (DBI), chloramine-T, 1,3-dibromo-5,5'-dimethylhydantoin, 1,3-iodo-5,5'-dimethylhydantoin, pyridinium bromoperbromide and the like can be mentioned. As the base, triethylamine, diisopropylethylamine, pyridine and the like can be mentioned. The solvent is not particularly limited as long as it does not adversely influence the reaction, tetrahydrofuran, dichloromethane, dichloroethane, chloroform, diethyl ether, dioxane, dimethoxyethane, acetonitrile, methyl alcohol, ethyl alcohol, water and the like can be mentioned. This reaction preferably proceeds at −78° C.-80° C., particularly 0° C.-70° C. It particularly preferably proceeds under reaction conditions described in Adv. Synth. Catal., 352, 1677-1687 or J. Org. Chem., 1989, 54, 3618-3624.

[Step 28c]

In the above-mentioned scheme, compound (AB6) can be produced by reacting compound (AB4) with compound (AB5) in a solvent in the presence of a transition metal complex and a base. The solvent is not particularly limited as long as it does not adversely influence the reaction and, for example, toluene, benzene, xylene, dichloromethane, dichloroethane, chloroform, tetrahydrofuran (THF), dimethoxyethane (DME), dioxane, diethyl ether, acetonitrile, ethyl acetate, N,N-dimethylformamide (DMF), dimethyl sulfoxide (DMSO), N-methylpyrrolidone (NMP), methyl alcohol, ethyl alcohol, i-propyl alcohol, n-butyl alcohol, water or a mixed solvent and the like can be appropriately used. Examples of the transition metal complex to be used include 0 valent palladium complexes such as tetrakis(triphenylphosphine)palladium(0), tris(dibenzylideneacetone)dipalladium(0), bis(dibenzylideneacetone)palladium(0), bis(tri-tert-butylphosphine)palladium(0), bis(tricyclohexylphosphine)palladium(0), and divalent palladium complexes such as palladium(II) acetate, palladium(II) trifluoroacetate, bis(triphenylphosphine)palladium(II) dichloride, bis(tri-O-tolylphosphine)palladium(II) dichloride, bis(tricyclohexylphosphine)palladium(II) dichloride, bis(benzonitrile)palladium(II) dichloride, bis(acetonitrile)palladium(II) dichloride, bis(acetylacetone)palladium(II), [1,1'-bis(diphenylphosphino)ferrocene]palladium(II) dichloride, bis(di-tert-butyl(4-dimethylaminophenyl)phosphine) dichloropalladium(II)(A-$^{ta}$Phos), bis(dicyclohexyl(4-dimethylaminophenyl)phosphine) dichloropalladium(II)(A-$^{CA}$Phos), η3-allylpalladium(II) chloride (dimer). In addition, a suitable ligand may be added and, for example, tri-tert-butylphosphine, tri-cyclohexylphosphine, 1,1'-bis(diphenylphosphino)ferrocene (DPPF), 1-[2-[bis(tert-butyl)phosphino]phenyl]-3,5-diphenyl-1H-pyrazole (TrippyPhos), (±)-2,2'-bis(diphenylphosphino)-1,1'-binaphthyl (BINAP), 2-dicyclohexylphosphino-2-(N,N-dimethylamino)biphenyl, tri(ortho-tolyl)phosphine, 1,3-bis(diphenylphosphino)propane, 1,2,3,4,5-pentaphenyl-1-(di-tert-butylphosphino)ferrocene (Q-Phos), 4,5-bis(diphenylphosphino)-9,9-dimethylxanthene (Xantphos), di(1-adamantyl)-n-butylphosphine (CataCXium A), (2-biphenyl) di-tert-butylphosphine (JohnPhos), (S)-1-[(1R)-2-(diphenylphosphino)ferrocenyl]ethyldicyclohexylphosphine (CyPFtBu JosiPhos), 2-dicyclohexylphosphino-2',6'-diisopropoxybiphenyl (RuPhos), 2-dicyclohexylphosphino-2',6'-dimethoxybiphenyl (SPhos), 2-dicyclohexylphosphino-2'-(N,N-dimethylamino)biphenyl (DavePhos), 2-dicyclohexylphosphino-2',4',6'-triisopropylbiphenyl (XPhos), 2-di-tert-butylphosphino-2',4',6'-triisopropyl-1,1'-biphenyl (tert-butyl-X-Phos), 2-(dicyclohexylphosphino)-3,6-dimethoxy-2',4',6'-triisopropyl-1,1'-biphenyl (BrettPhos) and the like can be mentioned.

Examples of the base include sodium hydrogen carbonate, sodium carbonate, potassium carbonate, cesium carbonate, sodium acetate, potassium acetate, lithium tert-butoxide, sodium tert-butoxide, potassium tert-butoxide, tripotassium phosphate, dipotassium hydrogen phosphate, potassium dihydrogen phosphate, triethylamine, diisopropylethylamine, 1,8-diazabicyclo[5.4.0]undecene (DBU), diazabicyclononene (DBN), 1,4-diazabicyclo[2.2.2]octane (DABCO) and the like can be mentioned. The amount of the transition metal complex to be used may be 0.01-0.3 equivalents, preferably 0.03-0.1 equivalents, relative to compound (AB4). The amount of the base to be used may be 1-10 equivalents, preferably 2-7 equivalents, relative to compound (AB4). Particularly, it can be preferably produced by a method using reaction conditions such as those described in J. Org. Chem., 1978, 43, 2941-2946 or Tetrahedron, 61, 4569-4576.

[Step 28d]

In the above-mentioned scheme, compound (AB7) can be produced from compound (AB6) by a Corey-Chaykovsky reaction. Particularly, it can be preferably produced by a method using reaction conditions such as those described in J. Am. Chem. Soc., 1965, 87, 1353-1364.

The thus-obtained compound of the present invention can be isolated and purified by a separation means known per se, for example, concentration, concentration under reduced pressure, solvent extraction, crystallization, recrystallization, phase transfer, chromatography and the like. When the compound of the present invention is obtained as a free form, it can be converted to an object salt by a method known per se or a method analogous thereto. When the compound is obtained as a salt, it can be converted to a free form or other object salt by a method known per se or a method analogous thereto.

When the compound of the present invention has an isomer such as optical isomer, stereoisomer, regio isomer, rotamer and the like, all these isomers and mixtures are encompassed in the compound of the present invention. For example, when the compound of the present invention contains an optical isomer, an optical isomer resolved from a racemate is also encompassed in the compound of the present invention. These isomers can be obtained as respective single products by a synthesis method, a separation method (e.g., concentration, solvent extraction, column chromatography, recrystallization) known per se.

The compound of the present invention may be a crystal, which is encompassed in the compound of the present invention whether it has a single crystal form or it is a crystal form mixture. The crystal can be produced by crystallization by applying a crystallization method known per se. In addition, the compound of the present invention may be a pharmaceutically acceptable cocrystal or co-crystal salt. As used herein, the cocrystal or co-crystal salt means a crystalline substance consisting of two or more particular solids at room temperature, wherein each has different physical properties (e.g., structure, melting point, melting heat, hygroscopicity, stability). The cocrystal or co-crystal salt can be produced by cocrystallization method known per se.

A compound labeled with an isotope (e.g., $^2$H, $^3$H, $^{13}$C, $^{14}$C, $^{15}$N, $^{35}$S) and the like are also encompassed in the compound of the present invention.

In the present specification, the diseases caused by autotoxin are those relating to autotoxin; for example, various diseases such as cancer or tumor such as malignant melanoma, brain tumor, neuroblastoma, glioblastoma multiforme, EBV positive Hodgkin lymphoma, glioblastoma, non-small cell lung cancer, lung tumor, breast tumor, ovary tumor, pancreas tumor, prostatic intraepithelial neoplasia, prostate tumor, thyroid tumor, follicular lymphoma, liver tumor, renal cell carcinoma and the like, fibrosis such as pulmonary fibrosis, hepatic fibrosis, renal fibrosis, atherosclerosis and the like, asthma, rheumatoid arthritis, type II diabetes-related obesity, acute coronary syndrome, cholestatic pruritus, or an inflammatory disease such as inflammatory bowel disease, Crohn's disease, ulcerative colitis, neuropathic pain and the like.

The subject of the administration of the compound of the present invention includes, for example, mammals such as human, dog, cat, bovine, horse, swine, monkey, rat and the like, and the like.

In the present specification, "prophylaxis" means an act of administering the compound of the present invention or a pharmaceutical composition containing the compound to an individual who has not developed a disease, condition or symptom. In addition, "treatment" means an act of administering the compound of the present invention or a pharmaceutical composition containing the compound to an individual who has developed a disease, condition or symptom. Therefore, an act of administration to an individual who has developed a disease, condition or symptom, for the prevention of aggravation of the symptom and the like, and for the prevention of attack and recurrence is one embodiment of the "treatment".

When the compound of the present invention is used as a medicament, the compound of the present invention can be administered orally or parenterally in the form of a pharmaceutical composition or preparation (oral preparation, injection and the like) obtained by mixing with a pharmaceutically acceptable carrier (excipient, binder, disintegrant, corrigent, flavor, emulsifier, diluent, solubilizing agents and the like). A pharmaceutical composition can be formulated by a general method.

In the present specification, "parenteral" includes subcutaneous injection, intravenous injection, intramuscular injection, intraperitoneal injection, drip or topical administration (transdermal administration, transocular administration, transpulmonary or bronchial administration, transnasal administration, transrectal administration and the like) and the like.

The content of the compound of the present invention that can be combined with a carrier can vary according to the individual to be treated and a particular administration form. However, a particular dose of a particular patient is determined according to various factors including age, body weight, general health conditions, sex, diet, administration time, administration method, excretion ratio and the level of a particular disease under treatment.

The dose of the compound of the present invention is determined according to the age, body weight, general health condition, sex, diet, administration time, administration method, excretion rate, and the level of disease for which patients are undergoing treatments at that time, or further in consideration of other factors. The compound of the present invention does not influence the heart rate and can be used safely. While the daily dose thereof varies depending on the condition and body weight of patient, the kind of the compound, administration route and the like, it is parenterally administered at, for example, about 0.0001-500 mg/patient/day by subcutaneous, intravenous, intramuscular, transdermal, transocular, transpulmonary or bronchial, transnasal or rectal administration, or about 0.001-5000 mg/patient/day by oral administration.

EXAMPLES

The present invention is explained in detail in the following by referring to Examples and Experimental Examples, which are not to be construed as limitative.

In the Examples, the following abbreviations are used.
Me: methyl
Et: ethyl
tBu: tert-butyl
Boc: tert-butoxycarbonyl
Bn: benzyl
Tf: trifluoromethanesulfonate
HPLC: high performance liquid chromatography Example 1

2-[6-(3-trifluoromethoxy-benzylamino)-pyridin-3-yl]-3H-benzimidazole-5-carboxylic acid

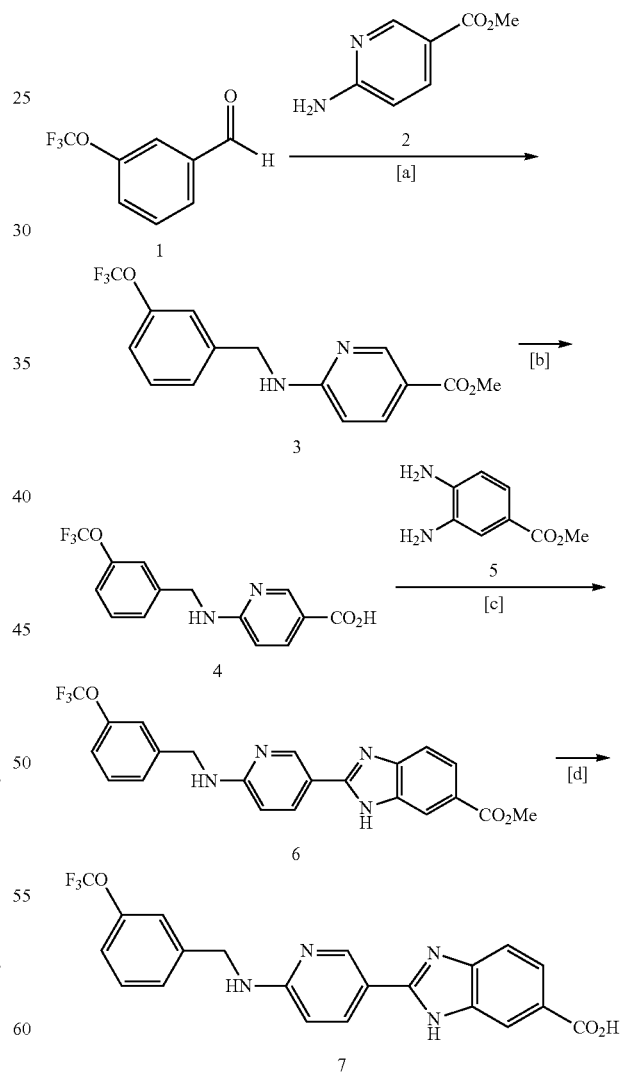

[Step a]

To a solution of compound 1 (7.50 g, 39.4 mmol) and compound 2 (5.00 g, 32.9 mmol) in N-methylpyrrolidone (50.0 mL) was added trifluoroacetic acid (3.75 mg, 32.9 mmol), and the mixture was ice-cooled. To the reaction solution was added sodium triacetoxyborohydride (8.36 g, 39.4 mmol), and the mixture was stirred for 3 days while raising the temperature to room temperature. To the reaction solution was added water, and the mixture was extracted with ethyl acetate. The organic layer was washed with water and saturated brine, dried over anhydrous sodium sulfate, filtered, and concentrated under reduced pressure. The residue was purified by silica gel chromatography. The obtained solid was suspended and washed in hexane to give compound 3 (4.20 g, 39.2%).

MS(ESI)m/z: 327(M+1)+.

[Step b]

To a mixed solution of compound 3 (3.50 g, 10.7 mmol) in tetrahydrofuran (18.0 mL) and methanol (18.0 mL) was added 4 M-aqueous sodium hydroxide solution (8.05 mL, 32.2 mmol), and the mixture was stirred at room temperature overnight. The reaction solution was neutralized with concentrated hydrochloric acid, water (40.0 mL) was added and the precipitated solid was collected by filtration and washed with water to give compound 4 (2.79 g, 83.3%).

MS(ESI)m/z: 313(M+1)+.

[Step c]

A mixed solution of compound 4 (200 mg, 0.64 mmol), compound 5 (106 mg, 0.641 mmol), diisopropylethylamine (167 μL, 961 μmol) and 50% solution (377 μL, 0.641 mmol) of propanephosphonic acid anhydride (T3P) in ethyl acetate was heated under microwave radiation at 160° C., and the mixture was stirred for 30 min. To the reaction solution was further added diisopropylethylamine (167 μL, 961 μmol) and 50% solution (377 μL, 641 μmol) of propanephosphonic acid anhydride (T3P) in ethyl acetate, and the mixture was heated under microwave radiation at 160° C. and stirred for 90 min. The reaction solution was allowed to cool to room temperature, saturated aqueous sodium hydrogen carbonate solution (20.0 mL) was added, and the mixture was extracted with chloroform. The organic layer was dried over anhydrous sodium sulfate, filtered, and concentrated under reduced pressure. The residue was purified by silica gel chromatography, the obtained solid was dissolved in chloroform, hexane was added, and the precipitated solid was collected by filtration, and suspended and washed in a chloroform-hexane (4:1) mixed solution to give compound 6 (125 mg, 44.0%).

MS(ESI)m/z: 443(M+1)+.

[Step d]

To a mixed solution of compound 6 (120 mg, 277 μmol) in tetrahydrofuran (2.40 mL) and methanol (1.20 mL) was added 4 M-aqueous sodium hydroxide solution (208 μL, 0.831 mmol), and the mixture was stirred at room temperature overnight, and stirred with heating at 50° C. for 5 hr. To the reaction solution was added water, and 1 M-hydrochloric acid was added to pH4. The precipitated solid was collected by filtration and washed with water to give compound 7 (118.7 mg, 100%).

MS(ESI)m/z: 429(M+1)+.

Example 2

2-[6-(3-trifluoromethoxy-benzylamino)-pyridin-3-yl]-3H-benzimidazole-4-carboxylic acid

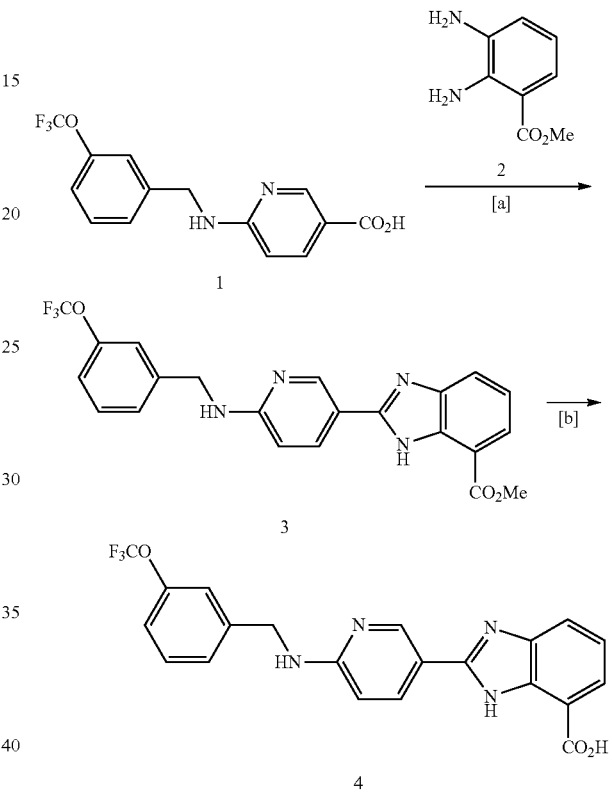

[Step a]

A mixed solution of compound 1 (200 mg, 0.64 mmol) which was obtained in Example 1, Step b, compound 2 (106 mg, 0.641 mmol), diisopropylethylamine (167 μL, 961 μmol) and 50% solution (377 μL, 0.641 mmol) of propanephosphonic acid anhydride (T3P) in ethyl acetate was heated under microwave radiation at 160° C., and the mixture was stirred for 30 min. To the reaction solution was added saturated aqueous sodium hydrogen carbonate solution (20.0 mL), and the mixture was extracted with chloroform. The organic layer was dried over anhydrous sodium sulfate, filtered, and concentrated under reduced pressure. The residue was purified by silica gel chromatography to give compound 3 (83 mg, 29.3%).

MS(ESI)m/z: 443(M+1)+.

[Step b]

To a mixed solution of compound 3 (80.0 mg, 180 μmol) in tetrahydrofuran (1.60 mL) and methanol (800 μL) was added 4 M-aqueous sodium hydroxide solution (136 μL, 542 μmol), and the mixture was stirred at room temperature for 3 hr. To the reaction solution was further added 4 M-aqueous sodium hydroxide solution (136 μL, 542 μmol), and the mixture was stirred at room temperature overnight. To the reaction solution was added 1 M-hydrochloric acid to pH4, and the mixture was extracted with chloroform. The organic layer was dried over sodium sulfate, filtered, and concentrated under reduced pressure to give compound 4 (69.8 mg, 90.1%).

MS(ESI)m/z: 429(M+1)+.

Example 3

2-[6-(3-trifluoromethoxy-benzylamino)-pyridin-3-yl]-benzoxazole-6-carboxylic acid

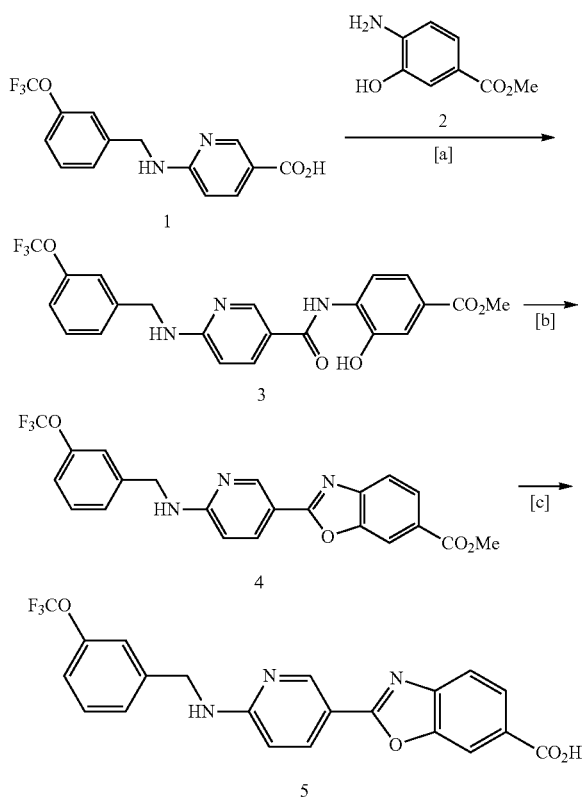

[Step a]

To a solution of compound 1 (150 mg, 0.480 mmol) which was obtained in Example 1, Step b, and compound 2 (73.0 mg, 0.4326 mmol) in N-methylformamide (3.00 mL) were added 1-ethyl-3-(3-dimethylaminopropyl)carbodiimide hydrochloride (WSC.HCl) (109 mg, 0.556 mmol) and 1-hydroxybenzotriazole (HOBt) (65.0 mg, 0.480 mmol), and the mixture was stirred at room temperature for 20 hr. Diisopropylethylamine (228 μL, 1.31 mmol) was added and the mixture was further stirred for 20 hr. To the reaction solution was added water, and the mixture was extracted with ethyl acetate. To the aqueous layer was added 1N-hydrochloric acid to adjust to pH6, and the mixture was extracted with ethyl acetate. The organic layers were combined, dried over anhydrous sodium sulfate, filtered, and concentrated under reduced pressure. The residue was purified by silica gel chromatography to give compound 3 (99.0 mg, 49.2%).

MS(ESI)m/z: 462(M+1)+.

[Step b]

To a solution of compound 3 (95.0 mg, 0.206 mmol) in xylene (3.00 mL) was added pyridinium paratoluenesulfonate (PPTS) (10.0 mg, 0.0412 mmol), and the mixture was heated under reflux for 3 hr. To the reaction solution were further added pyridinium paratoluenesulfonate (PPTS) (20.0 mg, 0.0824 mmol) and dioxane (3.00 mL), and the mixture was stirred for 41 hr. The reaction solution was allowed to cool to room temperature, saturated sodium hydrogen carbonate solution was added, and the mixture was extracted with chloroform. The organic layer was dried over anhydrous sodium sulfate, filtered, and concentrated under reduced pressure. The residue was purified by silica gel chromatography to give compound 4 (75.0 mg, 82.2%).

MS(ESI)m/z: 444(M+1)+.

[Step c]

To a mixed solution of compound 4 (38.0 mg, 0.0857 mmol) in tetrahydrofuran (2.00 mL) and methanol (1.00 mL) was added 2N-aqueous sodium hydroxide solution (1.00 mL), and the mixture was stirred at room temperature for 1 hr. To the reaction solution was added 1N-hydrochloric acid to adjust to pH3-4, and the mixture was extracted with chloroform. The aqueous layer was sequentially extracted with a methanol-chloroform (1:9) mixed solvent, and a methanol-ethyl acetate (1:9) mixed solvent, the organic layers were combined, dried over anhydrous sodium sulfate, filtered, and concentrated under reduced pressure. The residue was suspended and washed in a diisopropyl ether and hexane (1:1) mixed solution to give compound 5 (25.0 mg, 68.0%).

MS(ESI)m/z: 430(M+1)+.

Example 4

2-[6-(3-trifluoromethoxy-benzylamino)-pyridin-3-yl]-benzoxazole-7-carboxylic acid

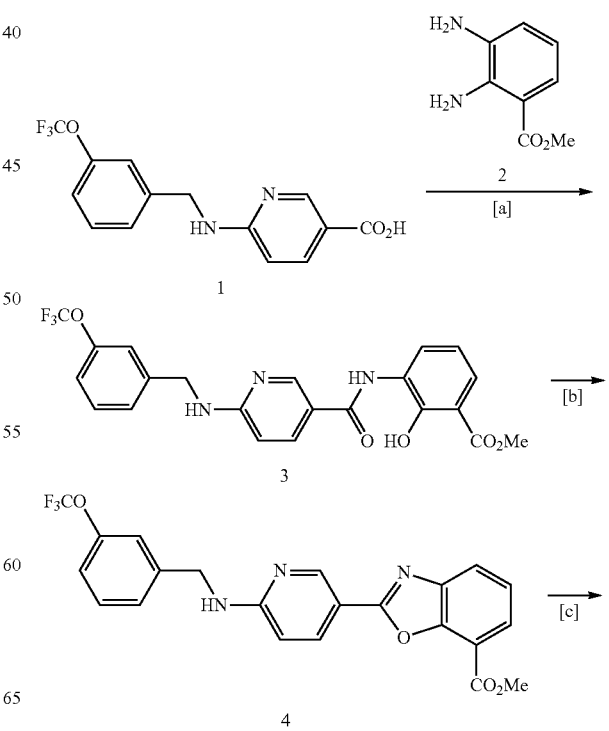

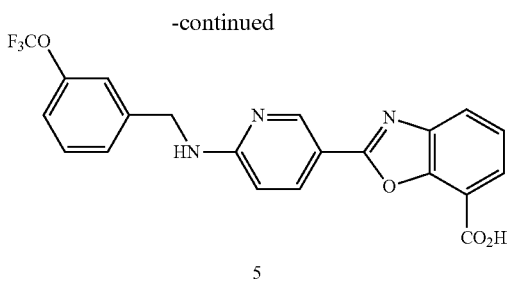

[Step a]
To a solution of compound 1 (150 mg, 0.480 mmol) which was obtained in Example 1, Step b, and compound 2 (73.0 mg, 0.4326 mmol) in N-methylformamide (3.00 mL) were added 1-ethyl-3-(3-dimethylaminopropyl)carbodiimide hydrochloride (WSC.HCl) (109 mg, 0.556 mmol) and 1-hydroxybenzotriazole (HOBt) (65.0 mg, 0.480 mmol), and the mixture was stirred at room temperature for 20 hr. Diisopropylethylamine (228 µL, 1.31 mmol) was added and the mixture was further stirred for 27 hr. To the reaction solution was added saturated aqueous sodium hydrogen carbonate solution, and the mixture was extracted with ethyl acetate. To the aqueous layer was added 1N-hydrochloric acid to adjust to pH4, and the mixture was extracted with chloroform. The organic layers were combined, dried over anhydrous sodium sulfate, filtered, and concentrated under reduced pressure. The residue was purified by silica gel chromatography to give compound 3 (40.0 mg, 19.9%).

MS(ESI)m/z: 462(M+1)+.

[Step b]
To a mixed solution of compound 3 (38.0 mg, 82.4 µmol) in xylene (3.00 mL) and dioxane (3.00 mL) was added pyridinium paratoluenesulfonate (PPTS) (12.0 mg, 49.4 µmol), and the mixture was heated under reflux for 17 hr. To the reaction solution were further added pyridinium paratoluenesulfonate (PPTS) (12.0 mg, 49.4 µmol), xylene (3.00 mL), dioxane (3.00 mL), and the mixture was stirred for 8 hr. To the reaction solution were added xylene (3.00 mL), dioxane (3.00 mL), and the mixture was stirred for 24 hr. The reaction solution was allowed to cool to room temperature, saturated sodium hydrogen carbonate solution was added, and the mixture was extracted with chloroform. The organic layer was dried over anhydrous sodium sulfate, filtered, and concentrated under reduced pressure. The residue was purified by silica gel chromatography to give compound 4 (21.0 mg, 57.5%).

MS(ESI)m/z: 444(M+1)+.

[Step c]
To a mixed solution of compound 4 (20.0 mg, 45.1 µmol) in tetrahydrofuran (1.00 mL) and methanol (1.00 mL) was added 2N-aqueous sodium hydroxide solution (1.00 mL), and the mixture was stirred at room temperature for 1 hr. To the reaction solution was added 1N-hydrochloric acid to adjust to pH3-4, and the mixture was extracted with chloroform. The organic layer was dried over anhydrous sodium sulfate, filtered, and concentrated under reduced pressure. The residue was suspended and washed in a diisopropyl ether and hexane (1:1) mixed solution to give compound 5 (13.5 mg, 69.8%).

MS(ESI)m/z: 430(M+1)+.

Example 5

2-[6-(3-trifluoromethoxy-benzylamino)-pyridin-3-yl]-benzothiazole-6-carboxylic acid

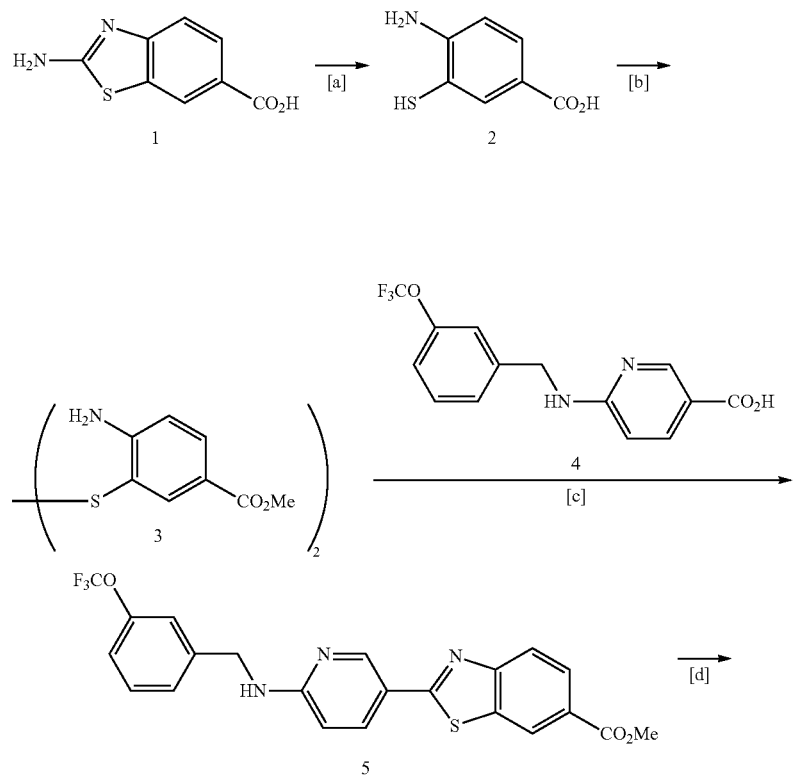

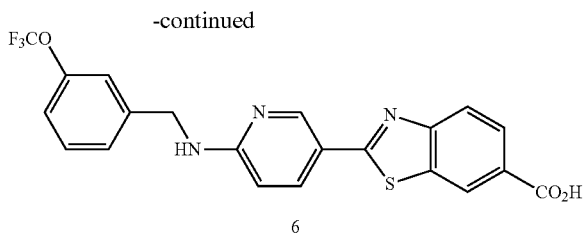

6

[Step a]

To a solution of potassium hydroxide (5.20 g, 92.7 mmol) in water (10.0 mL) was added compound 1 (1.00 g, 5.15 mmol), and the mixture was heated under reflux for 3 hr. The reaction solution was ice-cooled, concentrated hydrochloric acid was added to adjust to acidic. The precipitated solid was collected by filtration, and washed with water to give compound 2 as hydrochloride (699 mg, 66.1%).

MS(ESI)m/z: 170(M+1)+.

[Step b]

To a solution of compound 2 hydrochloride (600 mg, 2.67 mmol) in methanol (12 mL) was added concentrated sulfuric acid (286 mg, 2.67 mmol), and the mixture was heated under reflux for 8 hr. The reaction solution was concentrated under reduced pressure, neutralized with saturated aqueous sodium hydrogen carbonate solution, and extracted with chloroform. The organic layer was washed with water and saturated brine, dried over anhydrous sodium sulfate, filtered, and concentrated under reduced pressure. The residue was purified by silica gel chromatography to give compound 3 (256 mg, 52.2%).

MS(ESI)m/z: 365(M+1)+.

[Step c]

A mixed solution of compound 3 (88.0 mg, 240 μmol), compound 4 (150 mg, 480 μmol) which was obtained in Example 1, Step b, diisopropylethylamine (250 μL, 1.44 mmol) and 50% solution (565 μL, 961 μmol) of propane-phosphonic acid anhydride (T3P) in ethyl acetate was heated under microwave radiation at 100° C., and stirred for 30 min. The reaction solution was allowed to cool to room temperature, and purified by silica gel chromatography to give compound 5 (73.7 mg, 33.4%).

MS(ESI)m/z: 460(M+1)+.

[Step d]

To a mixed solution of compound 5 (70.0 mg, 162 μmol) in tetrahydrofuran (2.80 mL) and methanol (1.40 mL) was added 4 M-aqueous sodium hydroxide solution (121 μL, 485 μmol), and the mixture was stirred at room temperature for 3 hr. To the reaction solution were further added 4 M-aqueous sodium hydroxide solution (121 μL, 485 μmol) and methanol (1.40 mL), and the mixture was stirred at room temperature for 36 hr. To the reaction solution was added 1 M-hydrochloric acid to pH4, water (10.0 mL) was added, and the mixture was extracted with chloroform. The organic layer was dried over sodium sulfate, filtered and concentrated under reduced pressure, and the residue was suspended and washed in chloroform to give compound 6 (40.7 mg, 56.6%).

MS(ESI)m/z: 446(M+1)+.

Example 6

{5-[6-(3-trifluoromethoxy-benzylamino)-pyridin-3-yl]-[1,3,4]oxadiazol-2-yl}-acetic acid

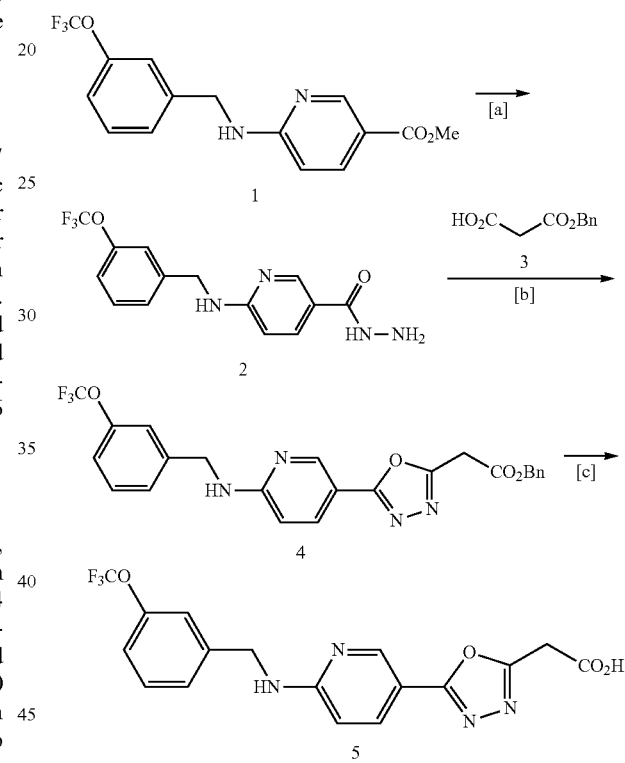

[Step a]

To a solution of compound 1 (600 mg, 1.84 mmol) which was obtained in Example 1, Step a, in methanol (12.0 mL) was added hydrazine monohydrate (716 μL, 14.7 mmol), and the mixture was stirred at room temperature overnight. To the reaction solution were further added methanol (12.0 mL) and hydrazine monohydrate (716 μL, 14.7 mmol), and the mixture was stirred with heating under reflux for 9 hr. The reaction solution was concentrated under reduced pressure, ethanol (24 mL) and hydrazine monohydrate (716 μL, 14.7 mmol) were added to the obtained residue, and the mixture was heated under reflux for 9 hr. The reaction solution was concentrated under reduced pressure, hydrazine monohydrate (715 μL, 14.7 mmol) was added, and the mixture was heated under reflux overnight. The reaction solution was concentrated under reduced pressure, and the residue was suspended and washed in diisopropyl ether to give compound 2 (536 mg, 89.3%).

MS(ESI)m/z: 327(M+1)+.

[Step b]

To a solution of compound 2 (150 mg, 460 μmol) and compound 3 (85.0 mg, 460 μmol) in ethyl acetate (2.00 mL) was added triethylamine (182 μL, 1.38 mmol) and 50% solution (676 μL, 1.15 mmol) of propanephosphonic acid anhydride (T3P) in ethyl acetate, and the mixture was heated under reflux for 3 hr. To the reaction solution was further added 50% solution (676 μL, 1.15 mmol) of propanephosphonic acid anhydride (T3P) in ethyl acetate, and the mixture was heated under reflux for 2 hr. To the reaction solution was added water, and the mixture was extracted with ethyl acetate. The organic layer was washed with water and saturated brine, dried over anhydrous sodium is sulfate, filtered, and concentrated under reduced pressure. The residue was purified by silica gel chromatography to give compound 4 (32.5 mg, 14.6%).

MS(ESI)m/z: 485(M+1)+.

[Step c]

To a mixed solution of compound 4 (40.0 mg, 89.8 μmol) in tetrahydrofuran (800 μL) and methanol (400 μL) was added 4 M-aqueous sodium hydroxide solution (67.2 μL, 269 μmol), and the mixture was stirred at room temperature overnight. To the reaction solution was added 1 M-hydrochloric acid to pH4, water (10.0 mL) was added, and the mixture was extracted with chloroform. The organic layer was dried over sodium sulfate, filtered, and concentrated under reduced pressure to give compound 5 (30.2 mg, 85.5%).

MS(ESI)m/z: 395(M+1)+.

Example 7

1-methyl-5-[6-(3-trifluoromethoxy-benzylamino)-pyridin-3-yl]-1H-indazole-3-carboxylic acid

[Step a]

To compound 1 (177 mg, 447 μmol) obtained in Reference Example 65, Step b and compound 2 (100 mg, 373 μmol) obtained in Reference Example 1, Step b in a mixed solvent of dioxane (1.80 mL) and water (0.20 mL) were added tripotassium phosphate (238 mg, 1.12 mmol) and bis(di-tert-butyl(4-dimethylaminophenyl)phosphine)dichloropalladium(II) (13 mg, 18.6 μmol), and the mixture was stirred under a nitrogen atmosphere with heating at 100° C. for 2 hr. To the reaction solution were added ethyl acetate, activated carbon and NH-silica gel (FUJI SILYSIA CHEMICAL LTD. CHROMATOREX), and the mixture was stirred at room temperature for 15 min. The is reaction solution was filtered through celite, saturated aqueous sodium hydrogen carbonate solution was added to the filtrate, and the mixture was extracted with ethyl acetate. The organic layer was washed with water and saturated brine, dried over anhydrous sodium sulfate, filtered, and concentrated under reduced pressure. The residue was purified by silica gel chromatography to give compound 3 (155 mg, 91.1%).

MS(ESI)m/z: 457(M+1)+.

[Step b]

To a mixed solution of compound 3 (150 mg, 328 μmol) in tetrahydrofuran (4.00 mL) and methanol (2.00 mL) was added 2 M-aqueous sodium hydroxide solution (2.00 mL), and the mixture was stirred at room temperature for 5 hr. The reaction solution was concentrated under reduced pressure, water and chloroform were added, and the mixture was adjusted with 1 M-hydrochloric acid to pH4, and extracted with chloroform. The organic layer was dried over anhydrous sodium sulfate, filtered, and concentrated under reduced pressure. The residue was suspended and washed in a mixed solution of diisopropyl ether and hexane to give compound 4 (107 mg, 73.8%).

MS(ESI)m/z: 443(M+1)+.

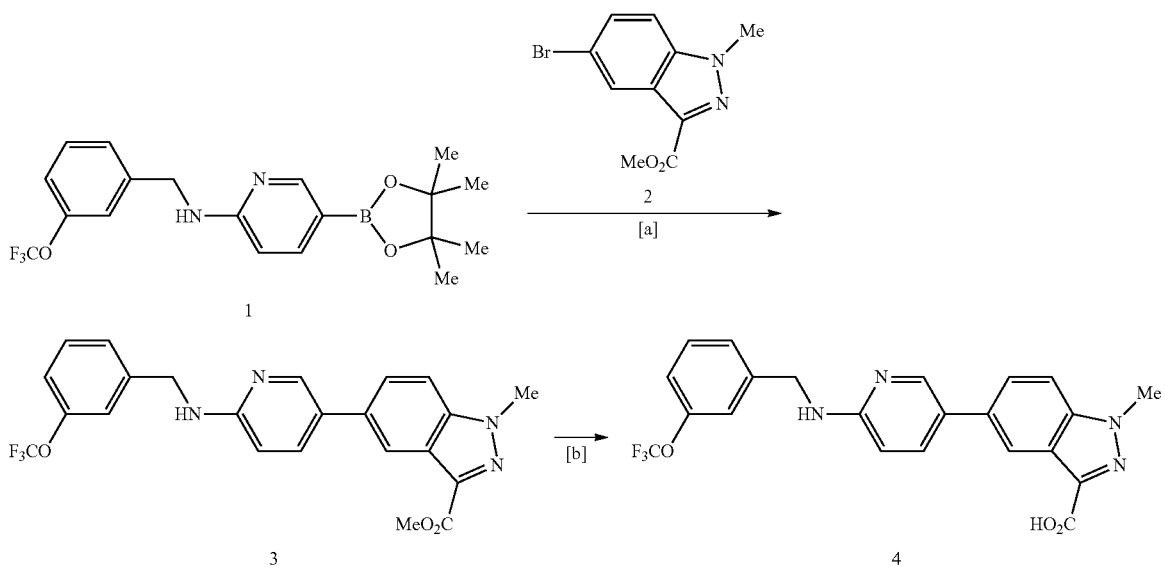

Example 8

5-[6-(3-trifluoromethoxy-benzylamino)-pyridin-3-yl]-1H-indazole-3-carboxylic acid

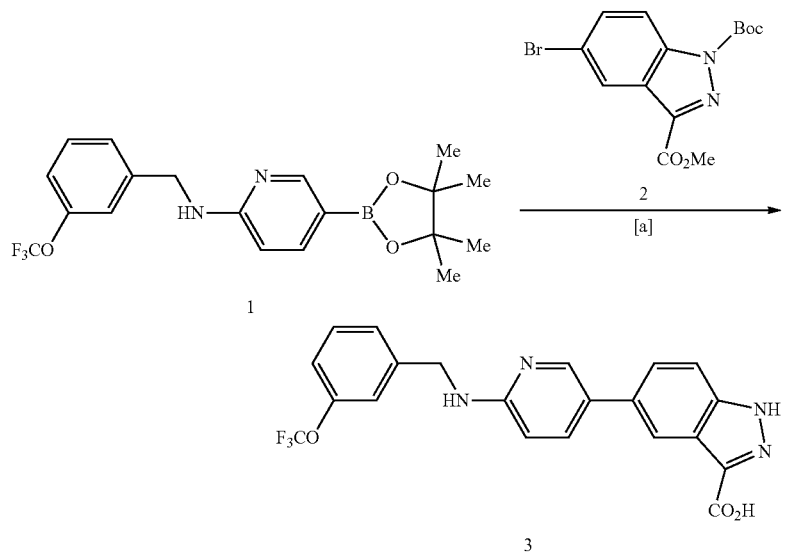

[Step a]

To compound 1 (267 mg, 677 μmol) obtained in Reference Example 65, Step b and compound 2 (200 mg, 564 mmol) obtained in Reference Example 2, Step a, in a mixed solvent of dioxane (2.50 mL) and water (280 μL) were added tripotassium phosphate (359 mg, 1.69 mmol) and bis(di-tert-butyl(4-dimethylaminophenyl)phosphine)dichloropalladium(II) (20 mg, 28.2 μmol), and the mixture was stirred under a nitrogen atmosphere with heating at 100° C. for 5 hr. The reaction solution was allowed to cool to room temperature, and ethyl acetate and water were added. The precipitated solid was collected by filtration, and washed with water, ethyl acetate to give compound 3 (53.0 mg, 21.3%).

MS(ESI)m/z: 429(M+1)+.

Example 9

6-[6-(3-trifluoromethoxy-benzylamino)-pyridin-3-yl]-imidazo[1,2-a]pyridine-3-carboxylic acid

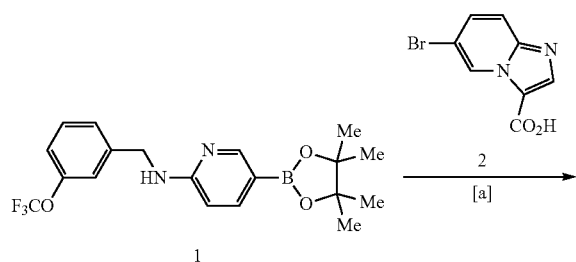

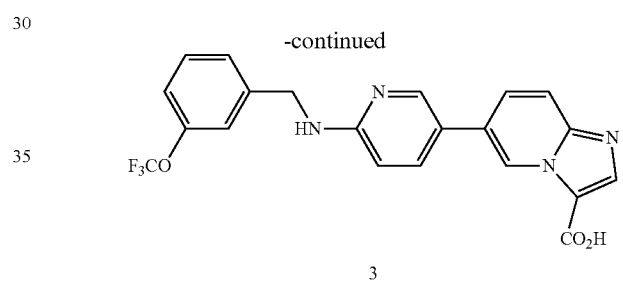

[Step a]

To a mixed solution of compound 1 (210 mg, 533 μmol) obtained in Reference Example 65, Step b, in dioxane (4.00 mL) and water (500 μL) were added potassium carbonate (170 mg, 1.23 mmol), compound 2 (CAS No. 944896-42-8, 100 mg, 415 μmol), bis(di-tert-butyl (4-dimethylaminophenyl)phosphine)dichloropalladium(II) (30 mg, 42.3 μmol), and the mixture was heated in a nitrogen atmosphere under microwave radiation at 150° C., and stirred for 1 hr. The reaction solution was allowed to cool to room temperature, 1 M-hydrochloric acid (3.5 mL) was added, and the mixture was extracted with a tetrahydrofuran and ethyl acetate mixed solution (1:1). The aqueous layer was further extracted with a tetrahydrofuran and chloroform mixed solution (1:1), and the organic layers were combined, washed with saturated brine, and concentrated. The residue was subjected to solid phase extraction purification with a cation exchange resin column (Waters, PoraPak™, RxnCX), and the obtained solid was suspended and washed in ethyl acetate (2.00 mL) to give compound 3 (70.0 mg, 39.4%).

MS(ESI)m/z: 429(M+1)+.

Example 10

3-{3-cyano-2-methoxy-5-[6-(3-trifluoromethoxy-benzylamino)-pyridin-3-yl]-phenyl}-propionic acid

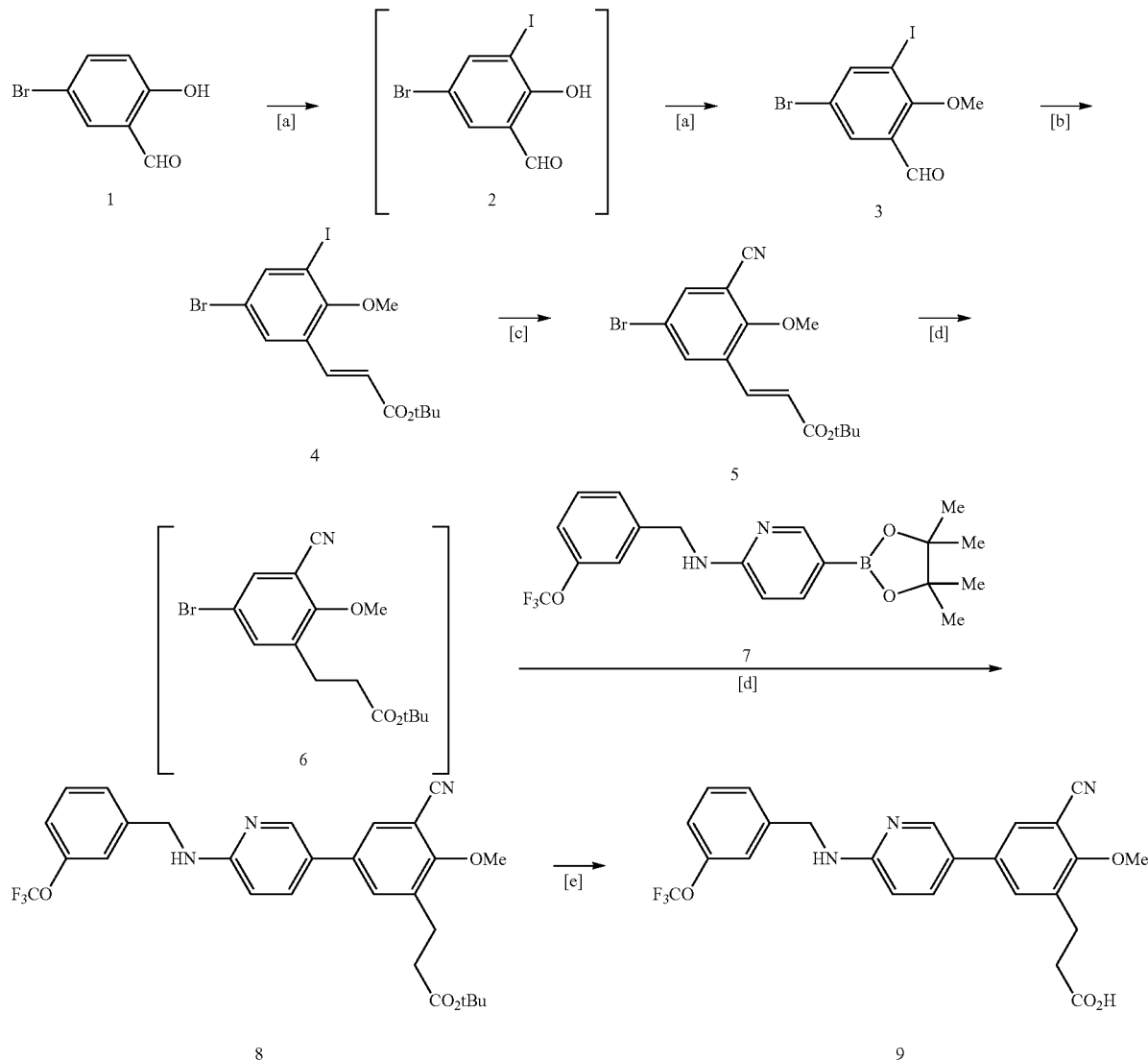

the resulting solid was collected by filtration, and washed with water. The obtained solid was purified by silica gel chromatography to give compound 3 (2.08 mg, 61.5%).

$^1$H-NMR (400 MHz, CDCl$_3$) δ: 3.94 (3H, s), 7.93 (1H, d, J=2.1 Hz), 8.15 (1H, d, J=2.1 Hz), 10.2 (1H, s).

[Step a]

To a solution (40.0 mL) of compound 1 (2.00 g, 9.95 mmol) in acetonitrile was added N-iodosuccinimide (2.35 g, 10.4 mmol), and the mixture was stirred at room temperature overnight, and with heating at 65° C. for 8 hr. The reaction solution was concentrated under reduced pressure, 0.5N-aqueous hydrochloric acid solution (20 mL) was added, and the mixture was extracted with ethyl acetate. The organic layer was washed with water and saturated brine, dried over anhydrous sodium sulfate, filtered, and concentrated under reduced pressure. The obtained residue was dissolved in dimethylformamide (25.0 mL), potassium carbonate (4.13 g, 29.9 mmol) and methyl iodide (3.53 g, 24.9 mmol) were added, and the mixture was stirred at room temperature for 7.5 hr. To the reaction solution was added 0.5N-aqueous hydrochloric acid solution (60 mL) under ice-cooling, and

[Step b]

To a solution of tert-butyl diethylphosphonoacetate (450 mg, 1.78 mmol) in tetrahydrofuran (10.0 mL) was added sodium hydride (60 wt %, 65.0 mg, 1.63 mmol) under ice-cooling, and the mixture was stirred for 30 min. To the reaction solution was added a solution (3.00 mL) of compound 3 (435 mg, 1.28 mmol) in tetrahydrofuran, and the mixture was stirred under ice-cooling for 1 hr. To the reaction solution were added saturated aqueous ammonium chloride solution and water, and the mixture was extracted with ethyl acetate. The organic layer was washed with water and saturated brine, dried over anhydrous sodium sulfate, filtered and concentrated under reduced pressure, and the residue was purified by silica gel chromatography to give compound 4 (630 mg, 100%).

¹H-NMR (400 MHz, CDCl₃) δ: 1.53 (9H, s), 3.78 (3H, s), 6.38 (1H, d, J=16.4 Hz), 7.63 (1H, d, J=2.1 Hz), 7.72 (1H, d, J=15.9 Hz), 7.89 (1H, d, J=2.6 Hz).

[Step c]

To a solution of compound 4 (630 mg, 1.28 mmol) in N-methylpyrrolidone (10.0 mL) was added copper cyanide (460 mg, 5.14 mmol), and the mixture was stirred with heating at 125° C. overnight. The reaction solution was allowed to cool to room temperature, water and ethyl acetate were added, celite filtration was performed, and the filtrate was extracted with ethyl acetate. The organic layer was washed with water and saturated brine, dried over anhydrous sodium sulfate, filtered and concentrated under reduced pressure, and the residue was purified by silica gel chromatography to give compound 5 (190 mg, 43.8%).

MS(ESI)m/z: 338, 340(M+1)+.

[Step d]

To a mixed solution of compound 5 (60.0 mg, 177 μmol) and cobalt(II) chloride (5.00 mg, 38.5 μmol) in tetrahydrofuran (2.00 mL)-methanol (2.00 mL) was added sodium borohydride (13.00 mg, 344 μmol) under cooling at −10° C., and the mixture was stirred for 45 min. To the reaction solution was added saturated aqueous ammonium chloride solution, the temperature was raised to room temperature, and the mixture was extracted with ethyl acetate. The organic layer was washed with water and saturated brine, dried over anhydrous sodium sulfate, filtered, and concentrated under reduced pressure. The residue was dissolved in dioxane (3.50 mL), water (600 μL), potassium carbonate (70.0 mg, 507 μmol), compound 7 (100 mg, 254 μmol) obtained in Reference Example 65, Step b, bis(di-tert-butyl (4-dimethylaminophenyl)phosphine)dichloropalladium(II) (12.0 mg, 16.9 μmol) were added, and the mixture was stirred in a nitrogen atmosphere with heating at 95° C. for 6 hr. To the reaction solution was added bis(di-tert-butyl(4-dimethylaminophenyl)phosphine)dichloropalladium(II) (18 mg, 25.4 μmol), and the mixture was stirred in a nitrogen atmosphere with heating at 95° C. for 3.5 hr. The reaction solution was allowed to cool to room temperature, water was added, and the mixture was extracted with ethyl acetate. The organic layer was washed with water and saturated brine, dried over anhydrous sodium sulfate, filtered and concentrated under reduced pressure, and the residue was purified by silica gel chromatography to give compound 8 (25.0 mg, 26.8%).

MS(ESI)m/z: 528(M+1)+.

[Step e]

To a solution of compound 8 (35 mg, 66.4 μmol) in dichloromethane (2.50 mL) was added trifluoroacetic acid (0.50 mL), and the mixture was stirred at room temperature for 4.5 hr. The reaction solution was concentrated under reduced pressure, and the residue was subjected to solid phase extraction purification using a cation exchange resin column (Waters, PoraPak™, RxnCX), and the obtained solid was suspended and washed in a diisopropyl ether (1.50 mL)-hexane (1.50 mL) mixed solution to give compound 9 (10.0 mg, 32.1%).

MS(ESI)m/z: 472(M+1)+.

Example 11

3-{2-chloro-5-[2-(3-trifluoromethoxy-benzylamino)-pyrimidin-5-yl]-phenyl}-propionic acid

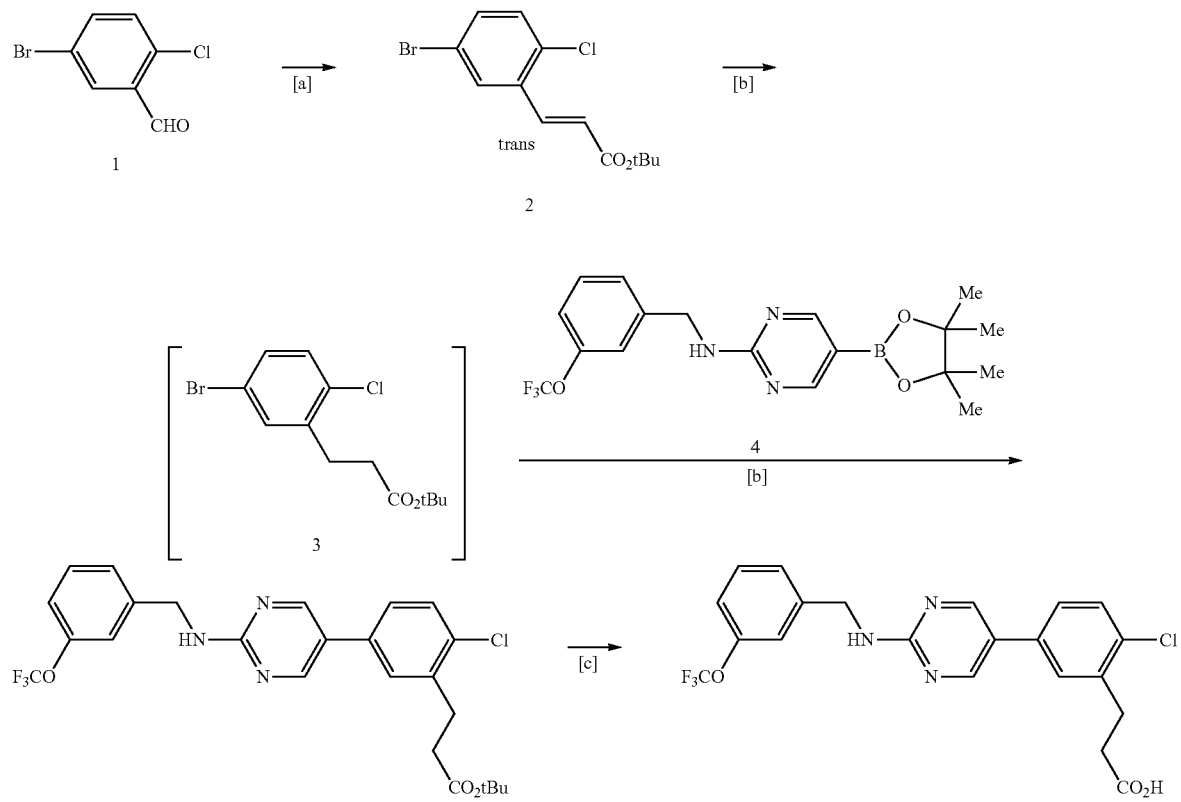

[Step a]

To a solution of tert-butyl diethylphosphonoacetate (3.00 mL, 12.8 mmol) in tetrahydrofuran (20.0 mL) was added sodium hydride (60 wt %, 474 mg, 11.8 mmol) under ice-cooling, compound 1 (2.00 g, 9.11 mmol) was added, and the mixture was stirred under ice-cooling for 2 hr. To the reaction solution was added saturated aqueous ammonium chloride solution (50.0 mL), and the mixture was extracted with ethyl acetate. The organic layer was washed with saturated brine, dried over anhydrous sodium sulfate, filtered and concentrated under reduced pressure, and the residue was purified by silica gel chromatography to give compound 2 (2.78 g, 95.9%).

$^1$H-NMR (400 MHz, CDCl$_3$) δ: 1.49 (9H, s), 6.74 (1H, d, J=15.9 Hz), 7.50 (1H, d, J=8.2 Hz), 7.62 (1H, dd, J=2.6, 8.7 Hz), 7.74 (1H, d, J=15.9 Hz), 8.18 (1H, d, J=2.6 Hz).

[Step b]

To a mixed solution of compound 2 (1.75 g, 5.51 mmol) and cobalt(II) chloride (143 mg, 1.10 mmol) in tetrahydrofuran (17.5 mL) and methanol (17.5 mL) was added sodium borohydride (417 mg, 11.0 mmol) by small portions under cooling at −10° C., and the mixture was stirred for 2 hr. To the reaction solution was further added cobalt(II) chloride (143 mg, 1.10 mmol), sodium borohydride (417 mg, 11.0 mmol) was added by small portions, and the mixture was stirred under cooling at −10° C. for 2 hr. To the reaction solution was added saturated aqueous ammonium chloride solution (70.0 mL), the temperature was raised to room temperature, and the mixture was extracted with ethyl acetate. The organic layer was washed with saturated brine, dried over anhydrous sodium sulfate, filtered, and concentrated under reduced pressure to give a solid (1.64 g). The obtained solid (300 mg) was dissolved in dioxane (2.70 mL), water (300 μL), tripotassium phosphate (569 mg, 2.68 mmol), compound 4 (353 mg, 894 μmol) obtained in Reference Example 66, Step b, bis(di-tert-butyl(4-dimethylaminophenyl)phosphine)dichloropalladium(II) (31.6 mg, 44.7 μmol) were added, and the mixture was stirred in a nitrogen atmosphere with heating at 100° C. for 2 hr. The reaction solution was allowed to cool to room temperature, water was added, and the mixture was extracted with ethyl acetate. The organic layer was dried over anhydrous sodium sulfate, filtered, and concentrated under reduced pressure. The obtained residue was purified by silica gel chromatography, and the obtained solid was suspended and washed in a mixed solution of diisopropyl ether (9.00 mL) and hexane (27.0 mL), and washed with a mixed solution of diisopropyl ether (5.00 mL) and hexane (15.0 mL) to give compound 5 (44.5 mg). The obtained filtrate was purified by reversed-phase HPLC to give compound 5 (207 mg).

MS(ESI)m/z: 508, 510(M+1)+.

[Step c]

To a solution of compound 5 (200 mg, 394 μmol) in dichloromethane (2.00 mL) was added trifluoroacetic acid (1.00 mL), and the mixture was stirred at room temperature overnight. The reaction solution was concentrated under reduced pressure, and the residue was subjected to solid phase extraction purification using a cation exchange resin column (Waters, PoraPak™, RxnCX). The obtained purification product was dissolved in tetrahydrofuran (2.00 mL) and methanol (2.00 mL), 4 M-aqueous sodium hydroxide solution (500 μL) was added, and the mixture was stirred at room temperature overnight. To the reaction solution was added 1 M-hydrochloric acid (2.00 mL) to neutralize same, and water (20.0 mL) was added. The precipitated solid was collected by filtration and washed with water to give compound 6 (151 mg, 85.0%).

MS(ESI)m/z: 452, 454(M+1)+.

Example 12

3-{3-cyano-2-methoxy-5-[6-(3-trifluoromethoxybenzylamino)-pyridin-3-yl]-phenyl}-2-methyl-propionic acid

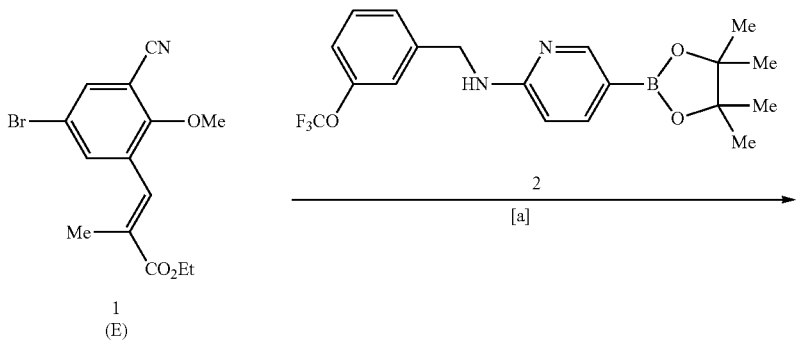

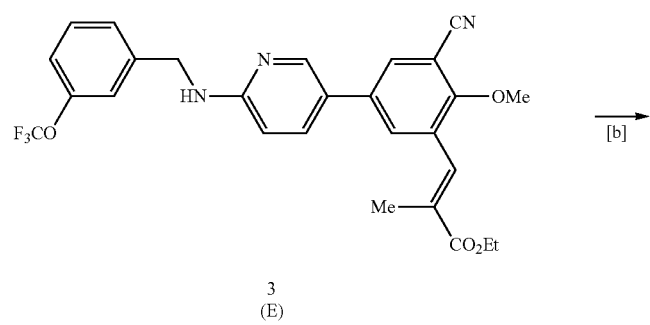

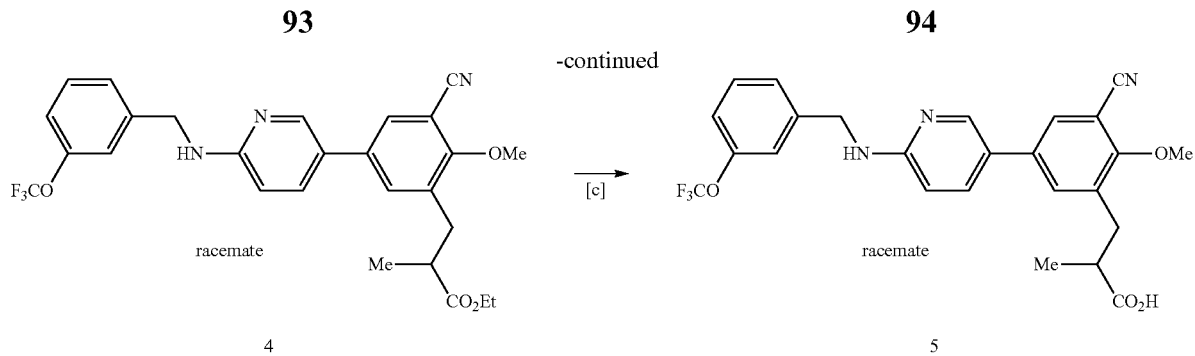

[Step a]

To a solution of compound 1 (100 mg, 308 μmol) obtained in Reference Example 45 in toluene (3.00 mL) were added water (500 μL), potassium carbonate (130 mg, 941 μmol), compound 2 (170 mg, 431 μmol) obtained in Reference Example 65, Step b, bis(di-tert-butyl(4-dimethylaminophenyl) phosphine) dichloropalladium (II) (22.0 mg, 31.1 μmol), and the mixture was heated in a nitrogen atmosphere, under microwave radiation at 135° C. and stirred for 1 hr. The reaction solution was allowed to cool to room temperature, water was added, and the mixture was extracted with ethyl acetate. The organic layer was washed with saturated brine, dried over anhydrous sodium sulfate, filtered and concentrated under reduced pressure, and the residue was purified by silica gel chromatography to give compound 3 (140 mg, 89.0%).

MS(ESI)m/z: 512(M+1)+.

[Step b]

To a solution of compound 3 (70.0 mg, 137 μmol) in ethanol (4.00 mL) was added palladium/carbon (10 wt %, 100 mg), and the mixture was stirred in a hydrogen atmosphere at room temperature for 32 hr. The reaction solution was filtered through celite, concentrated, and the residue was purified by silica gel chromatography to give compound 4 (50.0 mg, 71.9%).

MS(ESI)m/z: 514(M+1)+.

[Step c]

To a mixed solution of compound 4 (48.0 mg, 93.0 μmol) in tetrahydrofuran (2.00 mL), methanol (1.00 mL) was added 2 M-aqueous sodium hydroxide solution (1.00 mL), and the mixture was stirred at room temperature overnight. To the reaction is solution was added, under ice-cooling, 0.5 M-hydrochloric acid (4.50 mL), and the mixture was extracted with chloroform. The organic layer was washed with saturated brine, dried over anhydrous sodium sulfate, filtered and concentrated under reduced pressure, and the residue was purified by silica gel chromatography to give compound 5 (46.0 mg).

MS(ESI)m/z: 486(M+1)+.

Example 13

2-{2-methoxy-5-[6-(3-trifluoromethoxy-benzylamino)-pyridin-3-yl]-phenyl}-cyclopropanecarboxylic acid

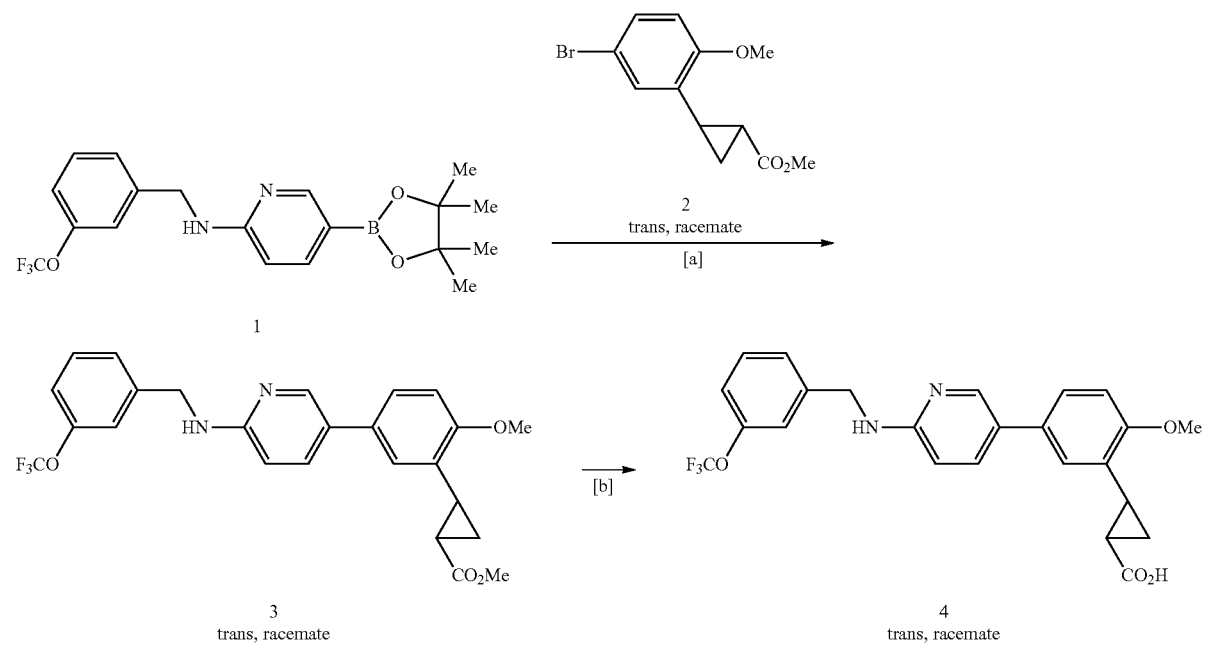

95

[Step a]

To a solution of compound 2 (170 mg, 596 μmol) obtained in Reference Example 11 in dioxane (6.00 mL) were added water (1.00 mL), potassium carbonate (245 mg, 1.78 mmol), compound 1 (280 mg, 710 μmol) obtained in Reference Example 65, Step b, bis(di-tert-butyl(4-dimethylaminophenyl)phosphine)dichloropalladium(II) (40.0 mg, 56.5 μmol), and the mixture was stirred in a nitrogen atmosphere with heating at 90° C. for 6 hr. The reaction solution was allowed to cool to room temperature, 0.2 M-hydrochloric acid (5.00 mL) was added, and the mixture was extracted with ethyl acetate. The organic layer was washed with saturated brine, dried over anhydrous sodium sulfate, filtered and concentrated under reduced pressure, and the residue was purified by silica gel chromatography to give compound 3 (280 mg, 99.4%).

MS(ESI)m/z: 473(M+1)+.

[Step b]

To a mixed solution of compound 3 (275 mg, 585 μmol) in tetrahydrofuran (3.00 mL), methanol (1.50 mL) was added 2 M-aqueous sodium hydroxide solution (1.50 mL), and the mixture was stirred at room temperature for 2.5 hr. To the reaction solution was added 0.5 M-hydrochloric acid (6.50 mL) under ice-cooling, and the mixture was extracted with chloroform. The organic layer was washed with saturated brine, dried over anhydrous sodium sulfate, filtered and concentrated under reduced pressure, and the residue was purified by silica gel chromatography to give compound 4 (220 mg, 82.0%).

MS(ESI)m/z: 459(M+1)+.

Example 14

(1S,2S)-2-{2-methoxy-5-[6-(3-trifluoromethoxy-benzylamino)-pyridin-3-yl]-phenyl}-cyclopropanecarboxylic acid (1R,2R)-2-{2-methoxy-5-[6-(3-trifluoromethoxy-benzylamino)-pyridin-3-yl]-phenyl}-cyclopropanecarboxylic acid

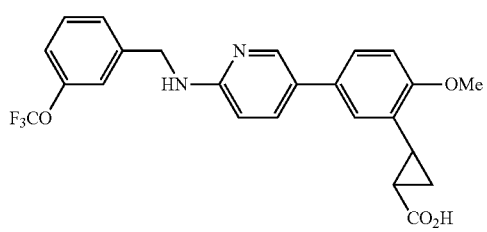

1
trans, racemate

→ [a]

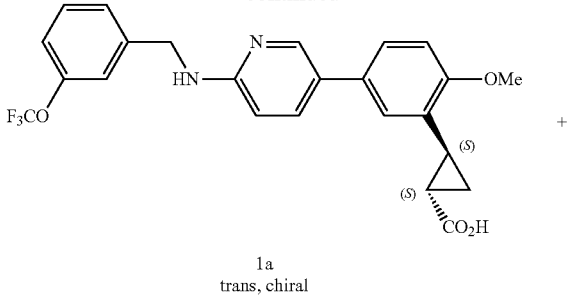

1a
trans, chiral

+

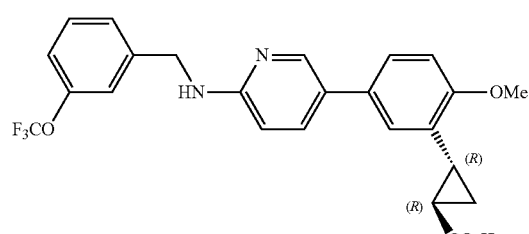

1b
trans, chiral

[Step a]

Chiral resolution of compound 1 (160 mg) obtained in Example 13, Step b, by chiral HPLC (CHIRAL PAK IA, 30×250, tetrahydrofuran:isopropyl alcohol:acetic acid=5: 95:0.1, 15 mL/min) gave compound 1a (80.0 mg, 99.9% ee) and compound 1b (79.0 mg, 99.8% ee).

MS(ESI)m/z: 459(M+1)+.

MS(ESI)m/z: 459(M+1)+.

Example 15

(trans)-2-[5-methoxy-6'-(3-trifluoromethoxy-benzylamino)-[2,3']bipyridinyl-6-yl]-cyclopropanecarboxylic acid

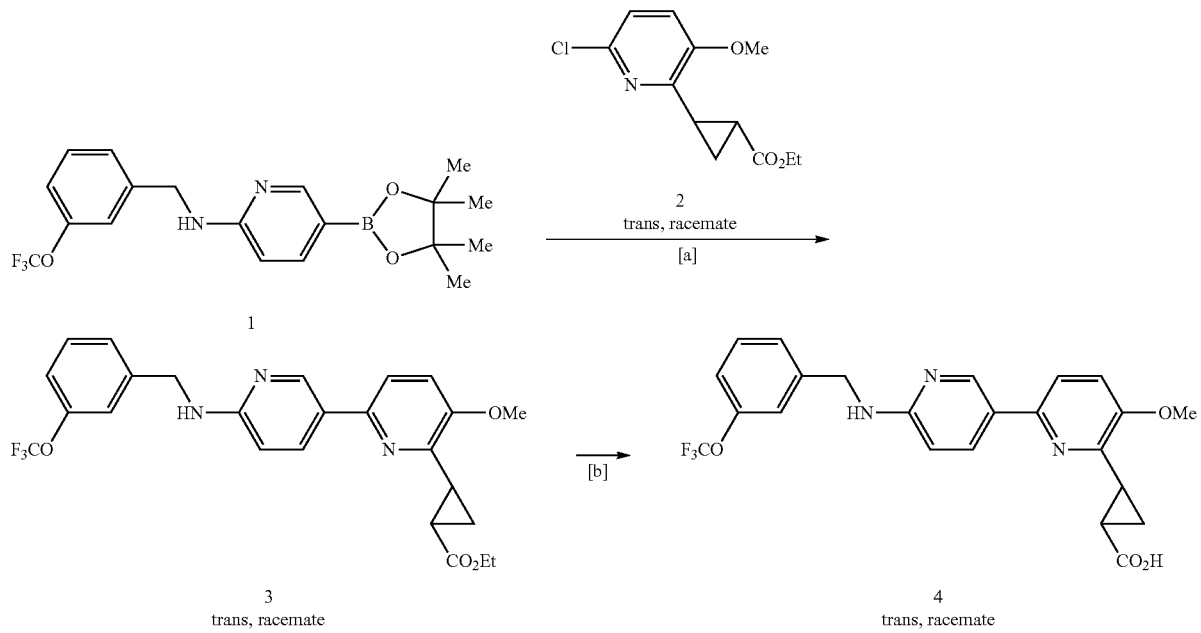

[Step a]

To a solution of compound 2 (110 mg, 430 µmol) obtained in Reference Example 17, Step b, in toluene (4.50 mL) were added water (500 µL), potassium carbonate (180 mg, 1.30 mmol), compound 1 (220 mg, 558 µmol) obtained in Reference Example 65, Step b, bis(di-tert-butyl(4-dimethylaminophenyl) phosphine) dichloropalladium(II) (30.0 mg, 42.4 Fpmol), and the mixture was heated in a nitrogen atmosphere, under microwave radiation at 130° C., and stirred for 30 min. The reaction solution was allowed to cool to room temperature, water was added, and the mixture was extracted with ethyl acetate. The organic layer was washed with saturated brine, dried over anhydrous sodium sulfate, filtered and concentrated under reduced pressure, and the residue was purified by silica gel chromatography to give compound 3 (200 mg, 95.5%).

MS(ESI)m/z: 488(M+1)+.

[Step b]

To a mixed solution of compound 3 (195 mg, 400 µmol) in tetrahydrofuran (4.00 mL), methanol (2.00 mL) was added 2 M-aqueous sodium hydroxide solution (2.00 mL), and the mixture was stirred at room temperature for 4 hr. To the reaction solution was added 0.5 M-hydrochloric acid (9.00 mL) under ice-cooling, and the mixture was extracted with chloroform. The organic layer was washed with saturated brine, dried over anhydrous sodium sulfate, filtered and concentrated under reduced pressure, and the residue was purified by silica gel chromatography to give compound 4 (170 mg, 92.5%).

MS(ESI)m/z: 460(M+1)+.

Example 16

(1S,2S)-2-[5-methoxy-6'-(3-trifluoromethoxy-benzylamino)-[2,3']bipyridinyl-6-yl]-cyclopropanecarboxylic acid (1R,2R)-2-[5-methoxy-6'-(3-trifluoromethoxy-benzylamino)-[2,3']bipyridinyl-6-yl]-cyclopropanecarboxylic acid

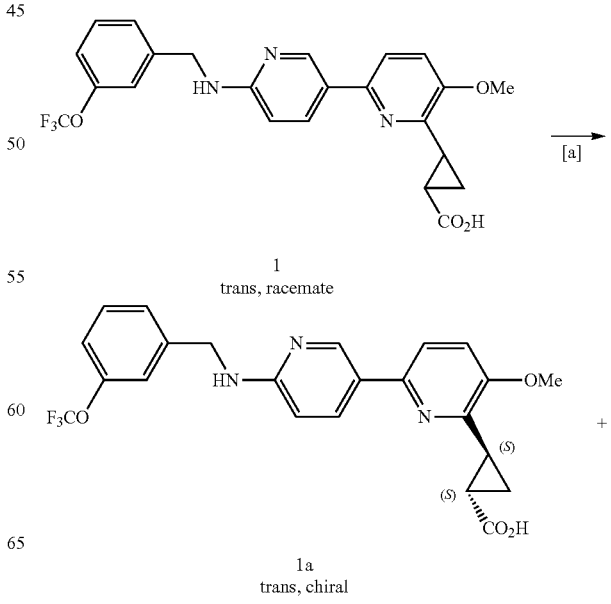

-continued

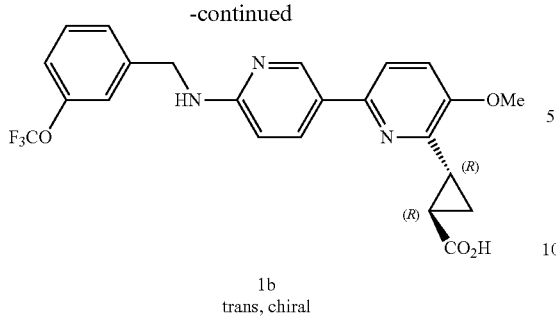

1b
trans, chiral

[Step a]

Chiral resolution of compound 1 (110 mg) obtained in Example 15, Step b, by chiral HPLC (CHIRAL PAK IA, 30×250, hexane:tetrahydrofuran:isopropyl alcohol:acetic acid=70:15:15:0.5, 20 mL/min) gave compound 1a (42.0 mg, 99.3% ee) and compound 1b (47.0 mg, 92.8% ee).

MS(ESI)m/z: 460(M+1)+.

MS(ESI)m/z: 460(M+1)+.

Example 17

(1S,2S)-2-{3-methoxy-6-[2-(3-trifluoromethoxy-benzylamino)-pyrimidin-5-yl]-pyridin-2-yl}-cyclopropanecarboxylic acid (1R,2R)-2-{3-methoxy-6-[2-(3-trifluoromethoxy-benzylamino)-pyrimidin-5-yl]-pyridin-2-yl}-cyclopropanecarboxylic acid

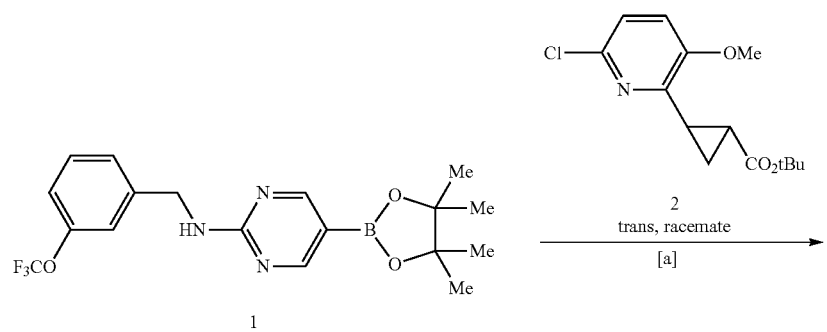

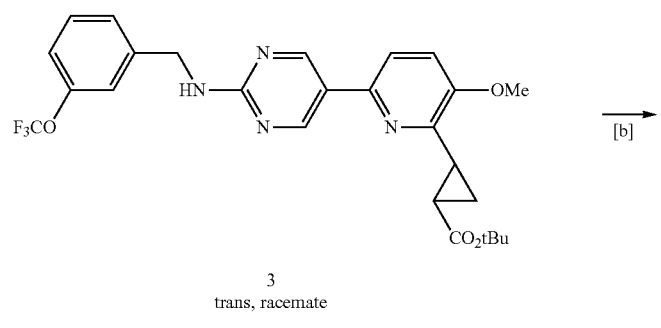

3
trans, racemate

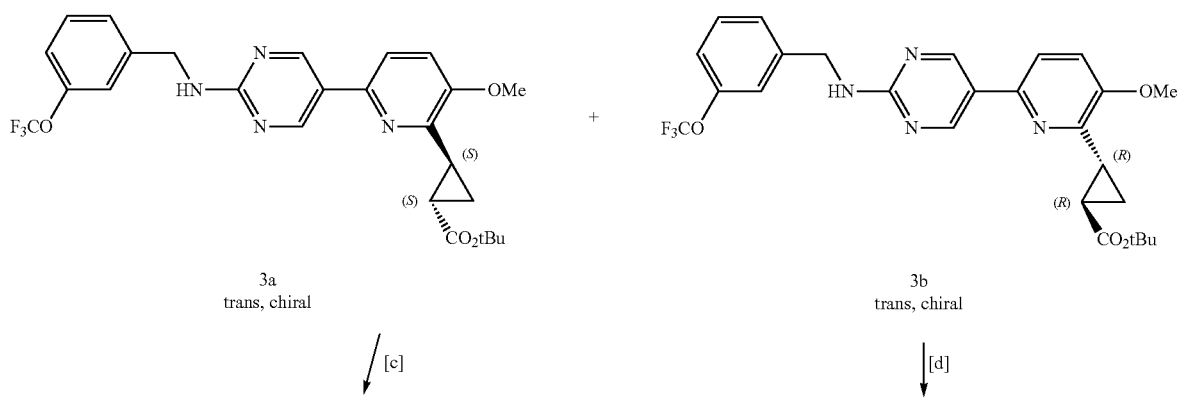

3a
trans, chiral 3b
trans, chiral

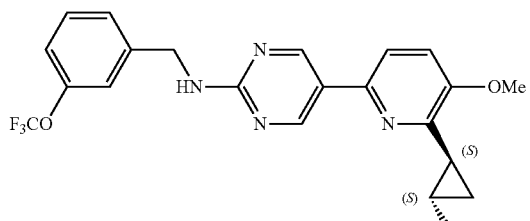

4a
trans, chiral

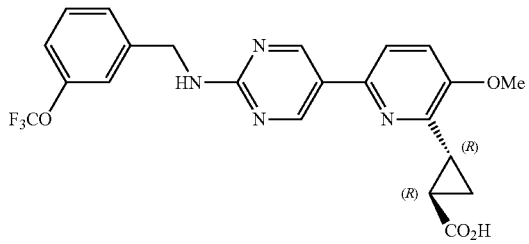

4b
trans, chiral

[Step a]

To a solution of compound 2 (95.0 mg, 335 μmol) obtained in Reference Example 18, Step a, in toluene (3.50 mL) were added water (500 μL), potassium carbonate (140 mg, 1.01 mmol), compound 1 (185 mg, 468 μmol) obtained in Reference Example 66, Step b, bis(di-tert-butyl(4-dimethylaminophenyl)phosphine) dichloropalladium(II) (25.0 mg, 35.3 μmol), and the mixture was heated in a nitrogen atmosphere, under microwave radiation at 130° C., and stirred for 30 min. The reaction solution was allowed to cool to room temperature, water was added, and the mixture was extracted with ethyl acetate. The organic layer was washed with saturated brine, dried over anhydrous sodium sulfate, filtered and concentrated under reduced pressure, and the residue was purified by silica gel chromatography to give compound 3 (200 mg).

MS(ESI)m/z: 517(M+1)+.

[Step b]

Chiral resolution of compound 3 (190 mg) by chiral HPLC (CHIRAL PAK IF, 30×250, hexane:ethanol:tetrahydrofuran:diethylamine=85:5:10:0.1, 20 mL/min) gave compound 3a (75 mg, 99.9% ee) and compound 3b (72.0 mg, 99.8% ee).

MS(ESI)m/z: 517(M+1)+.
MS(ESI)m/z: 517(M+1)+.

[Step c]

To a solution of compound 3a (74.0 mg, 143 μmol) in dichloromethane (3.00 mL) was added trifluoroacetic acid (600 μL), and the mixture was stirred at room temperature for 5.5 hr. The reaction solution was concentrated, diluted with ethyl acetate (6.00 mL), 2 M-ethyl acetate solution (150 μL) of hydrochloric acid was added, and the mixture was concentrated again. The obtained residue was suspended in diisopropyl ether, concentrated, dissolved in methanol, and concentrated. The obtained residue was suspended and washed in diisopropyl ether (6.00 mL) to give compound 4a (65.0 mg, 91.6%) as hydrochloride.

MS(ESI)m/z: 461(M+1)+.

[Step d]

To a solution of compound 3b (72.0 mg, 139 μmol) in dichloromethane (3.00 mL) was added trifluoroacetic acid (600 μL), and the mixture was stirred at room temperature for 3.5 hr. The reaction solution was concentrated, diluted with ethyl acetate (6.00 mL), 2 M-ethyl acetate solution (150 μL) of hydrochloric acid was added, and the mixture was concentrated again. The obtained residue was suspended in diisopropyl ether, concentrated, dissolved in methanol, and concentrated. The obtained residue was suspended and washed in diisopropyl ether (6.00 mL) to give compound 4b (65.0 mg, 94.2%) as hydrochloride.

MS(ESI)m/z: 461(M+1)+.

Example 18

(1S,2S)-2-[5-chloro-6'-(3-trifluoromethoxy-benzylamino)-[2,3']bipyridinyl-6-yl]-cyclopropanecarboxylic acid (1R,2R)-2-[5-chloro-6'-(3-trifluoromethoxy-benzylamino)-[2,3']bipyridinyl-6-yl]-cyclopropanecarboxylic acid

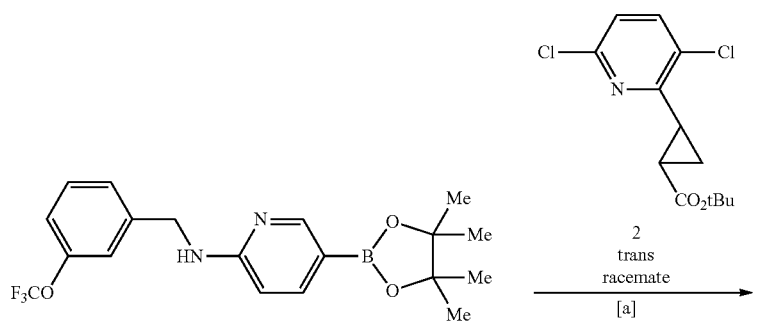

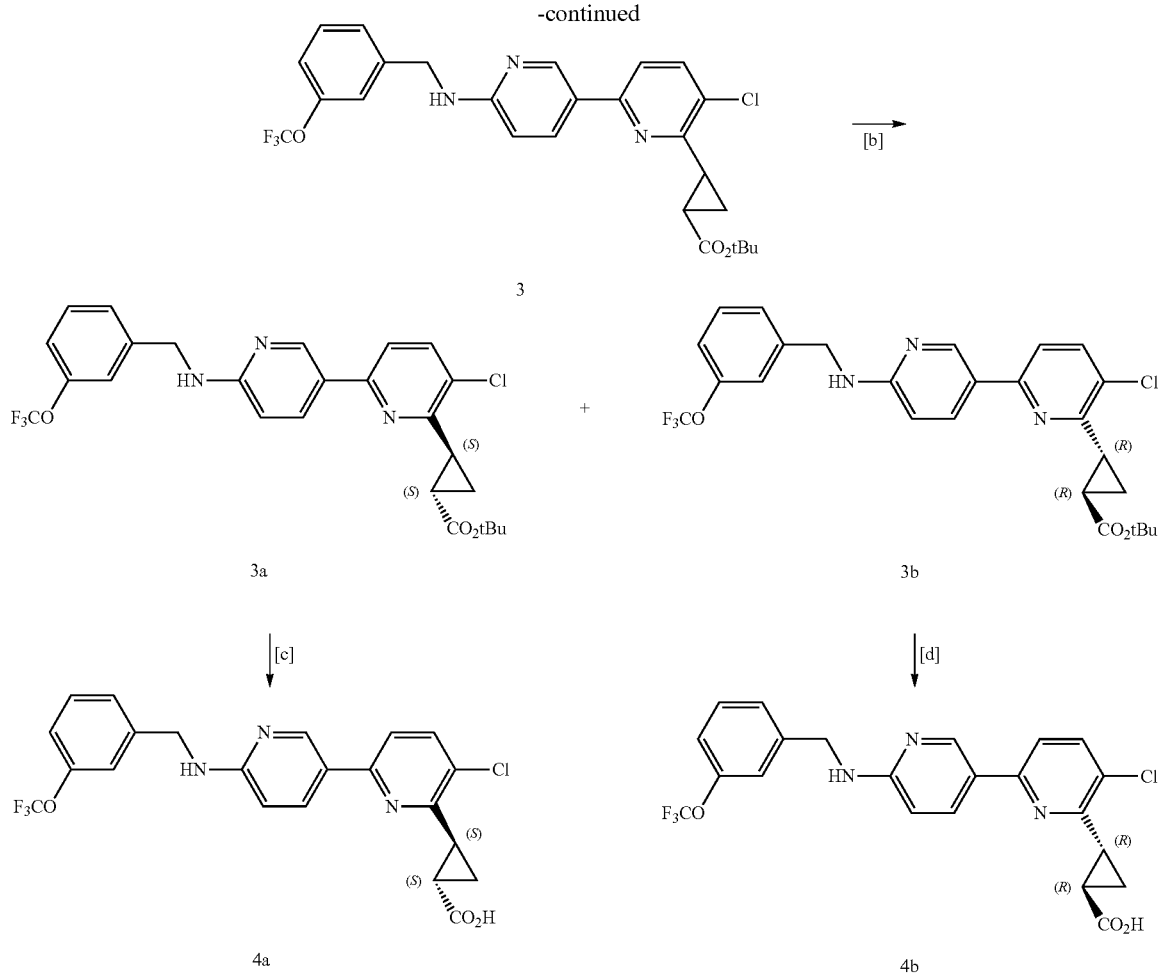

[Step a]

To a mixed solution of compound 2 (270 mg, 937 μmol) obtained in Reference Example 12, Step b, in dioxane (10.0 mL) and water (2.50 mL) were added potassium carbonate (389 mg, 2.81 mmol), compound 1 (443 mg, 1.12 mmol) obtained in Reference Example 65, Step b, tetrakis(triphenylphosphine)palladium(0) (54.0 mg, 46.7 μmol), and the mixture was stirred in a nitrogen atmosphere with heating at 100° C. for 4 hr. The reaction solution was allowed to cool to room temperature, water and chloroform were added, and the mixture was filtered through celite. The obtained filtrate was extracted with chloroform. The organic layer was concentrated under reduced pressure, and the residue was purified by silica gel chromatography. The obtained purification product was dissolved in ethyl acetate (10.0 mL), SH silica (FUJI SILYSIA CHEMICAL LTD) (50.0 mg) was added, and the mixture was stirred for 1 hr and filtered through celite. The obtained filtrate was concentrated under reduced pressure, the residue was dissolved in ethyl acetate, SH silica (FUJI SILYSIA CHEMICAL LTD) (50.0 mg) was added, and the mixture was stirred overnight and filtered through celite. The filtrate was concentrated under reduced pressure. The obtained residue was suspended and washed in hexane to give compound 3 (423 mg, 86.8%).

MS(ESI)m/z: 520(M+1)+.

[Step b]

Chiral resolution of compound 3 (400 mg) by chiral HPLC (CHIRAL PAK IA, 30×250, hexane:isopropyl alcohol:diethylamine=80:20:0.1, 20 mL/min) gave compound 3a (182 mg, 99.9% ee) and compound 3b (183 mg, 99.4% ee).

MS(ESI)m/z: 520(M+1)+.

MS(ESI)m/z: 520(M+1)+.

[Step c]

To a solution of compound 3a (182 mg, 352 μmol) in dichloromethane (4.00 mL) was added trifluoroacetic acid (500 μL), and the mixture was stirred at room temperature for 2 hr. To the reaction solution was further added trifluoroacetic acid (500 μL), and the mixture was stirred at room temperature overnight. The reaction solution was subjected to solid phase extraction purification using a cation exchange resin column (Waters, PoraPak™, RxnCX), and suspended and washed in hexane to give compound 4a (98.6 mg, 60.8%, 99.9% ee).

MS(ESI)m/z: 464(M+1)+.

[Step d]

To a solution of compound 3b (183 mg, 352 μmol) in dichloromethane (4.00 mL) was added trifluoroacetic acid (1.00 L), and the mixture was stirred at room temperature overnight. The reaction solution was subjected to solid phase extraction purification using a cation exchange resin column (Waters, PoraPak™, RxnCX), and suspended and washed in hexane to give compound 4b (154 mg, 94.3%, 99.6% ee).

MS(ESI)m/z: 464(M+1)+.

Example 19

(1S,2S)-2-[5-ethoxy-6'-(3-trifluoromethoxy-benzylamino)-[2,3']bipyridinyl-6-yl]-cyclopropanecarboxylic acid

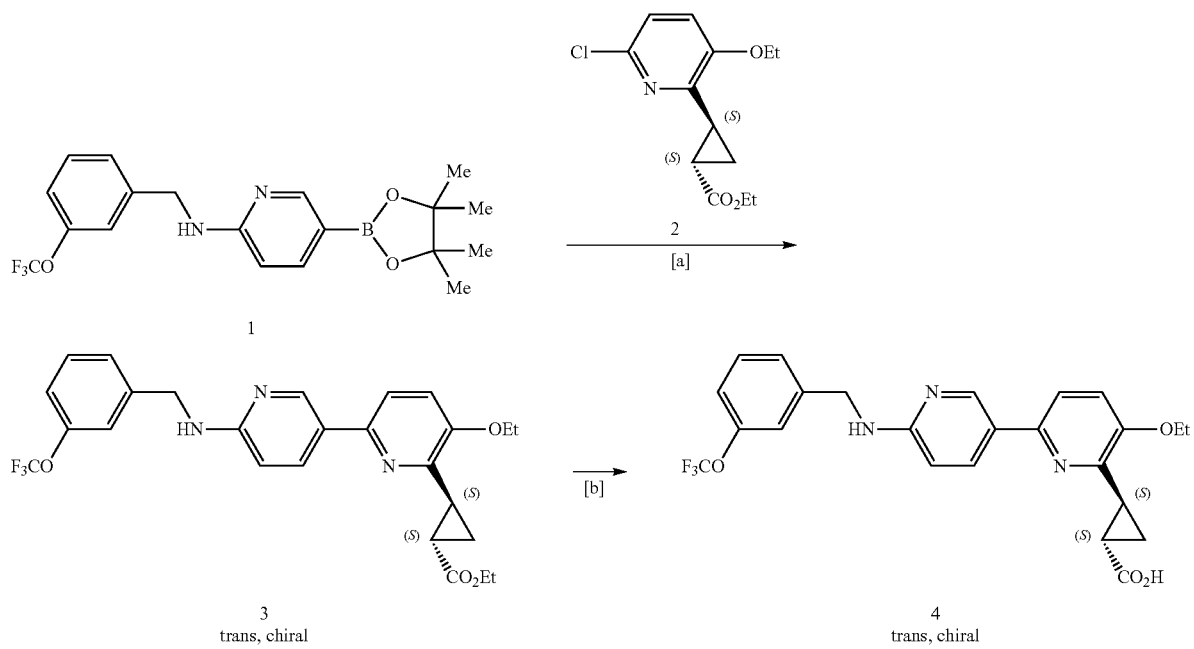

[Step a]

To a solution of compound 1 (298 mg, 756 μmol) obtained in Reference Example 65, Step b, compound 2 (170 mg, 632 μmol) obtained in Reference Example 20, Step b, in toluene (1.80 mL) were added water (200 μL), tripotassium phosphate (401 mg, 1.89 mmol), bis(di-tert-butyl(4-dimethylaminophenyl)phosphine)dichloropalladium(II) (23.0 mg, 32.5 μmol), and the mixture was stirred in a nitrogen atmosphere with heating at 100° C. for 2.5 hr. To the reaction solution were added compound 1 (249 mg, 632 μmol), bis(di-tert-butyl(4-dimethylaminophenyl)phosphine)dichloropalladium(II) (23.0 mg, 32.0 μmol), and the mixture was stirred in a nitrogen atmosphere with heating at 100° C. for 3.5 hr. To the reaction solution were added water (800 μL), toluene (1.00 mL), compound 1 (249 mg, 632 μmol), bis(di-tert-butyl(4-dimethylaminophenyl)phosphine)dichloropalladium(II) (23.0 mg, 32.0 μmol), and the mixture was stirred in a nitrogen atmosphere with heating at 100° C. overnight. The reaction solution was allowed to cool to room temperature, ethyl acetate (10.0 mL) and activated carbon (300 mg) were added, and the mixture was stirred at room temperature for 30 min. The reaction solution was filtered through celite, washed with water and ethyl acetate, and the obtained filtrate was extracted with ethyl acetate. The organic layer was washed with saturated brine, dried over anhydrous sodium sulfate, filtered and concentrated under reduced pressure, and the residue was purified by silica gel chromatography to give compound 3 (285 mg, 90.2%).

MS(ESI)m/z: 502(M+1)+.

[Step b]

To a mixed solution of compound 3 (95.0 mg, 190 μmol) in tetrahydrofuran (380 μL), methanol (190 μL) was added 2 M-aqueous sodium hydroxide solution (190 μL), and the mixture was stirred at room temperature for 1 hr. To the reaction solution was further added 4 M-aqueous sodium hydroxide solution (190 μL), and the mixture was stirred at room temperature overnight. To the reaction solution was added 1 M-hydrochloric acid (1.14 mL) to neutralize same, and the mixture was extracted with ethyl acetate. The organic layer was washed with saturated brine, dried over anhydrous sodium sulfate, filtered, and concentrated under reduced pressure. The residue was dissolved in methanol (20.0 mL), SH silica (FUJI SILYSIA CHEMICAL LTD) (500 mg) was added, and the mixture was stirred overnight and filtered through celite. The obtained filtrate was concentrated under reduced pressure, the residue was suspended and washed in diisopropyl ether, and purified by silica gel chromatography to give compound 4 (80.1 mg, 89.2%).

MS(ESI)m/z: 474(M+1)+.

Example 20

(1S,2S)-2-[5-methyl-6'-(3-trifluoromethoxy-benzylamino)-[2,3']bipyridinyl-6-yl]-cyclopropanecarboxylic acid

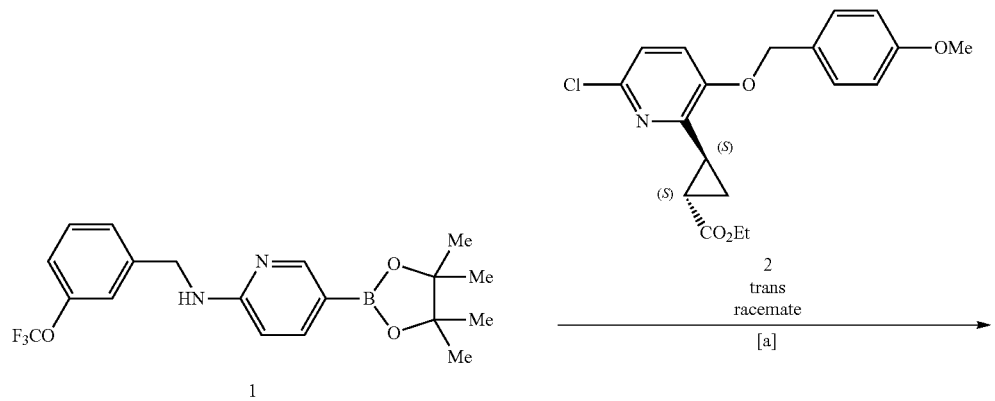

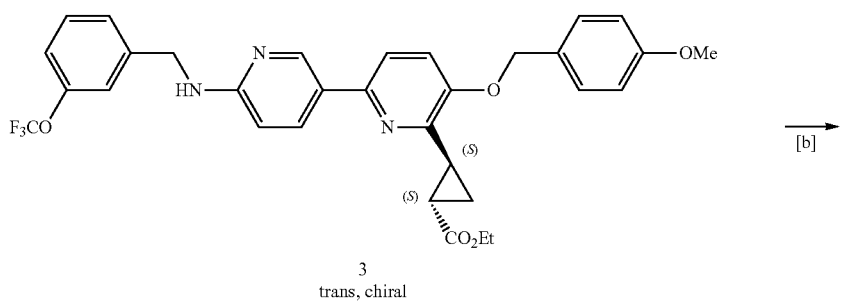

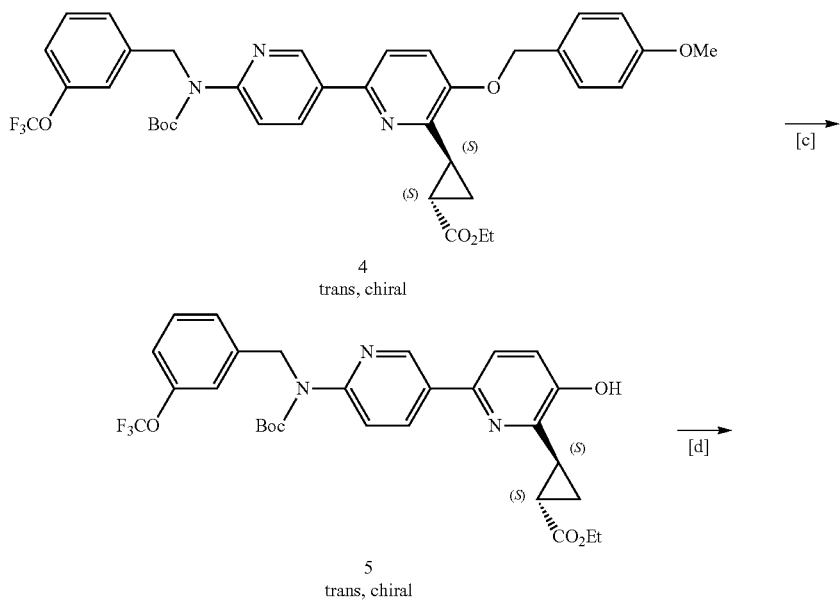

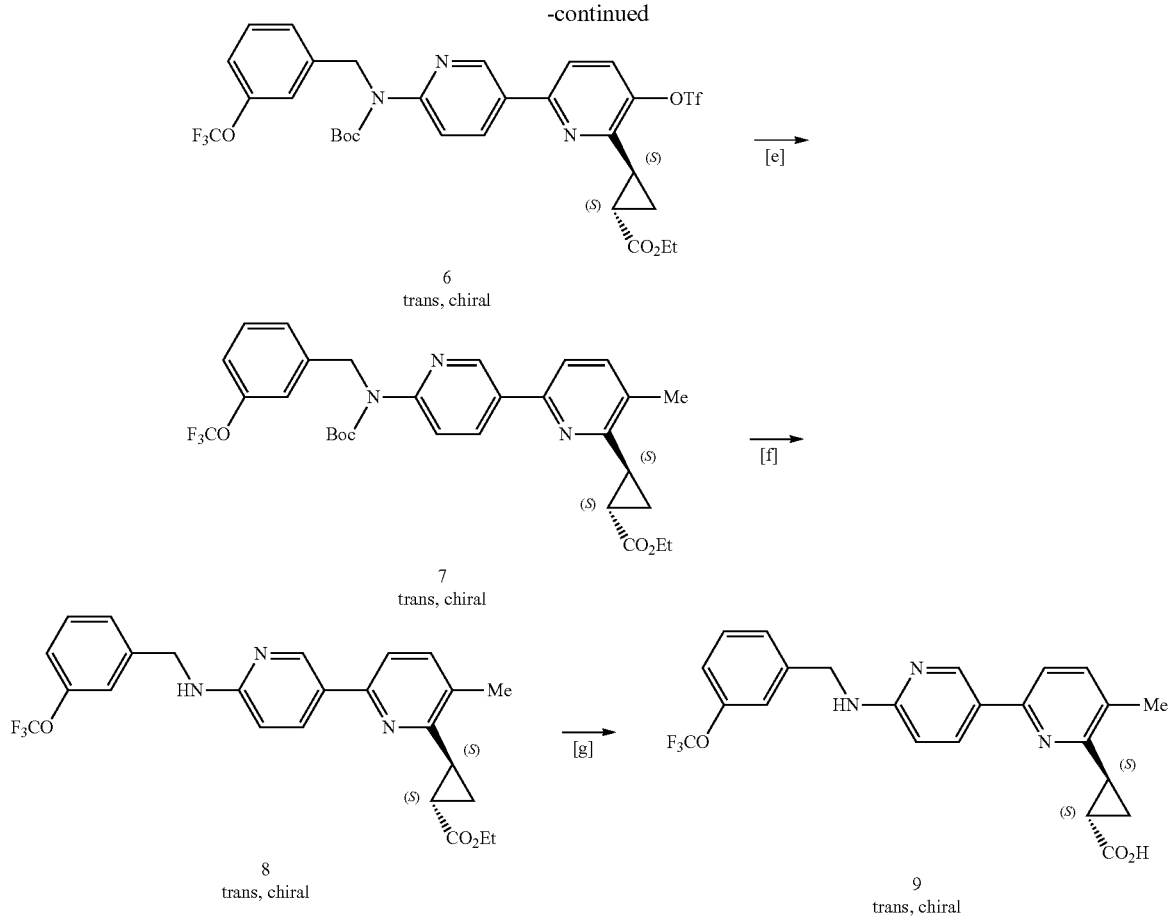

6
trans, chiral 7
trans, chiral 8
trans, chiral 9
trans, chiral

[Step a]

To a solution of compound 1 (131 mg, 332 μmol) obtained in Reference Example 65, Step b, compound 2 (100 mg, 277 μmol) obtained in Reference Example 21, Step a, in dioxane (2.00 mL) were added 2 M-aqueous tripotassium phosphate solution (416 μL, 831 μmol), tris(dibenzylideneacetone)dipalladium(0) (25.0 mg, 27.7 μmol), 2-dicyclohexylphosphino-2',4',6'-triisopropylbiphenyl (XPhos), and the mixture was stirred in a nitrogen atmosphere, with heating at 100° C. for 3 hr. The reaction solution was allowed to cool to room temperature, ethyl acetate (15.0 mL) and activated carbon (200 mg) were added, and the mixture was stirred at room temperature overnight. The reaction solution was filtered through celite, washed with water and ethyl acetate, and the obtained filtrate was extracted with ethyl acetate. The organic layer was washed with saturated brine, dried over anhydrous sodium sulfate, filtered and concentrated under reduced pressure, and the residue was purified by silica gel chromatography to give compound 3 (107 mg, 65.1%).

MS(ESI)m/z: 594(M+1)+.

[Step b]

To a solution of compound 3 (107 mg, 180 μmol) in acetonitrile (520 μL) were added di-tert-butyl dicarbonate (47.0 mg, 216 μmol) and triethylamine (60.0 μL, 432 μmol) under ice-cooling, and the mixture was stirred overnight while raising the temperature to room temperature, and stirred for 3 hr with heating under reflux. The reaction solution was allowed to cool to room temperature, di-tert-butyl dicarbonate (78.8 mg, 361 μmol) and triethylamine (100 μL, 721 μmol) were added, and the mixture was stirred overnight with heating under reflux. The reaction solution was allowed to cool to room temperature, water (3.00 mL) and ethyl acetate (3.00 mL) were added, and the mixture was extracted with ethyl acetate. The organic layer was washed with saturated brine, dried over anhydrous sodium sulfate, filtered and concentrated under reduced pressure, and the residue was purified by silica gel chromatography to give compound 4 (98.5 mg, 79.0%).

$^1$H-NMR (400 MHz, CDCl$_3$) δ: 1.25-1.30 (3H, m), 1.42 (9H, s), 1.58-1.63 (1H, m), 1.64-1.71 (1H, m), 2.31-2.40 (1H, m), 3.09-3.18 (1H, m), 3.82 (3H, s), 4.08-4.26 (2H, m), 5.08 (2H, s), 5.22 (2H, s), 6.92 (2H, d, J=8.7 Hz), 7.07 (1H, brd, J=8.2 Hz), 7.19 (2H, d, J=8.7 Hz), 7.25 (1H, d, J=8.2 Hz), 7.30 (1H, dd, J=7.7, 7.7 Hz), 7.36 (2H, d, J=8.7 Hz), 7.44 (1H, d, J=8.7 Hz), 7.77 (1H, d, J=8.7 Hz), 8.15 (1H, dd, J=2.6, 8.7 Hz), 8.90 (1H, d, J=2.1 Hz).

[Step c]

To a solution of compound 4 (85.0 g, 123 μmol) in ethyl acetate (350 μL) was added 10%-palladium/carbon (20 mg), and the mixture was stirred in a hydrogen atmosphere at room temperature for 2.5 hr. To the reaction solution was added 10%-palladium/carbon (20 mg), and the mixture was stirred in a hydrogen atmosphere at room temperature for 6 hr. The reaction solution was filtered through celite, and concentrated to give compound 5 (68.0 mg, 97.2%).

MS(ESI)m/z: 574(M+1)+.

[Step d]

To a solution of compound 5 (68.0 mg, 119 μmol) in dichloromethane (600 μL) were added triethylamine (37 μL, 264 µmol), trifluoromethanesulfonic anhydride (21 µL, 125 µmol) under ice-cooling, and the mixture was stirred for 1 hr. To the reaction solution were further added triethylamine (10.0 µL, 71.2 µmol), trifluoromethanesulfonic anhydride (6.00 µL, 35.6 µmol) under ice-cooling, and the mixture was stirred for 4 hr. To the reaction solution were added chloroform (3.00 mL) and water (2.00 mL), and the mixture was extracted with chloroform. The organic layer was washed with saturated brine, dried over anhydrous sodium sulfate, filtered, and concentrated under reduced pressure to give compound 6 (85.0 mg).

$^1$H-NMR (400 MHz, CDCl$_3$) δ: 1.28 (3H, t, J=7.2 Hz), 1.43 (9H, s), 1.73 (1H, ddd, J=3.6, 5.5, 8.9 Hz), 1.80 (1H, ddd, J=3.9, 6.0, 8.6 Hz), 2.37-2.45 (1H, m), 2.86-2.94 (1H, m), 4.19 (2H, q, J=7.2 Hz), 5.26 (2H, s), 7.09 (1H, d, J=8.2 Hz), 7.19 (1H, s), 7.25 (1H, d, J=7.2 Hz), 7.30 (1H, dd, J=7.7, 8.2 Hz), 7.58 (1H, d, J=8.7 Hz), 7.65 (1H, d, J=8.7 Hz), 7.92 (1H, d, J=8.7 Hz), 8.18 (1H, dd, J=2.6, 8.7 Hz), 8.93 (1H, d, J=2.6 Hz).

[Step e]

To a solution of compound 6 (85.0 mg, 121 µmol) in dioxane (960 µL) were added tripotassium phosphate (51.0 mg, 240 µmol), 2,4,6-trimethylboroxine (25 µL, 182 µmol), 2-dicyclohexylphosphino-2',6'-dimethoxybiphenyl (SPhos) (7.4 mg, 18.0 µmol), tris(dibenzylideneacetone)dipalladium (0) (8.0 mg, 8.74 µmol), and the mixture was stirred in a nitrogen atmosphere with heating at 100° C. for 2 hr. To the reaction solution was further added 2,4,6-trimethylboroxine (34 µL, 242 µmol), and the mixture was stirred in a nitrogen atmosphere with heating at 100° C. for 2 hr. The reaction solution was allowed to cool to room temperature, ethyl acetate (10.0 mL) and activated carbon (10.0 mg) were added, and the mixture was stirred at room temperature for 15 min. The reaction solution was filtered through celite, washed with water and ethyl acetate, and the obtained filtrate was extracted with ethyl acetate. The organic layer was washed with saturated brine, dried over anhydrous sodium sulfate, filtered and concentrated under reduced pressure, and the residue was purified by silica gel chromatography to give compound 7 (47.0 mg, 68.0%).

MS(APCI)m/z: 572(M+1)+.

[Step f]

To a solution of compound 7 (47.0 mg, 82.3 µmol) in dichloromethane (160 µL) was added trifluoroacetic acid (160 µL) under ice-cooling, and the mixture was stirred for 1.5 hr while raising the temperature to room temperature. The reaction solution was ice-cooled, chloroform (5.00 mL), saturated aqueous sodium hydrogen carbonate solution (3.00 mL) were added, and the mixture was extracted with chloroform. The organic layer was concentrated under reduced pressure, and the residue was purified by silica gel chromatography to give compound 8 (37.0 mg, 95.5%).

MS(ESI)m/z: 472(M+1)+.

[Step g]

To a mixed solution of compound 8 (37.0 mg, 78.6 µmol) in tetrahydrofuran (400 µL), methanol (200 µL) was added 4 M-aqueous sodium hydroxide solution (200 µL), and the mixture was stirred at room temperature overnight. To the reaction solution was added 1 M-hydrochloric acid (800 µL) under ice-cooling, and the mixture was extracted with ethyl acetate. The organic layer was washed with saturated brine, dried over anhydrous sodium sulfate, filtered and concentrated under reduced pressure, and the residue was purified by silica gel chromatography, and suspended and washed in a diethyl ether-hexane (1:2) mixed solution to give compound 9 (34.0 mg, 97.6%).

MS(ESI)m/z: 444(M+1)+.

Example 21

3-{2-methoxy-5-[2-(3-trifluoromethoxy-benzylamino)-pyrimidin-5-yl]-phenyl}-propionic acid

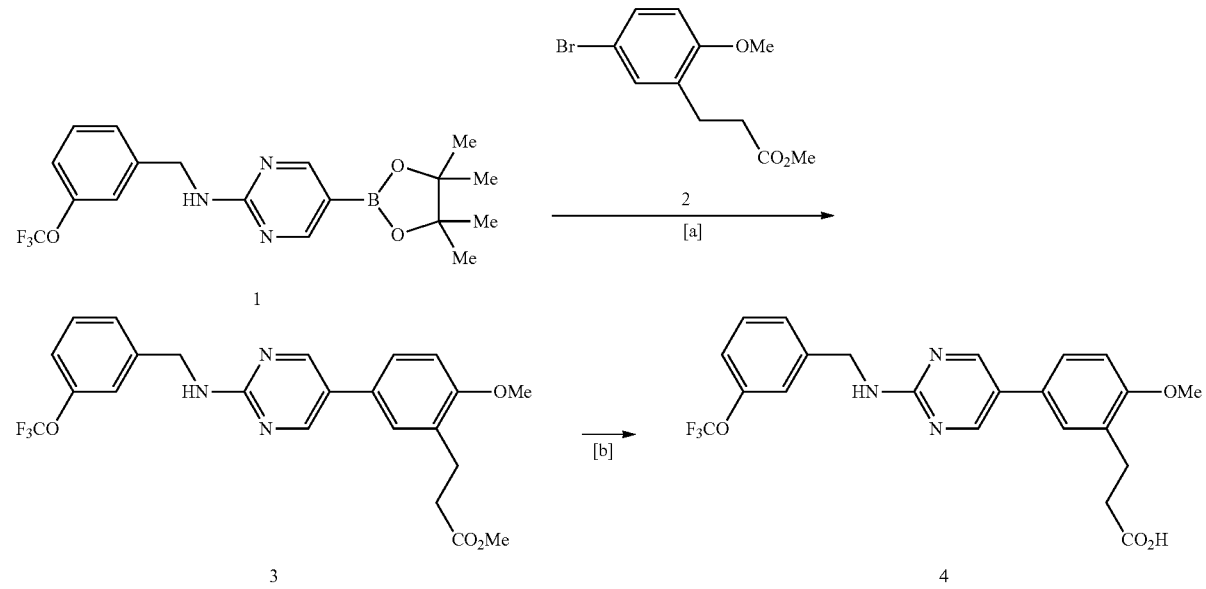

[Step a]

To a solution of compound 1 (300 mg, 759 µmol) obtained in Reference Example 66, Step b in dioxane (4.00 mL) were added water (500 µL), potassium carbonate (300 mg, 2.17 mmol), compound 2 (185 mg, 677 µmol) obtained in Reference Example 10, Step b, bis(di-tert-butyl(4-dimethylaminophenyl)phosphine)dichloropalladium(II) (25.0 mg, 35.3 µmol), and the mixture was stirred in a nitrogen atmosphere with heating at 90° C. for 8 hr. The reaction solution was allowed to cool to room temperature, 0.5 M-hydrochloric acid (2.70 mL) was added, and the mixture was extracted with ethyl acetate. The organic layer was washed with saturated brine, dried over anhydrous sodium sulfate, filtered and concentrated under reduced pressure, and the residue was purified by silica gel chromatography to give compound 3 (140 mg, 44.8%).

MS(ESI)m/z: 462(M+1)+.

[Step b]

To a mixed solution of compound 3 (130 mg, 282 µmol) in tetrahydrofuran (2.80 mL), methanol (1.40 mL) was added 2 M-aqueous sodium hydroxide solution (1.40 mL), and the mixture was stirred at room temperature for 2.5 hr. To the reaction solution was added 0.5 M-hydrochloric acid (6.00 mL) under ice-cooling, and the mixture was extracted with chloroform. The organic layer was washed with saturated brine, dried over anhydrous sodium sulfate, filtered and concentrated under reduced pressure, and the residue was purified by silica gel chromatography to give compound 4 (100 mg, 79.1%).

MS(ESI)m/z: 448(M+1)+.

Example 22

3-{2-methoxy-5-[6-(3-trifluoromethoxy-benzylamino)-pyridin-3-yl]-phenyl}-propionic acid ethylaminophenyl)phosphine)dichloropalladium(II) (40.0 mg, 56.4 µmol), and the mixture was stirred in a nitrogen atmosphere with heating at 90° C. for 4 hr. The reaction solution was allowed to cool to room temperature, 0.5 M-hydrochloric acid (3.00 mL) was added, and the mixture was extracted with ethyl acetate. The organic layer was washed with saturated brine, dried over anhydrous sodium sulfate, filtered and concentrated under reduced pressure, and the residue was purified by silica gel chromatography to give compound 3 (400 mg, 79.0%).

MS(ESI)m/z: 461(M+1)+.

[Step b]

To a mixed solution of compound 3 (395 mg, 858 µmol) in tetrahydrofuran (4.00 mL), methanol (2.00 mL) was added 2 M-aqueous sodium hydroxide solution (2.00 mL), and the mixture was stirred at room temperature for 2 hr. To the reaction solution was added 0.5 M-hydrochloric acid (9.00 mL) under ice-cooling, and the mixture was extracted with chloroform. The organic layer was washed with saturated brine, dried over anhydrous sodium sulfate, filtered and concentrated under reduced pressure, and the residue was purified by silica gel chromatography to give a white solid (370 mg). The obtained white solid (320 mg) was dissolved in ethyl acetate (6.00 mL) under heating at 80° C.,

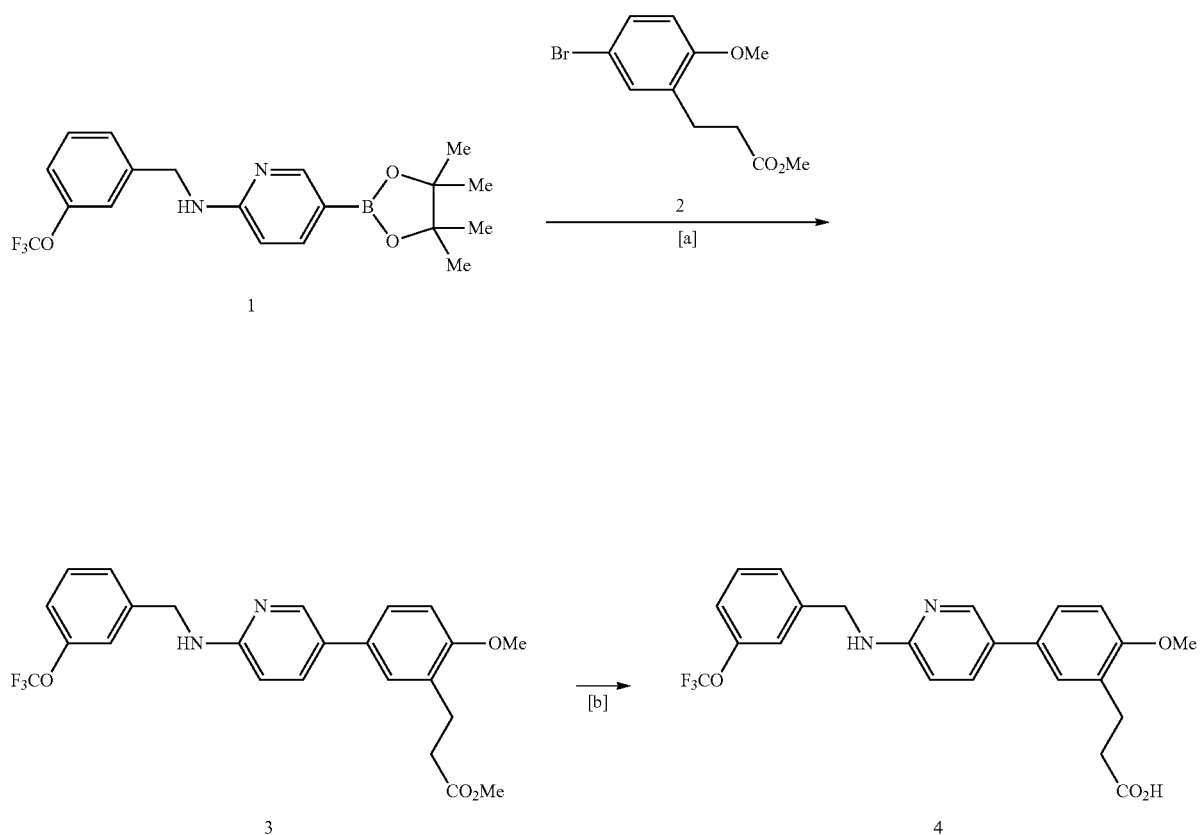

[Step a]

To a solution of compound 1 (435 mg, 1.11 mmol) obtained in Reference Example 65, Step b, in dioxane (5.00 mL) were added water (1.00 mL), potassium carbonate (365 mg, 2.64 mmol), compound 2 (300 mg, 1.10 mmol) obtained in Reference Example 10, Step b, bis(di-tert-butyl(4-dimhexane (6.00 mL) was added, and the mixture was allowed to cool to room temperature. The precipitated solid was collected by filtration, and washed with an ethyl acetate-hexane mixed solution (1:2) to give compound 4 (295 mg).

MS(ESI)m/z: 447(M+1)+.

Example 23

{2-methoxy-4-[6-(3-trifluoromethoxy-benzylamino)-pyridin-3-yl]-phenoxy}-acetic acid

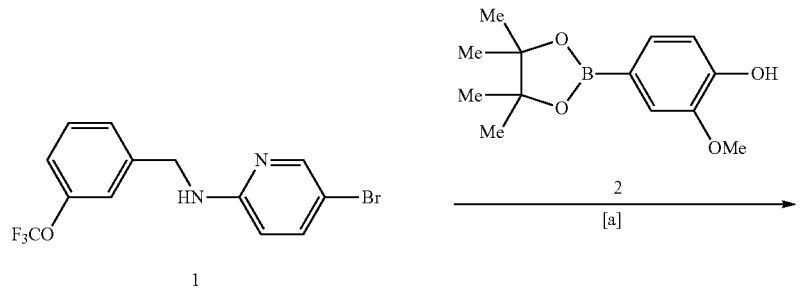

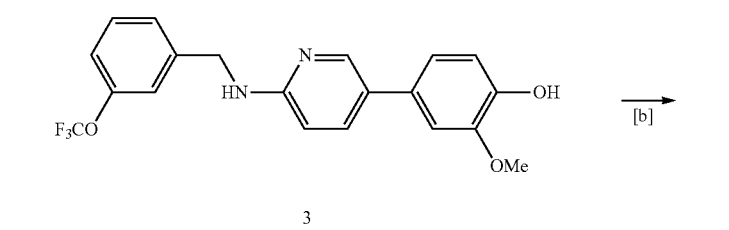

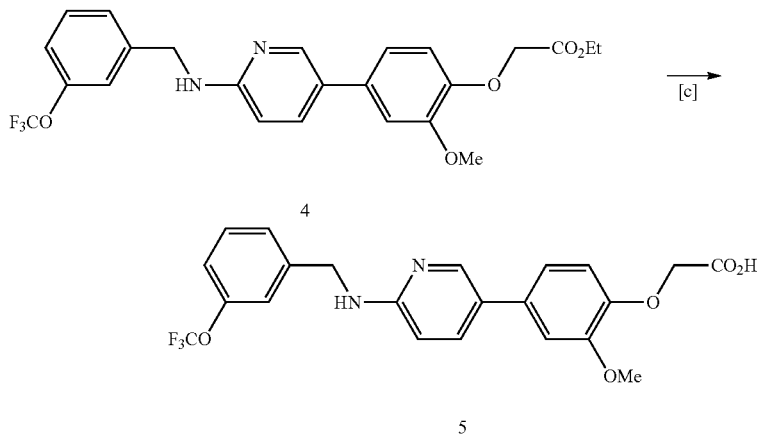

[Step a]

To compound 1 (5.00 g, 14.4 mmol) obtained in Reference Example 65, Step a, and compound 2 (5.40 g, 21.6 mmol) in a mixed solvent of dimethoxyethane (150 mL) and water (50.0 mL) were added sodium carbonate (4.60 g, 43.4 mmol) and tetrakis(triphenylphosphine)palladium(0) (830 mg, 720 μmol), and the mixture was stirred in a nitrogen atmosphere with heating at 100° C. for 6 hr. The reaction solution was allowed to cool to room temperature, saturated brine was added, and the mixture was extracted with ethyl acetate. The organic layer was dried over anhydrous sodium sulfate, filtered, and concentrated under reduced pressure. The residue was purified by silica gel chromatography. The obtained solid was suspended and washed in diisopropyl ether to give compound 3 (3.70 g, 65.8%).

MS(APCI)m/z: 391(M+1)+.

[Step b]

To a solution of compound 3 (350 mg, 897 μmol) in acetone (5.00 mL) were added potassium carbonate (248 mg, 1.79 mmol), ethyl bromoacetate (180 mg, 1.08 mmol), and the mixture was stirred for 3 hr with heating under reflux. The reaction solution was allowed to cool to room temperature, ethyl bromoacetate (90 mg, 53.9 μmol) was further added, and the mixture was stirred for 3 hr with heating under reflux. The reaction solution was allowed to cool to room temperature, and filtered through celite. The obtained filtrate was concentrated. The residue was purified by silica gel chromatography to give compound 4 (331 mg, 77.5%).

MS(APCI)m/z: 477(M+1)+.

[Step c]

To a solution of compound 4 (261 mg, 548 μmol) in methanol (4.00 mL) was added 1 M-aqueous sodium hydroxide solution (2.00 mL), and the mixture was stirred at room temperature overnight. To the reaction solution was added 1 M-hydrochloric acid under ice-cooling to adjust to pH=6-7, and the mixture was extracted with chloroform. The organic layer was washed with saturated brine, dried over anhydrous sodium sulfate, filtered and concentrated under reduced pressure, and the residue was purified by silica gel chromatography to give compound 5 (67.0 mg, 27.3%).

MS(APCI)m/z: 449(M+1)+.

Example 24

4-{2-methoxy-5-[6-(3-trifluoromethoxy-benzylamino)-pyridin-3-yl]-phenoxymethyl}-cyclohexanecarboxylic acid

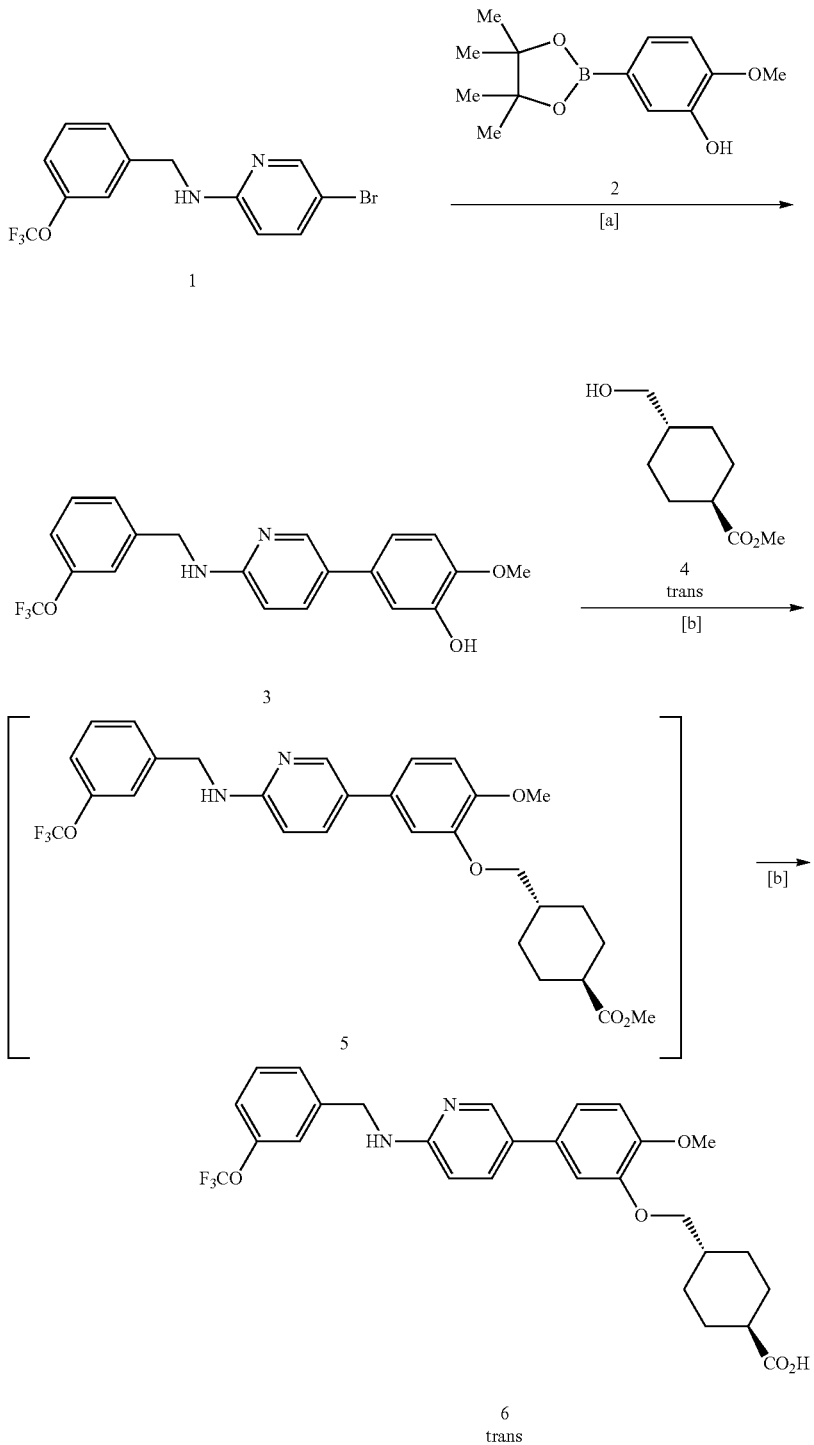

[Step a]

To compound 1 (3.50 g, 10.1 mmol) obtained in Reference Example 65, Step a, and compound 2 (3.00 g, 12.1 mmol) in a mixed solvent of dimethoxyethane (105 mL) and water (35.0 mL) were added sodium carbonate (3.20 g, 30.2 mmol) and tetrakis(triphenylphosphine)palladium(0) (580 mg, 504 μmol), and the mixture was stirred in a nitrogen atmosphere with heating at 100° C. for 6 hr. The reaction solution was allowed to cool to room temperature, saturated brine was added, and the mixture was extracted with ethyl acetate. The organic layer was dried over anhydrous sodium sulfate, filtered, and concentrated under reduced pressure. The residue was purified by silica gel chromatography. The obtained solid was suspended and washed in a mixed solution of diisopropyl ether and ethyl acetate to give compound 3 (1.70 g, 43.3%).

MS(APCI)m/z: 391(M+1)+.

[Step b]

To a solution of compound 3 (30.0 mg, 77.0 μmol) in tetrahydrofuran (800 μL) were added compound 4 (CAS No. 110928-44-4, 26.5 mg, 154 μmol), tri-n-butylphosphine (31.0 mg, 154 μmol), N,N,N',N'-tetramethylazodicarboxamide (TMAD) (27.0 mg, 154 μmol), and the mixture was stirred at room temperature for 3.0 hr, and under heating at 80° C. overnight. The reaction solution was concentrated, the residue was dissolved in tetrahydrofuran (1.00 mL), 1 M-aqueous sodium hydroxide solution (154 μL, 154 μmol) was added, and the mixture was stirred with heating at 80° C. for 2 hr. The reaction solution is was concentrated and purified by reversed-phase HPLC to give compound 6 (2.50 mg, 6.1%).

MS(ESI)m/z: 531(M+1)+.

Example 25

2-{2-methoxy-5-[6-(3-trifluoromethoxy-benzylamino)-pyridin-3-yl]-phenyl}-2-methyl-propionic acid

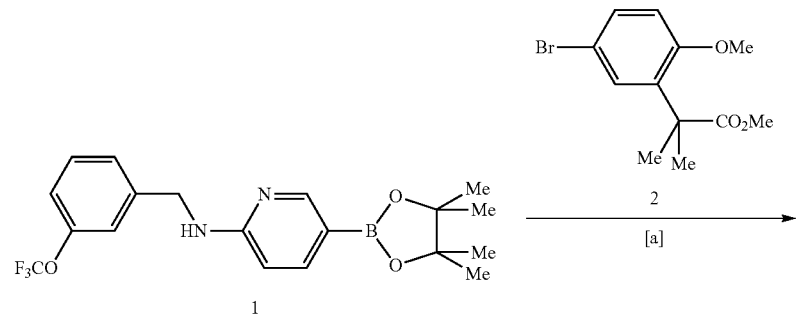

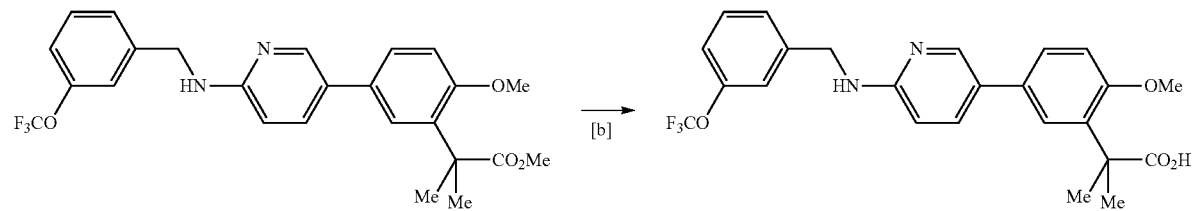

[Step a]

To a solution of compound 1 (314 mg, 797 µmol) obtained in Reference Example 65, Step b, in toluene (2.70 mL) were added water (300 µL), tripotassium phosphate (423 mg, 1.99 mmol), compound 2 (190 mg, 664 µmol) obtained in Reference Example 51, bis(di-tert-butyl(4-dimethylaminophenyl)phosphine)dichloropalladium(II) (24.0 mg, 33.2 µmol), and the mixture was stirred in a nitrogen atmosphere with heating at 100° C. for 2 hr. The reaction solution was allowed to cool to room temperature, diluted with ethyl acetate, activated carbon and NH-silica gel (FUJI SILYSIA CHEMICAL LTD. CHROMATOREX) were added, and the mixture was stirred at room temperature for 15 min, and filtered through celite. To the obtained filtrate was added saturated aqueous sodium hydrogen carbonate solution, and the mixture was extracted with ethyl acetate. The organic layer was washed with saturated brine, dried over anhydrous sodium sulfate, filtered and concentrated under reduced pressure, and the residue was purified by silica gel chromatography to give compound 3 (268 mg, 85.1%).

MS(ESI)m/z: 475(M+1)+.

[Step b]

To a solution of compound 3 (265 mg, 558 µmol) in ethanol (5.00 mL) was added 4 M-aqueous sodium hydroxide solution (5.00 mL), and the mixture was stirred with heating under reflux for 17 hr. The reaction solution was allowed to cool to room temperature, and concentrated under reduced pressure. The residue was diluted with chloroform and water, ice-cooled, 6-M hydrochloric acid was added to adjust to pH=4, and the mixture was extracted with chloroform. The organic layer was washed with saturated brine, dried over anhydrous sodium sulfate, filtered and concentrated under reduced pressure, and the residue was purified by silica gel chromatography to give compound 4 (134 mg, 52.2%).

MS(ESI)m/z: 461(M+1)+.

Example 26

2-{3-cyano-2-methoxy-5-[6-(3-trifluoromethoxy-benzylamino)-pyridin-3-yl]-phenyl}-2-methyl-propionic acid

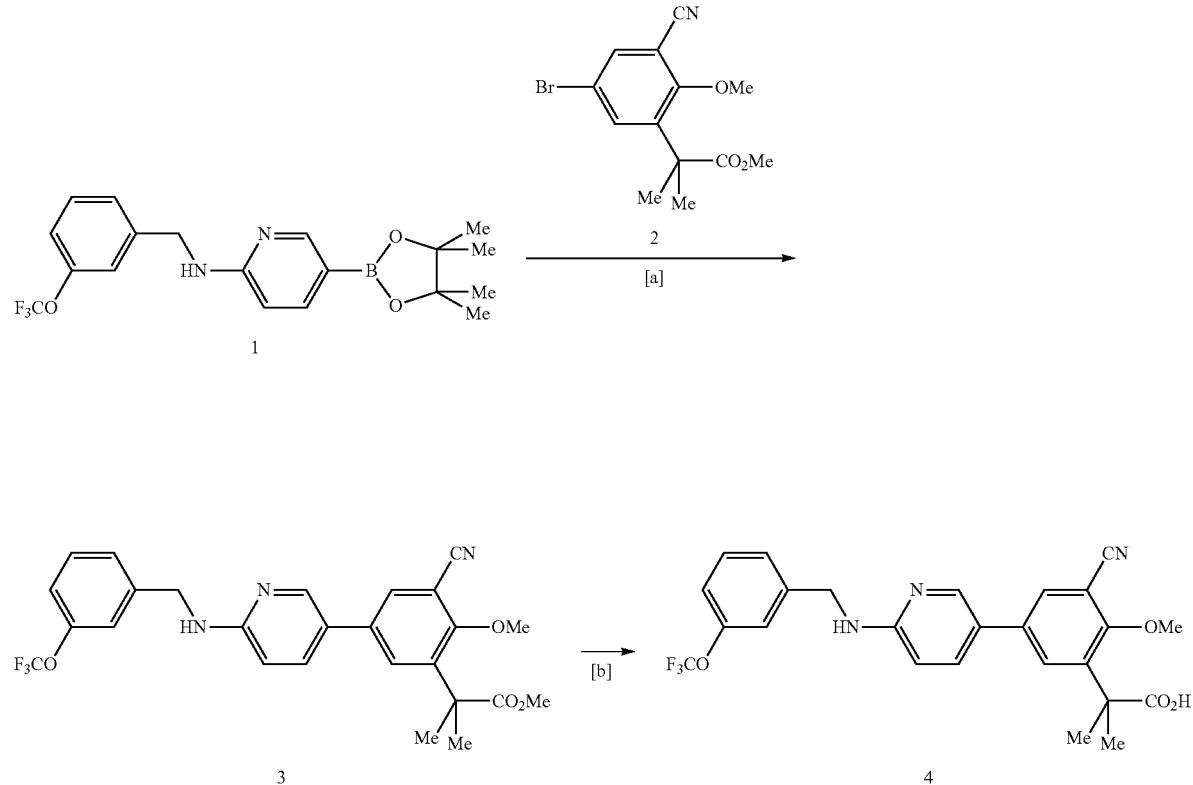

[Step a]

To a solution of compound 1 (129 mg, 327 µmol) obtained in Reference Example 65, Step b, in dioxane (3.00 mL) were added water (300 µL), potassium carbonate (113 mg, 819 µmol), compound 2 (85.1 mg, 273 µmol) obtained in Reference Example 36, Step b, bis(di-tert-butyl(4-dimethylaminophenyl)phosphine)dichloropalladium(II) (9.67 mg, 13.7 µmol), and the mixture was stirred in a nitrogen atmosphere with heating at 100° C. for 3.5 hr. The reaction solution was allowed to cool to room temperature, water was added, and the mixture was extracted with ethyl acetate. The organic layer was washed with saturated brine, dried over anhydrous sodium sulfate, filtered and concentrated under reduced pressure, and the residue was purified by silica gel chromatography to give compound 3 (76.1 mg, 55.9%).

MS(ESI)m/z: 500(M+1)+.

[Step b]

To a solution of compound 3 (30.0 mg, 60.1 µmol) in methanol (1.00 mL) was added 2 M-aqueous sodium hydroxide solution (100 µL), and the mixture was stirred with heating at 80° C. overnight. The reaction solution was allowed to cool to room temperature, methanol (1.00 mL), 2 M-aqueous sodium hydroxide solution (200 μL) were further added, and the mixture was stirred with heating at 80° C. for 5 hr. The reaction solution was allowed to cool to room temperature, water was added and the mixture was stirred. The precipitated solid was removed by filtration, the filtrate was adjusted to pH5-6 with 1 M-hydrochloric acid, and the mixture was extracted with chloroform. The organic layer was washed with saturated brine, dried over anhydrous sodium sulfate, filtered, and concentrated under reduced pressure to give compound 4 (7.5 mg, 25.7%).

MS(ESI)m/z: 486(M+1)+.

Example 27

6'-(3-trifluoromethoxy-benzylamino)-3,4,5,6-tetra-hydro-2H-[1,3']bipyridinyl-3-carboxylic acid

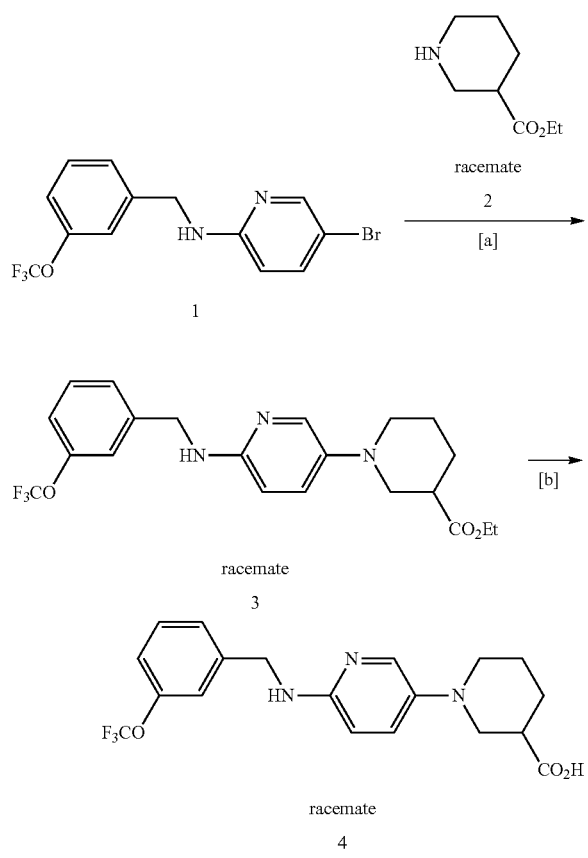

[Step a]

To a solution of compound 1 (250 mg, 720 μmol) obtained in Reference Example 65, Step a, and compound 2 (340 μL, 2.18 mmol) in dimethoxyethane (3.00 mL) were added tripotassium phosphate (615 mg, 2.90 mmol), tris(dibenzylideneacetone)dipalladium(0) (35.0 mg, 38.2 μmol), 2-dicyclohexylphosphino-2'-(N,N-dimethylamino)biphenyl (DavePhos) (60.0 mg, 152 μmol), and the mixture was heated in a nitrogen atmosphere under microwave radiation at 130° C., and stirred for 30 min. The reaction solution was allowed to cool to room temperature, compound 2 (225 μL, 1.45 mmol), tripotassium phosphate (305 mg, 1.44 mmol), tris(dibenzylideneacetone)dipalladium(0) (30.0 mg, 32.8 μmol), 2-dicyclohexylphosphino-2'-(N,N-dimethylamino)biphenyl (DavePhos) (55.0 mg, 140 μmol) were further added, and the mixture was heated in a nitrogen atmosphere under microwave radiation at 130° C., and stirred for 30 min. The reaction solution was allowed to cool to room temperature, 0.5 M-hydrochloric acid (7.00 mL) was added, and the mixture was extracted with ethyl acetate. The organic layer was washed with water and saturated brine, dried over anhydrous sodium sulfate, filtered and concentrated under reduced pressure, and the residue was purified by silica gel chromatography to give compound 3 (95.0 mg, 31.1%).

MS(ESI)m/z: 424(M+1)+.

[Step b]

To a mixed solution of compound 3 (90.0 mg, 213 μmol) in tetrahydrofuran (4.00 mL), methanol (2.00 mL) was added 2 M-aqueous sodium hydroxide solution (2.00 mL), and the mixture was stirred at room temperature for 2 hr. To the reaction solution was added 0.5 M-hydrochloric acid (8.50 mL) under ice-cooling, and the mixture was extracted with chloroform. The organic layer was washed with saturated brine, dried over anhydrous sodium sulfate, filtered and concentrated under reduced pressure, and the residue was purified by silica gel chromatography to give compound 4 (35.0 mg, 41.6%).

MS(ESI)m/z: 396(M+1)+.

Example 28

2-chloro-3-(1-methyl-pyrrolidin-3-yloxy)-5-[2-(3-trifluoromethoxy-benzylamino)-pyrimidin-5-yl]-benzoic acid

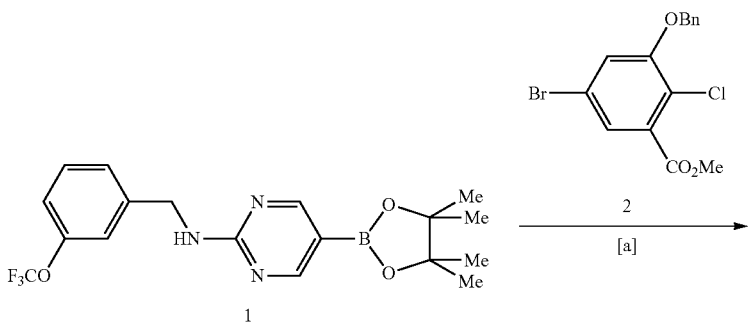

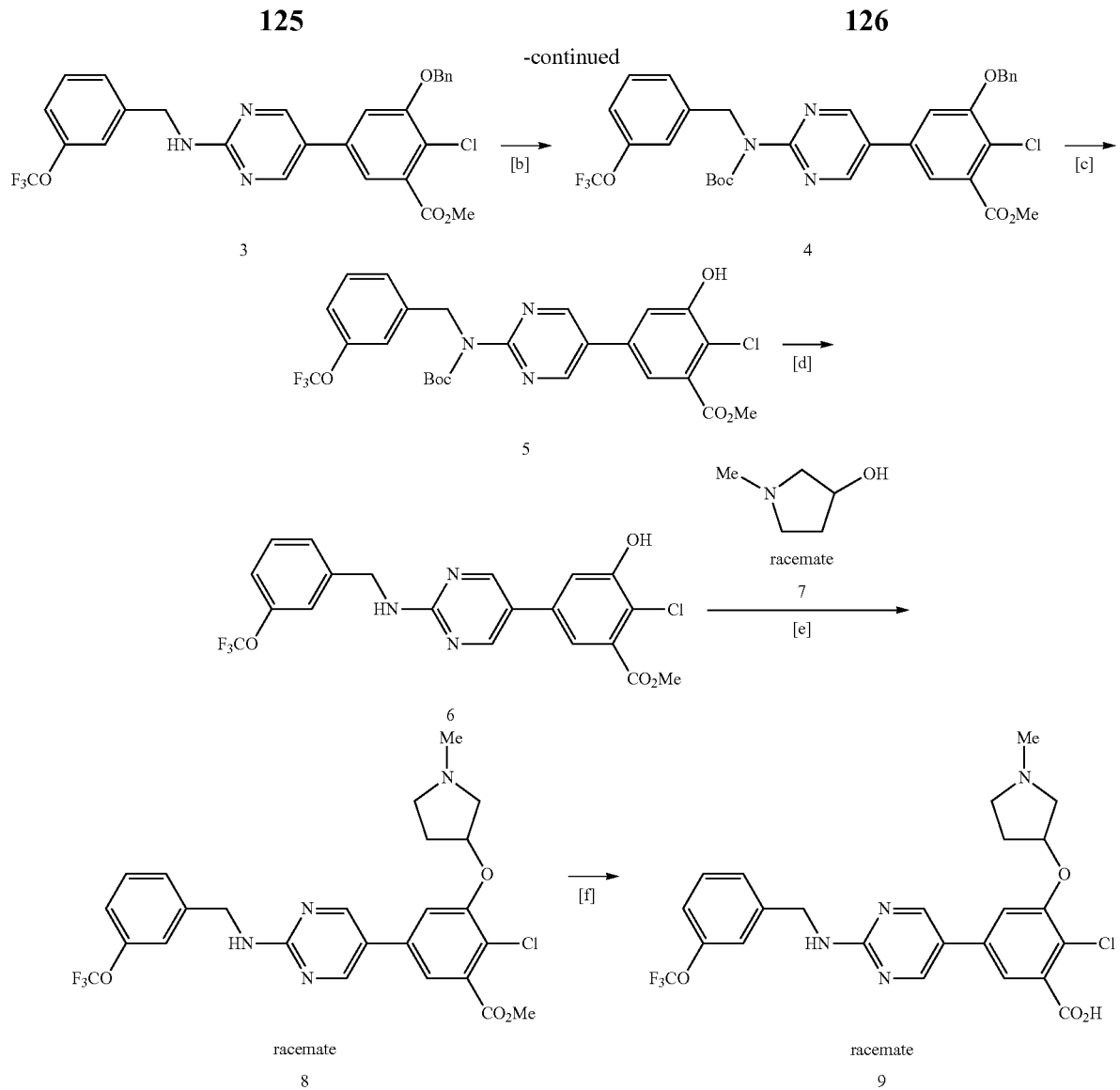

[Step a]

To a mixed solution of compound 1 (4.18 g, 10.6 mmol) obtained in Reference Example 66, Step b, in dioxane (70.0 mL) and water (7.00 mL) were added tripotassium phosphate (5.60 g, 26.4 mmol), compound 2 (3.13 g, 8.80 mmol) obtained in Reference Example 37, Step f, bis(di-tert-butyl (4-dimethylaminophenyl)phosphine)dichloropalladium(II) (311 mg, 440 μmol), and the mixture was stirred in a nitrogen atmosphere with heating at 100° C. for 2 hr. The reaction solution was filtered through celite, concentrated and purified by silica gel chromatography to give compound 3 (3.76 g, 78.4%).

MS(APCI)m/z: 544, 546(M+1)+.

[Step b]

To a solution of compound 3 (3.76 g, 6.90 mmol) in tetrahydrofuran (75.0 mL) were added di-tert-butyl dicarbonate (3.01 g, 13.8 mmol) and N,N-dimethyl-4-aminopyridine (843 mg, 6.90 mmol), and the mixture was stirred at room temperature overnight. The reaction solution was concentrated and purified by silica gel chromatography to give compound 4 (4.05 g, 91.0%).

MS(ESI)m/z: 644, 646(M+1)+.

[Step c]

To a solution of compound 4 (4.05 g, 4.05 mmol) in ethyl acetate (81.0 mL) was added 10%-palladium/carbon (405 mg), and the mixture was stirred in a hydrogen atmosphere at room temperature for 8 hr. The reaction solution was filtered through celite, and concentrated to give compound 5 (3.21 g, 92.2%).

MS(APCI)m/z: 554, 556(M+1)+.

[Step d]

To a solution of compound 5 (2.00 g, 3.61 mmol) in dichloromethane (20.0 mL) was added trifluoroacetic acid (10.0 mL) under ice-cooling, and the mixture was stirred for 1.5 hr while raising the temperature to room temperature. The reaction solution was concentrated, saturated aqueous sodium hydrogen carbonate solution was added, and the mixture was extracted with ethyl acetate. The organic layer was washed with water and saturated brine, dried over anhydrous sodium sulfate, filtered and concentrated under reduced pressure, and the residue was purified by silica gel chromatography to give compound 6 (1.47 g, 89.5%).

MS(ESI)m/z: 454, 456(M+1)+.

[Step e]

To a solution of compound 6 (100 mg, 220 μmol) in tetrahydrofuran (1.10 mL) were added compound 7 (46.9 mg, 441 μmol), triphenylphosphine (116 mg, 441 μmol), bis(2-methoxyethyl)azodicarboxylate (106 mg, 440 μmol) under ice-cooling, and the mixture was stirred overnight while raising the temperature to room temperature. To the reaction solution was added water, and the mixture was extracted with ethyl acetate. The organic layer was washed with water and saturated brine, dried over anhydrous sodium sulfate, filtered and concentrated under reduced pressure, and the residue was purified by silica gel chromatography to give compound 8 (92.9 mg, 78.5%).

MS(ESI)m/z: 537, 539(M+1)+.

while raising the temperature to room temperature, and stirred for 1 hr with heating under reflux. The reaction solution was concentrated and suspended and washed in diethyl ether to give a sodium salt of compound 8 (43.4 mg, 50.3%).

MS(ESI)m/z: 523, 525(M+H−Na+1)+.

Example 29

2-chloro-3-(pyrrolidin-3-yloxy)-5-[2-(3-trifluoromethoxy-benzylamino)-pyrimidin-5-yl]-benzoic acid

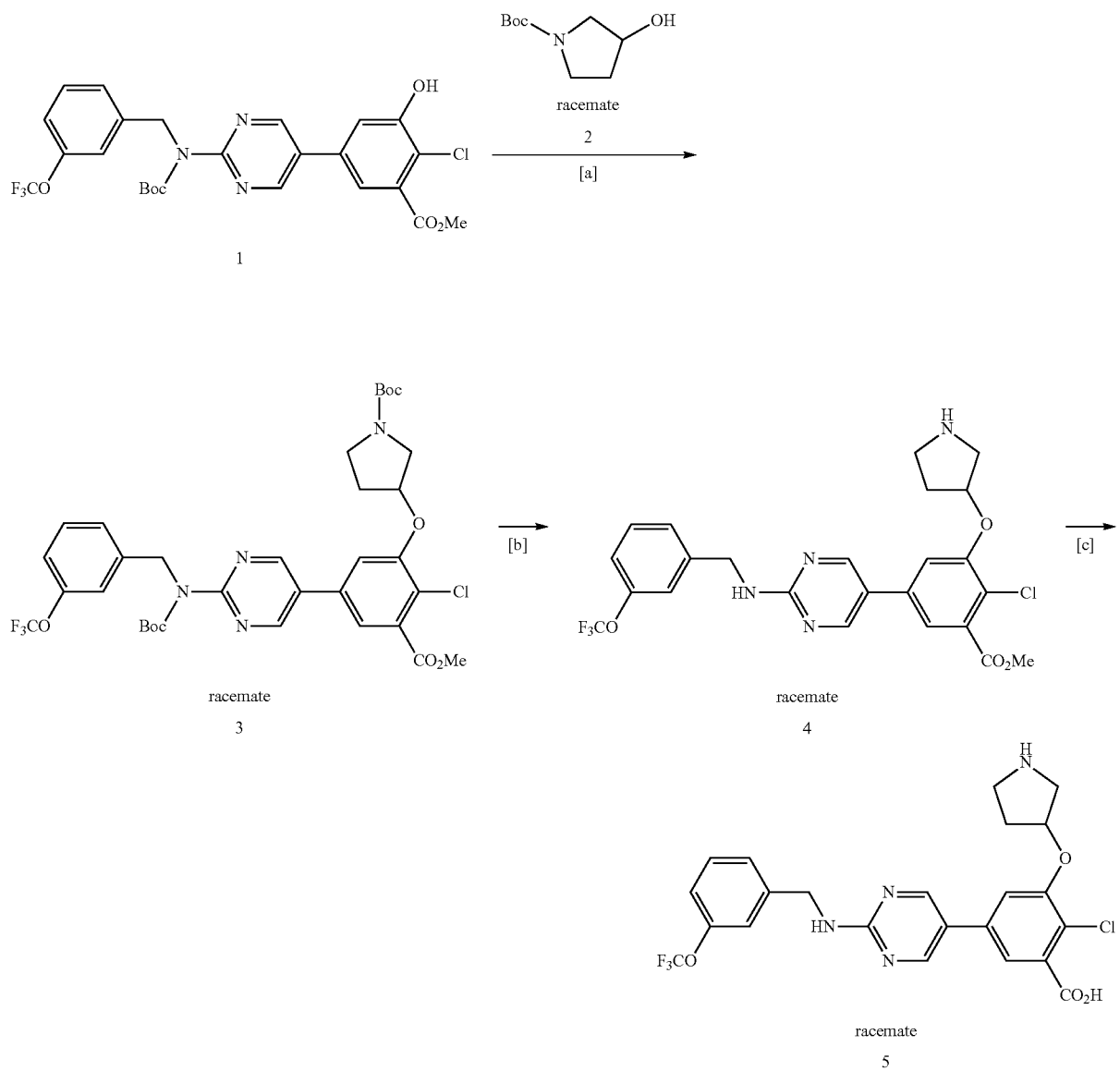

[Step f]

To a mixed solution of compound 8 (85.1 mg, 156 μmol) in tetrahydrofuran (1.00 mL), methanol (1.00 mL) was added 1 M-aqueous sodium hydroxide solution (156 μL) under ice-cooling, and the mixture was stirred overnight

[Step a]

To a solution of compound 1 (150 mg, 271 μmol) obtained in Example 28, Step c, in tetrahydrofuran (1.35 mL) were added compound 2 (77.6 mg, 405 μmol), triphenylphosphine (107 mg, 406 μmol), bis(2-methoxyethyl)azodicarboxylate (98.1 mg, 406 μmol) under ice-cooling, and the mixture was stirred overnight while raising the temperature to room temperature. To the reaction solution were further added compound 2 (152 mg, 813 μmol), triphenylphosphine (213 mg, 813 μmol), bis(2-methoxyethyl)azodicarboxylate (190 mg, 813 μmol) under ice-cooling, and the mixture was stirred for 4 hr while raising the temperature to room temperature. To the reaction solution was added water, and the mixture was extracted with ethyl acetate. The organic layer was washed with saturated brine, and filtered through celite, and concentrated under reduced pressure. The obtained residue was purified by silica gel chromatography to give compound 3 (156 mg, 79.9%).

MS(ESI)m/z: 723, 725(M+1)+.

[Step b]

To a solution of compound 3 (147 mg, 204 μmol) in dichloromethane (2.94 mL) was added tetrafluoroacetic acid (1.47 mL), and the mixture was stirred at room temperature for 2 hr. The reaction solution was concentrated, excess saturated aqueous sodium hydrogen carbonate solution was under ice-cooling, and the mixture was stirred overnight while raising the temperature to room temperature, and stirred for 1 hr with heating under reflux. To the reaction solution was further added 1 M-aqueous sodium hydroxide solution (154 μL), and the mixture was stirred for 1 hr with heating under reflux. The reaction solution was allowed to cool to room temperature, neutralized with 1 M-hydrochloric acid (308 μL), and water was added. The precipitated solid was collected by filtration, washed with water, and suspended and washed in diethyl ether to give compound 5 (72.3 mg, 92.0%).

MS(ESI)m/z: 509, 511(M+1)+.

Example 30

3-(azetidin-3-yloxy)-2-chloro-5-[2-(3-trifluoromethoxy-benzylamino)-pyrimidin-5-yl]-benzoic acid

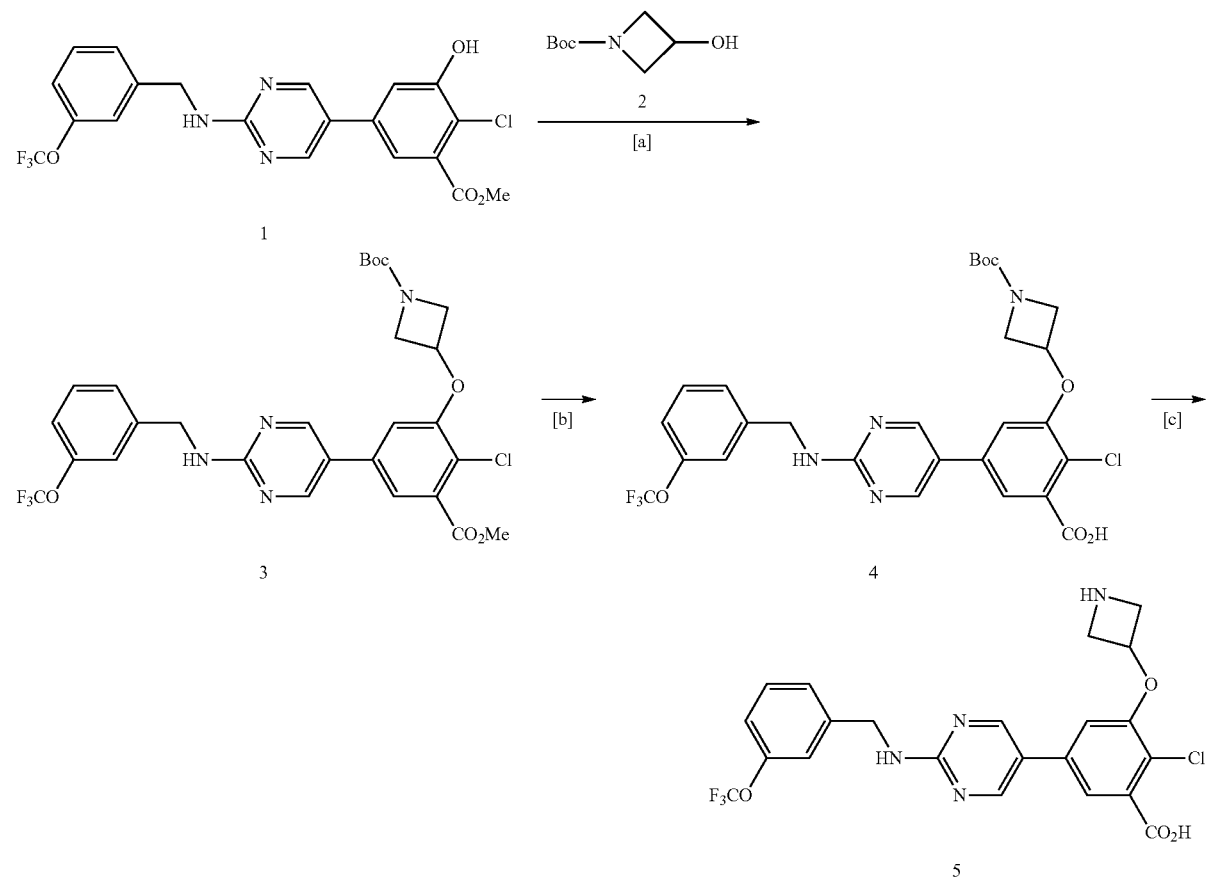

added, and the mixture was extracted with ethyl acetate. The organic layer is was washed with water and saturated brine, dried over anhydrous sodium sulfate, filtered and concentrated under reduced pressure, and the residue was purified by silica gel chromatography to give compound 4 (93.1 mg, 87.5%).

MS(ESI)m/z: 523, 525(M+1)+.

[Step c]

To a mixed solution of compound 4 (87.8 mg, 154 μmol) in tetrahydrofuran (1.00 mL) and methanol (1.00 mL) was added 1 M-aqueous sodium hydroxide solution (154 μL)

[Step a]

To a solution of compound 1 (245 mg, 540 μmol) obtained in Example 28, Step d, in tetrahydrofuran (2.70 mL) were added compound 2 (193 mg, 1.08 mmol), triphenylphosphine (283 mg, 1.08 mmol), bis(2-methoxyethyl)azodicarboxylate (261 mg, 1.08 mmol) under ice-cooling, and the mixture was stirred with heating under reflux for 4 hr. To the reaction solution was added water, and the mixture was extracted with ethyl acetate. The organic layer was washed with water and saturated brine, and filtered through celite, and concentrated under reduced pressure. The obtained residue was purified by silica gel chromatography to give compound 3 (297 mg, 90.2%).

MS(ESI)m/z: 601, 611(M+1)+.

[Step b]

To a mixed solution of compound 3 (291 mg, 477 μmol) in tetrahydrofuran (2.91 mL) and methanol (2.91 mL) was added 1 M-aqueous sodium hydroxide solution (716 μL) under ice-cooling, and the mixture was stirred overnight while raising the temperature to room temperature. The reaction solution was neutralized with 1 M-hydrochloric acid (716 μL), water was added, and the mixture was extracted with ethyl acetate. The organic layer was washed with saturated brine, and filtered through celite, and concentrated under reduced pressure. The obtained residue was suspended and washed in diethyl ether to give compound 4 (269 mg, 94.7%).

MS(ESI)m/z: 595, 597(M+1)+.

[Step c]

To a solution of compound 4 (120 mg, 202 μmol) in dioxane (2.40 mL) was added 4 M-hydrochloric acid dioxane solution (2.40 mL), and the mixture was stirred at room temperature for 2.5 hr. The reaction solution was concentrated, and the residue was suspended and washed in a mixed solution of ethyl acetate and diethyl ether to give hydrochloride of compound 5 (79.8 mg, 99.1%).

MS(ESI)m/z: 495, 407(M+1)+.

Example 31

2-chloro-3-(l-methyl-azetidin-3-yloxy)-5-[2-(3-trifluoromethoxy-benzylamino)-pyrimidin-5-yl]-benzoic acid

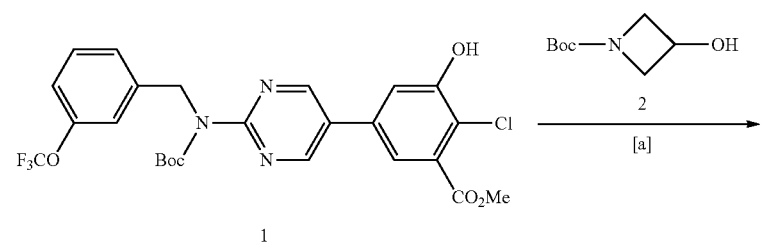

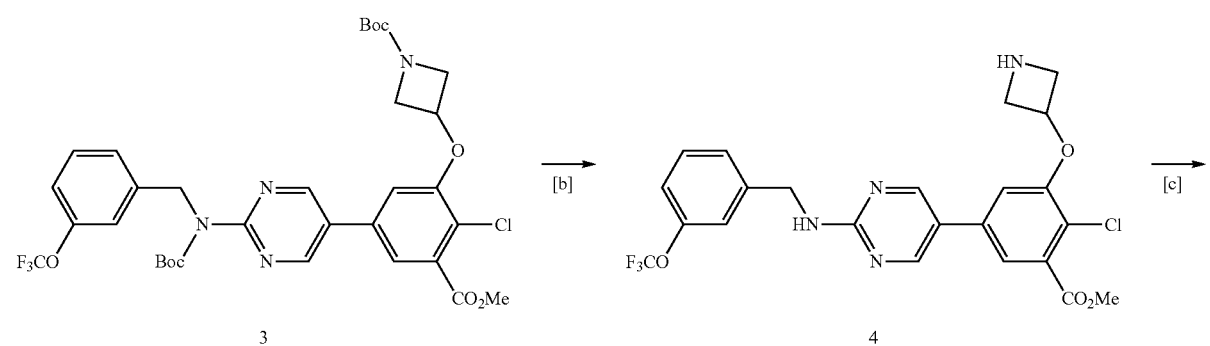

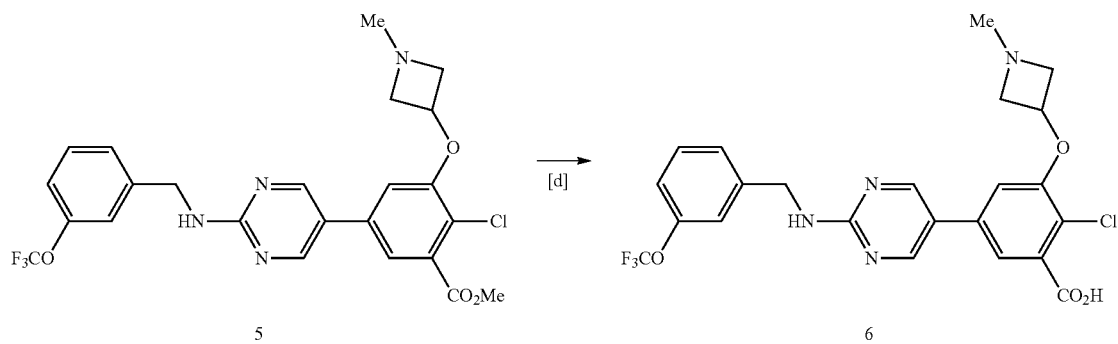

[Step a]

To a solution of compound 1 (150 mg, 271 μmol) obtained in Example 28, Step c, in tetrahydrofuran (1.35 mL) were added compound 2 (72.5 mg, 406 μmol), triphenylphosphine (107 mg, 406 μmol), bis(2-methoxyethyl)azodicarboxylate (98.1 mg, 406 μmol) under ice-cooling, and the mixture was stirred overnight while raising the temperature to room temperature. To the reaction solution were further added compound 2 (152 mg, 813 μmol), triphenylphosphine (213 mg, 0.813 mmol), bis(2-methoxyethyl)azodicarboxylate (190 mg, 813 μmol) under ice-cooling, and the mixture was stirred for 4 hr while raising the temperature to room temperature. To the reaction solution was added water, and the mixture was extracted with ethyl acetate. The organic layer was washed with saturated brine, and filtered through celite, and concentrated under reduced pressure. The obtained residue was purified by silica gel chromatography to give compound 3 (136 mg, 70.7%).

MS(ESI)m/z: 709, 711(M+1)+.

[Step b]

To a solution of compound 3 (128 mg, 180 μmol) in dichloromethane (2.56 mL) was added tetrafluoroacetic acid (1.28 mL), and the mixture was stirred at room temperature for 2 hr. The reaction solution was concentrated, excess saturated aqueous sodium hydrogen carbonate solution was added, and the mixture was extracted with ethyl acetate. The organic layer was washed with saturated brine, dried over anhydrous sodium sulfate, filtered and concentrated under reduced pressure, and the residue was purified by silica gel chromatography to give compound 4 (83.3 mg, 90.8%).

MS(ESI)m/z: 509, 511(M+1)+.

[Step c]

To a solution of compound 4 (174 mg, 341 μmol), acetic acid (39.0 μL, 682 μmol), para-formaldehyde (56.9 mg, 1.71 mmol) in 1,2-dichloroethane (1.71 mL) was added sodium triacetoxyborohydride (304 mg, 1.36 mmol) under ice-cooling, and the mixture was stirred for 19 hr while raising the temperature to room temperature. To the reaction solution were further added para-formaldehyde (22.8 mg, 682 μmol), sodium triacetoxyborohydride (152 mg, 682 μmol), and the mixture was stirred at room temperature for 3 hr. To the reaction solution were further added para-formaldehyde (22.8 mg, 682 μmol), sodium triacetoxyborohydride (152 mg, 682 μmol), and the mixture was stirred at room temperature for 2 hr. To the reaction solution was added excess saturated sodium hydride aqueous solution, and the mixture was extracted with ethyl acetate. The organic layer was dried over anhydrous sodium sulfate, filtered and concentrated under reduced pressure, and the residue was purified by silica gel chromatography to give compound 5 (73.4 mg, 41.2%).

MS(ESI)m/z: 523, 525(M+1)+.

[Step d]

To a mixed solution of compound 5 (70.2 mg, 134 μmol) in tetrahydrofuran (1.00 mL) and methanol (1.00 mL) was added 1 M-aqueous sodium hydroxide solution (134 μL) under ice-cooling, and the mixture was stirred overnight while raising the temperature to room temperature, and stirred for 1 hr with heating under reflux. The reaction solution was concentrated, and the precipitated solid was suspended and washed in diethyl ether to give a sodium salt of compound 6 (67.7 mg, 97.6%).

MS(ESI)m/z: 509, 511(M+H−Na+1)+.

Example 32

2-chloro-3-(2,2,2-trifluoro-ethoxy)-5-[2-(3-trifluoromethoxy-benzylamino)-pyrimidin-5-yl]-benzoic acid

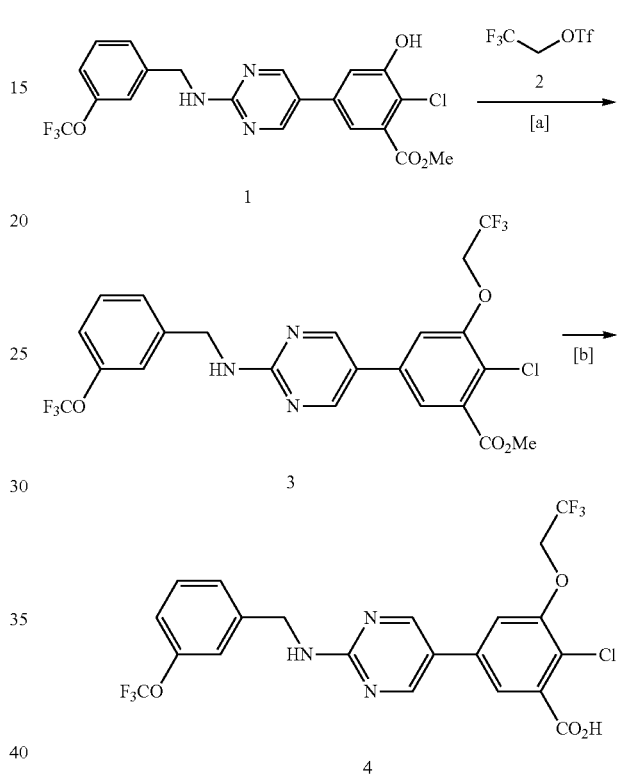

[Step a]

To a solution of compound 1 (100 mg, 220 μmol) which was obtained in Example 28, Step d, and compound 2 (76.7 mg, 331 μmol) in N,N-dimethylformamide (1.10 mL) was added potassium carbonate (45.7 mg, 331 μmol) under ice-cooling, and the mixture was stirred for 3 hr while raising the temperature to room temperature. To the reaction solution was added water, and the mixture was extracted with ethyl acetate. The organic layer was washed with water and saturated brine, concentrated under reduced pressure, and the residue was purified by silica gel chromatography to give compound 3 (114.8 mg, 97.2%).

MS(ESI)m/z: 536, 538(M+1)+.

[Step b]

To a mixed solution of compound 3 (108 mg, 202 μmol) in tetrahydrofuran (1.00 mL) and methanol (1.00 mL) was added 1 M-aqueous sodium hydroxide solution (303 μL) under ice-cooling, and the mixture was stirred overnight while raising the temperature to room temperature. To the reaction solution was added 1 M-hydrochloric acid (303 μL), and the mixture was diluted with water, and extracted with ethyl acetate. The organic layer was washed with saturated brine, dried over anhydrous sodium sulfate, filtered, concentrated under reduced pressure, the obtained residue was suspended and washed in diethyl ether to give compound 4 (94.6 mg, 99.4%).

MS(ESI)m/z: 522, 524(M+1)+.

Example 33
2-methoxy-3-pyridin-4-yl-5-[2-(3-trifluoromethoxy-benzylamino)-pyrimidin-5-yl]-benzoic acid
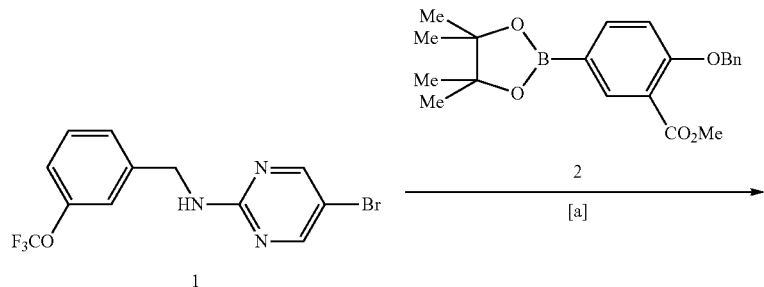
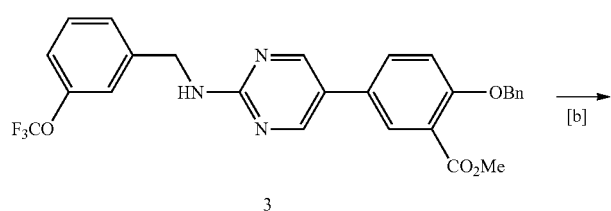
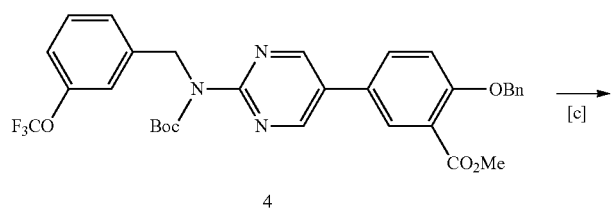
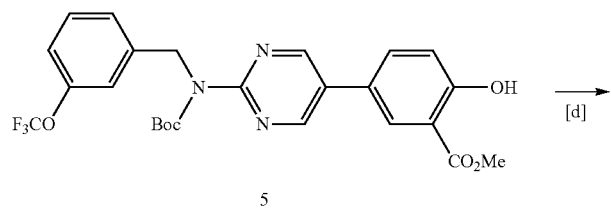
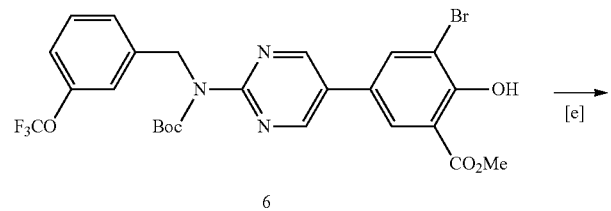
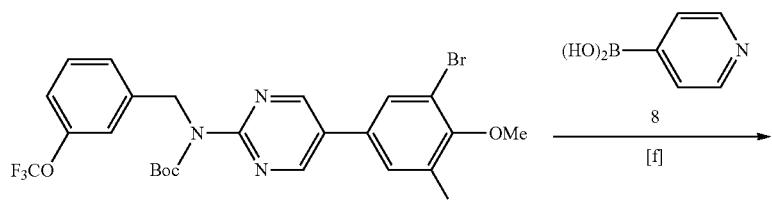

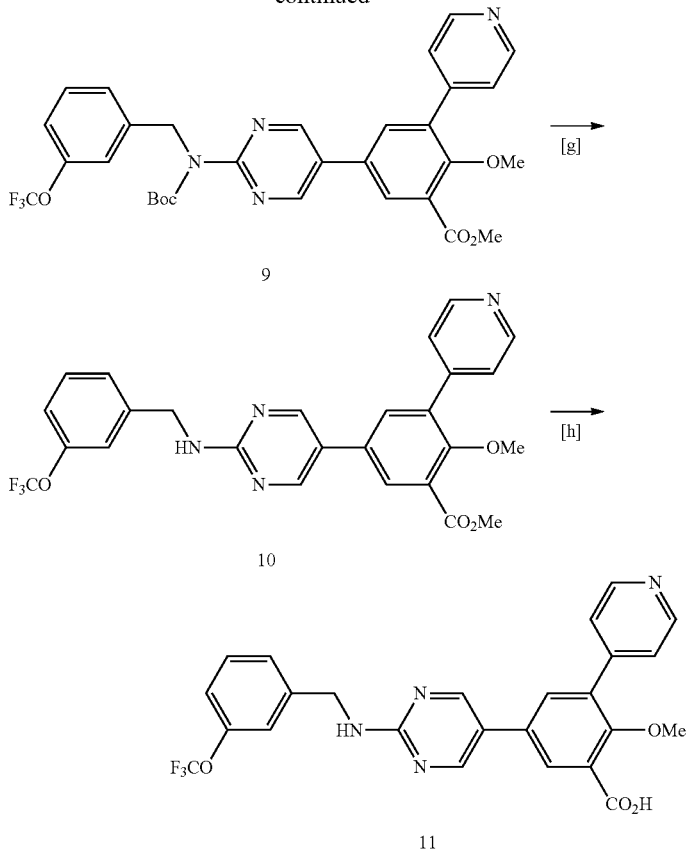

[Step a]

To a mixed solution of compound 2 (4.00 g, 11.5 mmol) obtained in Reference Example 38, Step b, and compound 1 (5.08 g, 13.8 mmol) obtained in Reference Example 66, Step a, in dioxane (100 mL) and water (10.0 mL) were added tripotassium phosphate (7.32 g, 34.5 mmol), bis(di-tert-butyl(4-dimethylaminophenyl)phosphine)dichloropalladium(II) (407 mg, 575 μmol), and the mixture was stirred in a nitrogen atmosphere with heating at 100° C. for 10 hr. The reaction solution was filtered through celite, water and ethyl acetate were added, and the mixture was extracted with ethyl acetate. The organic layer was washed with water and saturated brine, dried over anhydrous sodium sulfate, filtered and concentrated under reduced pressure, and the residue was purified by silica gel chromatography to give compound 3 (2.66 g, 45.5%).

MS(APCI)m/z: 510(M+1)+.

[Step b]

To a solution of compound 3 (3.26 g, 6.40 mmol) in tetrahydrofuran (65.0 mL) were added N,N-dimethyl-4-aminopyridine (781 mg, 6.40 mmol), di-tert-butyl dicarbonate (2.79 g, 12.8 mmol), and the mixture was stirred at room temperature overnight. The reaction solution was concentrated and purified by silica gel chromatography to give compound 4 (4.02 g, 97.1%).

MS(APCI)m/z: 610(M+1)+.

[Step c]

To a solution of compound 4 (3.96 g, 6.40 mmol) in ethyl acetate (80.0 mL) was added 10%-palladium/carbon (400 mg), and the mixture was stirred in a hydrogen atmosphere at room temperature for 8 hr. The reaction solution was filtered through celite, and concentrated to give compound 5 (3.38 g).

MS(APCI)m/z: 520(M+1)+.

[Step d]

To a solution of compound 5 (1.00 g, 1.93 mmol) in dichloromethane (5.00 mL) were added diisopropylamine (109 μL, 0.775 mmol), N-bromosuccinimide (344 mg, 1.93 mmol), and the mixture was stirred at room temperature for 1 hr. To the reaction solution was added saturated aqueous sodium thiosulfate solution, and the mixture was stirred at room temperature for 30 min. The reaction solution was extracted with ethyl acetate, and the organic layer was washed with saturated brine, dried over anhydrous sodium sulfate, filtered, and concentrated under reduced pressure. The obtained residue was suspended and washed in hexane to give compound 6 (783 mg, 67.8%).

MS(ESI)m/z: 598(M+1)+.

[Step e]

To a solution of compound 6 (500 mg, 0.816 mmol) in dimethylformamide (5.00 mL) were added methyl iodide (67.0 μL, 1.08 mmol), potassium carbonate (147 mg, 1.06 mmol), and the mixture was stirred at room temperature overnight. To the reaction solution was further added methyl iodide (67.0 μL, 1.08 mmol), and the mixture was stirred at room temperature for 8 hr. To the reaction solution was added water, and the mixture was extracted with ethyl acetate. The organic layer was washed with saturated brine, dried over anhydrous sodium sulfate, filtered and concentrated under reduced pressure, and the residue was purified by silica gel chromatography to give compound 7 (437 mg, 87.6%).

MS(ESI)m/z: 612, 614(M+1)+.

[Step f]

To a mixed solution of compound 7 (100 mg, 163 μmol), compound 8 (21.9 mg, 195 μmol), potassium carbonate (70.0 mg, 506 μmol) in dioxane (1.00 mL) and water (100 μL) was added bis(di-tert-butyl(4-dimethylaminophenyl) phosphine) dichloropalladium(II) (10.0 mg, 14.1 μmol) in a nitrogen atmosphere, and the mixture was stirred with heating at 100° C. for 5 hr. The reaction solution was allowed to cool to room temperature, water was added, and the mixture was extracted with ethyl acetate. The organic layer was washed with saturated brine, dried over anhydrous sodium sulfate, filtered and concentrated under reduced pressure, and the residue was purified by silica gel chromatography to give compound 9 (56.9 mg, 57.2%).

MS(ESI)m/z: 611(M+1)+.

[Step g]

To compound 9 (56.0 mg, 91.7 μmol) was added trifluoroacetic acid (1.00 mL), and the mixture was stirred at room temperature for 3.0 hr. The reaction solution was purified by solid phase extraction (Waters, PoraPak™, Rxn CX) to give compound 10 (45.1 mg, 96.0%).

MS(ESI)m/z: 511(M+1)+.

[Step h]

To a solution of compound 10 (45.0 mg, 88.2 μmol) in methanol (1.00 mL) was added 2 M-aqueous sodium hydroxide solution (100 μL, 200 μmol), and the mixture was stirred at room temperature for 7 hr. To the reaction solution was further added 2 M-aqueous sodium hydroxide solution (100 μL, 200 μmol), and the mixture was stirred at room temperature overnight. To the reaction solution was added 1 M-hydrochloric acid to adjust to pH 6-7 and the mixture was purified by solid phase extraction (Waters, PoraPak™, Rxn CX) to give compound 11 (42.7 mg, 97.5%).

MS(ESI)m/z: 497(M+1)+.

Example 34

2-methoxy-5-[6-(3-trifluoromethoxy-benzylamino)-pyridin-3-yl]-benzoic acid

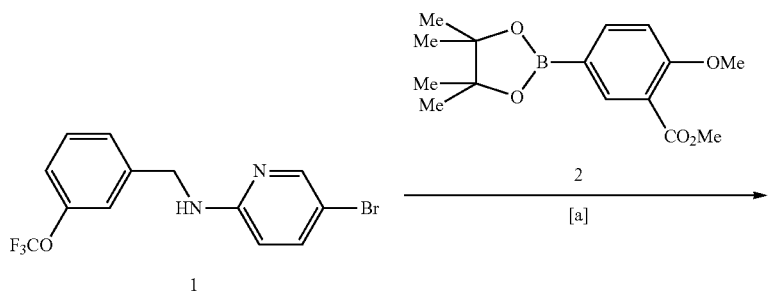

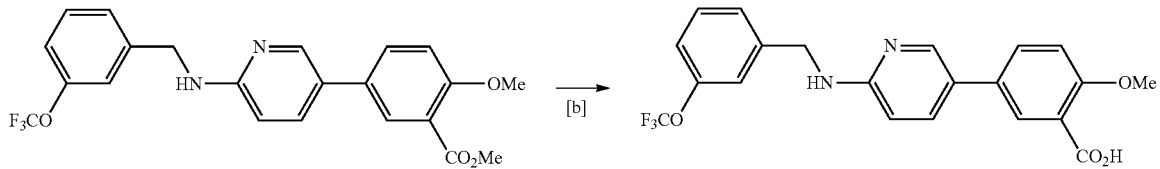

[Step a]

To a mixed solution of compound 1 (19.8 g, 57.3 mmol) obtained in Reference Example 65, Step a, and compound 2 (20.1 g, 68.8 mmol) obtained in Reference Example 39, Step a, in toluene (120 mL) and water (12.0 mL) were added potassium carbonate (23.7 g, 172 mmol), bis(di-tert-butyl (4-dimethylaminophenyl)phosphine)dichloropalladium(II) (406 mg, 0.573 mmol), and the mixture was stirred in a nitrogen atmosphere with heating at 100° C. for 2 hr. The reaction solution was allowed to cool to room temperature, diluted with ethyl acetate, NH silica gel (FUJI SILYSIA CHEMICAL LTD. CHROMATOREX) and activated carbon were added, and the mixture was stirred at room temperature for 15 min, and filtered through celite. To the obtained filtrate was added saturated aqueous sodium hydrogen carbonate solution, and the mixture was extracted with ethyl acetate. The organic layer was washed with saturated brine, dried over anhydrous sodium sulfate, filtered and concentrated under reduced pressure, and the residue was purified by silica gel chromatography to give compound 3 (23.4 g, 94.5%).

MS(ESI)m/z: 433(M+1)+.

[Step b]

To a mixed solution of compound 3 (31.4 g, 67.0 mmol) in tetrahydrofuran (100 mL) and methanol (200 mL) was added 2 M-aqueous sodium hydroxide solution (109 mL, 218 mmol), and the mixture was stirred at room temperature for 6 hr. To the reaction solution was added 6 M-hydrochloric acid under ice-cooling to adjust to pH3-4, and the mixture was extracted with chloroform. The organic layer was washed with saturated brine, dried over anhydrous sodium sulfate, filtered, concentrated under reduced pressure, and the obtained residue was suspended and washed in ethanol to give compound 4 (15.4 g, 54.9%).

MS(ESI)m/z: 419(M+1)+.

Example 35

2-methoxy-5-[4-methyl-6-(3-trifluoromethoxy-benzylamino)-pyridin-3-yl]-benzoic acid

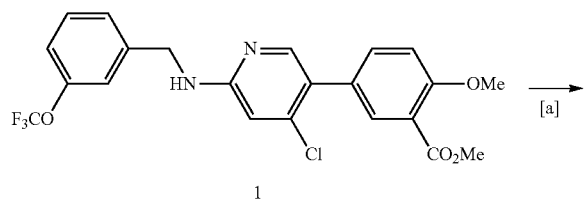

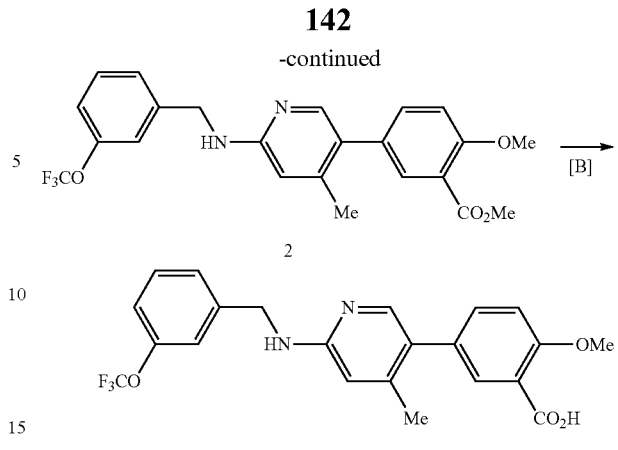

[Step a]

To a solution of compound 1 (230 mg, 493 μmol) obtained in Reference Example 69 in dimethoxyethane (1.30 mL) were added [1,3-bis(2,6-diisopropylphenyl)imidazol-2-ylidene](3-chloropyridyl) palladium (trivalent) dichloride (PEPPSI™-IPr) (30.0 mg, 44 μmol), 50% solution (1.30 mL, 4.66 mmol) of 2,4,6-trimethylboroxine in tetrahydrofuran, potassium carbonate (260 mg, 1.88 mmol), and the mixture was stirred under microwave radiation with heating at 125° C. for 1 hr. The reaction solution was allowed to cool to room temperature, water was added, and the mixture was extracted with ethyl acetate. The organic layer was washed with saturated brine, dried over anhydrous sodium sulfate, filtered and concentrated under reduced pressure, and the residue was purified by silica gel chromatography to give compound 2 (220 mg).

MS(ESI)m/z: 447(M+1)+.

[Step b]

To a mixed solution of compound 2 (215 mg, 482 μmol) in tetrahydrofuran (4.00 mL) and methanol (2.00 mL) was added 2 M-aqueous sodium hydroxide solution (2.00 mL, 2.00 mmol), and the mixture was stirred at room temperature for 2 hr. The reaction solution was ice-cooled, 0.5 M-hydrochloric acid (9.00 mL) was added, and the mixture was extracted with chloroform. The organic layer was washed with saturated brine, dried over anhydrous sodium sulfate, filtered, and concentrated under reduced pressure. The obtained residue was suspended and washed in ethanol, and the obtained solid was purified by silica gel chromatography to give compound 3 (190 mg, 91.2%).

MS(ESI)m/z: 433(M+1)+.

Example 36

{2-methoxy-5-[6-(3-trifluoromethoxy-benzylamino)-pyridin-3-yl]-benzoylamino}-acetic acid

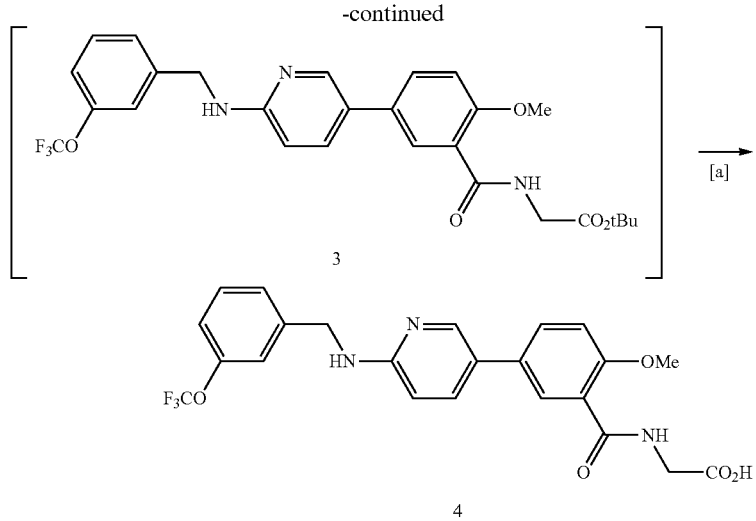

[Step a]

To a solution of compound 1 (40.0 mg, 95.6 μmol) obtained in Example 34, Step b, in dimethylformamide (300 μL) were added hydrochloride of compound 2 (19.3 mg, 115 μmol), 1-ethyl-3-(3-dimethylaminopropyl)carbodiimide hydrochloride (WSC.HCl) (22.0 mg, 115 μmol), 1-hydroxy-7-azabenzotriazole (HOAt) (16.0 mg, 115 μmol), diisopropylethylamine (40.0 μL, 231 μmol), and the mixture was stirred with heating at 40° C. overnight. The reaction solution was concentrated, and the residue was dissolved in dichloromethane (1.00 mL), trifluoroacetic acid (1.00 mL) was added, and the mixture was stirred at room temperature for 1 day. The reaction solution was concentrated, is neutralized with 1 M-aqueous sodium hydroxide solution, and extracted with ethyl acetate. The organic layer was concentrated and purified by reversed-phase HPLC to give compound 4 (6.8 mg, 15.0%).

MS(ESI)m/z: 476(M+1)+.

Example 37

5-{2-methoxy-5-[6-(3-trifluoromethoxy-benzylamino)-pyridin-3-yl]-benzoylamino}-nicotinic acid

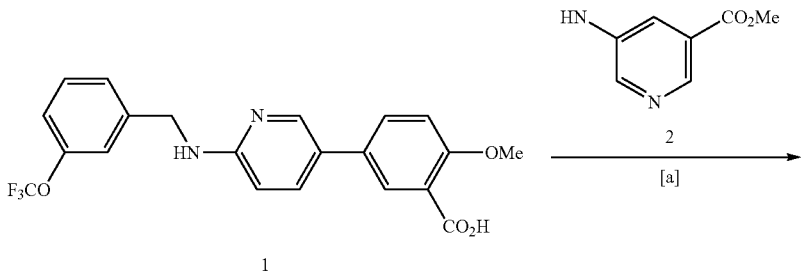

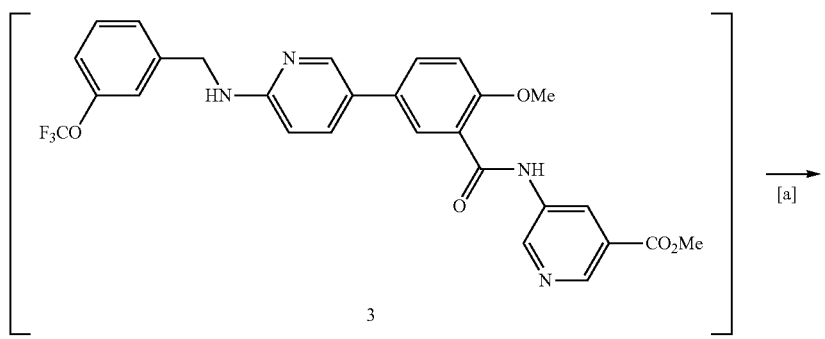

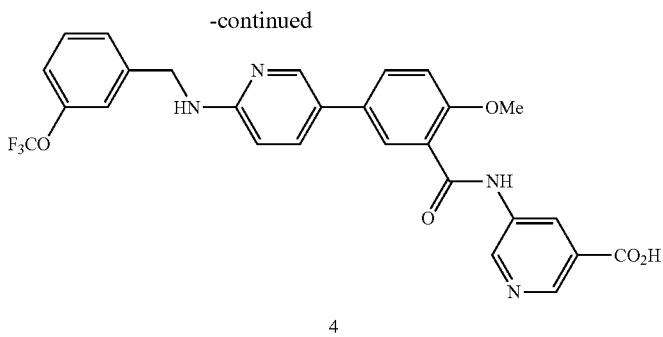

4

[Step a]

To a solution of compound 1 (40.0 mg, 95.6 µmol) obtained in Example 34, Step b, in dimethylformamide (300 µL) were added compound 2 (17.5 mg, 115 µmol), 1-ethyl-3-(3-dimethylaminopropyl)carbodiimide hydrochloride (WSC.HCl) (22.0 mg, 115 µmol), 1-hydroxy-7-azabenzotriazole (HOAt) (16.0 mg, 115 µmol), diisopropylethylamine (40.0 µL, 231 µmol), and the mixture was stirred with heating at 40° C. overnight. The reaction solution was concentrated, and the residue was dissolved in ethanol (1.00 mL), 1 M-aqueous sodium hydroxide solution (77.0 µL) was added, and the mixture was stirred with heating at 80° C. for 1 day. The reaction solution was allowed to cool to room temperature, neutralized with 1 M-hydrochloric acid, and extracted with ethyl acetate. The organic layer was concentrated and purified by reversed-phase HPLC to give compound 4 (15.4 mg, 29.9%).

MS(ESI)m/z: 539(M+1)+.

Example 38

5-{6-[(biphenyl-3-ylmethyl)-amino]-pyridin-3-yl}-2-methoxy-benzoic acid

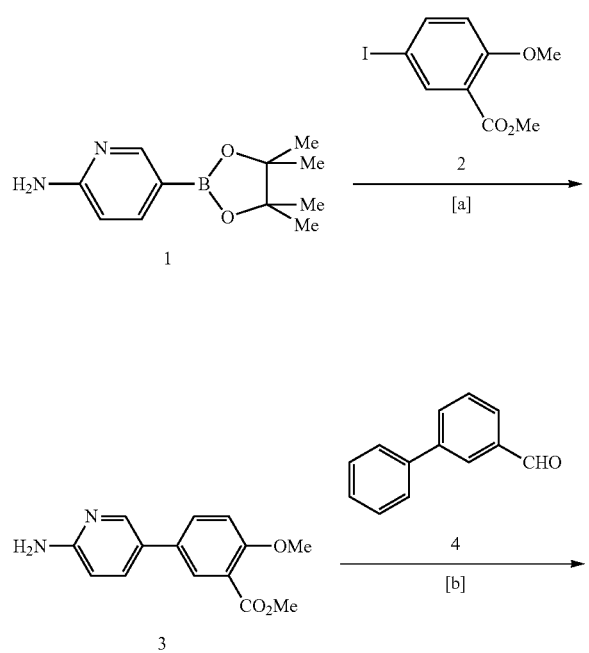

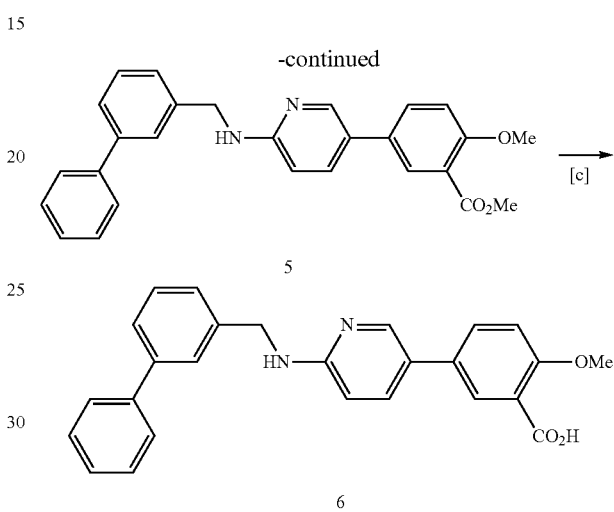

[Step a]

To a mixed solution of compound 1 (320 mg, 1.45 mmol) and compound 2 (510 mg, 1.75 mmol) in dioxane (4.00 mL), acetonitrile (4.00 mL), water (2.00 mL) were added tripotassium phosphate (740 mg, 3.49 mmol), bis(di-tert-butyl (4-dimethylaminophenyl)phosphine)dichloropalladium(II) (50.0 mg, 70.6 µmol), and the mixture was stirred in a nitrogen atmosphere with heating at 90° C. for 3 hr. The reaction solution was allowed to cool to room temperature, 0.2 M-hydrochloric acid (10.0 mL) was added, and the mixture was extracted with ethyl acetate. The organic layer was washed with saturated brine, dried over anhydrous sodium sulfate, filtered and concentrated under reduced pressure, and the residue was purified by silica gel chromatography to give compound 3 (300 mg, 80.1%).

MS(ESI)m/z: 259(M+1)+.

[Step b]

To a solution of compound 3 (90.0 mg, 348 µmol) and compound 4 (95.0 mg, 521 µmol) in dichloromethane (5.00 mL) were added trifluoroacetic acid (33 µL, 431 µmol), sodium triacetoxyborohydride (190 mg, 896 µmol), and the mixture was stirred at room temperature overnight. To the reaction solution were further added compound 4 (95.0 mg, 521 µmol), sodium triacetoxyborohydride (90.0 mg, 424 µmol), and the mixture was stirred at room temperature for 6 hr. To the reaction solution was added saturated aqueous sodium hydrogen carbonate solution (1.00 mL) and the mixture was filtered through a diatomaceous earth column, and the obtained filtrate was concentrated. The residue was purified by silica gel chromatography to give compound 5 (155 mg).

MS(ESI)m/z: 425(M+1)+.

[Step c]

To a mixed solution of compound 5 (150 mg, 348 μmol) in tetrahydrofuran (3.50 mL) and methanol (1.75 mL) was added 2 M-aqueous sodium hydroxide solution (1.75 mL), and the mixture was stirred at room temperature for 3 hr. To the reaction solution was added 0.2 M-hydrochloric acid (19.0 mL) under ice-cooling, the organic solvent in the reaction solution was evaporated by concentration under reduced pressure. The precipitated solid was collected by filtration, and washed with 0.2 M-hydrochloric acid to give compound 6 (130 mg, 91.1%).

MS(ESI)m/z: 411(M+1)+.

Example 39

2-methoxy-5-[6-(3-pyrrolidin-1-yl-benzylamino)-pyridin-3-yl]-benzoic acid

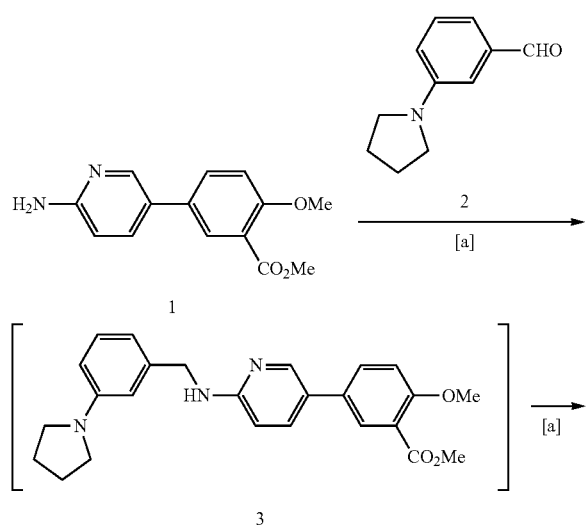

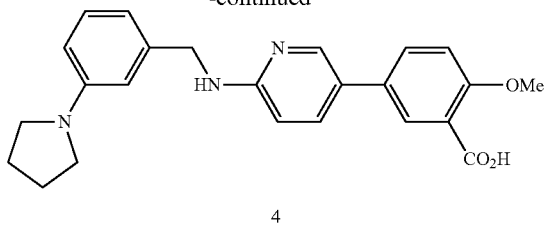

[Step a]

To a solution of compound 1 (135 mg, 523 μmol) which was obtained in Example 38, Step a, and compound 2 (185 mg, 1.05 mmol) in dichloromethane (5.00 mL) were added trifluoroacetic acid (50 μL, 653 μmol), sodium triacetoxyborohydride (330 mg, 1.55 mmol), and the mixture was stirred at room temperature for 1 day. To the reaction solution was added saturated aqueous sodium hydrogen carbonate solution (1.00 mL), and the mixture was filtered through a diatomaceous earth column, and the obtained filtrate was concentrated. The residue was dissolved in a mixed solution of tetrahydrofuran (3.00 mL) and methanol (1.50 mL), 4 M-aqueous sodium hydroxide solution (1.50 mL) was added, and the mixture was stirred at room temperature for 3 hr. To the reaction solution were added 1 M-hydrochloric acid (6.50 mL), water (10.0 mL), the precipitated solid was collected by filtration and suspended and washed in ethyl acetate to give compound 4 (185 mg, 87.7%).

MS(ESI)m/z: 404(M+1)+.

The following compounds were produced according to Production Methods 1-28, Examples, and Reference Examples.

TABLE 1

| Example 41 | 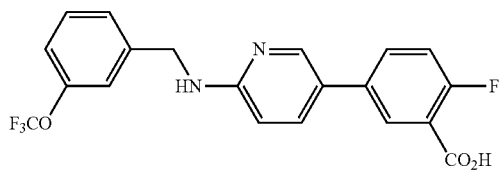 | MS (ESI) m/z: 407 (M + 1)+ |
|---|---|---|
| Example 42 | 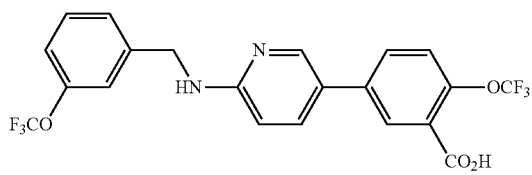 [SMILES: O=C(O)c1cc(-c2ccc(NCc3cccc(OC(F)(F)F)c3)nc2)ccc1OC(F)(F)F] | MS (ESI) m/z: 473 (M + 1)+ |
| Example 43 | 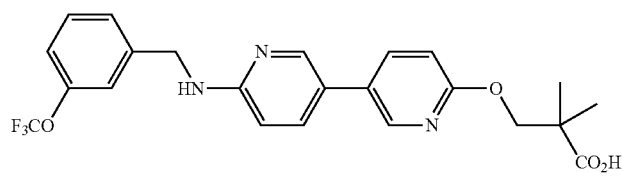 | MS (ESI) m/z: 462 (M + 1)+ |

TABLE 1-continued

| Example | Structure | MS |
|---|---|---|
| Example 44 | 3-F₃CO-benzyl-NH-pyridine-5-yl-(2-fluoro-4-)-phenyl-N-(2-oxoimidazolidin-1-yl)-CH₂CO₂H | MS (ESI) m/z: 505 (M + 1)+ |
| Example 45 | 3-F₃CO-benzyl-NH-pyridine-5-yl-(3-amino-5-)phenyl-CO₂H | MS (ESI) m/z: 404 (M + 1)+. |
| Example 46 | 3-F₃CO-benzyl-NH-pyridine-5-yl-phenyl-(trans-cyclohexyl)-CH₂CO₂H | MS (ESI) m/z: 485 (M + 1)+ |
| Example 47 | 3-F₃CO-benzyl-NH-pyridine-5-yl-phenyl-C(=O)-CH₂-C(CH₃)₂-CO₂H | MS (ESI) m/z: 473 (M + 1)+ |
| Example 48 | 3-F₃CO-benzyl-NH-pyridine-5-yl-cyclohexenyl-CH₂CO₂H | MS (ESI) m/z: 407 (M + 1)+ |
| Example 49 | 3-F₃CO-benzyl-NH-pyridine-5-yl-pyridine-2-CO₂H | MS (ESI) m/z: 309 (M + 1)+ |
| Example 50 | 3-F₃CO-benzyl-NH-pyridine-5-yl-(5-OMe)-pyridine-4-CO₂H | MS (ESI) m/z: 420 (M + 1)+ |

TABLE 2

| Example | Structure | MS |
|---|---|---|
| Example 51 | 3-F₃CO-benzyl-NH-pyridine-5-yl-(4-Cl-3-CO₂H)-phenyl | MS (APCI) m/z: 423, 425 (M + 1)+ |

TABLE 2-continued

| Example | Structure | MS |
|---|---|---|
| Example 52 | (structure) | MS (APCI) m/z: 403 (M + 1)+ |
| Example 53 | (structure) | MS (ESI) m/z: 420 (M + 1)+ |
| Example 54 | (structure) | MS (ESI) m/z: 420 (M + 1)+ |
| Example 55 | (structure) | MS (ESI) m/z: 433 (M + 1)+ |
| Example 56 | (structure) | MS (ESI) m/z: 433 (M + 1)+ |
| Example 57 | (structure) | MS (ESI) m/z: 431 (M + 1)+ |
| Example 58 | (structure) | MS (ESI) m/z: 420 (M + 1)+ |
| Example 59 | (structure) | MS (ESI) m/z: 437 (M + 1)+ |

TABLE 2-continued
| Example 60 | 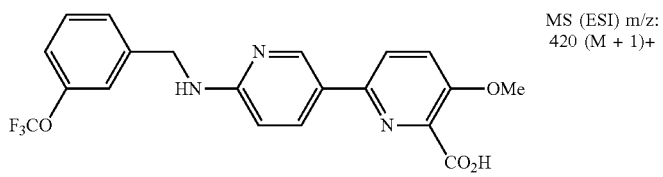 | MS (ESI) m/z: 420 (M + 1)+ |
TABLE 3
| Example 61 | 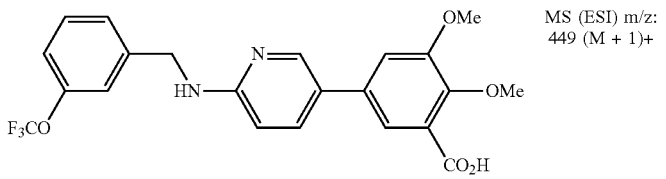 | MS (ESI) m/z: 449 (M + 1)+ |
| Example 62 | 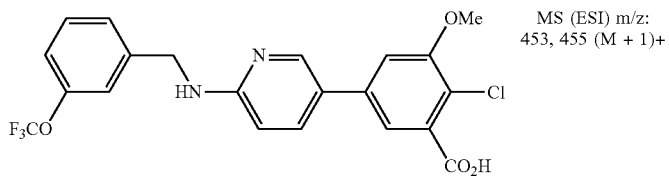 | MS (ESI) m/z: 453, 455 (M + 1)+ |
| Example 63 | 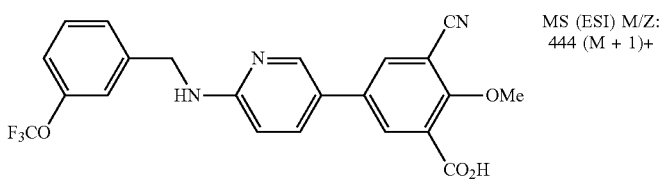 | MS (ESI) M/Z: 444 (M + 1)+ |
| Example 64 | 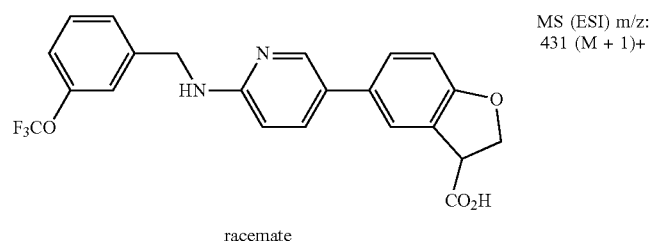 racemate | MS (ESI) m/z: 431 (M + 1)+ |
| Example 65 | 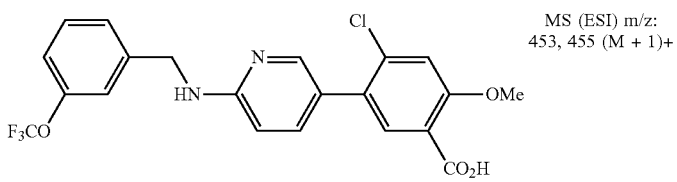 | MS (ESI) m/z: 453, 455 (M + 1)+ |
| Example 66 | 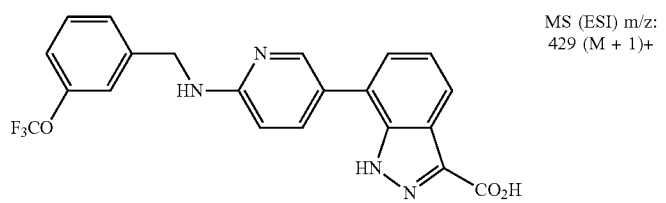 | MS (ESI) m/z: 429 (M + 1)+ |

TABLE 3-continued
| Example 67 | 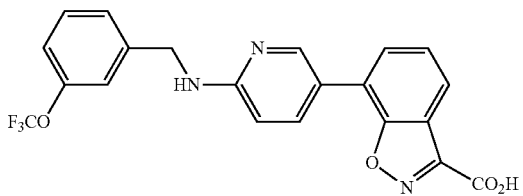 [SMILES: O=C(O)c1noc2c(-c3ccc(NCc4cccc(OC(F)(F)F)c4)nc3)cccc12] | MS (ESI) m/z: 430 (M + 1)+ |
| Example 68 | 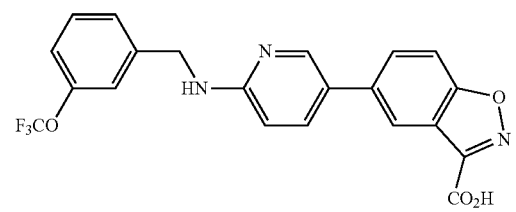 [SMILES: O=C(O)c1noc2ccc(-c3ccc(NCc4cccc(OC(F)(F)F)c4)nc3)cc12] | MS (ESI) m/z: 430 (M + 1)+ |
| Example 69 | 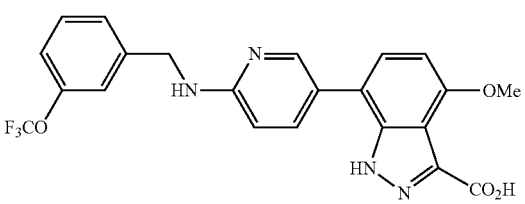 [SMILES: COc1ccc(-c2ccc(NCc3cccc(OC(F)(F)F)c3)nc2)c2[nH]nc(C(=O)O)c12] | MS (ESI) m/z: 459 (M + 1)+ |
TABLE 4
| Example 70 | 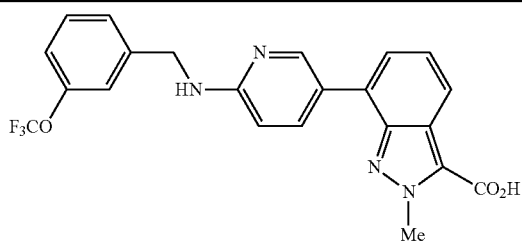 | MS (ESI) m/z: 443 (M + 1)+ |
| Example 71 | 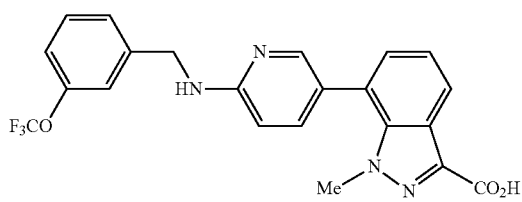 [SMILES: Cn1nc(C(=O)O)c2cccc(-c3ccc(NCc4cccc(OC(F)(F)F)c4)nc3)c21] | MS (ESI) m/z: 443 (M + 1)+ |
| Example 72 | 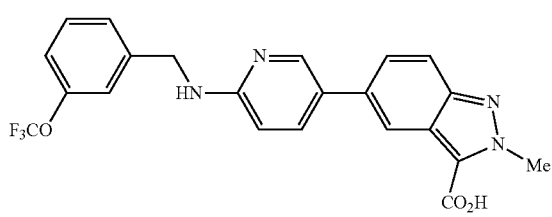 [SMILES: Cn1nc2ccc(-c3ccc(NCc4cccc(OC(F)(F)F)c4)nc3)cc2c1C(=O)O] | MS (ESI) m/z: 443 (M + 1)+ |
| Example 73 | 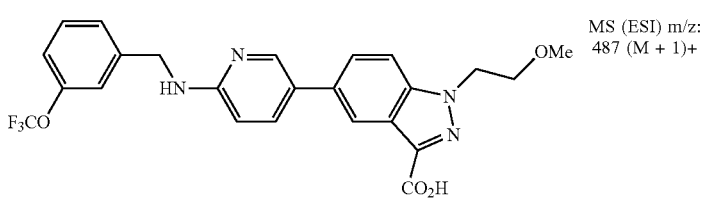 | MS (ESI) m/z: 487 (M + 1)+ |

TABLE 4-continued
| Example 74 | 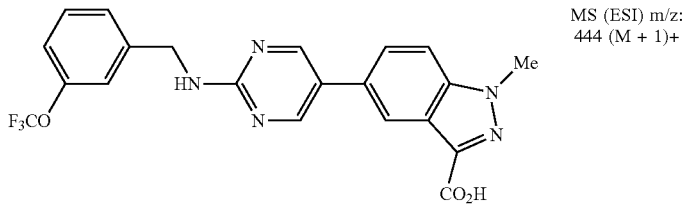 | MS (ESI) m/z: 444 (M + 1)+ |
| Example 75 | 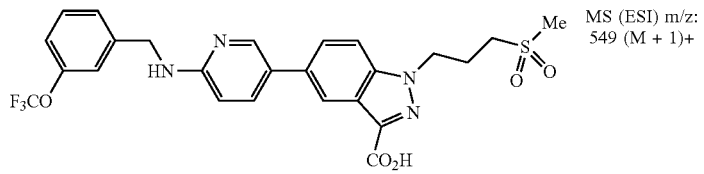 | MS (ESI) m/z: 549 (M + 1)+ |
| Example 76 | 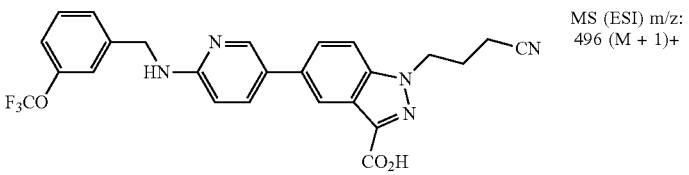 | MS (ESI) m/z: 496 (M + 1)+ |
| Example 77 | 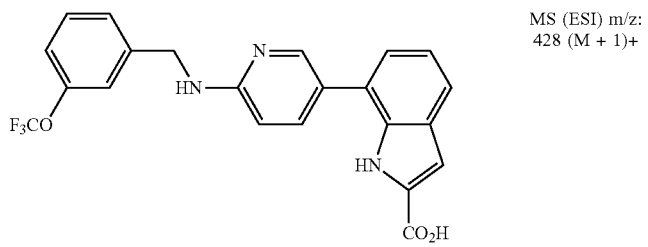 | MS (ESI) m/z: 428 (M + 1)+ |
TABLE 5
| Example 78 | 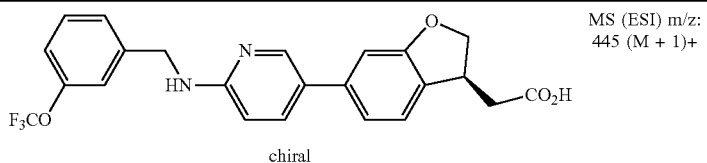 chiral | MS (ESI) m/z: 445 (M + 1)+ |
| Example 79 | 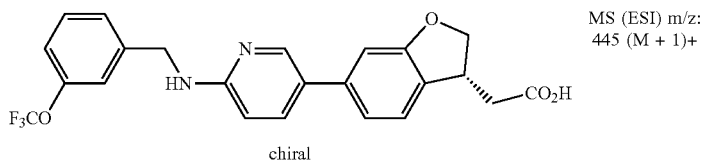 chiral | MS (ESI) m/z: 445 (M + 1)+ |
| Example 80 | 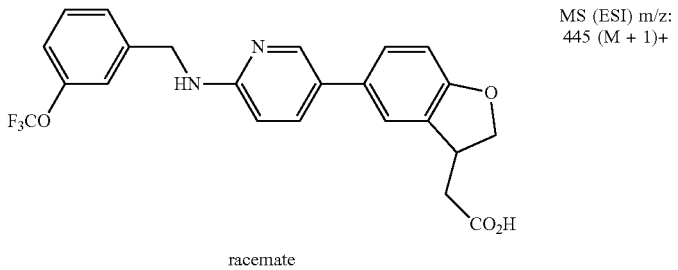 racemate | MS (ESI) m/z: 445 (M + 1)+ |

TABLE 5-continued
| Example 81 | 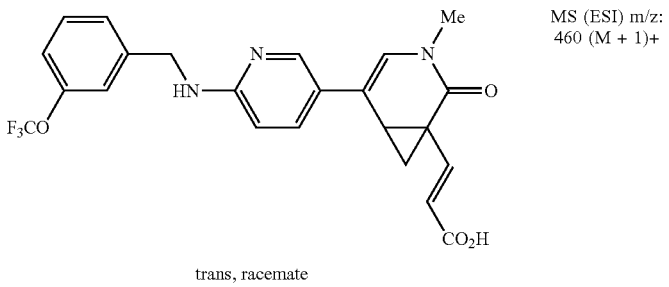 trans, racemate | MS (ESI) m/z: 460 (M + 1)+ |
| --- | --- | --- |
| Example 82 | 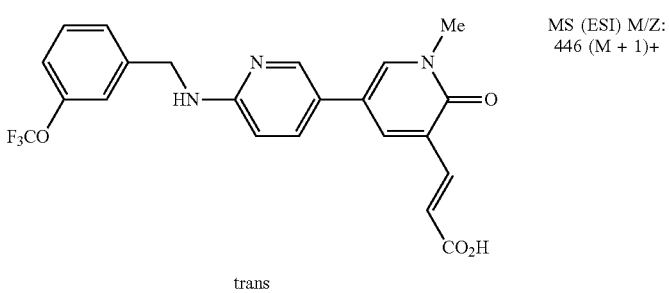 trans | MS (ESI) M/Z: 446 (M + 1)+ |
| Example 83 | 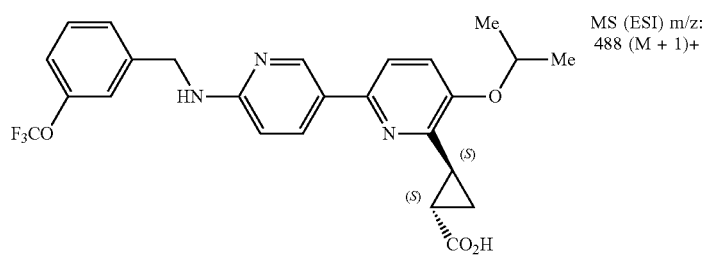 | MS (ESI) m/z: 488 (M + 1)+ |
| Example 84 | 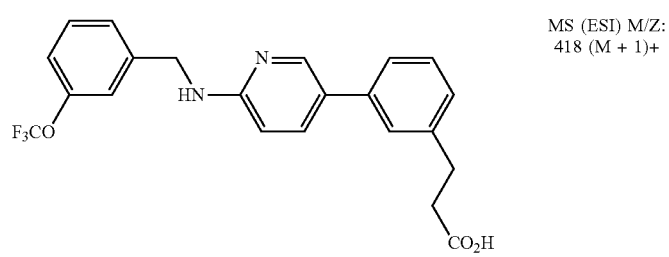 | MS (ESI) M/Z: 418 (M + 1)+ |
TABLE 6
| Example 85 | 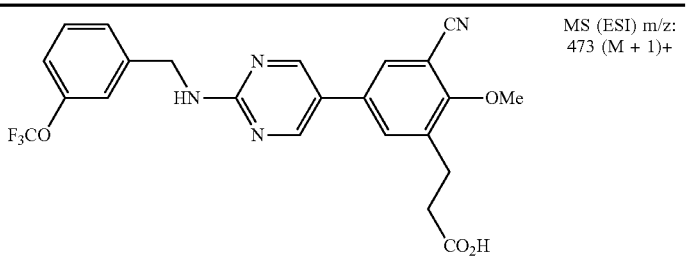 | MS (ESI) m/z: 473 (M + 1)+ |
| --- | --- | --- |

TABLE 6-continued
| | | |
|---|---|---|
| Example 86 | 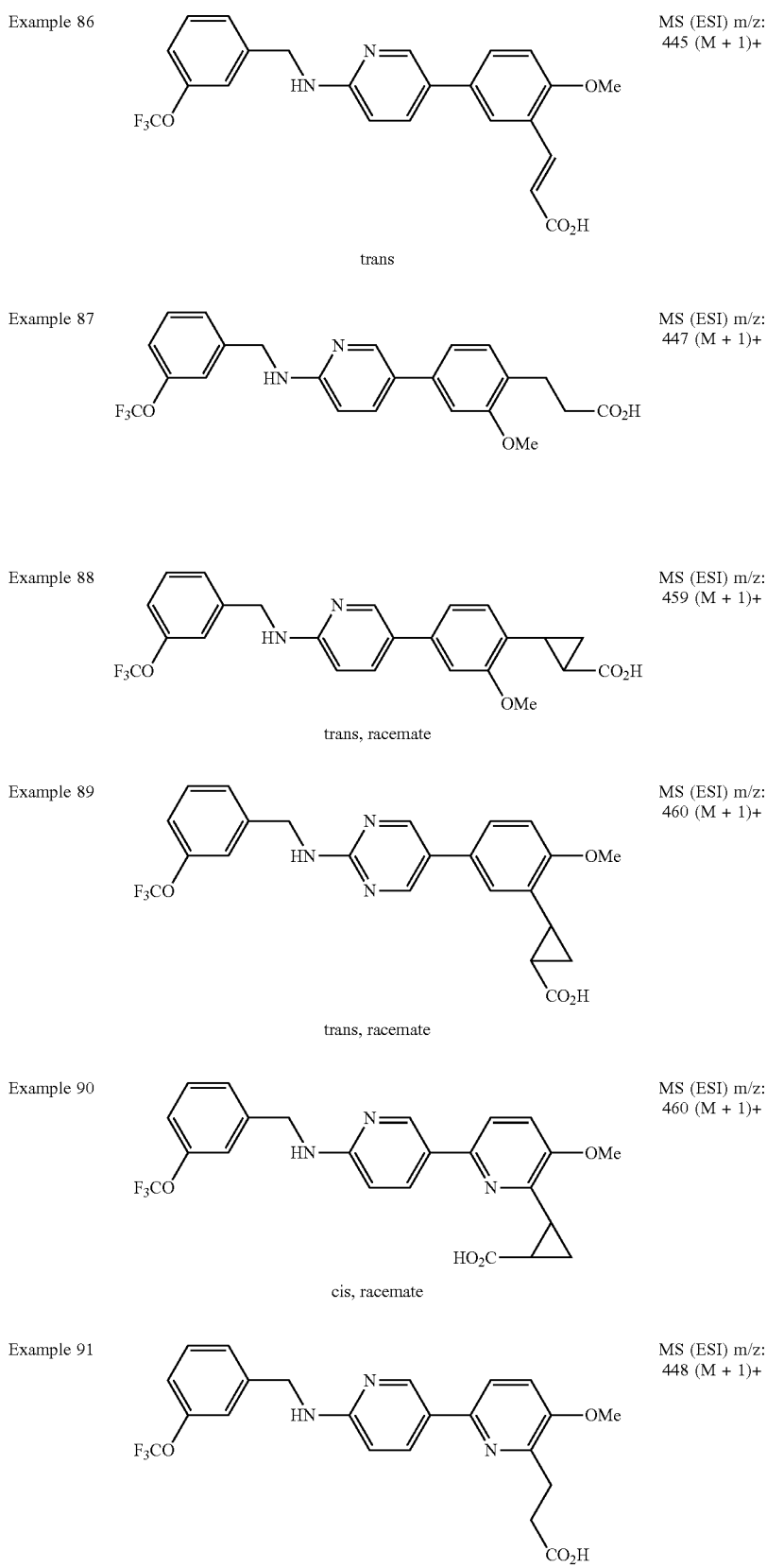 | MS (ESI) m/z: 445 (M + 1)+ |
| | trans | |
| Example 87 | | MS (ESI) m/z: 447 (M + 1)+ |
| Example 88 | | MS (ESI) m/z: 459 (M + 1)+ |
| | trans, racemate | |
| Example 89 | | MS (ESI) m/z: 460 (M + 1)+ |
| | trans, racemate | |
| Example 90 | | MS (ESI) m/z: 460 (M + 1)+ |
| | cis, racemate | |
| Example 91 | | MS (ESI) m/z: 448 (M + 1)+ |

TABLE 7
| Example 92 | 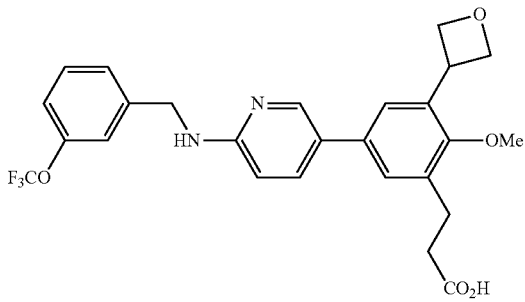 [SMILES: COc1c(CCC(=O)O)cc(-c2ccc(NCc3cccc(OC(F)(F)F)c3)nc2)cc1C1COC1] | MS (ESI) m/z: 503 (M + 1)+ |
| --- | --- | --- |
| Example 93 | 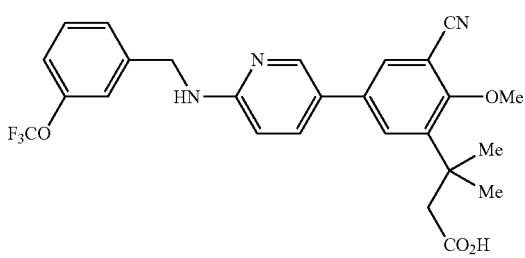 [SMILES: COc1c(C#N)cc(-c2ccc(NCc3cccc(OC(F)(F)F)c3)nc2)cc1C(C)(C)CC(=O)O] | MS (ESI) m/z: 500 (M + 1)+ |
| Example 94 | 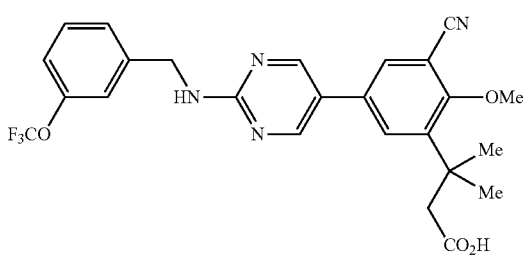 [SMILES: COc1c(C#N)cc(-c2cnc(NCc3cccc(OC(F)(F)F)c3)nc2)cc1C(C)(C)CC(=O)O] | MS (ESI) m/z: 501 (M + 1)+ |
| Example 95 | 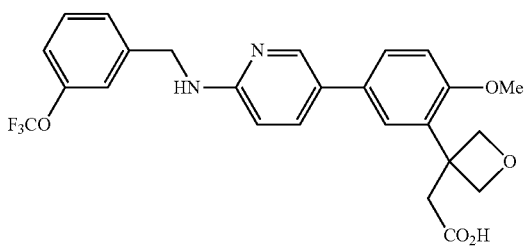 [SMILES: COc1ccc(-c2ccc(NCc3cccc(OC(F)(F)F)c3)nc2)cc1C1(CC(=O)O)COC1] | MS (ESI) m/z: 489 (M + 1)+ |
| Example 96 | 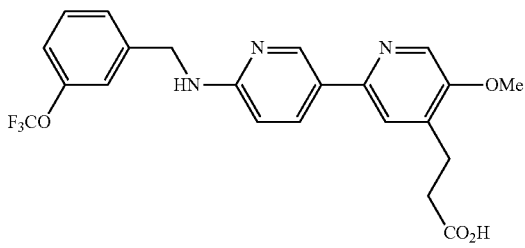 | MS (ESI) m/z: 448 (M + 1)+ |
| Example 97 | 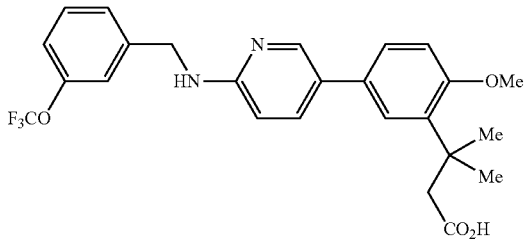 [SMILES: COc1ccc(-c2ccc(NCc3cccc(OC(F)(F)F)c3)nc2)cc1C(C)(C)CC(=O)O] | MS (ESI) m/z: 475 (M + 1)+ |

TABLE 7-continued
| Example 98 |  | MS (ESI) m/z: 477 (M + 1)+ |
TABLE 8
| Example 99 | 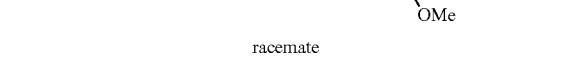 racemate | MS (ESI) m/z: 491 (M + 1)+ |
| Example 100 | 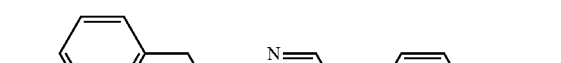 | MS (ESI) m/z: 403 (M + 1)+ |
| Example 101 | 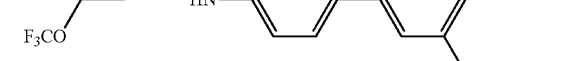 | MS (ESI) m/z: 449 (M + 1)+ |
| Example 102 |  | MS (ESI) m/z: 462 (M + 1)+ |
| Example 103 |  | MS (ESI) m/z: 460 (M + 1)+ |
| Example 104 |  | MS (ESI) m/z: 463 (M + 1)+ |

TABLE 8-continued

| Example 105 | (structure) | MS (ESI) m/z: 461 (M + 1)+ |
| Example 106 | (structure) | MS (ESI) m/z: 462 (M + 1)+ |

TABLE 9

| Example 107 | (structure) | MS (ESI) m/z: 541 (M + 1)+ |
| Example 108 | (structure) | MS (ESI) m/z: 541 (M + 1)+ |
| Example 109 | (structure) | MS (ESI) m/z: 433 (M + 1)+ |
| Example 110 | (structure) | MS (ESI) m/z: 459 (M + 1)+ |
| Example 111 | (structure) | MS (ESI) m/z: 462 (M + 1)+ |

TABLE 9-continued
| Example 112 | 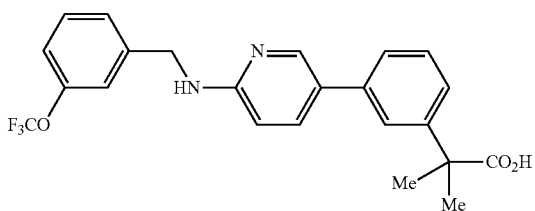 | MS (ESI) m/z: 431 (M + 1)+ |
| Example 113 | 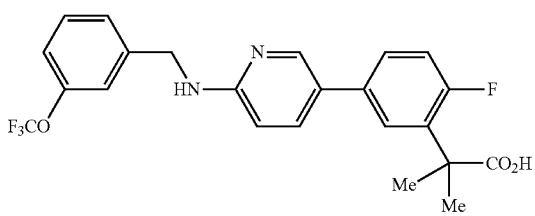 [SMILES: COc1cnc(-c2ccc(NCc3cccc(OC(F)(F)F)c3)nc2)cc1C(C)(C)C(=O)O] | MS (ESI) m/z: 449 (M + 1)+ |
| Example 114 | 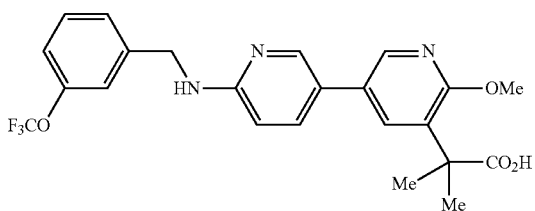 | MS (ESI) m/z: 462 (M + 1)+ |
TABLE 10
| Example 115 | 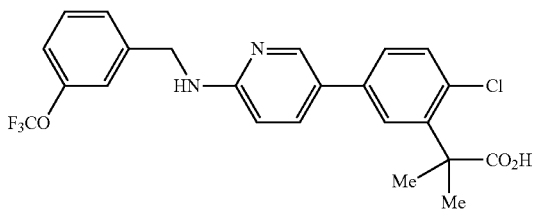 [SMILES: CC(C)(C(=O)O)c1cc(-c2ccc(NCc3cccc(OC(F)(F)F)c3)nc2)ccc1F] | MS (ESI) m/z: 465 (M + 1)+ |
| Example 116 | 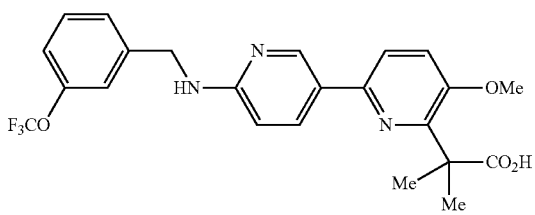 [SMILES: COc1ccc(-c2ccc(NCc3cccc(OC(F)(F)F)c3)nc2)nc1C(C)(C)C(=O)O] | MS (ESI) m/z: 462 (M + 1)+ |
| Example 117 | 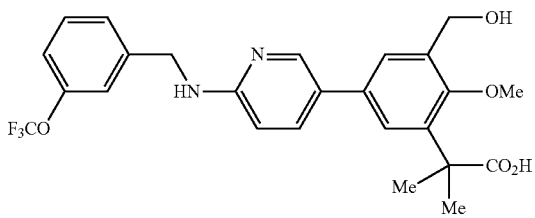 [SMILES: COc1c(CO)cc(-c2ccc(NCc3cccc(OC(F)(F)F)c3)nc2)cc1C(C)(C)C(=O)O] | MS (ESI) m/z: 491 (M + 1)+ |
| Example 118 | 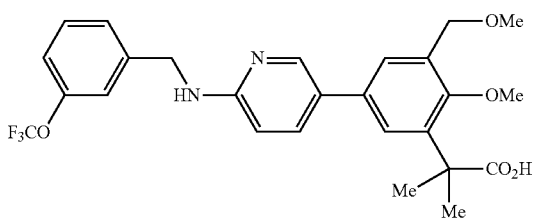 [SMILES: COc1c(CC(=O)O)cc(-c2ccc(NCc3cccc(OC(F)(F)F)c3)nc2)cc1C(C)(C)C(=O)O] | MS (ESI) m/z: 505 (M + 1)+ |

TABLE 10-continued

| Example 119 | (structure) | MS (ESI) m/z: 572 (M + 1)+ |
| Example 120 | (structure) | MS (ESI) m/z: 493 (M + 1)+ |
| Example 121 | (structure) | MS (ESI) m/z: 505 (M + 1)+ |
| Example 122 | (structure) | MS (ESI) m/z: 518 (M + 1)+ |

TABLE 11

| Example 123 | (structure) | MS (ESI) m/z: 532 (M + 1)+ |
| Example 124 | (structure) | MS (ESI) m/z: 519 (M + 1)+ |

TABLE 11-continued

| Example 125 | (structure: 3-F3CO-benzyl-NH-pyridine-phenyl(OMe)-tetrazole-CH2-CO2H) | MS (ESI) m/z: 501 (M + 1)+ |
| --- | --- | --- |
| Example 126 | (structure: 3-F3CO-benzyl-NH-pyridine-phenyl(OMe)-O-CH2-cyclohexyl(trans)-CO2H) | MS (ESI) m/z: 531 (M + 1)+ |
| | trans | |
| Example 127 | (structure: 3-F3CO-benzyl-NH-pyridine-phenyl-O-C(Me)(Me)-CO2H) | MS (ESI) m/z: 461 (M + 1)+ |
| Example 128 | (structure: 3-F3CO-benzyl-NH-pyrimidine-phenyl(OMe)-O-CH2-CO2H) | MS (ESI) m/z: 450 (M + 1)+ |
| Example 129 | (structure: 3-F3CO-benzyl-NH-pyridine-phenyl(OMe)-O-CH2-CO2H) | MS (APCI) m/z: 449 (M + 1)+ |
| Example 130 | (structure: 3-F3CO-benzyl-NH-pyridine-phenyl(OMe)-O-C(Me)(Me)-CO2H) | MS (APCI) m/z: 477 (M + 1)+ |

TABLE 12

| Example 131 | (structure: 3-F3CO-benzyl-NH-pyridine-phenyl(OMe)-O-CH(Me)-CO2H) | MS (APCI) m/z: 463 (M + 1)+ |
| --- | --- | --- |
| | racemate | |

TABLE 12-continued
| Example 132 | 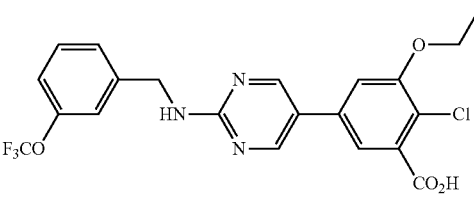 | MS (ESI) m/z: 498, 500 (M + 1)+ |
| Example 133 | 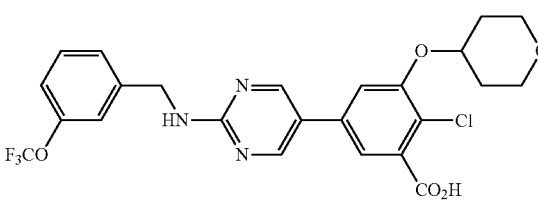 | MS (ESI) m/z: 524, 526 (M + 1)+ |
| Example 134 | 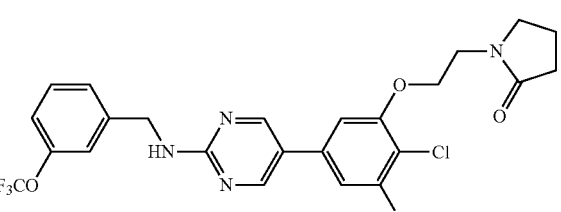 | MS (ESI) m/z: 551, 553 (M + 1)+ |
| Example 135 | 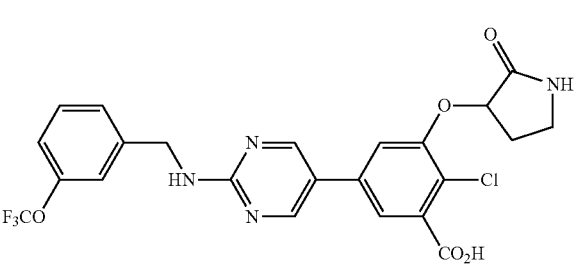<br>racemate | MS (ESI) m/z: 523, 525 (M + 1)+ |
| Example 136 | 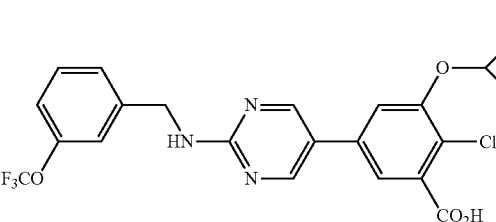 | MS (ESI) m/z: 496, 498 (M + 1)+ |
| Example 137 | 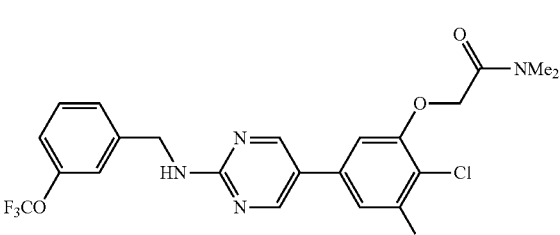 | MS (ESI) m/z: 525, 527 (M + 1)+ |
| Example 138<br>Na salt | 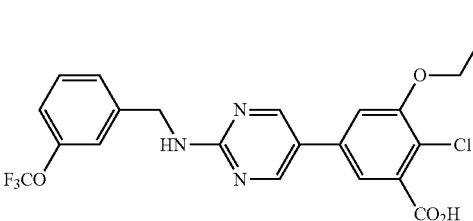 | MS (ESI) m/z: 511, 513 (M + 1)+ |

TABLE 13
| Example 139 Na salt | 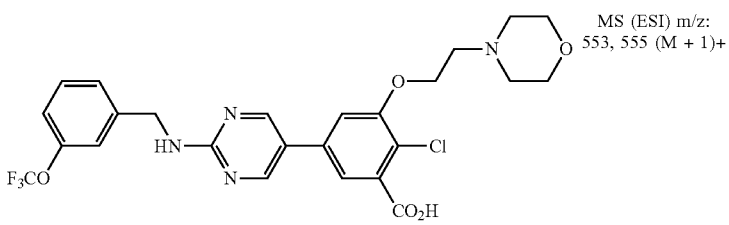 | MS (ESI) m/z: 553, 555 (M + 1)+ |
| --- | --- | --- |
| Example 140 | 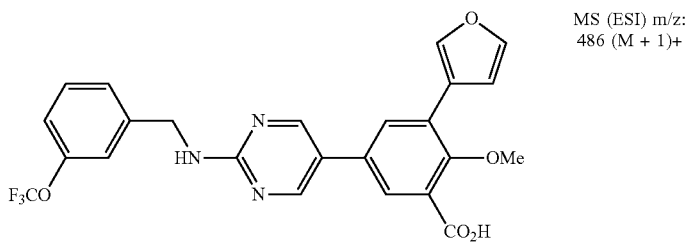 | MS (ESI) m/z: 486 (M + 1)+ |
| Example 141 | 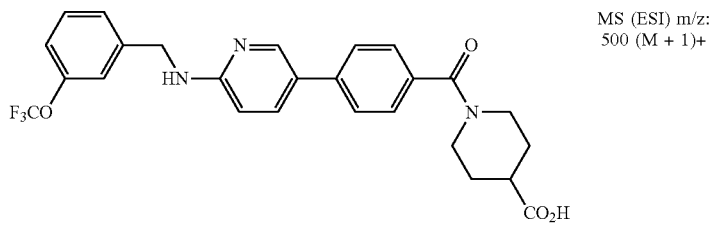 | MS (ESI) m/z: 500 (M + 1)+ |
| Example 142 | 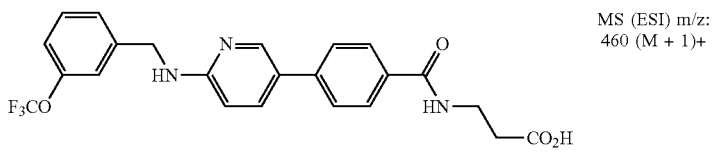 | MS (ESI) m/z: 460 (M + 1)+ |
| Example 143 | 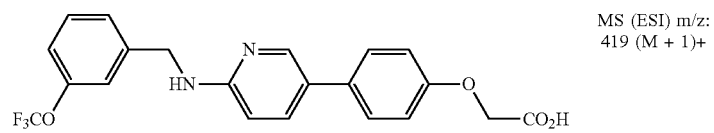 | MS (ESI) m/z: 419 (M + 1)+ |
| Example 144 | 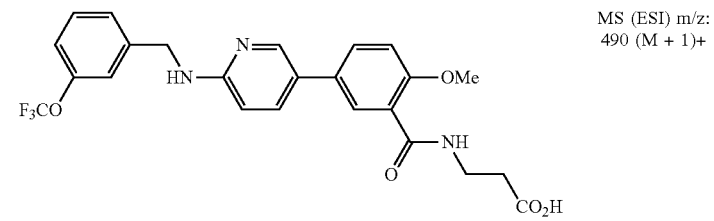 | MS (ESI) m/z: 490 (M + 1)+ |
| Example 145 | 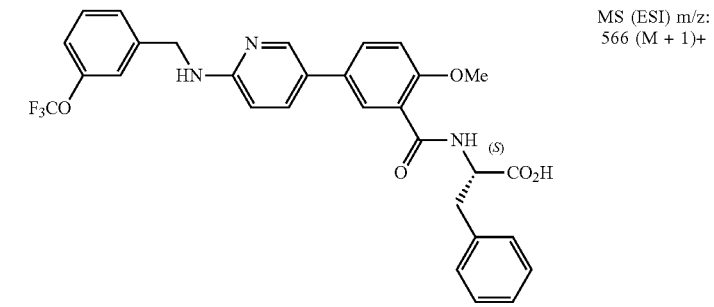 | MS (ESI) m/z: 566 (M + 1)+ |

TABLE 14

| Example 146 | (structure) | MS (ESI) m/z: 516 (M + 1)+ |
| Example 147 | (structure) | MS (ESI) m/z: 506 (M + 1)+ |
| Example 148 | (structure) | MS (ESI) m/z: 518 (M + 1)+ |
| Example 149 | (structure) | MS (ESI) m/z: 530 (M + 1)+ |
| Example 150 | (structure) racemate | MS (ESI) m/z: 530 (M + 1)+ |
| Example 151 | (structure) racemate | MS (ESI) m/z: 490 (M + 1)+ |

TABLE 14-continued
| Example 152 | 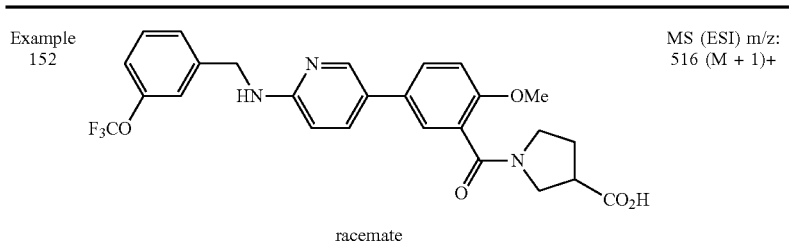 racemate | MS (ESI) m/z: 516 (M + 1)+ |
TABLE 15
| Example 153 | 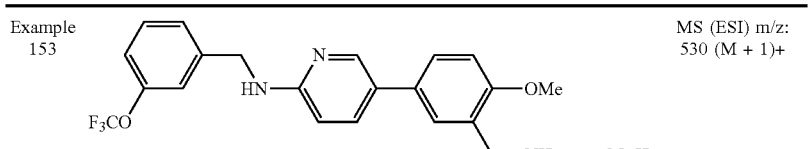 cis, racemate | MS (ESI) m/z: 530 (M + 1)+ |
| Example 154 | 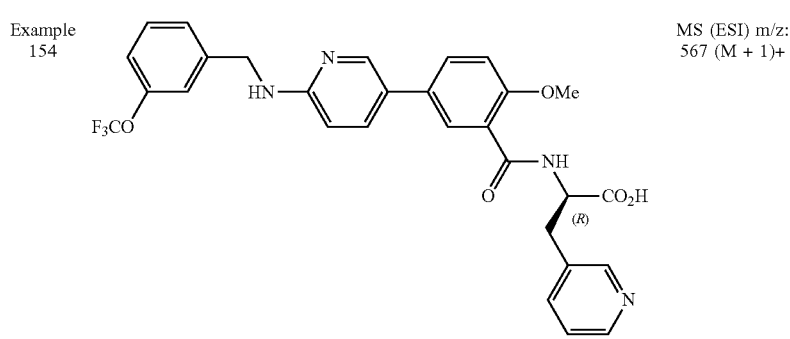 | MS (ESI) m/z: 567 (M + 1)+ |
| Example 155 | 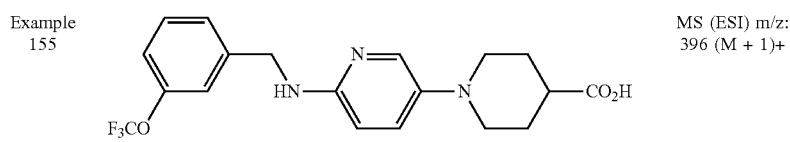 | MS (ESI) m/z: 396 (M + 1)+ |
| Example 156 | 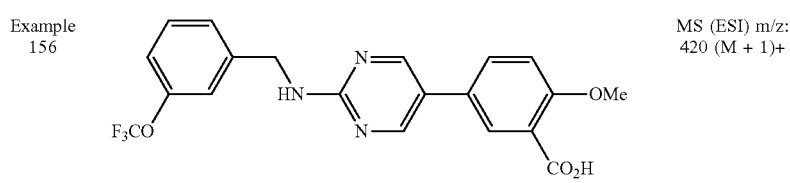 | MS (ESI) m/z: 420 (M + 1)+ |
| Example 157 | 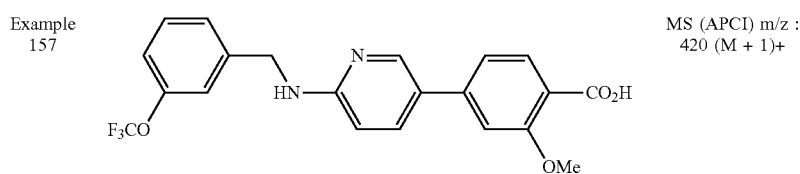 | MS (APCI) m/z: 420 (M + 1)+ |
| Example 158 | 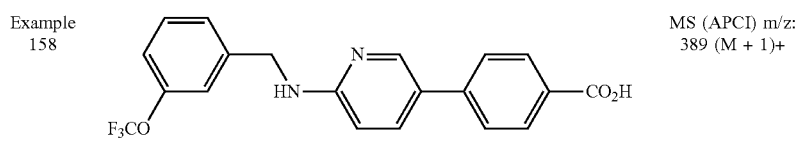 | MS (APCI) m/z: 389 (M + 1)+ |

TABLE 15-continued

| Example 159 | (3-trifluoromethoxybenzyl)amino-pyridine-phenyl-CO2H structure | MS (APCI) m/z: 389 (M + 1)+ |
| Example 160 | (3-trifluoromethoxybenzyl)amino-fluoropyridine-methoxyphenyl-CO2H structure | MS (APCI) m/z: 437 (M + 1)+ |
| Example 161 | (3-trifluoromethoxybenzyl)amino-chloropyridine-methoxyphenyl-CO2H structure | MS (ECI) m/z: 453, 455 (M + 1)+ |

TABLE 16

| Example 162 | (3-chlorobenzyl)amino-pyridine-methoxyphenyl-CO2H structure | MS (ECI) m/z: 369, 371 (M + 1)+ |
| Example 163 | (3-cyanobenzyl)amino-pyridine-methoxyphenyl-CO2H structure | MS (ECI) m/z: 360 (M + 1)+ |
| Example 164 | (pyridin-4-ylmethyl)amino-pyridine-methoxyphenyl-CO2H structure | MS (ECI) m/z: 336 (M + 1)+ |
| Example 165 | [3-(3,5-dimethylpyrazol-1-yl)benzyl]amino-pyridine-methoxyphenyl-CO2H structure | MS (ECI) m/z: 429 (M + 1)+ |
| Example 166 | (3-trifluoromethylbenzyl)amino-pyridine-methoxyphenyl-CO2H structure | MS (ECI) m/z: 403 (M + 1)+ |

TABLE 16-continued
| Example 167 | 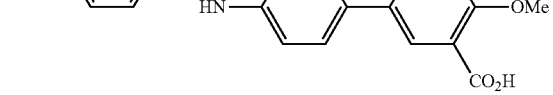 | MS (ECI) m/z: 403 (M + 1)+ |
| Example 168 | | MS (ECI) m/z: 403 (M + 1)+ |
| Example 169 | | MS (ECI) m/z: 393 (M + 1)+ |
| Example 170 | | MS (ECI) m/z: 437 (M + 1)+ |
TABLE 17
| Example 171 | 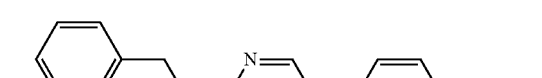 | MS (ECI) m/z: 453, 455 (M + 1)+ |
| Example 172 | | MS (ECI) m/z: 453, 455 (M + 1)+ |
| Example 173 | | MS (ECI) m/z: 433 (M + 1)+ |

TABLE 17-continued

| Example 174 | (structure: 3-F₃CO, 2-F benzyl-NH-pyridine-phenyl with OMe and CO₂H) | MS (ECI) m/z: 437 (M + 1)+ |
| --- | --- | --- |
| Example 175 | (structure: 4-F, 3-F₃CO benzyl-NH-pyridine-phenyl with OMe and CO₂H) | MS (ECI) m/z: 437 (M + 1)+ |
| Example 176 | (structure: 3-(1-Me-ethyl) benzyl-NH-pyridine-phenyl with OMe and CO₂H) | MS (ECI) m/z: 377 (M + 1)+ |

Example 177

(1S,2S)-2-[5-cyano-6'-(3-trifluoromethoxy-benzylamino)-[2,3']bipyridinyl-6-yl]-cyclopropanecarboxylic acid

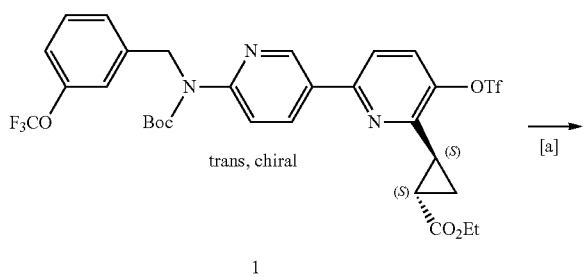

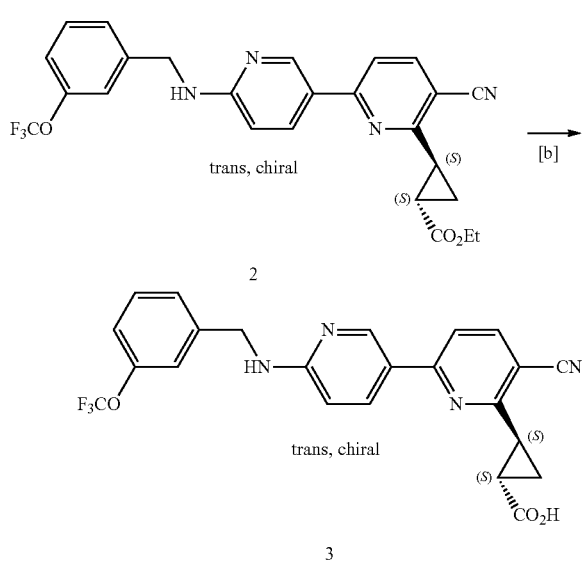

[Step a]

To a solution of compound 1 (105 mg, 149 μmol) obtained in Example 20, Step d, in N-methylpyrrolidone (1.5 mL) were added zinc cyanide (50 mg, 426 μmol), 1,1'-bis(diphenylphosphino)ferrocene (DPPF) (17 mg, 30.7 μmol), tris(dibenzylideneacetone)dipalladium(0) (14 mg, 15.3 μmol), and the mixture was stirred in a nitrogen atmosphere with heating at 100° C. for 2.5 hr. The reaction solution was allowed to cool to room temperature, ethyl acetate (15 mL) and water (15 mL) were added, and the mixture was filtered through celite, washed with water and ethyl acetate, and the obtained filtrate was extracted with ethyl acetate. The organic layer was washed with water and saturated brine, dried over anhydrous sodium sulfate, filtered, and concentrated under reduced pressure. The residue was dissolved in dichloromethane (3 mL), trifluoroacetic acid (600 μL) was added, and the mixture was stirred at room temperature for 3.5 hr. The reaction solution was ice-cooled, saturated aqueous sodium hydrogen carbonate solution was added, and the mixture was extracted with chloroform. The organic layer was washed with saturated brine, dried over anhydrous sodium sulfate, filtered, and concentrated under reduced pressure. The residue was purified by silica gel chromatography to give compound 2 (52 mg, 72.5%).

MS(ESI)m/z: 483(M+1)+.

[Step b]

To a mixed solution of compound 2 (50 mg, 104 μmol) in tetrahydrofuran (2 mL), methanol (1 mL) was added 2 M-aqueous sodium hydroxide solution (1 mL), and the mixture was stirred at room temperature for 1.5 hr. To the reaction solution was added 0.5 M-hydrochloric acid (4.5 mL) under ice-cooling, and the mixture was extracted with chloroform. The organic layer was washed with saturated brine, dried over anhydrous sodium sulfate, filtered, and concentrated under reduced pressure. The residue was purified by silica gel chromatography to give compound 3 (42 mg, 88.9%).

MS(ESI)m/z: 455(M+1)+.

Example 178

(1S,2S)-2-[6'-(3-trifluoromethoxy-benzylamino)-[2,3']bipyridinyl-6-yl]-cyclopropanecarboxylic acid

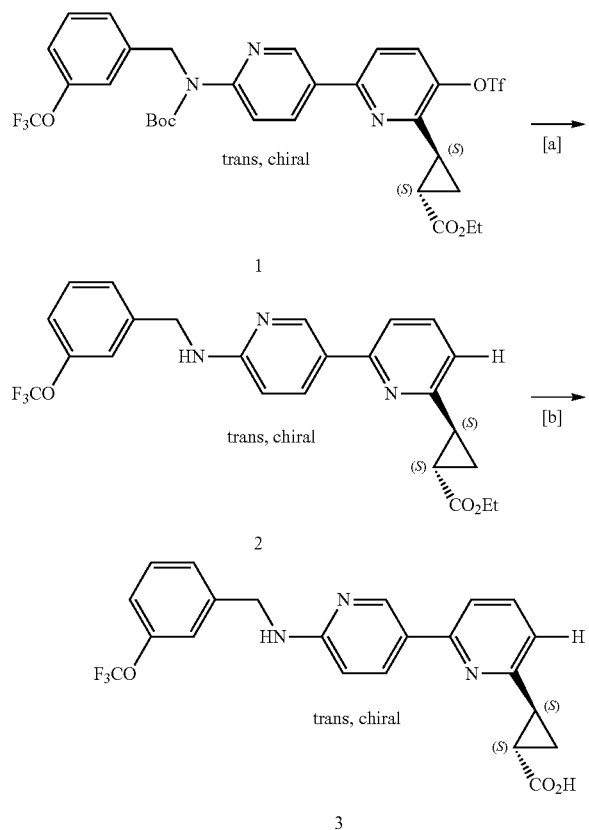

[Step a]

To a solution of compound 1 (100 mg, 142 μmol) obtained in Example 20, Step d, in N,N-dimethylformamide (1.4 mL) were added 1,3-bis(diphenylphosphino)propane (DPPP) (2.9 mg, 7.1 μmol), palladium(II) acetate (1.6 mg, 7.1 μmol), formic acid (11 μL, 284 μmol), triethylamine (59 μL, 426 μmol), and the mixture was stirred in a nitrogen atmosphere with heating at 80° C. for 1 hr. The reaction solution was allowed to cool to room temperature, ethyl acetate (15 mL) and water (8 mL) were added, and the mixture was filtered through celite, washed with water and ethyl acetate, and the obtained filtrate was extracted with ethyl acetate. The organic layer was washed with saturated brine, dried over anhydrous sodium sulfate, filtered, and concentrated under reduced pressure. To a solution of the residue in dichloromethane (1 mL) was added trifluoroacetic acid (500 μL) under ice-cooling, and the mixture was stirred for 2 hr while raising the temperature to room temperature. The reaction solution was ice-cooled, saturated aqueous sodium hydrogen carbonate solution (3.00 mL) was added, and the mixture was extracted with ethyl acetate. The organic layer was washed with saturated brine, dried over anhydrous sodium sulfate, filtered, and concentrated under reduced pressure. The residue was purified by solid phase extraction using a cation exchange resin column (Waters, PoraPak™, RxnCX) to give compound 2 (59.0 mg, 90.9%).

MS(ESI)m/z: 458(M+1)+.

[Step b]

To a mixed solution of compound 2 (59.0 mg, 130 μmol) in tetrahydrofuran (600 μL), methanol (300 μL) was added 4 M-aqueous sodium hydroxide solution (300 μL), and the mixture was stirred at room temperature for 3.5 hr. To the reaction solution was added 1 M-hydrochloric acid (1.2 mL) under ice-cooling, and the mixture was extracted with ethyl acetate. The organic layer was washed with saturated brine, dried over anhydrous sodium sulfate, filtered and concentrated under reduced pressure. The residue was subjected to solid phase extraction purification using a cation exchange resin column (Waters, PoraPak™, RxnCX) and suspended and washed in a mixed solution of diisopropyl ether and hexane (1:1) to give compound 3 (53.0 mg, 95.0%).

MS(ESI)m/z: 430(M+1)+.

Example 179

3-{trans-4-[6-(3-trifluoromethoxy-benzylamino)-pyridin-3-yl]-tetrahydropyran-2-yl}propionic acid

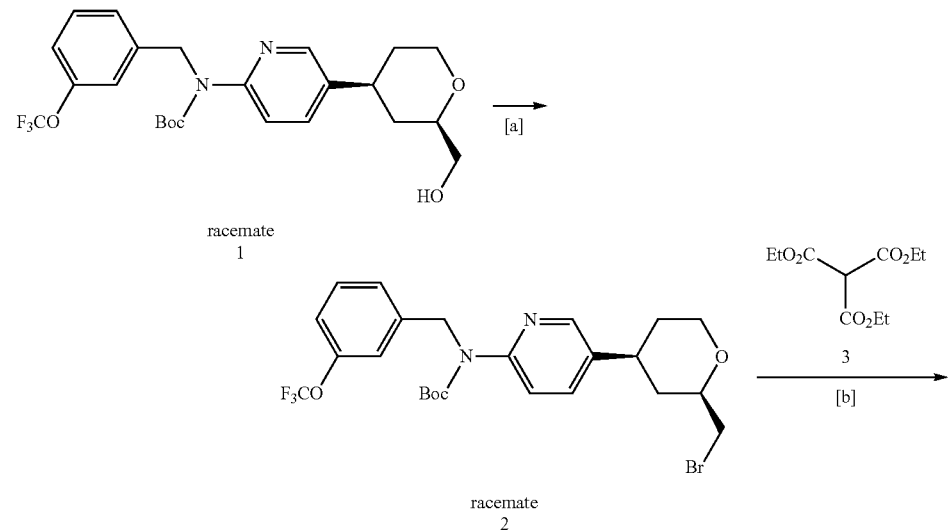

-continued

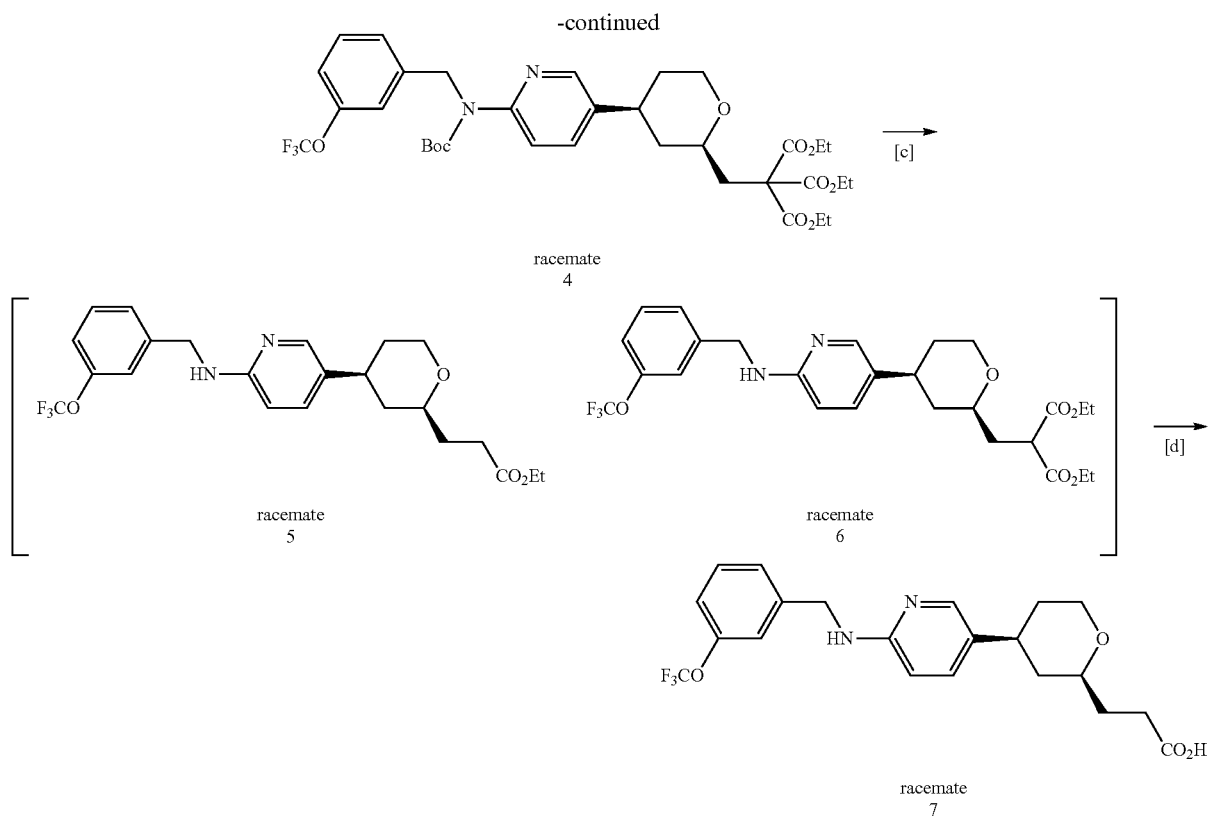

[Step a]

To a solution of compound 1 (95 mg, 0.20 mmol) obtained in Reference Example 71, Step f, in dichloromethane (4 mL) were added carbon tetrabromide (133 mg, 0.394 mmol), triphenylphosphine (107 mg, 0.394 mmol), and the mixture was stirred at room temperature for 16 hr. The reaction solution was concentrated under reduced pressure, and the residue was purified by silica gel chromatography to give compound 2 (24 mg, 22%)

MS(ESI)m/z: 545,547(M+1)+.

[Step b]

To a solution of compound 2 (24 mg, 44 μmol) in N-methylpyrrolidone (0.5 mL) were added compound 3 (51 mg, 0.22 mmol), potassium carbonate (36 mg, 0.26 mmol), and the mixture was stirred under microwave radiation at 135° C. for 1 hr. The reaction solution was allowed to cool to room temperature, water was added, and the mixture was extracted with ethyl acetate. The organic layer was washed with saturated brine, dried over anhydrous sodium sulfate, filtered, and concentrated under reduced pressure. The residue was purified by silica gel chromatography to give compound 4 (13 mg, 42%).

MS(ESI)m/z: 697(M+1)+.

[Step c]

To a solution of compound 4 (13 mg, 19 μmol) in dichloromethane (3 mL) was added trifluoroacetic acid (1 mL), and the mixture was stirred at room temperature for 3 hr. The reaction solution was concentrated under reduced pressure, and the residue was dissolved in chloroform, washed with saturated aqueous sodium bicarbonate solution, dried over anhydrous sodium sulfate, filtered, and concentrated under reduced pressure. The residue was dissolved in ethanol (1 mL), a solution of potassium hydroxide (4.2 mg, 75 μmol) in ethanol (1 mL) was added, and the mixture was stirred at room temperature for 5 days. To the reaction solution was added 2 M-hydrochloric acid (0.05 mL), and the mixture was concentrated under reduced pressure. The residue was suspended in toluene (3.5 mL), N,N-diisopropylethylamine (32 μL) was added, and the mixture was stirred with heating at 110° C. for 26 hr. The reaction mixture was allowed to cool to room temperature, and concentrated under reduced pressure. The residue was purified by silica gel chromatography to give a mixture of compound 5 and compound 6 (8.5 mg, compound 5:compound 6=4:1, 100%).

MS(ESI)m/z: 453(M+1)+, 525(M+1)+.

[Step d]

To a mixed solution of a mixture of compound 5 and compound 6 (8.5 mg, compound 5:compound 6=4:1) in tetrahydrofuran (1 mL), methanol (0.5 mL) was added 4 M-aqueous sodium hydroxide solution (0.5 mL), and the mixture was stirred at room temperature for 3 hr. To the reaction solution was added 2 M-hydrochloric acid (1.1 mL), and the mixture was concentrated under reduced pressure. The residue was dissolved in acetic acid (3.5 mL), and the mixture was stirred with heating at 125° C. for 11 hr. The reaction solution was allowed to cool to room temperature, and concentrated under reduced pressure. The residue was dissolved in chloroform, washed with saturated brine, dried over anhydrous sodium sulfate, filtered, and concentrated under reduced pressure to give compound 7 (9 mg).

MS(ESI)m/z: 425(M+1)+.

The following compounds were produced according to Production Methods 1-28, Examples, and Reference Examples.
TABLE 18
| Example 180 | 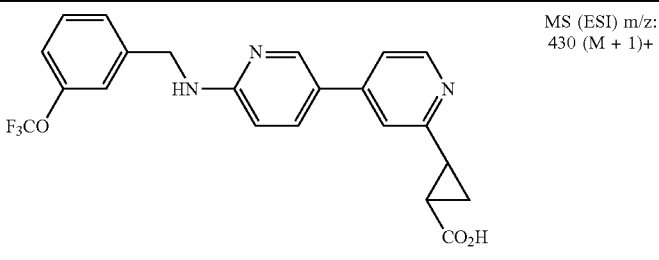 trans, racemate | MS (ESI) m/z: 430 (M + 1)+ |
|---|---|---|
| Example 181 | 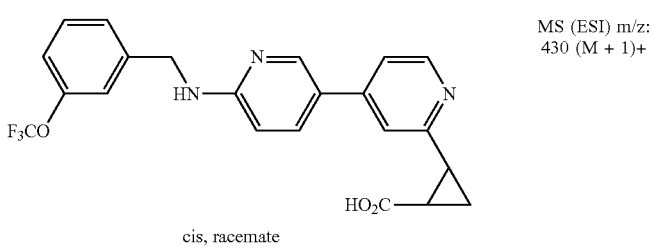 cis, racemate | MS (ESI) m/z: 430 (M + 1)+ |
| Example 182 | 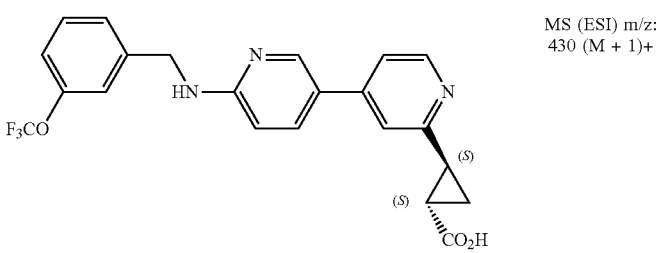 | MS (ESI) m/z: 430 (M + 1)+ |
| Example 183 | 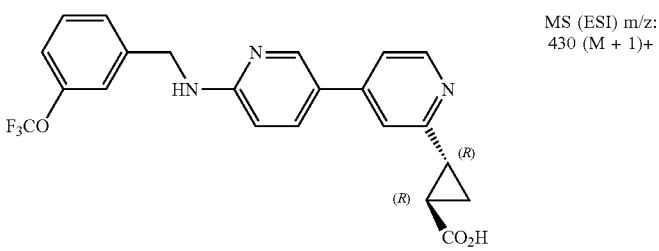 | MS (ESI) m/z: 430 (M + 1)+ |
| Example 184 | 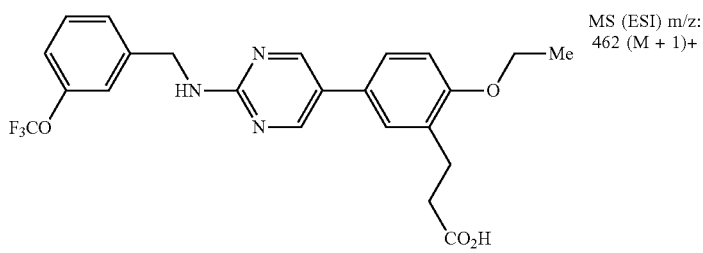 | MS (ESI) m/z: 462 (M + 1)+ |
| Example 185 | 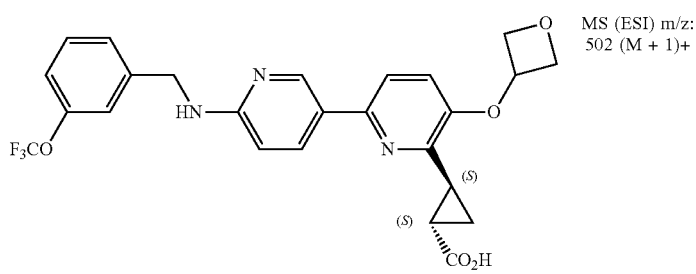 | MS (ESI) m/z: 502 (M + 1)+ |

TABLE 18-continued

Example 186

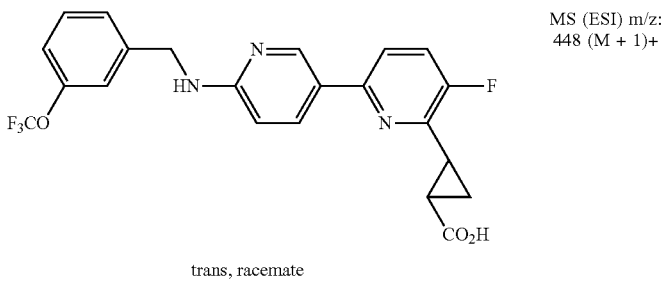

trans, racemate

MS (ESI) m/z: 448 (M + 1)+

Reference Example 1

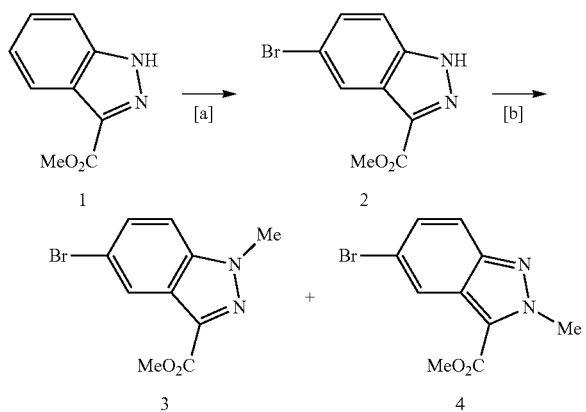

[Step a]

To a solution of compound 1 (5.00 g, 28.3 mmol) in N,N-dimethylformamide (30.0 mL) was added dropwise bromine (1.74 mL, 34.1 mmol) under ice-cooling, and the mixture was stirred for 1 day while raising the temperature to room temperature. The reaction solution was ice-cooled again, bromine (1.74 mL, 34.1 mmol) was added, and the mixture was stirred for 17 hr while raising the temperature to room temperature. To the reaction solution were added 10% aqueous sodium thiosulfate solution and saturated aqueous sodium hydroxide solution, and the mixture was extracted with ethyl acetate. The organic layer was washed with water and saturated brine, dried over anhydrous sodium sulfate, filtered, and concentrated under reduced pressure. The residue was purified by silica gel chromatography. The obtained solid was suspended and washed in hexane to give compound 2 (4.51 g, 63.0%).

MS(ESI)m/z: 255, 257(M+1)+.

[Step b]

To a solution of compound 2 (470 mg, 1.85 mmol) and potassium carbonate (639 mg, 4.62 mmol) in N,N-dimethylformamide (8.00 mL) was added iodomethane (289 mg, 2.03 mmol) under ice-cooling, and the mixture was stirred for 17 hr while raising the temperature to room temperature. To the reaction solution was added saturated aqueous sodium hydroxide solution, and the mixture was extracted with ethyl acetate. The organic layer was washed with saturated brine, dried over anhydrous sodium sulfate, filtered, and concentrated under reduced pressure. The residue was purified by silica gel chromatography to give compound 3 (220 mg, 44.4%) and compound 4 (197 mg, 39.7%).

MS(ESI)m/z: 269, 271(M+1)+.
MS(ESI)m/z: 269, 271(M+1)+.

Reference Example 2

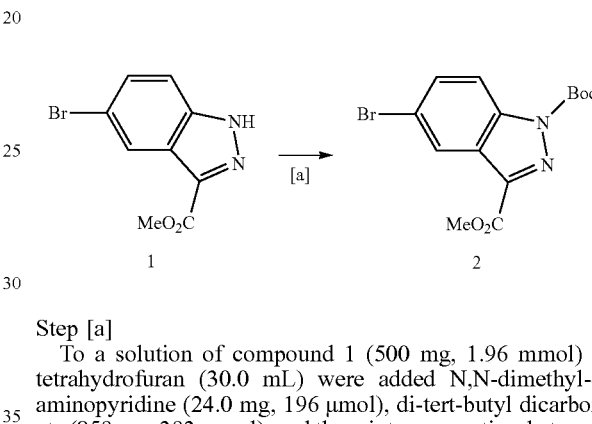

Step [a]

To a solution of compound 1 (500 mg, 1.96 mmol) in tetrahydrofuran (30.0 mL) were added N,N-dimethyl-4-aminopyridine (24.0 mg, 196 μmol), di-tert-butyl dicarbonate (859 mg, 393 mmol), and the mixture was stirred at room temperature overnight. To the reaction solution was added saturated aqueous sodium hydrogen carbonate solution, and the mixture was extracted with ethyl acetate. The organic layer was washed with saturated brine, dried over anhydrous sodium sulfate, filtered, and concentrated under reduced pressure. The residue was purified by silica gel chromatography to give compound 2 (662 mg, 95.4%).

MS(ESI)m/z: 355, 357(M+1)+.

Reference Example 3

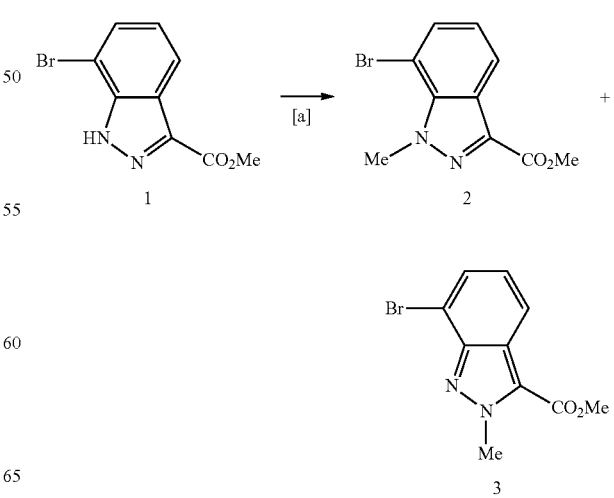

[Step a]

To a solution of compound 1 (200 mg, 784 μmol) and cesium carbonate (306 mg, 939 μmol) in N,N-dimethylformamide (8.00 mL) was added iodomethane (53.7 μL, 863 μmol) at room temperature, and the mixture was stirred for 3.5 hr. To the reaction solution was added water, and the mixture was extracted with ethyl acetate. The organic layer was washed with saturated brine, dried over anhydrous sodium sulfate, filtered, and concentrated under reduced pressure. The residue was purified by silica gel chromatography to give compound 2 (46.7 mg, 22.1%) and compound 3 (83.7 mg, 39.7%).

MS(ESI)m/z: 269, 271(M+1)+.
MS(ESI)m/z: 269, 271(M+1)+.

Reference Example 4

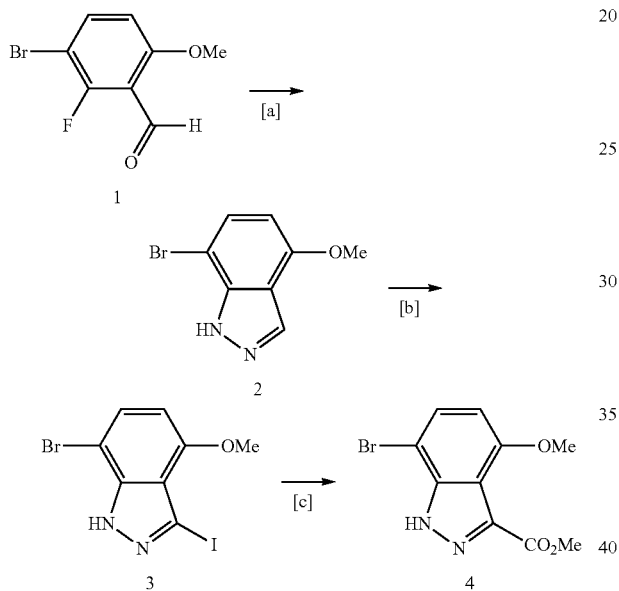

[Step a]

To a solution of compound 1 (1.00 g, 4.29 mmol) in dimethoxyethane (4.00 mL) was added hydrazine monohydrate (4.00 mL, 12.8 mmol), and the mixture was stirred with heating at 90° C. overnight. The reaction solution was allowed to cool to room temperature, water was added, and the precipitated solid was collected by filtration, the obtained solid was washed with water to give compound 2 (785 mg, 77.8%).

MS(ESI)m/z: 227(M+1)+.

[Step b]

To a solution of compound 2 (350.0 mg, 1.54 mmol) in N,N-dimethylformamide (8.00 mL) was added N-iodosuccinimide (451 mg, 2.00 mmol), and the mixture was stirred at room temperature for 1 day. To the reaction solution were added saturated aqueous sodium thiosulfate solution, saturated aqueous sodium hydrogen carbonate solution, and the precipitated solid was collected by filtration, and the obtained solid was washed with water to give compound 3 (428 mg, 78.8%).

MS(ESI)m/z: 353, 355(M+1)+.

[Step c]

To a mixed solution of compound 3 (100 mg, 284 μmol) in N,N-dimethylformamide (1.50 mL) and methanol (1.50 mL) were added triethylamine (60.0 μL, 426 μmol), [1,1'-bis(diphenylphosphino)ferrocene]palladium(II) dichloride (10.0 mg, 14.2 μmol) and 1,1'-bis(diphenylphosphino)ferrocene (8.00 mg, 14.2 μmol), and the mixture was stirred in a carbon monoxide atmosphere with heating at 70° C. overnight. The reaction solution was allowed to cool to room temperature. Furthermore, triethylamine (60.0 μL, 426 μmol), [1,1'-bis(diphenylphosphino)ferrocene]palladium(II) dichloride (10.0 mg, 14.2 μmol) and 1,1'-bis(diphenylphosphino)ferrocene (8.00 mg, 14.2 μmol) were added, and the mixture was stirred in a carbon monoxide atmosphere with heating at 70° C. overnight. To the reaction solution was added water, and the mixture was extracted with ethyl acetate. The organic layer was washed with saturated brine, dried over anhydrous sodium sulfate, filtered, and concentrated under reduced pressure. The residue was purified by silica gel chromatography to give compound 4 (75.0 mg, 93.0%).

MS(ESI)m/z: 285, 287(M+1)+.

Reference Example 5

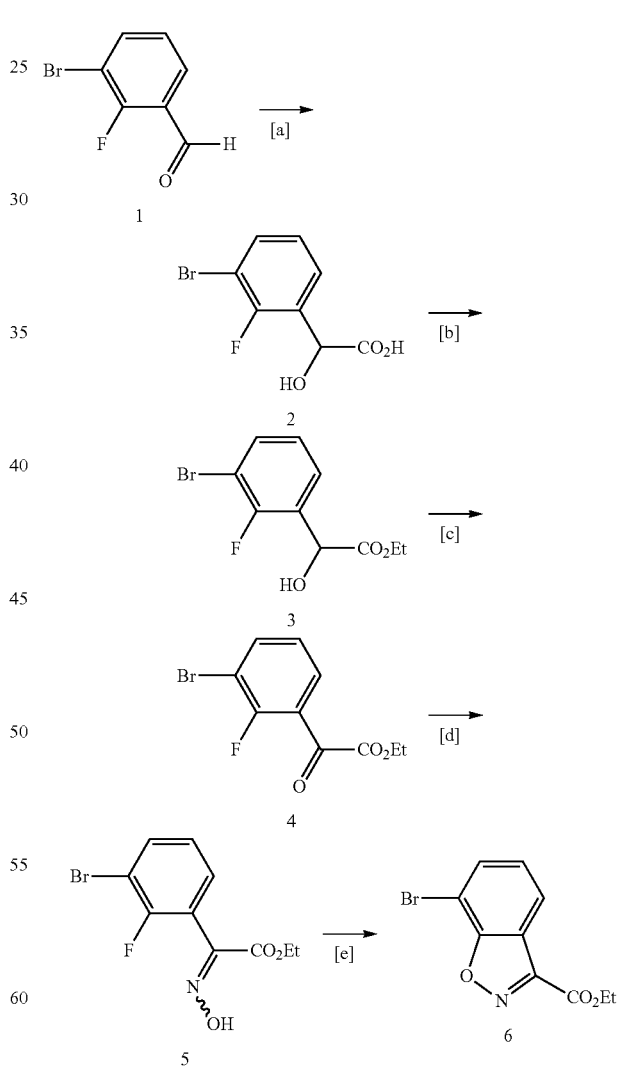

[Step a]

To a solution of compound 1 (1.00 g, 4.93 mmol) and N,N-dimethyl-4-aminopyridine (DMAP) (6.00 mg, 49.1

μmol) in tetrahydrofuran (10.0 mL) was added trimethylsilyl cyanide (587 mg, 5.92 mmol) under ice-cooling, and the mixture was stirred for 1 day while raising the temperature to room temperature. The reaction solution was concentrated under reduced pressure, water (1.00 mL) was added, concentrated sulfuric acid (3.00 mL) was further added under ice-cooling, and the mixture was stirred with heating under reflux for 3.5 hr. The reaction solution was allowed to cool to room temperature, adjusted to pH=10 with 2 M-aqueous sodium hydroxide solution, and washed with diethyl ether. The obtained aqueous layer was adjusted to pH2-3 with 1 M-hydrochloric acid, and the precipitated solid was collected by filtration, and washed with water to give compound 2 (298 mg, 24.3%).

MS(ESI)m/z: 247, 249(M−1)−.

[Step b]

To a solution of compound 2 (280 mg, 1.12 mmol) in ethanol (3.00 mL) was added concentrated sulfuric acid (300 μL), and the mixture was stirred with heating at 85° C. for 6 hr. The reaction solution was allowed to cool to room temperature, neutralized with 1 M-aqueous sodium hydroxide solution, and extracted with ethyl acetate. The organic layer was washed with saturated brine, dried over anhydrous sodium sulfate, filtered, and concentrated under reduced pressure to give compound 3 (233 mg, 75.1%).

$^1$H-NMR (400 MHz, CDCl$_3$) δ: 1.23 (3H, t, J=7.2 Hz), 3.56 (1H, d, J=5.1 Hz), 4.16-4.34 (2H, m), 5.39 (1H, d, J=4.6 Hz), 7.01-7.08 (1H, m), 7.33 (1H, td, J=7.2, 1.5 Hz), 7.53 (1H, ddd, J=8.0, 6.4, 1.5 Hz).

[Step c]

To a solution of compound 3 (230 mg, 830 μmol) in N,N-dimethyl sulfoxide (2.00 mL) was added acetic anhydride (98.0 μL, 1.04 mmol), and the mixture was stirred with heating at 90° C. for 8 hr. To the reaction solution was further added acetic anhydride (98.0 μL, 1.04 mmol), and the mixture was stirred with heating at 90° C. for 7.5 hr. The reaction solution was allowed to cool to room temperature, water was added, and the mixture was extracted with ethyl acetate. The organic layer was washed with saturated brine, dried over anhydrous sodium sulfate, filtered and concentrated under reduced pressure, and the residue was purified by silica gel chromatography to give compound 4 (51.0 mg, 22.3%).

$^1$H-NMR (400 MHz, CDCl$_3$) δ: 1.42 (3H, t, J=7.2 Hz), 4.45 (2H, q, J=7.0 Hz), 7.36-7.42 (1H, m), 7.79-7.90 (2H, m).

[Step d]

To a solution of compound 4 (51.0 mg, 185 μmol) in ethanol (1.00 mL) were added hydroxyamine hydrochloride (17.4 mg, 0.250 mmol) and sodium acetate (21.5 mg, 0.262 mmol), and the mixture was stirred with heating at 50° C. for 3 hr, and further at room temperature overnight. To the reaction solution was added water, and the mixture was extracted with ethyl acetate. The organic layer was washed with saturated brine, dried over anhydrous sodium sulfate, filtered, and concentrated under reduced pressure to give compound 5 (57.5 mg).

MS(ESI)m/z: 290, 292(M+1)+.

[Step e]

To a solution of compound 5 (57.5 mg, 198 μmol) in dimethyl sulfoxide (1.00 mL) was added potassium carbonate (30.0 mg, 217 μmol), and the mixture was stirred with heating at 70° C. for 4 hr. The reaction solution was allowed to cool to room temperature, water was added, and the precipitated solid was collected by filtration, and washed with water to give compound 6 (22.7 mg, 64.5%).

$^1$H-NMR (400 MHz, CDCl$_3$) δ: 1.50 (3H, t, J=7.2 Hz), 4.57 (2H, q, J=7.2 Hz), 7.33 (1H, t, J=8.0 Hz), 7.79 (1H, dd, J=7.7, 1.0 Hz), 8.05-8.12 (1H, m).

Reference Example 6

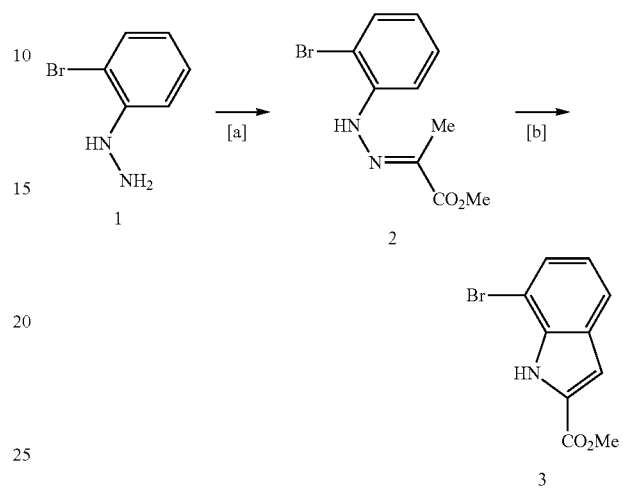

[Step a]

To a solution of compound 1 (500 mg, 2.23 mmol) in methanol (5.00 mL) were added methyl pyruvate (300 μL, 2.65 mmol) and sodium acetate (210 mg, 2.56 mmol), and the mixture was stirred at room temperature for 1 hr 30 min. To the reaction solution was added water, and the mixture was extracted with diethyl ether. The organic layer was washed with saturated brine, dried over anhydrous sodium sulfate, filtered, and concentration under reduced pressure to give a yellow solid (571 mg). The obtained yellow solid (471 mg) was purified by silica gel chromatography to give compound 2 (345 mg).

MS(ESI)m/z: 271, 273(M+1)+.

[Step b]

To a solution of compound 2 (100 mg, 0.369 mmol) in toluene (4.00 mL) was added p-toluenesulfonic acid monohydrate (70.2 mg, 0.369 mmol), and the mixture was stirred with heating under reflux for 2 hr by using Dean-Stark apparatus. Then, toluene (5.00 mL) was added to the reaction solution, and heating under reflux was continued for 8 hr. The reaction solution was allowed to cool to room temperature, concentrated under reduced pressure, and the residue was purified by silica gel chromatography to give compound 3 (72.4 mg, 77.2%).

MS(ESI)m/z: 254,256 (M+1)+.

Reference Example 7

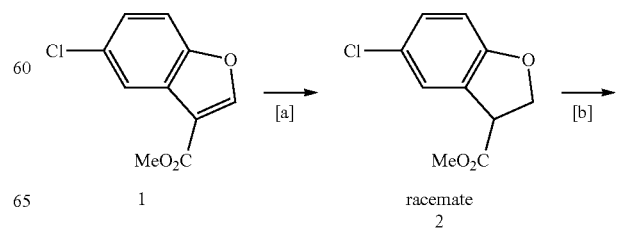

-continued

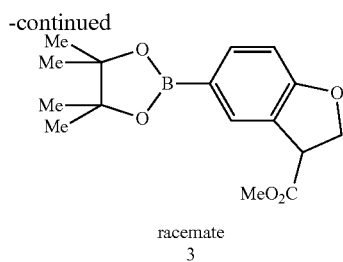

racemate
3

[Step a]

To a solution of compound 1 (500 mg, 2.23 mmol) in methanol (25.0 mL) was added magnesium (270 mg, 11.1 mmol), and the mixture was stirred at room temperature overnight. The reaction solution was ice-cooled, 1 M-aqueous hydrochloric acid solution (25 mL) was added, and the mixture was extracted with ethyl acetate. The organic layer was washed with water and saturated brine, dried over anhydrous sodium sulfate, filtered and concentrated under reduced pressure, and the residue was purified by silica gel chromatography to give compound 2 (330 mg, 69.6.%).

$^1$H-NMR (400 MHz, CDCl$_3$) δ: 3.80 (3H, s), 4.32 (1H, dd, J=6.7, 9.8 Hz), 4.69 (1H, dd, J=9.8, 9.8 Hz), 4.95 (1H, dd, 6.7, 9.8 Hz), 6.74 (1H, d, J=8.7 Hz), 7.14 (1H, dd, J=2.4, 8.7 Hz), 7.34 (1H, dd, J=2.4, 1.0 Hz).

[Step b]

To a solution of compound 2 (330 mg, 1.45 mmol) and bis(pinacolato)diborane (740 mg, 2.91 mmol) and potassium acetate (430 mg, 4.38 mmol) in dimethoxyethane (6.00 mL) were added palladium acetate (34 mg, 0.145 mmol) and 2-dicyclohexylphosphino-2',4',6'-triisopropylbiphenyl (140 mg, 0.294 mmol), and the mixture was stirred under microwave radiation at 135° C. for 1 hr. The reaction solution was diluted with water and ethyl acetate, filtered through celite, and the filtrate was extracted with ethyl acetate. The organic layer was washed with saturated brine, dried over anhydrous sodium sulfate, filtered and concentrated under reduced pressure, and the residue was purified by silica gel chromatography to give compound 3 (500 mg).

MS(ESI)m/z: 305(M+1)+.

Reference Example 8

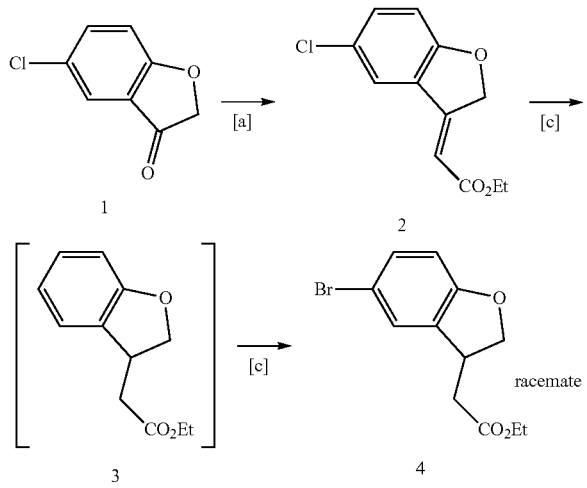

[Step a]

To a solution of ethyl diethylphosphonoacetate (2.66 g, 11.9 mmol) in tetrahydrofuran (15.0 mL) was added sodium hydride (60 wt %, 0.43 g, 10.8 mmol) under ice-cooling, and the mixture was stirred at room temperature for 30 min. To the reaction solution was added a solution (10.0 mL) of compound 1 (1.00 g, 5.93 mmol) in tetrahydrofuran, and the mixture was stirred at room temperature for 3 hr. To the reaction solution were added saturated aqueous ammonium chloride solution (2.00 mL) and water (50.0 mL), and the mixture was extracted with ethyl acetate. The organic layer was washed with water and saturated brine, dried over anhydrous sodium sulfate, filtered and concentrated under reduced pressure, and the residue was purified by silica gel chromatography to give compound 2 (835 mg, 59.0%).

$^1$H-NMR (400 MHz, CDCl$_3$) δ: 1.29 (3H, t, J=7.2 Hz), 3.66 (2H, d, J=1.0 Hz), 4.20 (2H, q, J=7.2 Hz), 7.26 (1H, dd, 2.1, 8.7 Hz), 7.39 (1H, d, J=8.7 Hz), 7.55 (1H, d, J=2.0 Hz), 7.65 (1H, s).

[Step c]

To a solution of compound 2 (280 mg, 1.17 mmol) in ethanol (12.0 mL) was added palladium/carbon (10 wt %, 120 mg), and the mixture was stirred overnight at room temperature in a hydrogen atmosphere. The reaction solution was filtered through celite, and the obtained filtrate was concentrated under reduced pressure. The residue was dissolved in acetonitrile (6.00 mL), N-bromosuccinimide (270 mg, 1.52 mmol) was added at room temperature, and the mixture was stirred for 4 hr. To the reaction solution was added water, and the mixture was extracted with ethyl acetate. The organic layer was washed with saturated brine, dried over anhydrous sodium sulfate, filtered and concentrated under reduced pressure, and the residue was purified by silica gel chromatography to give compound 3 (250 mg, 75.2%).

MS(ESI)m/z: 285, 287(M+1)+.

Reference Example 9

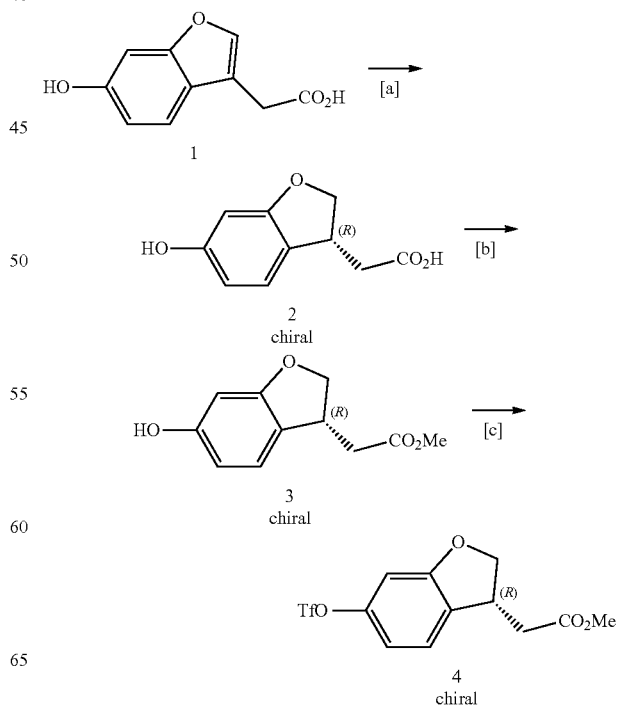

[Step a]

To a solution of compound 1 (20.9 g, 109 mmol) in methanol (200 mL) was added sodium methoxide (2.94 g, 54.5 mmol), and the mixture was stirred with nitrogen bubbling at room temperature until the reagent was completely dissolved. To the reaction solution was added a solution of (+)-1,1-bis[(2R,4R)-2,4-diethylphosphotano]ferrocene (482 mg, 1.09 mmol) and bis(1,5-cyclooctadiene) rhodium (I) tetrafluoroborate (510 mg, 1.09 mmol) in methanol (100 mL), and the mixture was stirred in an autoclave reaction apparatus in a hydrogen atmosphere at 0.5-0.7 MPa for 5 hr. The reaction solution was concentrated under reduced pressure, 10% aqueous citric acid solution (1.0 L) was added, and the mixture was extracted with ethyl acetate. The obtained organic layer was washed with saturated brine, dried over anhydrous magnesium sulfate, filtered, concentrated, and the residue was purified by silica gel chromatography to give compound 2 (17.6 g, 83.1%, 86.9% ee). The obtained compound 2 (17.1 g, 88.0 mmol) was dissolved in 1 M-aqueous sodium hydroxide solution (200 mL), 1 M-hydrochloric acid (200 mL) was added, and the mixture was stirred under ice-cooling overnight. The precipitated solid was removed by filtration, and the obtained filtrate was extracted with ethyl acetate. The organic layer was washed with saturated aqueous sodium chloride solution, dried over anhydrous sodium sulfate, filtered, and concentrated under reduced pressure. The obtained residue was dissolved in 1 M-aqueous sodium hydroxide solution (100 mL), 1 M-hydrochloric acid (100 mL) was added, and the mixture was stirred under ice-cooling overnight. To the obtained reaction solution was added water (50 mL), and the mixture was left standing at room temperature for 3 days. The precipitated solid was removed by filtration, and the filtrate was extracted with ethyl acetate. The organic layer was washed with saturated aqueous sodium chloride solution, dried over anhydrous sodium sulfate, filtered, and concentrated under reduced pressure to give compound 2 (12.5 g, 59.1%, 92.9% ee).

MS(ESI)m/z: 195(M+1)+.

[Step b]

To a solution of compound 2 (12.5 g, 64.2 mmol) in methanol (100 mL) was added concentrated sulfuric acid (140 μL), and the mixture was stirred with heating under reflux for 2 hr. The reaction solution was allowed to cool to room temperature, concentrated under reduced pressure, water was added, and the mixture was extracted with ethyl acetate. The organic layer was washed with water, washed with saturated aqueous sodium chloride solution (100 mL), dried over anhydrous sodium sulfate, filtered, and concentrated. The residue was purified by silica gel chromatography, and the solid obtained by concentration under reduced pressure was suspended and washed in hexane to give compound 3 (9.82 g, 99.8%, 93.4% ee).

MS(ESI)m/z: 209(M+1)+.

[Step c]

To a solution of compound 1 (998 mg, 4.79 mmol) in pyridine (10.0 mL) was added dropwise trifluoromethanesulfonic anhydride (1.63 g, 5.76 mmol) over 2 min under ice-cooling, and the mixture was stirred for 2 hr while raising the temperature to room temperature. The reaction solution was concentrated under reduced pressure, ethyl acetate (35.0 mL) and 1 M-hydrochloric acid (35.0 mL) were added, and the mixture was extracted with ethyl acetate. The organic layer was washed with water and saturated brine, dried over anhydrous sodium sulfate, filtered, and concentrated. The residue was purified by silica gel chromatography to give compound 2 (1.58 g, 96.8%).

$^1$H-NMR (400 MHz, CDCl$_3$) δ: 2.61 (1H, dd, J=9.2, 16.5 Hz), 2.79 (1H, dd, J=5.6, 16.5 Hz), 3.73 (3H, s), 3.89 (1H, ddddd, J=1.0, 5.6, 6.7, 9.2, 9.2 Hz), 4.34 (1H, dd, J=6.7, 9.2 Hz), 4.84 (1H, dd, J=9.2, 9.2 Hz), 6.70 (1H, d, J=2.6 Hz), 6.77 (1H, dd, J=2.6, 8.2 Hz), 7.19 (1H, dd, J=1.0, 8.2 Hz).

Reference Example 10

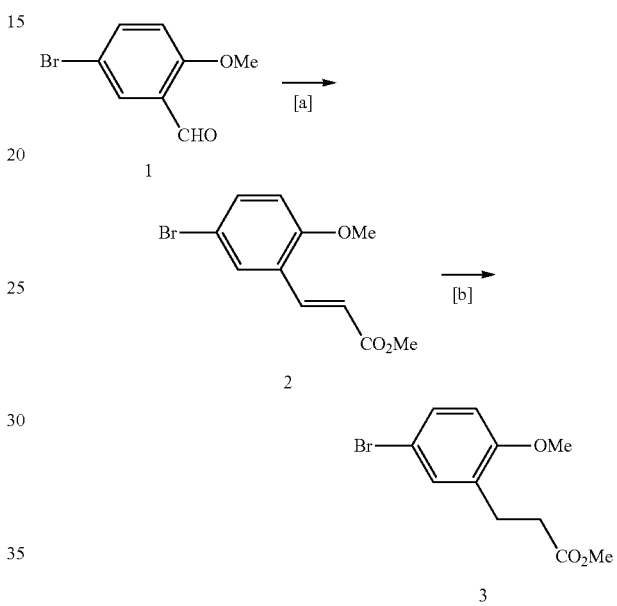

[Step a]

To a solution of compound 1 (10.0 g, 46.5 mmol) in toluene (100 mL) was added ethyl (triphenylphosphoranylidene)acetate (17.1 g, 51.2 mmol), and the mixture was stirred with heating at 105° C. for 2.5 hr. The reaction solution was allowed to cool to room temperature, concentration under reduced pressure, and toluene (50 mL) was added. The precipitated solid was removed by filtration, and the filtrate was concentrated under reduced pressure. The residue was purified by silica gel chromatography to give compound 2 (12.6 g).

MS(ESI)m/z: 273, 275(M+1)+.

[Step b]

To a solution of compound 2 (1.86 g, 6.85 mmol) in methanol (35 mL) was added cobalt(II) chloride (45.0 mg, 0.347 mmol), and the mixture was ice-cooled. Sodium borohydride (390 mg, 10.3 mmol) was added, and the mixture was stirred for 25 min. To the reaction solution were added saturated aqueous ammonium chloride solution and water, the organic solvent was concentrated under reduced pressure, and the mixture was extracted with ethyl acetate. The organic layer was washed with saturated brine, dried over anhydrous sodium sulfate, filtered, and concentrated. The residue was purified by silica gel chromatography to give compound 3 (2.00 g, 100%).

Reference Example 11

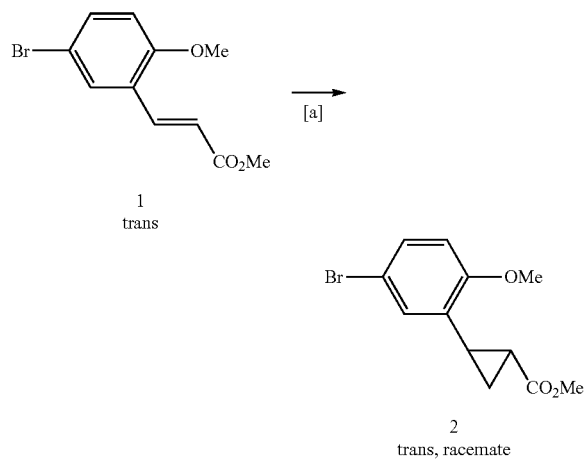

A solution of sodium hydride (60 wt %, 100 mg, 2.50 mmol) in dimethyl sulfoxide (8.00 mL) was stirred in a nitrogen atmosphere with heating at 60° C. for 35 min. To the reaction solution was added trimethylsulfoxonium iodide (590 mg, 2.68 mmol) at room temperature, and the mixture was stirred for 30 min. To the reaction solution was added a solution of compound 1 (560 mg, 2.06 mmol) in dimethyl sulfoxide (4.0 mL), and the mixture was stirred at room temperature overnight. To the reaction solution was added saturated aqueous ammonium chloride solution, and the mixture was extracted with ethyl acetate. The organic layer was washed with water and saturated brine, dried over anhydrous sodium sulfate, filtered, and concentrated. The residue was purified by silica gel chromatography to give compound 2 (175 mg, 29.8%).

MS(ESI)m/z: 285, 287(M+1)+.

Reference Example 12

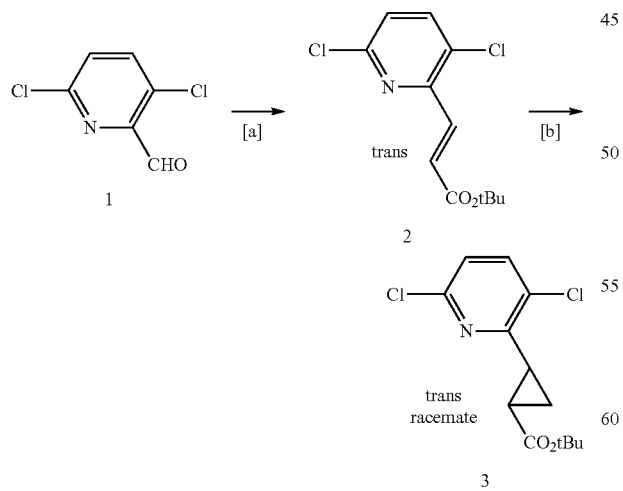

Step [a]

To a solution of sodium hydride (60 wt %, 545 mg, 13.6 mmol) in tetrahydrofuran (40.0 mL) was added tert-butyl diethylphosphonoacetate (3.23 mL, 13.7 mmol) under ice-cooling, and the mixture was stirred for 10 min. To the reaction solution was added a solution of compound 1 (2.00 g, 11.4 mmol) in tetrahydrofuran (40.0 mL) under ice-cooling, and the mixture was stirred for 1.3 hr while raising the temperature to room temperature. To the reaction solution was added water, and the mixture was extracted with ethyl acetate. The organic layer was washed with saturated brine, dried over anhydrous sodium sulfate, filtered and concentrated under reduced pressure, and the residue was purified by silica gel chromatography to give compound 2 (2.93 g, 93.8%).

MS(ESI)m/z: 274(M+1)+.

Step [b]

A solution of sodium hydride (60 wt %, 507 mg, 12.7 mmol) in dimethyl sulfoxide (40 mL) was stirred in a nitrogen atmosphere with heating at 70° C. for 15 min. The reaction solution was allowed to cool to room temperature, trimethylsulfoxonium iodide (2.80 g, 12.7 mmol) was added and the mixture was stirred for 30 min. To the reaction solution was added a solution of compound 2 (2.90 g, 10.6 mmol) in dimethyl sulfoxide (40 mL), and the mixture was stirred at room temperature overnight. To the reaction solution was added water, and the mixture was extracted with ethyl acetate. The organic layer was washed with water and saturated brine, dried over anhydrous sodium sulfate, filtered, and concentrated. The residue was purified by silica gel chromatography, the obtained solid was suspended and washed in hexane to give compound 3 (278 mg, 9.1%).

MS(ESI)m/z: 288(M+1)+.

Reference Example 13

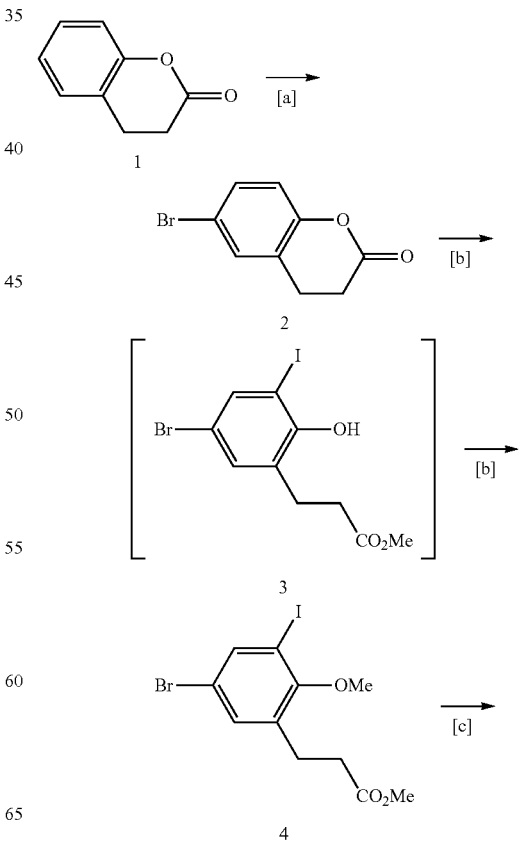

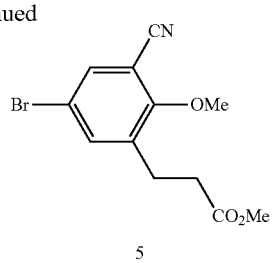

[Step a]

To a solution of compound 1 (5.00 g, 33.7 mmol) in dichloromethane (50.0 mL) was added dropwise a solution of bromine (1.80 mL, 35.4 mmol) in dichloromethane (20.0 mL) at room temperature, and the mixture was stirred for 7 hr. To the reaction solution was added water, and the mixture was extracted with chloroform. The organic layer was washed with saturated aqueous sodium hydrogen carbonate solution, and saturated brine, dried over anhydrous sodium sulfate, filtered, and concentrated. The precipitated solid was suspended and washed in diisopropyl ether (10.0 mL), collected by filtration and washed with diisopropyl ether and hexane to give compound 2 (3.56 g, 46.5%).

MS(ESI)m/z: 227, 229(M+1)+.

[Step b]

To a solution of compound 2 (1.02 g, 4.49 mmol) in tetrahydrofuran (10.0 mL) was added 2 M-aqueous sodium hydroxide solution (5.00 mL), and the mixture was stirred at room temperature for 10 hr. The reaction solution was concentrated under reduced pressure to evaporate the organic solvent, water (10.0 mL) and sodium iodide (1.01 g, 6.74 mmol) were added, and the mixture was cooled to −5° C. To the reaction solution was added 2% aqueous sodium hypochlorite solution (20.0 mL) over 40 min, and the mixture was stirred at −5° C. under cooling for 1 hr. To the reaction solution was added 2 M-aqueous hydrochloric acid solution, and the mixture was extracted with ethyl acetate. The organic layer was washed with saturated aqueous sodium thiosulfate solution, saturated brine, dried over anhydrous sodium sulfate, filtered, and concentrated. The residue was dissolved in N,N-dimethylformamide (20.0 mL), potassium carbonate (1.86 g, 13.46 mmol) and methyl iodide (0.850 mL, 13.65 mmol) were added, and the mixture was stirred at room temperature overnight. The reaction solution was ice-cooled, 0.1 M-hydrochloric acid (50.0 mL) was added, and the mixture was extracted with ethyl acetate. The organic layer was washed with water and saturated brine, dried over anhydrous sodium sulfate, filtered, and concentrated. The residue was purified by silica gel chromatography to give compound 4 (1.48 g, 82.6%).

MS(ESI)m/z: 399, 401 (M+1)+.

[Step c]

To a solution of compound 4 (460 mg, 1.15 mmol) in N-methylpyrrolidone (10.0 mL) was added copper cyanide (520 mg, 1.31 mmol), and the mixture was stirred with heating at 120° C. for 1 day. The reaction solution was allowed to cool to room temperature, ethyl acetate (40.0 mL) and water (40.0 mL) were added, and the mixture was filtered through celite, and the filtrate was extracted with ethyl acetate. The organic layer was washed with water and saturated brine, dried over anhydrous sodium sulfate, filtered, and concentrated. The residue was purified by silica gel chromatography to give compound 5 (160 mg, 46.7%).

MS(ESI)m/z: 298, 300 (M+1)+.

Reference Example 14

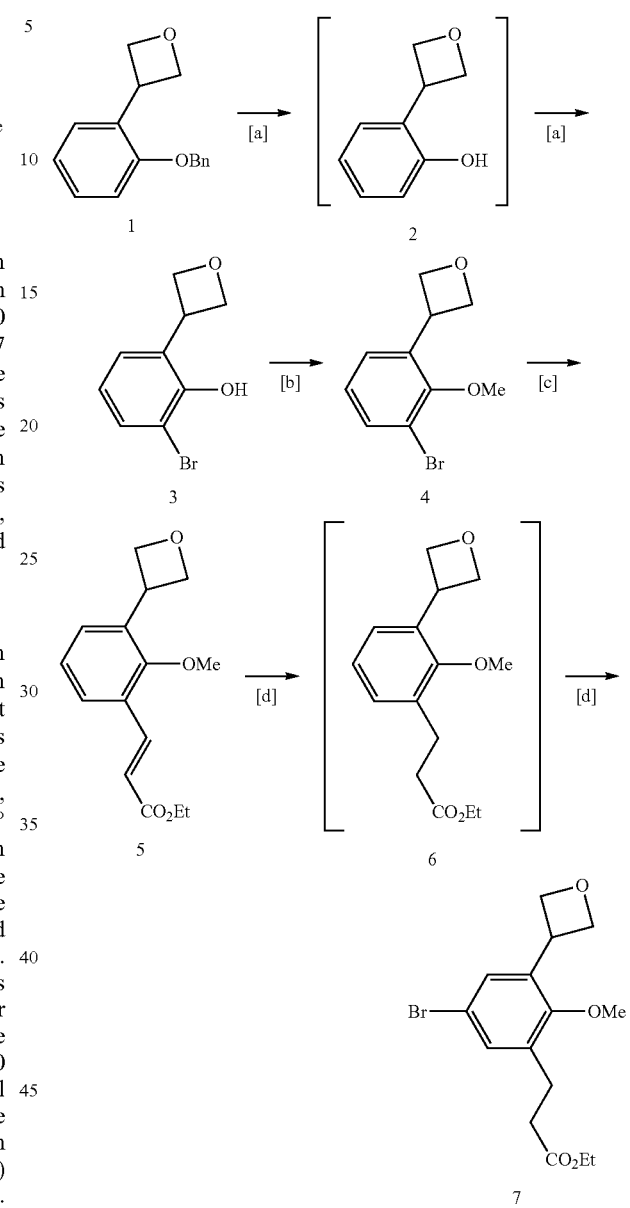

[Step a]

To a solution of compound 1 (900 mg, 3.74 mmol) in ethyl acetate (40.0 mL) was added palladium/carbon (10 wt %, 400 mg). The reaction solution was stirred in a hydrogen atmosphere at room temperature for 6 hr. The reaction container was substituted with nitrogen, the reaction solution was filtered through celite, and the obtained filtrate was concentrated under reduced pressure. The residue was dissolved in dichloromethane (30.0 mL), diisopropylamine (130 µL, 0.928 mmol) was added and the mixture was ice-cooled. To the reaction solution was added dropwise a solution of N-bromosuccinimide (640 mg, 3.60 mmol) in dichloromethane (30.0 mL) over 5 min, and the mixture was stirred under ice-cooling for 1 hr. To the reaction solution was added 0.05 M-hydrochloric acid (40.0 mL), and the mixture was extracted with chloroform. The organic layer was washed with saturated brine, and dried over anhydrous sodium sulfate. The residue was purified by silica gel chromatography to give compound 3 (720 mg, 83.9%).

MS(ESI)m/z: 227, 229 (M−1)−.

[Step b]

To a solution of compound 3 (720 mg, 3.13 mmol) in N,N-dimethylformamide (12.0 mL) were added potassium carbonate (865 mg, 6.26 mmol) and methyl iodide (390 µL, 6.27 mmol), and the mixture was stirred at room temperature for 17 hr. To the reaction solution was added water, and the mixture was extracted with ethyl acetate. The organic layer was washed with water and saturated brine, dried over anhydrous sodium sulfate, filtered, and concentrated. The residue was purified by silica gel chromatography to give compound 4 (700 mg, 92.0%).

MS(ESI)m/z: 243,245 (M+1)+.

[Step c]

To a solution of compound 4 (160 mg, 658 µmol) in acetonitrile (3.00 mL) were added ethyl acrylate (143 µL, 1.32 mmol), diisopropylethylamine (350 µL, 2.01 mmol), tri-(O-tolyl)phosphine (80 mg, 263 µmol) and palladium(II) acetate (15.0 mg, 66.8 µmol), and the mixture was stirred with heating at 130° C. for 1 hr in a microwave reactor. To the reaction solution were added ethyl acrylate (143 µL, 1.32 mmol), tri-(O-tolyl)phosphine (40 mg, 131 µmol) and palladium(II) acetate (15.0 mg, 66.8 µmol), and the mixture was further stirred with heating at 130° C. for 1 hr in a microwave reactor. The reaction solution was allowed to cool to room temperature, water was added, and the mixture was extracted with ethyl acetate. The organic layer was washed with saturated brine, dried over anhydrous sodium sulfate, filtered, and concentrated. The residue was purified by silica gel chromatography to give compound 5 (130 mg, 75.3%).

MS(ESI)m/z: 263 (M+1)+.

[Step d]

To a mixed solution of compound 5 (125 mg, 477 µmol) in tetrahydrofuran (4.50 mL) and methanol (4.50 mL) was added cobalt chloride (6.0 mg, 46.0 µmol), and sodium borohydride (35.0 mg, 926 µmol) was added at −10° C. under cooling, and the mixture was stirred for 40 min. To the reaction solution were added saturated aqueous ammonium chloride solution and water, and the mixture was extracted with ethyl acetate. The organic layer was washed with saturated brine, dried over anhydrous sodium sulfate, filtered, and concentrated. The residue was purified by silica gel chromatography to give an object product (130 mg) as an oil. To a solution of the obtained oil (130 mg) in acetonitrile (45.0 mL) was added N-bromosuccinimide (170 mg, 0.955 mmol), and the mixture was stirred at room temperature for 9 hr. To the reaction solution was added water, and the mixture was extracted with ethyl acetate. The organic layer was washed with saturated brine, dried over anhydrous sodium sulfate, filtered, and concentrated. The residue was purified by silica gel chromatography to give compound 7 (125 mg, 76.4%)

MS(ESI)m/z: 343, 345 (M+1)+.

Reference Example 15

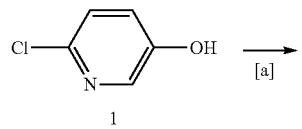

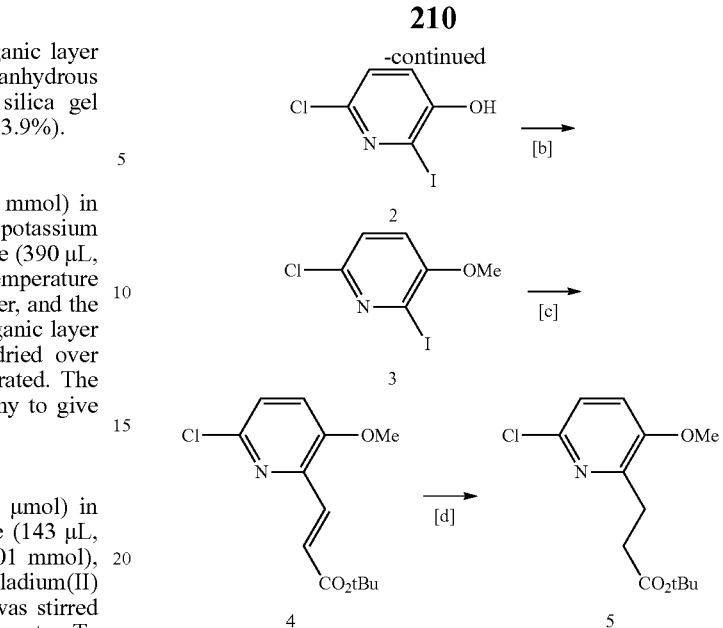

[Step a]

To a mixed solution of compound 1 (1.00 g, 7.71 mmol) and sodium carbonate (1.71 g, 16.2 mmol) in tetrahydrofuran (5.00 mL) and water (5.00 mL) was added iodine (2.94 g, 16.2 mmol) in 3 portions at room temperature, and the mixture was stirred for 1.5 hr. The reaction solution was neutralized with 1 M-hydrochloric acid, and extracted with ethyl acetate. The organic layer was washed with aqueous sodium thiosulfate solution, dried over anhydrous sodium sulfate, filtered, and concentrated to give compound 2 (2.04 g).

MS(ESI)m/z: 256 (M+1)+

[Step b]

To a solution of compound 2 (2.04 g) and potassium carbonate (1.60 g, 11.6 mmol) in dimethylformamide (15.4 mL) was added methyl iodide (0.58 mL, 11.6 mmol) at room temperature, and the mixture was stirred for 1 hr. To the reaction solution was added water (60.0 mL), and the mixture was stirred for 1 hr. The precipitated solid was collected by filtration, and washed with water (30.0 mL) to give compound 3 (1.81 g).

MS(ESI)m/z: 270 (M+1)+

[Step c]

To a solution of compound 3 (1.00 g, 3.71 mmol) in acetonitrile (11.0 mL) were added tert-butyl acrylate (1.08 mL, 7.41 mmol), diisopropylethylamine (1.94 mL, 11.1 mmol), palladium(II) acetate (45 mg, 0.200 mmol), tri-(O-tolyl)phosphine (225 mg, 0.739 mmol), and the mixture was stirred under microwave radiation in a nitrogen atmosphere at 150° C. for 2 hr. To the reaction solution was added water, and the mixture was extracted with ethyl acetate. The organic layer was washed with saturated brine, dried over anhydrous sodium sulfate, filtered, and concentrated. The residue was purified by silica gel chromatography to give compound 4 (925 mg, 92.8%).

MS(ESI)m/z: 270 (M+1)+.

[Step d]

To compound 4 (200 mg, 0.742 mmol) and cobalt(II) chloride (10 mg, 0.0770 mmol) in a mixed solvent of tetrahydrofuran (3.50 mL) and methanol (3.50 mL) was added sodium borohydride (40 mg, 1.06 mmol) under cooling at −10° C., and the mixture was stirred for 45 min. To the reaction solution were added saturated aqueous ammonium chloride solution and water, and the mixture was extracted with ethyl acetate. The organic layer was washed with water and saturated brine, dried over anhydrous sodium sulfate, filtered, and concentrated. The residue was purified by silica gel chromatography to give compound 5 (210 mg).

MS(ESI)m/z: 272 (M+1)+.

Reference Example 16

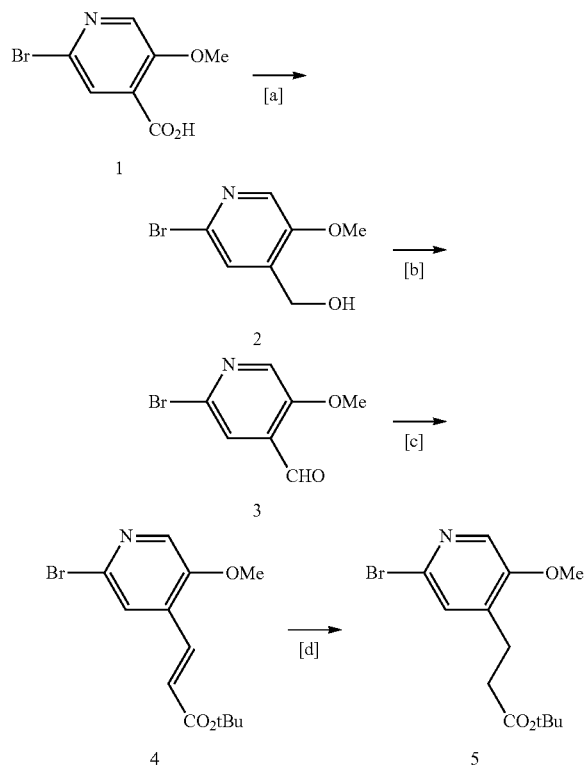

[Step a]

To a solution of compound 1 (2.00 g, 8.62 mmol) in tetrahydrofuran (40.0 mL) was added dropwise 0.95 M-borane-tetrahydrofuran complex in tetrahydrofuran solution (21.8 mL, 20.7 mmol) in a nitrogen atmosphere, and the mixture was stirred at room temperature overnight. To the reaction solution was added 3 M-aqueous sodium hydroxide solution (20.0 mL) to quench the reaction, and the mixture was stirred with heating at 90° C. for 1 hr. The organic solvent in the reaction solution was evaporated by concentration under reduced pressure, and water (40.0 mL) was added. The precipitated solid was washed with water to give compound 2 (1.50 g, 79.8%).

MS(ESI)m/z: 218, 220(M+1)+.

[Step b]

To a mixed solution of compound 2 (500 mg, 2.29 mmol) in dichloromethane (25.0 mL) and toluene (25.0 mL) was added manganese dioxide (995 mg, 11.4 mmol), and the mixture was stirred at room temperature overnight, and with heating at 50° C. for 1 day. The reaction solution was filtered through celite, the filtrate was concentrated, and the residue was purified by silica gel chromatography to give compound 3 (360 mg, 72.5%).

MS(ESI)m/z: 216, 218 (M+1)+.

[Step c]

To tert-butyl diethylphosphonoacetate (580 mg, 2.30 mmol) in tetrahydrofuran (6.00 mL) was added sodium hydride (60 wt %, 85 mg, 2.13 mmol) under ice-cooling, and the mixture was stirred for 30 min. To the reaction solution was added a solution of compound 3 (355 mg, 1.64 mmol) in tetrahydrofuran (4.0 mL) under ice-cooling, and the mixture was stirred for 2 hr. To the reaction solution were added saturated aqueous ammonium chloride solution and water to quench the reaction, and the mixture was extracted with ethyl acetate. The organic layer was washed with saturated brine, dried over anhydrous sodium sulfate, filtered, and concentrated. The residue was purified by silica gel chromatography to give compound 4 (480 mg, 93.3%).

MS(ESI)m/z: 314, 316(M+1)+.

[Step d]

To compound 4 (125 mg, 0.397 mmol) and cobalt(II) chloride (10 mg, 0.0770 mmol) in a mixed solvent of tetrahydrofuran (4.00 mL) and methanol (4.00 mL) was added sodium borohydride (30 mg, 7.93 μmol) under cooling at −10° C., and the mixture was stirred for 50 min. To the reaction solution were added saturated aqueous ammonium chloride solution and water under cooling at −10° C. to quench the reaction, and the mixture was extracted with ethyl acetate. The organic layer was washed with saturated brine, dried over anhydrous sodium sulfate, filtered, and concentrated. The residue was purified by silica gel chromatography to give compound 5 (85.0 mg, 67.7%).

MS(ESI)m/z: 316, 318 (M+1)+.

Reference Example 17

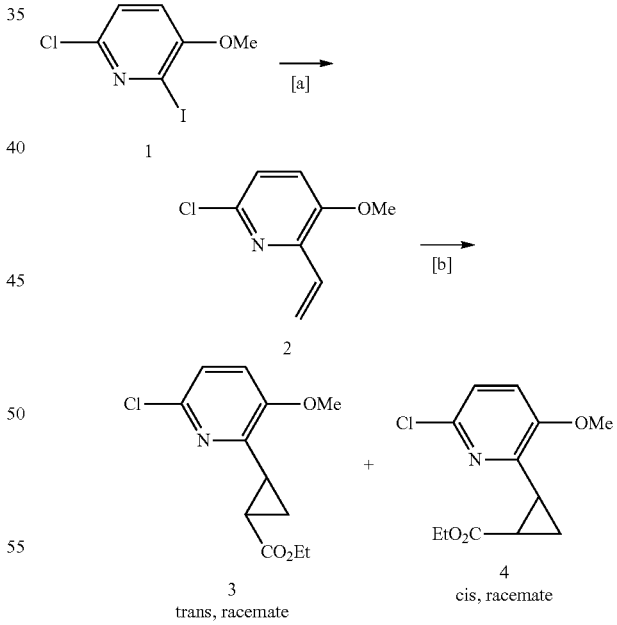

[Step a]

To a mixed solution of compound 1 (1.00 g, 3.71 mmol) in dioxane (20.0 mL) and water (5.00 mL) were added 4,4,5,5-tetramethyl-2-vinyl-1,3,2-dioxaborolane (695 μL, 4.10 mmol), potassium carbonate (1.03 g, 7.41 mmol) and tetrakis(triphenylphosphine)palladium(0) (220 mg, 0.190 mmol), and the mixture was stirred in a nitrogen atmosphere with heating at 90° C. for 4 hr. Furthermore, to the reaction solution were added 4,4,5,5-tetramethyl-2-vinyl-1,3,2-dioxaborolane (255 μL, 1.50 mmol) and tetrakis(triphenylphosphine)palladium(0) (130 mg, 0.112 mmol), and the mixture was stirred in a nitrogen atmosphere with heating at 90° C. for 4 hr. To the reaction solution was added water, and the mixture was extracted with ethyl acetate. The organic layer was washed with saturated brine, dried over anhydrous sodium sulfate, filtered, and concentrated. The residue was purified by silica gel chromatography to give compound 2 (420 mg, 66.8%).

MS(ESI)m/z: 170,172 (M+1)+.

[Step b]

To a solution of compound 2 (420 mg, 2.47 mmol) in toluene (10.0 mL) was added ethyl diazoacetate (85% toluene solution, 290 μL, 2.35 mmol), and the mixture was stirred with heating at 105° C. for 7 hr. To the reaction solution was further added ethyl diazoacetate (85% toluene solution, 1.22 mL, 8.34 mmol), and the mixture was stirred with heating at 105° C. for 1.5 hr. The reaction solution was concentrated under reduced pressure, and the residue was purified by silica gel chromatography to give compound 3 (320 mg, 50.6%) and compound 4 (140 mg, 22.1%).

MS(ESI)m/z: 256, 258 (M+1)+.
MS(ESI)m/z: 256, 258 (M+1)+.

Reference Example 18

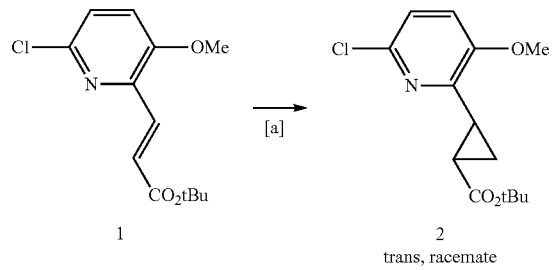 [SMILES: COc1ccc(Cl)nc1/C=C/C(=O)OC(C)(C)C ; COc1ccc(Cl)nc1C1CC1C(=O)OC(C)(C)C]

[Step a]

A solution of sodium hydride (60 wt %, 35.0 mg, 876 μmol) in dimethyl sulfoxide (4.00 mL) was stirred in a nitrogen atmosphere with heating at 60° C. for 30 min. To the reaction solution was added trimethylsulfoxonium iodide (220 mg, 1.00 mmol) at room temperature, and the mixture was stirred for 30 min. To the reaction solution was added a solution of compound 1 (200 mg, 742 μmol) in dimethyl sulfoxide (4.00 mL), and the mixture was stirred at room temperature for 6 hr. To the reaction solution were added saturated aqueous ammonium chloride solution and water, and the mixture was extracted with ethyl acetate. The organic layer was washed with water and saturated brine, dried over anhydrous sodium sulfate, filtered, and concentrated. The residue was purified by silica gel chromatography to give compound 2 (115 mg, 54.6%).

MS(ESI)m/z: 284, 286(M+1)+.

Reference Example 19

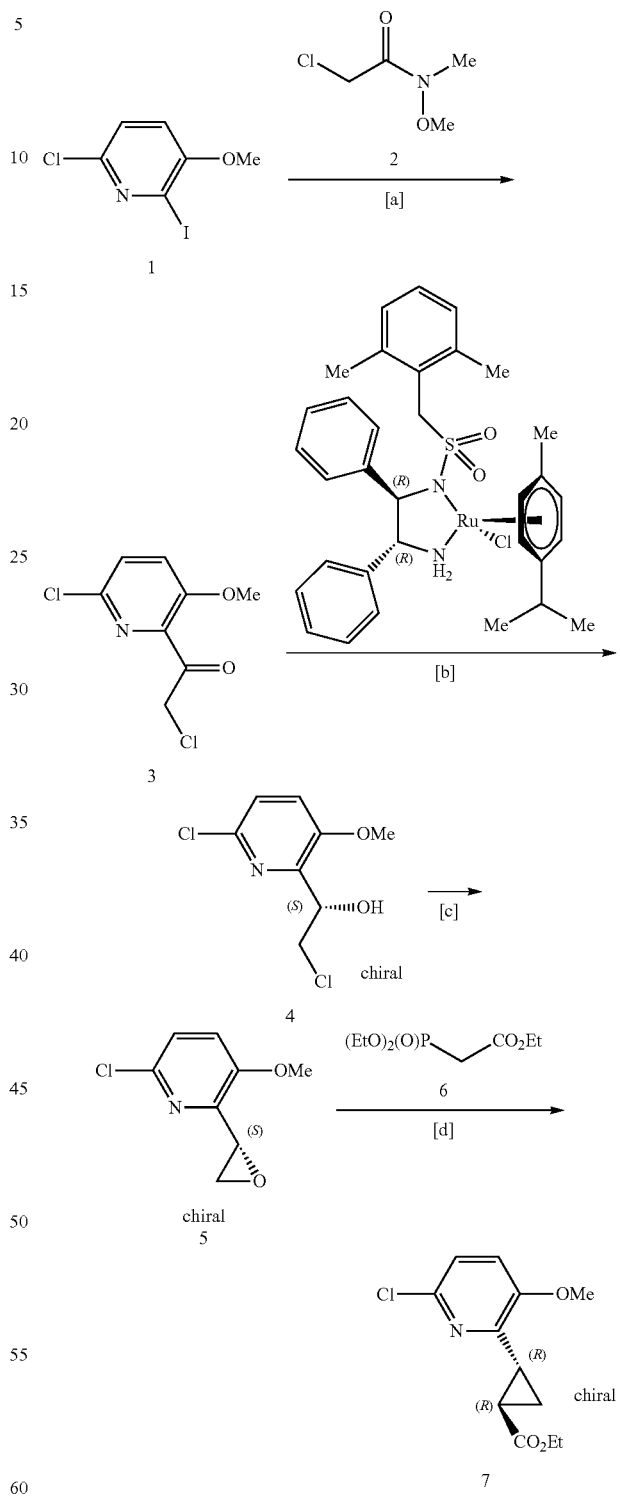

[Step a]

To a solution of 2 M solution (24.5 mL, 49.0 mmol) of isopropylmagnesium chloride in tetrahydrofuran in tetrahydrofuran (30.0 mL) was added dropwise a solution of compound 1 (12.0 g, 44.5 mmol) in tetrahydrofuran (30.0 mL) in a nitrogen atmosphere at room temperature and the mixture was stirred for 1 hr. To the reaction solution was further added dropwise 2 M solution (4.45 mL, 8.91 mmol) of isopropylmagnesium chloride in tetrahydrofuran, and the mixture was stirred at room temperature for 1 hr. To the reaction solution was added a solution of compound 2 (6.43 g, 46.8 mmol) in tetrahydrofuran (30.0 mL) under ice-cooling, and the mixture was stirred for 2 hr, and stirred overnight while raising the temperature to room temperature. To the reaction solution were added water (40.0 mL) and saturated aqueous ammonium chloride solution (160 mL), and the mixture was extracted with ethyl acetate. The organic layer was washed with saturated brine, dried over anhydrous sodium sulfate, filtered, and concentrated. The obtained residue was suspended and washed in chloroform (50.0 mL), to the suspension was added hexane (100 mL) and the mixture was suspension-washed again to give compound 3 (5.84 g, 59.6%).

MS(ESI)m/z: 220, 222(M+1)+.

[Step b]

To a solution of compound 3 (3.00 g, 13.6 mmol), chloro[(1R,2R)—N-(2',6'-dimethylbenzylsulfonyl)-1,2-diphenylethanediamine](p-cymene)ruthenium (II) (181 mg, 272 μmol) and triethylamine (3.78 mL, 27.2 mmol) in N,N-dimethylformamide (27.3 mL) was added formic acid (2.57 mL, 68.2 mmol) at room temperature, and the mixture was stirred at room temperature for 1 hr. To the reaction solution was added water (150 mL), and the mixture was extracted with ethyl acetate. The organic layer was washed with saturated aqueous sodium hydrogen carbonate solution, water, saturated brine, dried over anhydrous sodium sulfate, filtered, and concentrated. The residue was purified by silica gel chromatography to give compound 4 (3.08 g, 91.1% ee).

MS(ESI)m/z: 222, 224(M+1)+.

[Step c]

To a solution of compound 4 (3.08 g, 13.9 mmol) in diethyl ether (30.0 mL) were added water (30.0 mL) and potassium hydroxide (2.35 g, 41.9 mmol), and the mixture was stirred overnight. The reaction solution was extracted with ethyl acetate, the organic layer was washed with saturated brine, dried over anhydrous sodium sulfate, filtered, and concentrated to give compound 5 (2.39 g, 92.2%, 90.0% ee).

MS(APCI)m/z: 186, 188(M+1)+.

[Step d]

To a solution of compound 6 (556 mg, 2.48 mmol) in tetrahydrofuran (1.00 mL) was added dropwise 1 M solution (2.16 mL, 2.15 mmol) of potassium tert-butoxide in tetrahydrofuran, to the reaction solution was added compound 5 (200 mg, 1.08 mmol), and the mixture was stirred in a nitrogen atmosphere, with heating under reflux for 1 day. The reaction solution was allowed to cool to room temperature, water (10.0 mL) was added, and the mixture was extracted with ethyl acetate (30.0 mL). The organic layer was washed with saturated brine, dried over anhydrous sodium sulfate, filtered, and concentrated. The obtained residue was purified by silica gel chromatography to give compound 7 (236 mg, 85.7%, 89.6% ee).

MS(ESI)m/z: 256, 258(M+1)+.

Reference Example 20

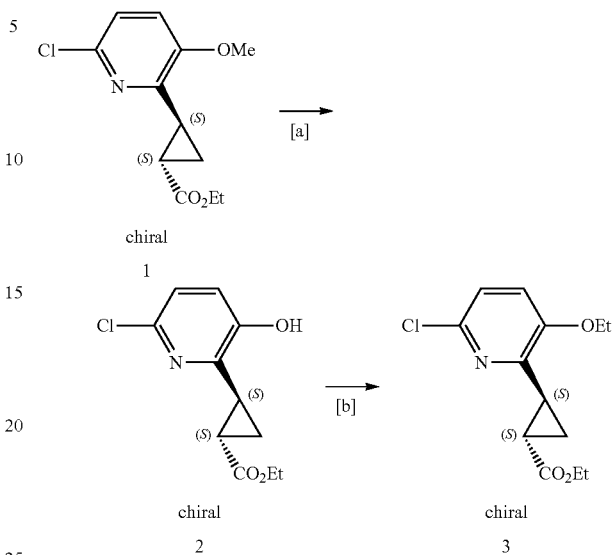

[Step a]

To a solution of compound 1 (2.00 g, 7.82 mmol, 99.27% ee) in dichloromethane (30.0 mL) was added dropwise 1 M solution (23.5 mL, 23.5 mmol) of boron tribromide in dichloromethane under cooling at −20° C., and the mixture was stirred for 5 hr while raising the temperature to room temperature. To the reaction solution was added ethanol (3.00 mL) under cooling at −20° C., the temperature was raised to room temperature, saturated aqueous sodium hydrogen carbonate solution and 4 M-aqueous sodium hydroxide solution (3.00 mL) were added to adjust to pH=7, and the mixture was extracted with chloroform. The organic layer was washed with saturated brine, dried over anhydrous sodium sulfate, filtered, and concentrated. The obtained residue was purified by silica gel chromatography to give compound 2 (1.60 g, 84.9%).

MS(ESI)m/z: 242(M+1)+.

[Step b]

To a solution of compound 2 (250 mg, 1.04 mmol) in N,N-dimethylformamide (5.2 mL) were added potassium carbonate (287 mg, 2.08 mmol), ethyl iodide (142 μL, 1.45 mmol), and the mixture was stirred at room temperature for 7 hr. To the reaction solution was added water (20.0 mL), and the precipitated solid was collected by filtration and washed with water to give compound 3 (258 mg, 92.1%).

MS(ESI)m/z: 270(M+1)+.

Reference Example 21

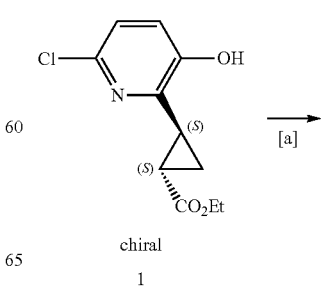

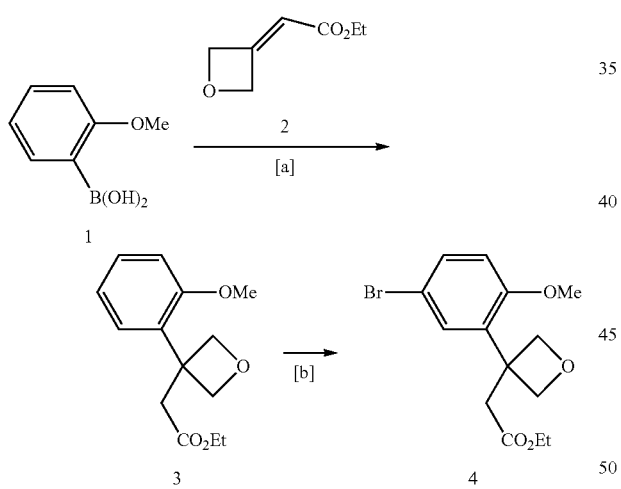

[Step a]

To a solution of compound 1 (1.00 g, 4.15 mmol) in N,N-dimethylformamide (20.0 mL) were added potassium carbonate (1.15 g, 8.31 mmol), 4-methoxybenzyl chloride (847 μL, 6.22 mmol), and the mixture was stirred at room temperature for 3 days. To the reaction solution was added water (20.0 mL), then 1 M-hydrochloric acid was added to neutralize the mixture, and the mixture was extracted with ethyl acetate. The organic layer was washed with saturated brine, dried over anhydrous sodium sulfate, filtered, and concentrated. The obtained residue was purified by silica gel chromatography to give compound 2 (1.40 g, 93.5%).

MS(ESI)m/z: 362(M+1)+.

Reference Example 22

[Step a]

To a solution of chloro(1,5-cyclooctadiene)rhodium (I) dimer (410 mg, 0.831 mmol) in dioxane (40.0 mL) was successively added 1.5 M-aqueous potassium hydroxide solution (14.5 mL, 2.17 mmol), a solution of compound 2 (2.38 g, 16.7 mmol) in dioxane (40.0 mL), and a solution of compound 1 (2.54 g, 16.8 mmol) in dioxane (40.0 mL), and the mixture was stirred at room temperature for 3 hr. To the reaction solution were added diethyl ether and water, and the mixture was extracted with diethyl ether. The organic layer was washed with saturated brine, dried over anhydrous sodium sulfate, filtered, and concentrated. The residue was purified by silica gel chromatography to give compound 3 (440 mg).

MS(ESI)m/z: 251 (M+1)+.

[Step b]

To a solution of the obtained compound 3 (440 mg) in acetonitrile (16.0 mL) was added N-bromosuccinimide (330 mg, 1.85 mmol), and the mixture was stirred at room temperature overnight. To the reaction solution was added water, and the mixture was extracted with ethyl acetate. The organic layer was washed with saturated brine, dried over anhydrous sodium sulfate, filtered, and concentrated. The residue was purified by silica gel chromatography to give compound 4 (335 mg).

MS(ESI)m/z: 329, 332 (M+1)+.

Reference Example 23

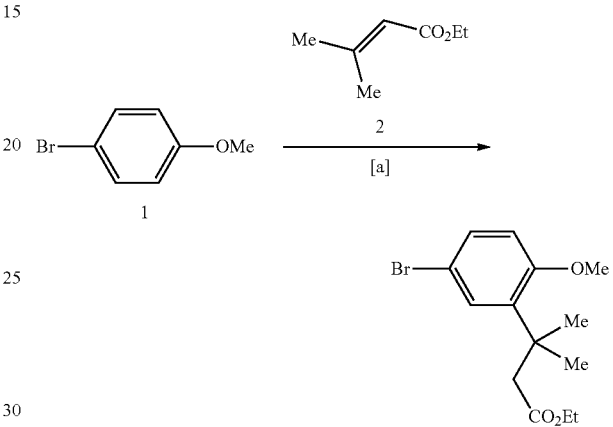

[Step a]

A solution of compound 1 (10.0 mL, 79.9 mmol) and compound 2 (7.20 g, 56.2 mmol) in methanesulfonic acid (24.0 mL) was stirred with heating at 65° C. for 42 hr. The reaction solution was ice-cooled, water was added, and the mixture was extracted with hexane. The organic layer was washed with water, 2 M-aqueous sodium hydroxide solution, water, saturated brine, is dried over anhydrous sodium sulfate, filtered, and concentrated. The residue was purified by silica gel chromatography to give compound 2 (11.0 g, 62.3%).

MS(ESI)m/z: 315, 317 (M+1)+.

Reference Example 24

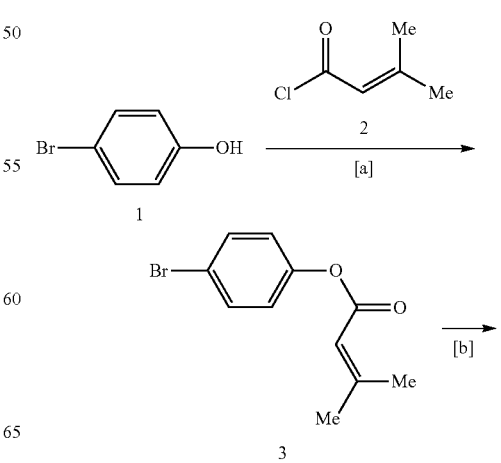

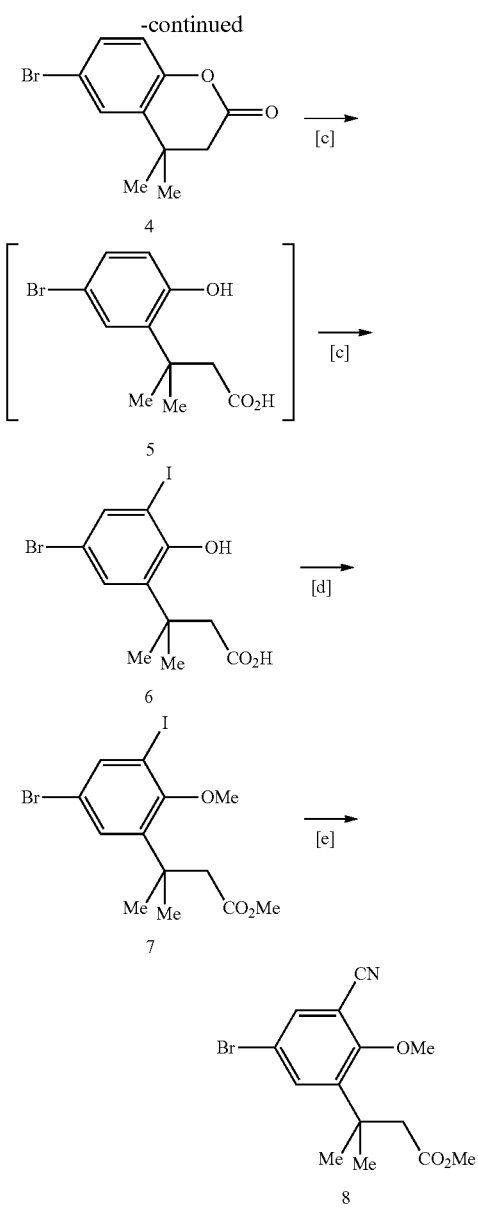

4

5

6

7

8

[Step a]

To a solution of sodium hydride (60 wt %, 1.00 g, 25.0 mmol) in THF (50.0 mL) was added compound 1 (4.33 g, 25.0 mmol) in 5 portions under ice-cooling, and the mixture was stirred for 25 min. To the reaction solution was further added compound 2 (2.80 g, 25.0 mmol), and the mixture was stirred for 6.5 hr while raising the temperature to room temperature. The reaction solution was ice-cooled, 2 M-aqueous sodium carbonate solution was added, and the mixture was extracted with ethyl acetate. The organic layer was washed with saturated brine, dried over anhydrous sodium sulfate, filtered, and concentrated. The residue was purified by silica gel chromatography to give compound 3 (6.70 g).

MS(ESI)m/z: 255,257(M+1)+.

[Step b]

To a solution of compound 3 (3.35 g, 12.5 mmol) in dichloromethane (100 mL) was added aluminum(III) chloride (3.15 g, 24.0 mmol) under ice-cooling, and the mixture was stirred overnight while raising the temperature to room temperature. To the reaction solution was added ice water, and the mixture was extracted with chloroform. The organic layer was washed with saturated brine, dried over anhydrous sodium sulfate, filtered, and concentrated. The residue was purified by silica gel chromatography to give compound 4 (1.30 g, 40.8%).

MS(ESI)m/z: 255,257(M+1)+.

[Step c]

To a mixed solution of compound 4 (1.30 g, 5.10 mmol) in tetrahydrofuran (10.0 mL) and methanol (5.00 mL) was added 2 M-aqueous sodium hydroxide solution (5.10 mL, 10.2 mmol), and the mixture was stirred at room temperature for 1.5 hr. To the reaction solution was added 0.5 M-hydrochloric acid (24.0 mL) under ice-cooling, and the mixture was extracted with ethyl acetate. The organic layer was washed with saturated brine, dried over anhydrous sodium sulfate, filtered, and concentrated. The residue was purified by silica gel chromatography to give a mixture (1.50 g) of compound 4 and compound 5 as a solid. The obtained solid (500 mg) was dissolved in methanol (10.0 mL), 1 M aqueous sodium hydroxide solution (3.5 mL, 3.5 mmol) was added, and the mixture was stirred at room temperature for 40 min. To the reaction solution was added sodium iodide (380 mg, 2.54 mmol), and the mixture was cooled to −10° C. Furthermore, aqueous sodium hypochlorite solution (1%, 15.0 mL, 2.02 mmol) was added, and the mixture was stirred for 30 min. To the reaction solution was added aqueous sodium thiosulfate solution (10%, 3.5 mL), and the mixture was stirred for 10 min, and 0.5 M-hydrochloric acid (14.0 mL) was added. The precipitated solid was washed with 5 mM-hydrochloric acid, dissolved in ethanol and toluene, and concentrated under reduced pressure to give compound 6 (645 mg).

MS(ESI)m/z: 399,401 (M+1)+.

[Step d]

To a solution of compound 6 (320 mg, 802 μmol) in N,N-dimethylformamide (4.00 mL) was added sodium hydride (60 wt %, 65 mg, 1.63 mmol) under ice-cooling, and the mixture was stirred for 20 min. To the reaction solution was further added methyl iodide (150 μL, 2.41 mmol), and the mixture was stirred overnight while raising the temperature to room temperature. To the reaction solution were added potassium carbonate (220 mg, 1.59 mmol) and methyl iodide (150 μL, 2.41 mmol), and the mixture was stirred at room temperature for 3 hr. To the reaction solution was added water, and the mixture was extracted with ethyl acetate. The organic layer was washed with 5 mM hydrochloric acid, saturated brine, dried over anhydrous sodium sulfate, filtered, and concentrated. The residue was purified by silica gel chromatography to give compound 7 (315 mg, 92.0%).

$^1$H-NMR (400 MHz, CDCl$_3$) δ: 1.45 (6H, s), 2.83 (2H, s), 3.52 (3H, s), 3.90 (3H, s), 7.38 (1H, d, J=2.1 Hz), 7.82 (1H, d, J=2.1 Hz).

[Step e]

To a solution of compound 7 (310 mg, 726 μmol) in N-methylpyrrolidone (3.50 mL) was added copper cyanide (330 mg, 3.68 mmol), and the mixture was stirred with heating at 150° C. for 4 hr. To the reaction solution was added water, and the mixture was filtered through celite, and the obtained filtrate was extracted with ethyl acetate. The organic layer was washed with water and saturated brine, dried over anhydrous sodium sulfate, filtered, and concentrated. The residue was purified by silica gel chromatography to give compound 8 (200 mg, 84.3%).

MS(ESI)m/z: 326,328(M+1)+.

Reference Example 25

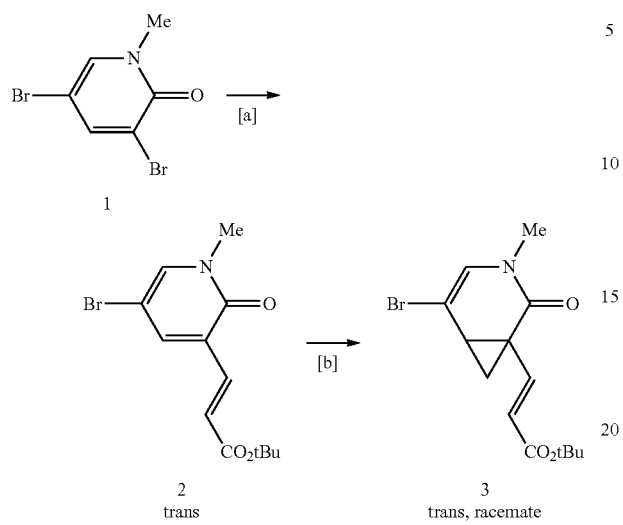

[Step a]

To compound 1 (CAS No. 14529-54-5, 500 mg, 1.87 mmol) in N,N-dimethylformamide (10.0 mL) solvent were added acrylic acid tert-butyl ester (240 mg, 1.87 mmol), palladium acetate (21.0 mg, 93.7 μmol), tri-(O-tolyl)phosphine (57.0 mg, 187 μmol), triethylamine (521 μL, 3.75 mmol), and the mixture was stirred in a nitrogen atmosphere with heating at 100° C. for 1 hr. The reaction solution was cooled to room temperature, water (50.0 mL) was added, and the mixture was extracted with ethyl acetate. The organic layer was washed with water and saturated brine, dried over anhydrous sodium sulfate, filtered, and concentrated. The residue was purified by silica gel chromatography to give compound 2 (245 mg, 41.1%).

MS(ESI)m/z: 314,316(M+1)+.

[Step b]

To dimethyl sulfoxide (4.00 mL) was added 1 M solution (1.30 mL, 1.30 mmol) of potassium tert-butoxide in tetrahydrofuran, trimethylsulfoxonium iodide (286 mg, 1.30 mmol) was added by small portions, and the mixture was stirred in a nitrogen atmosphere at room temperature. To the reaction solution was added a mixed solution of compound 2 (340 mg, 1.08 mmol) in dimethyl sulfoxide (2.00 mL) and tetrahydrofuran (2.00 mL) at room temperature, and the mixture was stirred overnight. To the reaction solution was added saturated aqueous ammonium chloride solution (30.0 mL), and the mixture was extracted with ethyl acetate. The organic layer was washed with water and saturated brine, dried over anhydrous sodium sulfate, filtered, and concentrated. The residue was purified by silica gel chromatography to give compound 3 (241 mg, 53.7%).

MS(ESI)m/z: 272,274(M+1)+.

Reference Example 26

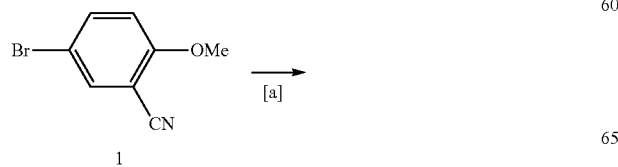

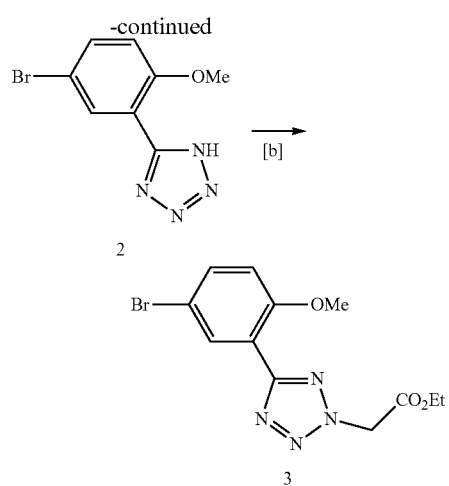

[Step a]

To a solution of compound 1 (3.00 g, 14.1 mmol) in N,N-dimethylformamide (30.0 mL) were added sodium azide (4.60 g, 70.7 mmol), pyridine hydrochloride (3.27 g, 28.3 mmol), and the mixture was stirred with heating at 130° C. for 2 hr. The reaction solution was allowed to cool to room temperature, water (200 mL), 1 M-hydrochloric acid were added to adjust to pH 4-5, and the mixture was extracted with ethyl acetate. The organic layer was washed with water and saturated brine, dried over anhydrous sodium sulfate, filtered and concentrated under reduced pressure, and the residue was purified by silica gel chromatography to give compound 2 (682 mg, 18.9%).

MS(ESI)m/z: 255, 257(M+1)+.

[Step b]

To a solution of compound 2 (500 mg, 1.96 mmol) in tetrahydrofuran (10.0 mL) were added triethylamine (492 μL, 3.53 mmol), ethyl bromoacetate (304 μL, 2.74 mmol), and the mixture was stirred with heating under reflux for 30 min. The reaction solution was concentrated, and the residue was purified by silica gel chromatography to give compound 3 (374 mg, 55.9%).

MS(ESI)m/z: 341, 343(M+1)+.

Reference Example 27

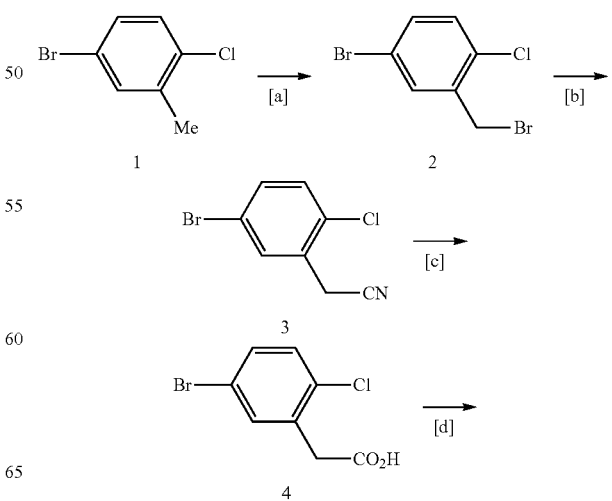

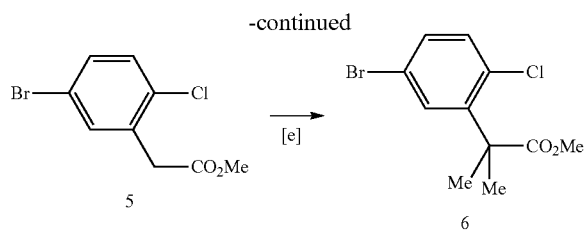

[Step a]

To a solution of compound 1 (2.00 g, 9.80 mmol) in carbon tetrachloride (50.0 mL) were added N-bromosuccinimide (1.92 g, 10.7 mmol) and benzoyl peroxide (24.0 mg, 99.1 μmol) at room temperature, and the mixture was stirred with heating under reflux for 5 hr. The reaction solution was filtered through celite, and the obtained filtrate was concentrated and the residue was purified by silica gel chromatography to give compound 2 (867 mg, 31.3%).

1H-NMR (400 MHz, CDCl$_3$) δ: 4.52 (2H, s), 7.26 (1H, d, J=8.7 Hz), 7.38 (1H, dd, J=8.7, 2.6 Hz), 7.58 (1H, d, J=2.6 Hz).

[Step b]

To a solution of compound 2 (533 mg, 1.89 mmol) in acetonitrile (5.00 mL) was added N,N,N,N-tetrabutylammonium cyanide (325 mg, 1.21 mmol) under ice-cooling, and the mixture was stirred for 5 hr while raising the temperature to room temperature. To the reaction solution was further added N,N,N,N-tetrabutylammonium cyanide (585 mg, 2.18 mmol), and the mixture was stirred at room temperature for 2 days. The reaction solution was concentrated, and ethyl acetate and aqueous sodium hydrogen carbonate solution were added to the residue, and the mixture was extracted with ethyl acetate. The organic layer was washed with saturated brine, dried over anhydrous sodium sulfate, filtered, and concentrated. The residue was purified by silica gel chromatography to give compound 3 (147 mg, 34.0%).

$^1$H-NMR (400 MHz, CDCl$_3$) δ: 3.82 (2H, s), 7.30 (1H, d, J=8.5 Hz), 7.44 (1H, dd, J=8.5, 2.3 Hz), 7.67 (1H, d, J=2.3 Hz).

[Step c]

To a solution of compound 3 (135 mg, 589 μmol) in ethanol (4.00 mL) were added water (1.00 mL), sodium hydroxide (94.0 mg, 2.35 mmol), and the mixture was stirred with heating under reflux for 7 hr. The reaction solution was allowed to cool to room temperature, concentrated, and chloroform was added to the residue. Under ice-cooling, 1 M-hydrochloric acid was added to adjust to pH 1-2, and the mixture was extracted with chloroform. The organic layer was washed with saturated brine, dried over anhydrous sodium sulfate, filtered, and concentrated to give compound 4 (116 mg, 79.4%).

MS(ESI)m/z: 247(M−1)−.

[Step d]

To a solution of compound 4 (116 mg, 468 μmol) in methanol (4.00 mL) was added concentrated sulfuric acid (22.0 μL, 412 μmol), and the mixture was stirred with heating under reflux for 2 hr. The reaction solution was allowed to cool to room temperature, aqueous sodium hydrogen carbonate solution and ethyl acetate were added, and the mixture was extracted with ethyl acetate. The organic layer was washed with saturated brine, dried over anhydrous sodium sulfate, filtered, and concentrated. The residue was purified by silica gel chromatography to give compound 5 (106 mg, 86.5%).

MS(ESI)m/z: 263,265(M+1)+.

[Step e]

To a solution of compound 5 (100 mg, 381 μmol) in N,N-dimethylformamide (4.00 mL) was added methyl iodide (95 μL, 1.52 mmol) under ice-cooling, sodium hydride (60 wt %, 46.0 mg, 1.14 mmol) was further added, and the mixture was stirred for 4 hr while raising the temperature to room temperature. To the reaction solution was added 1 M-hydrochloric acid to quench the reaction, aqueous hydrogencarbonate solution was added, and the mixture was extracted with ethyl acetate. The organic layer was washed with saturated brine, dried over anhydrous sodium sulfate, filtered, and concentrated. The residue was purified by silica gel chromatography to give compound 6 (95.0 mg, 86.0%).

MS(ESI)m/z: 291,293(M+1)+.

Reference Example 28

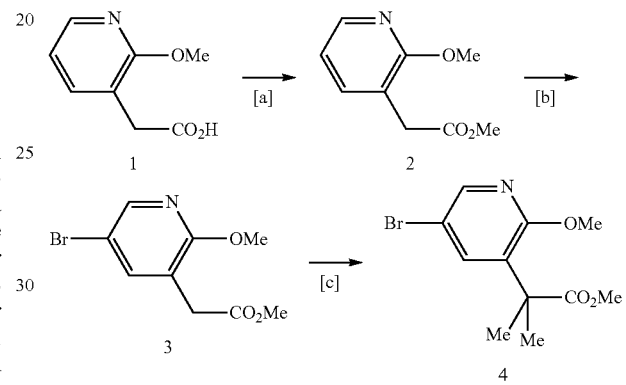

[Step a]

To a solution of compound 1 (CAS No. 351410-38-3, 1.00 g, 5.98 mmol) in N,N-dimethylformamide (12.0 mL) were added methyl iodide (745 μL, 11.9 mmol) and potassium carbonate (2.06 g, 14.9 mmol), and the mixture was stirred at room temperature for 5 hr. To the reaction solution were added saturated aqueous sodium hydrogen carbonate solution and ethyl acetate, and the mixture was extracted with ethyl acetate. The organic layer was washed with saturated brine, dried over anhydrous sodium sulfate, filtered, and concentrated. The residue was purified by silica gel chromatography to give compound 2 (1.02 g, 94.2%).

MS(ESI)m/z: 182(M+1)+.

[Step b]

To a solution of compound 2 (500 mg, 2.76 mmol) in chloroform (10.0 mL) was added bromine (155 μL, 3.03 mmol) over 5 min under ice-cooling, and the mixture was stirred for 3 hr while raising the temperature to room temperature. To the reaction solution was further added bromine (155 μL, 3.03 mmol) over 5 min under ice-cooling, and the mixture was stirred for 1 hr while raising the temperature to room temperature, and stirred under heating at 50° C. for 30 min. The reaction solution was allowed to cool to room temperature, aqueous sodium thiosulfate solution was added to quench the reaction, aqueous sodium hydrogen carbonate solution and ethyl acetate were added, and the mixture was extracted with ethyl acetate. The organic layer was washed with saturated brine, dried over anhydrous sodium sulfate, filtered, and concentrated. The residue was purified by silica gel chromatography to give compound 3 (380 mg, 53.2%).

MS(ESI)m/z: 260, 262(M+1)+.

[Step c]

To a solution of compound 3 (200 mg, 772 μmol) in N,N-dimethylformamide (4.00 mL) was added methyl iodide (192 μL, 3.08 mmol) under ice-cooling, sodium hydride (60 wt %, 93.0 mg, 2.31 mmol) was further added, and the mixture was stirred for 5 hr while raising the temperature to room temperature. To the reaction solution was added 1 M-hydrochloric acid to quench the reaction, aqueous sodium hydrogen carbonate solution was added, and the mixture was extracted with ethyl acetate. The organic layer was washed with saturated brine, dried over anhydrous sodium sulfate, filtered, and concentrated. The residue was purified by silica gel chromatography to give compound 4 (206 mg, 93.0%).

MS(ESI)m/z: 288,290(M+1)+.

Reference Example 29

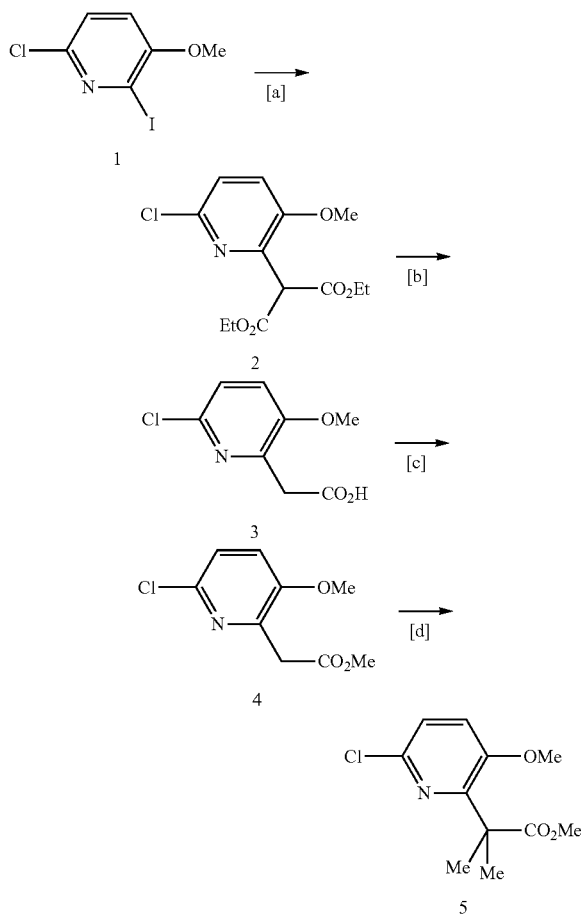

[Step a]

To a solution of compound 1 (1.00 g, 3.71 mmol) in dioxane (6.00 mL) were added diethyl malonate (1.12 mL, 7.43 mmol), copper(I) iodide (71 mg, 371 μmol), picolinic acid (91 mg, 742 μmol), cesium carbonate (3.62 g, 11.1 mmol), and the mixture was stirred in a nitrogen atmosphere with heating under reflux for 5 hr. The reaction solution was allowed to cool to room temperature, saturated aqueous ammonium chloride solution was added, and the mixture was extracted with ethyl acetate. The organic layer was washed with saturated brine, dried over anhydrous sodium sulfate, filtered, and concentrated. The residue was purified by silica gel chromatography to give compound 2 (1.04 g, 93.1%).

MS(ESI)m/z: 302(M+1)+.

[Step b]

To a solution of compound 2 (500 mg, 1.66 mmol) in ethanol (18.0 mL) was added potassium hydroxide (466 mg, 8.30 mmol), and the mixture was stirred with heating under reflux for 5 hr. The reaction solution was concentrated, chloroform was added and the mixture was ice-cooled. The mixture was adjusted to pH=4 with 1 M-hydrochloric acid, and extracted with chloroform. The organic layer was washed with saturated brine, dried over anhydrous sodium sulfate, filtered, and concentrated to give compound 3 (294 mg, 88.1%).

MS(ESI)m/z: 202(M+1)+.

[Step c]

To a mixed solution of compound 3 (290 mg, 1.44 mmol) in N,N-dimethylformamide (8.00 mL) and dichloromethane (4.00 mL) were added potassium carbonate (498 mg, 3.60 mmol) and methyl iodide (180 μL, 2.88 mmol), and the mixture was stirred in a nitrogen atmosphere at room temperature for 3 days. To the reaction solution was added water, and the mixture was extracted with ethyl acetate. The organic layer was washed with saturated brine, dried over anhydrous sodium sulfate, filtered, and concentrated. The residue was purified by silica gel chromatography to give compound 4 (294 mg, 94.9%).

MS(ESI)m/z: 216(M+1)+.

[Step d]

To a solution of compound 4 (153 mg, 0.711 mmol) in N,N-dimethylformamide (4.00 mL) was added methyl iodide (177 μL, 3.84 mmol) under ice-cooling, sodium hydride (60 wt %, 85.0 mg, 2.13 mmol) was further added, and the mixture was stirred for 17 hr while raising the temperature to room temperature. To the reaction solution was added water, and the mixture was extracted with ethyl acetate. The organic layer was washed with saturated brine, dried over anhydrous sodium sulfate, filtered, and concentrated. The residue was dissolved in dimethylformamide (4.00 mL), methyl iodide (177 μL, 2.84 mmol) was added under ice-cooling, sodium hydride (85.0 mg, 2.13 mmol) was further added, and the mixture was stirred for 4 hr while raising the temperature to room temperature. To the reaction solution was added water, and the mixture was extracted with ethyl acetate. The organic layer was washed with saturated brine, dried over anhydrous sodium sulfate, filtered, and concentrated. The residue was purified by silica gel chromatography to give compound 5 (142 mg, 82.2%).

MS(ESI)m/z: 244(M+1)+.

Reference Example 30

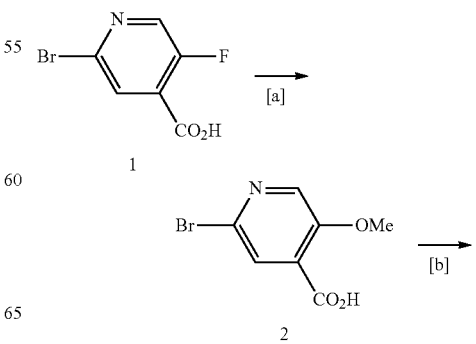

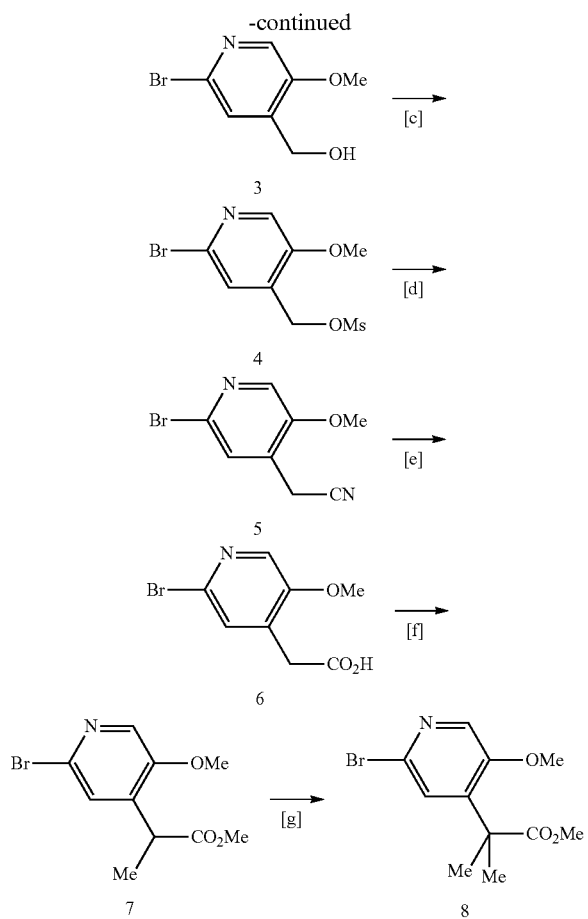

[Step a]

To a solution of compound 1 (8.00 g, 36.4 mmol) in methanol (120 mL) was added 5 M methanol solution (72.8 mL, 364 mmol) of sodium methoxide, and the mixture was stirred with heating at 60° C. for 1 day. The reaction solution was concentrated, water was added, and the mixture was adjusted to pH=3-4 with concentrated hydrochloric acid under ice-cooling. The precipitated solid was collected by filtration, and washed with water to give compound 2 (5.08 g, 60.2%).

MS(ESI)m/z: 232(M+1)+.

[Step b]

To a solution of compound 2 (1.00 g, 4.32 mmol) in tetrahydrofuran (20.0 mL) was added dropwise 0.95 M solution (11.4 mL, 10.8 mmol) of borane-tetrahydrofuran complex in tetrahydrofuran in a nitrogen atmosphere under ice-cooling, and the mixture was stirred for 1 day while raising the temperature to room temperature. To the reaction solution was added water to quench the reaction, 3 M-aqueous sodium hydroxide solution (15.0 mL) was added, and the mixture was stirred at room temperature for 1 hr. The organic solvent in the reaction solution was evaporated by concentration under reduced pressure, and the mixture was extracted with chloroform. The organic layer was washed with saturated brine, dried over anhydrous sodium sulfate, filtered, and concentrated. The residue was purified by silica gel chromatography to give compound 3 (880 mg, 93.9%).

MS(ESI)m/z: 218, 220(M+1)+.

[Step c]

To a solution of compound 3 (440 mg, 2.02 mmol) in tetrahydrofuran (10.0 mL) were added triethylamine (706 µL, 5.05 mmol), methanesulfonyl chloride (235 µL, 3.04 mmol) under ice-cooling in a nitrogen atmosphere, and the mixture was stirred for 1 hr. To the reaction solution were added saturated aqueous sodium hydrogen carbonate solution and ethyl acetate, and the mixture was extracted with ethyl acetate. The organic layer was washed with saturated brine, dried over anhydrous sodium sulfate, filtered, and concentrated to give compound 4 (590 mg, 99.0%).

MS(ESI)m/z: 296, 298(M+1)+.

[Step d]

To a solution of compound 4 (590 mg, 2.00 mmol) in tetrahydrofuran (5.00 mL) were added sodium cyanide (119 mg, 2.42 mmol) and triethylamine (706 µL, 5.05 mmol), and the mixture was stirred in a nitrogen atmosphere with heating at 50° C. for 4 hr. The reaction solution was allowed to cool to room temperature, saturated aqueous sodium hydrogen carbonate solution and ethyl acetate were added, and the mixture was extracted with ethyl acetate. The organic layer was washed with saturated brine, dried over anhydrous sodium sulfate, filtered, and concentrated. The residue was purified by silica gel chromatography to give compound 5 (130 mg, 28.8%).

MS(ESI)m/z: 227, 229(M+1)+.

[Step e]

To a solution of compound 5 (130 mg, 575 µmol) in ethanol (4.00 mL) were added water (1.00 mL), sodium hydroxide (92.0 mg, 2.30 mmol), and the mixture was stirred with heating under reflux for 5 hr. The reaction solution was allowed to cool to room temperature, and concentrated under reduced pressure. The obtained residue was dissolved in chloroform, 1 M-hydrochloric acid was added under ice-cooling to adjust to pH 4-5, and the mixture was extracted with chloroform. The organic layer was washed with saturated brine, dried over anhydrous sodium sulfate, filtered, and concentrated to give compound 6 (107 mg, 75.9%).

MS(ESI)m/z: 246, 248(M+1)+.

[Step f]

To a solution of compound 6 (107 mg, 437 µmol) in N,N-dimethylformamide (4.00 mL) were added potassium carbonate (199 mg, 1.43 mmol) and methyl iodide (72.0 µL, 1.15 mmol), and the mixture was stirred in a nitrogen atmosphere at room temperature for 12 hr. To the reaction solution was added saturated aqueous sodium hydrogen carbonate solution, and the mixture was extracted with ethyl acetate. The organic layer was washed with saturated brine, dried over anhydrous sodium sulfate, filtered, and concentrated. The residue was purified by silica gel chromatography to give compound 7 (76.0 mg, 63.4%).

MS(ESI)m/z: 274, 276(M+1)+.

[Step g]

To a solution of compound 7 (76 mg, 0.278 mmol) in N,N-dimethylformamide (4.00 mL) was added methyl iodide (107 µL, 1.72 mmol) under ice-cooling, sodium hydride (60 wt %, 69.0 mg, 1.72 mmol) was further added, and the mixture was stirred for 2 hr while raising the temperature to room temperature. To the reaction solution was added saturated aqueous sodium hydrogen carbonate solution, and the mixture was extracted with ethyl acetate. The organic layer was washed with saturated brine, dried over anhydrous sodium sulfate, filtered, and concentrated. The residue was purified by silica gel chromatography to give compound 8 (55.0 mg, 68.7%).

MS(ESI)m/z: 288, 290(M+1)+.

Reference Example 31

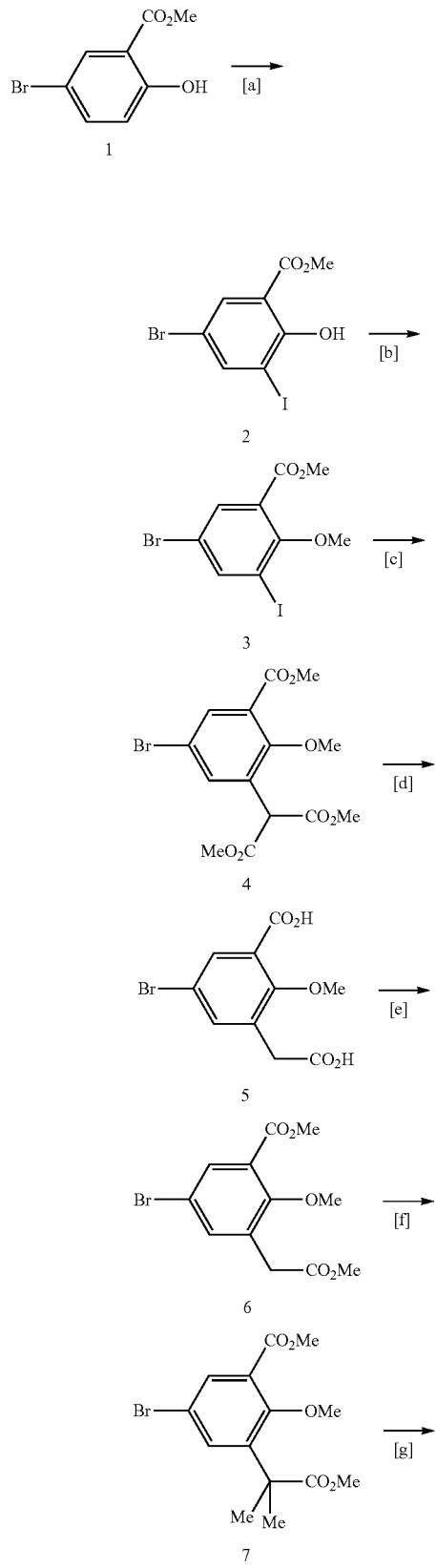

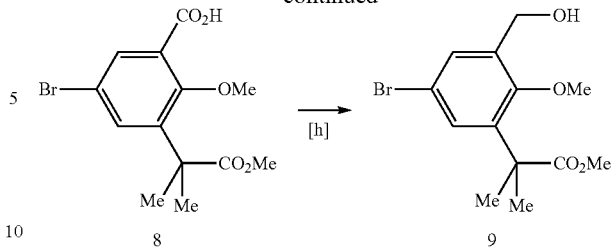

[Step a]
To a solution of compound 1 (10.0 g, 43.3 mmol) in N,N-dimethylformamide (50.0 mL) were added sodium iodide (7.82 g, 52.1 mmol) and chloramine-T trihydrate (14.4 g, 51.2 mmol) under a nitrogen atmosphere, and the mixture was stirred for 14 hr. The reaction solution was filtered through celite, to the obtained filtrate were added aqueous sodium thiosulfate solution and ethyl acetate, and the mixture was extracted with ethyl acetate. The organic layer was washed with 1 M-hydrochloric acid, saturated brine, dried over anhydrous sodium sulfate, filtered, and concentrated. The residue was recrystallized from ethyl acetate to give compound 2 (13.9 g, 90.3%).
MS(ESI)m/z: 356(M+1)+.
[Step b]
To a solution of compound 2 (2.00 g, 5.62 mmol) in N,N-dimethylformamide (10.0 mL) were added potassium carbonate (1.55 g, 11.2 mmol) and methyl iodide (490 μL, 7.86 mmol), and the mixture was stirred at room temperature for 17 hr. To the reaction solution were added saturated aqueous sodium hydrogen carbonate solution and ethyl acetate, and the mixture was extracted with ethyl acetate. The organic layer was washed with 1 M-hydrochloric acid, saturated brine, dried over anhydrous sodium sulfate, filtered, and concentrated. The residue was purified by silica gel chromatography to give compound 3 (2.08 g, 100%).
MS(ESI)m/z: 371, 373(M+1)+.
[Step c]
To a solution of compound 3 (6.00 g, 16.2 mmol) in dioxane (40.0 mL) were added diethyl malonate (5.56 mL, 48.6 mmol), copper(I) iodide (1.23 g, 6.48 mmol), picolinic acid (1.59 g, 12.9 mmol), cesium carbonate (15.8 g, 48.6 mmol), and the mixture was stirred in a nitrogen atmosphere with heating under reflux for 2 hr. The reaction solution was filtered through celite, saturated aqueous sodium hydrogen carbonate solution was added, and the mixture was extracted with ethyl acetate. The organic layer was washed with saturated brine, dried over anhydrous sodium sulfate, filtered, and concentrated. The residue was purified by silica gel chromatography to give compound 4 (3.92 g, 64.7%).
MS(ESI)m/z: 375, 377(M+1)+.
[Step d]
To a solution of compound 4 (8.00 g, 21.3 mmol) in methanol (100 mL) was added potassium hydroxide (3.60 g, 64.1 mmol), and the mixture was stirred for 1 hr with heating under reflux. To the reaction solution was further added potassium hydroxide (1.80 g, 32.0 mmol), and the mixture was stirred for 3 hr with heating under reflux. The reaction solution was allowed to cool to room temperature, concentrated, chloroform was added, and the mixture was adjusted to pH=2 with 6 M-hydrochloric acid under ice-cooling. The obtained solution was extracted with chloroform, the organic layer was washed with saturated brine, dried over anhydrous sodium sulfate, filtered, and concentrated. The obtained residue was suspended and washed in diisopropyl ether to give compound 5 (5.29 g, 86.2%).

MS(ESI)m/z: 289, 291(M+1)+.

[Step e]

To a solution of compound 5 (5.29 g, 18.3 mmol) in N,N-dimethylformamide (50.0 mL) were added potassium carbonate (10.1 g, 73.2 mmol) and methyl iodide (3.43 mL, 55.1 mmol), and the mixture was stirred in a nitrogen atmosphere at room temperature for 17 hr. To the reaction solution was added saturated aqueous sodium hydrogen carbonate solution, and the mixture was extracted with ethyl acetate. The organic layer was washed with 1 M-hydrochloric acid, saturated brine, dried over anhydrous sodium sulfate, filtered, and concentrated. The residue was purified by silica gel chromatography to give compound 6 (5.68 g, 98.2%).

MS(ESI)m/z: 317, 319(M+1)+.

[Step f]

To a solution of compound 6 (5.68 g, 17.9 mmol) in N,N-dimethylformamide (40.0 mL) was added methyl iodide (4.48 mL, 71.9 mmol) under ice-cooling, sodium hydride (60 wt %, 2.88 g, 71.9 mmol) was further added, and the mixture was stirred for 5 hr while raising the temperature to room temperature. The reaction solution was adjusted to weak acidic with 1 M-hydrochloric acid under ice-cooling, and the mixture was extracted with ethyl acetate. The organic layer was washed with aqueous sodium hydrogen carbonate solution, saturated brine, dried over anhydrous sodium sulfate, filtered, and concentrated. The residue was purified by silica gel chromatography to give compound 7 (5.12 g, 83.1%).

MS(ESI)m/z: 345(M+1)+.

[Step g]

To a mixed solution of compound 7 (3.30 g, 9.59 mmol) in tetrahydrofuran (20.0 mL) and methanol (10.0 mL) was added 2 M-aqueous sodium hydroxide solution (10.0 mL), and the mixture was stirred at room temperature for 17 hr. To the reaction solution was added 6 M-hydrochloric acid to adjust pH to 2 under ice-cooling, and the mixture was extracted with chloroform. The organic layer was washed with aqueous sodium hydrogen carbonate solution, saturated brine, dried over anhydrous sodium sulfate, filtered, and concentrated. The residue was purified by silica gel chromatography to give compound 8 (2.97 g, 93.8%).

MS(ESI)m/z: 329, 331(M−1)−.

[Step h]

To a solution of compound 8 (2.97 g, 9.00 mmol) in tetrahydrofuran (20.0 mL) was added 0.95 M solution (20.1 mL, 19.1 mmol) of borane-tetrahydrofuran complex in tetrahydrofuran in a nitrogen atmosphere under ice-cooling, and the mixture was stirred for 5 hr while allowing the mixture to cool to room temperature. To the reaction solution was added methanol under ice-cooling to quench the reaction, 1 M-hydrochloric acid and ethyl acetate were added, and the mixture was extracted with ethyl acetate. The organic layer was washed with aqueous sodium hydrogen carbonate solution, saturated brine, dried over anhydrous sodium sulfate, filtered, and concentrated. The residue was purified by silica gel chromatography to give compound 9 (2.79 g, 98.1%).

MS(ESI)m/z: 317(M+1)+.

Reference Example 32

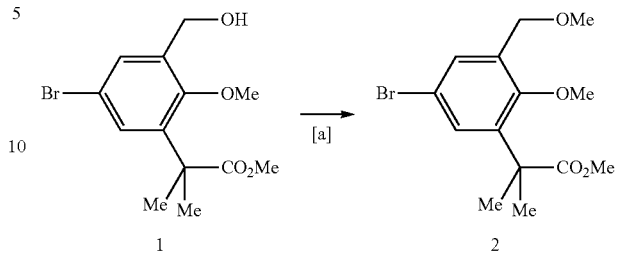

[Step a]

To a solution of compound 1 (100 mg, 316 μmol) in tetrahydrofuran (3.00 mL) were added methyl iodide (39.0 μL, 632 μmol), sodium hydride (60 wt %, 19.0 mg, 474 μmol) under ice-cooling, and the mixture was stirred for 5 hr while raising the temperature to room temperature. To the reaction solution was added saturated aqueous ammonium chloride solution, and the mixture was extracted with ethyl acetate. The organic layer was washed with saturated brine, dried over anhydrous sodium sulfate, filtered, and concentrated. The residue was purified by silica gel chromatography to give compound 2 (87 mg, 83.4%).

MS(ESI)m/z: 331(M+1)+.

Reference Example 33

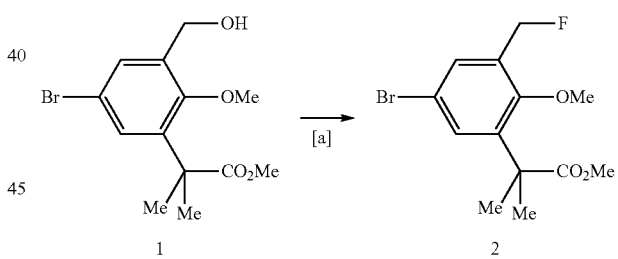

[Step a]

To a solution of compound 1 (100 mg, 316 μmol) in dichloromethane (3.00 mL) was added N,N-diethylaminosulfur trifluoride (DAST) (83.0 μL, 632 μmol) under ice-cooling, and the mixture was stirred for 5 hr while raising the temperature to room temperature. To the reaction solution was added methanol, and the mixture was concentrated, saturated aqueous sodium hydrogen carbonate solution and ethyl acetate were added, and the mixture was extracted with ethyl acetate. The organic layer was washed with saturated brine, dried over anhydrous sodium sulfate, filtered, and concentrated. The residue was purified by silica gel chromatography to give compound 2 (72.0 mg, 71.6%).

MS(ESI)m/z: 319, 321(M+1)+.

Reference Example 34

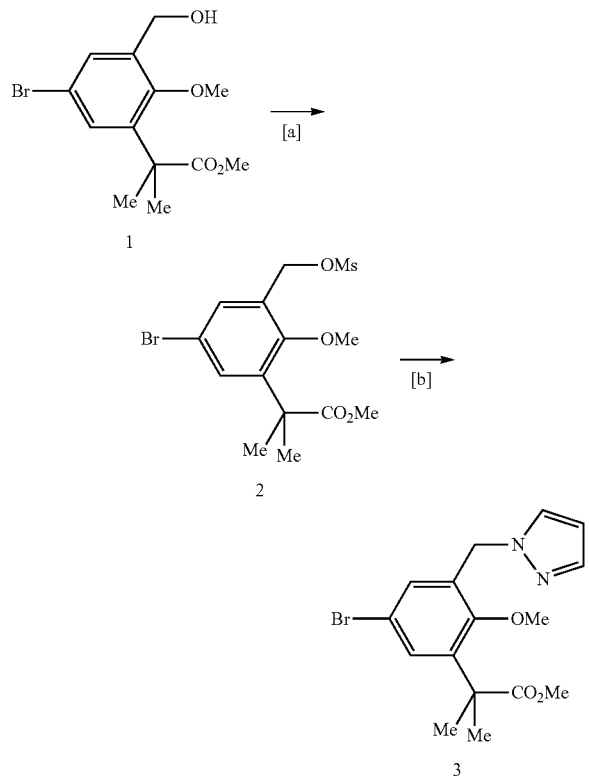

[Step a]

To a solution of compound 1 (300 mg, 949 μmol) in tetrahydrofuran (5.00 mL) were added triethylamine (331 μL, 2.37 mmol), methanesulfonyl chloride (110 μL, 1.42 mmol) under ice-cooling in a nitrogen atmosphere, and the mixture was stirred for 1 hr. To the reaction solution were added saturated aqueous sodium hydrogen carbonate solution and ethyl acetate under ice-cooling, and the mixture was extracted with ethyl acetate. The organic layer was washed with saturated aqueous ammonium chloride solution, saturated brine, dried over anhydrous sodium sulfate, filtered, and concentrated to give compound 2 (396 mg).

$^1$H-NMR (400 MHz, CDCl$_3$) δ: 1.51 (6H, s), 3.02 (3H, s), 3.67 (3H, s), 3.77 (3H, s), 5.24 (2H, s), 7.46 (1H, d, J=2.3 Hz), 7.49 (1H, d, J=2.3 Hz).

[Step b]

To a solution of compound 2 (80.0 mg, 203 μmol) in acetonitrile (4.00 mL) were added potassium carbonate (84.0 mg, 609 μmol), pyrazole (138 mg, 2.03 mmol), and the mixture was stirred in a nitrogen atmosphere with heating at 80° C. for 17 hr. The reaction solution was allowed to cool to room temperature, saturated aqueous sodium hydrogen carbonate solution and chloroform were added, and the mixture was extracted with chloroform. The organic layer was washed with saturated brine, dried over anhydrous sodium sulfate, filtered, and concentrated. The residue was purified by silica gel chromatography to give compound 3 (63.0 mg, 84.8%).

MS(ESI)m/z: 367, 369(M+1)+.

Reference Example 35

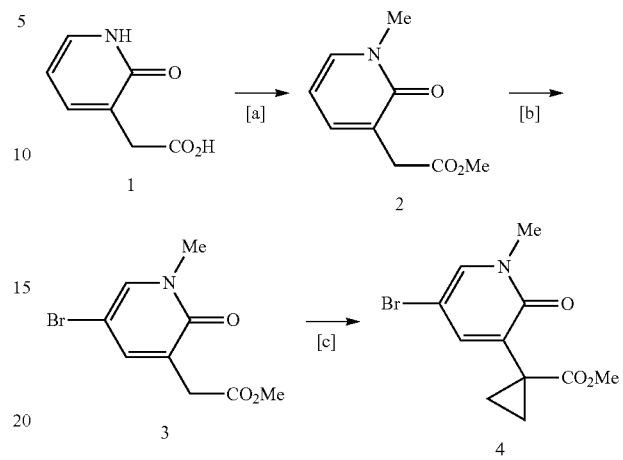

[Step a]

To a solution of compound 1 (CAS No. 100960-03-0, 2.00 g, 13.1 mmol) in N,N-dimethylformamide (20.0 mL) were added potassium carbonate (5.42 g, 39.2 mmol) and methyl iodide (2.44 mL, 39.2 mmol), and the mixture was stirred at room temperature for 6 hr. To the reaction solution was further added methyl iodide (1.22 mL, 19.6 mmol) and the mixture was stirred overnight. To the reaction solution was added water, and the mixture was extracted with chloroform. The organic layer was dried over anhydrous magnesium sulfate, filtered, and concentrated. The residue was purified by silica gel chromatography to give compound 2 (1.29 g, 54.7%).

MS(ESI)m/z: 182(M+1)+.

[Step b]

To a solution of compound 2 (1.25 g, 6.90 mmol) in N,N-dimethylformamide (12.5 mL) was added N-bromosuccinimide (1.29 g, 7.24 mmol), and the mixture was stirred at room temperature overnight. To the reaction solution was added water, and the mixture was extracted with ethyl acetate. The obtained aqueous layer was extracted with chloroform. The obtained organic layers were combined, dried over anhydrous sodium sulfate, filtered, and concentrated. The residue was purified by silica gel chromatography to give compound 3 (1.92 g).

MS(ESI)m/z: 260, 262 (M+1)+.

[Step c]

To a solution of compound 3 (1.10 g, 4.23 mmol) in N,N-dimethylformamide (11.0 mL) was added sodium hydride (60 wt %, 508 mg, 12.7 mmol) in a nitrogen atmosphere under ice-cooling, and the mixture was stirred for 10 min. To the reaction solution was added 1,2-dibromoethane (1.19 g, 6.34 mmol), and the mixture was stirred for 30 min while raising the temperature to room temperature. To the reaction solution was added water, and the mixture was extracted with ethyl acetate. The organic layer was dried over anhydrous magnesium sulfate, filtered, and concentrated. The residue was purified by silica gel chromatography to give compound 4 (555 mg, 48.6%).

MS(ESI)m/z: 286, 288(M+1)+.

235

Reference Example 36

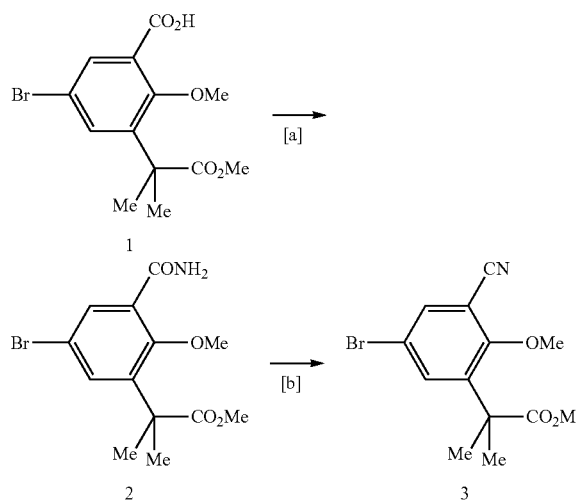

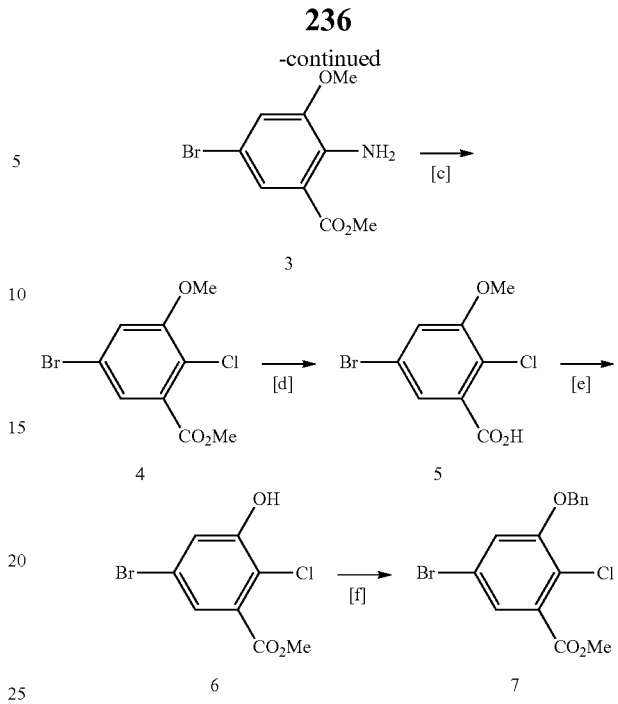

[Step a]
To a solution of compound 1 (100 mg, 302 μmol) in N,N-dimethylformamide (2.00 mL) were added 1-hydroxybenzotriazole (HOBt) (49.0 mg, 363 μmol), 1-ethyl-3-(3-dimethylaminopropyl)carbodiimide hydrochloride (WSC.HCl) (69 mg, 363 μmol), and the mixture was stirred at room temperature for 60 min. To the reaction solution were further added ammonium chloride (48.5 mg, 906 μmol), diisopropylethylamine (158 μL, 906 μmol), and the mixture was stirred at room temperature for 5 hr. To the reaction solution was added water, and the mixture was extracted with ethyl acetate. The organic layer was washed with saturated brine, dried over anhydrous magnesium sulfate, filtered, and concentrated to give compound 2 (96.3 mg, 96.6%).
MS(ESI)m/z: 330, 332(M+1)+.

[Step b]
To a solution of compound 2 (95 mg, 288 μmol) in tetrahydrofuran (2.00 mL) was added pyridine (70 μL, 869 μmol), trifluoroacetic anhydride (122 μL, 869 μmol) was further added under ice-cooling, and the mixture was stirred for 3.5 hr while raising the temperature to room temperature. To the reaction solution was added an excess amount of 1 M-hydrochloric acid, and the mixture was extracted with ethyl acetate. The organic layer was washed with saturated aqueous sodium hydrogen carbonate solution, saturated brine, dried over anhydrous magnesium sulfate, filtered, and concentrated to give compound 3 (85.1 mg, 94.6%).
$^1$H-NMR (400 MHz, CDCl$_3$) δ: 1.50 (6H, s), 3.68 (3H, s), 4.07 (3H, s), 7.59 (2H, q, J=2.4 Hz).

Reference Example 37

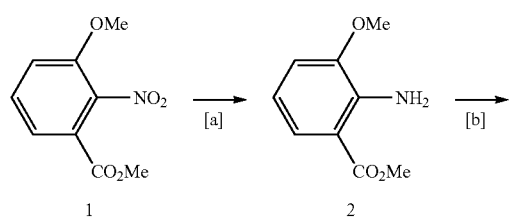

236

[Step a]
To a mixed solution of compound 1 (100 g, 473 mmol) in tetrahydrofuran (630 mL) and methanol (210 mL) was added palladium/carbon (10 wt %, 10.0 g), and the mixture was stirred in a hydrogen atmosphere at room temperature for 29 hr. The mixture was further stirred with heating at 40° C. for 19 hr. The reaction solution was substituted with nitrogen, filtered through celite, and concentrated to give compound 2 (86.7 g).
$^1$H-NMR (400 MHz, CDCl$_3$) δ: 3.87 (6H, s), 6.00 (2H, brs), 6.57 (1H, t, J=8.0 Hz), 6.85 (1H, dd, J=1.2, 8.0 Hz), 7.47 (1H, dd, J=1.2, 8.4 Hz).

[Step b]
To a solution of compound 2 (86.7 g, 473 mmol) in N,N-dimethylformamide (430 mL) was added N-bromosuccinimide over 15 min under ice-cooling, and the mixture was stirred for 1 hr. To the reaction solution were added saturated aqueous sodium hydrogen carbonate solution (500 mL) and water (500 mL), and the mixture was extracted with ethyl acetate (1.0 μL). The organic layer was washed with water and saturated brine, dried over anhydrous sodium sulfate, filtered, and concentrated. The residue was purified by silica gel chromatography, and suspended and washed in n-hexane (120 mL) to give compound 3 (108 g, 88.1%).
$^1$H-NMR (400 MHz, CDCl$_3$) δ: 3.87 (6H, s), 6.03 (2H, brs), 6.90 (1H, d, J=2.0 Hz), 7.26 (1H, s), 7.60 (1H, d, J=2.4 Hz).

[Step c]
To a solution of compound 3 (45.1 g, 174 mmol) in dioxane (90.0 mL) were added 4 M solution (135 mL) of hydrochloric acid in dioxane and water (90.0 mL), a solution of sodium nitrite (13.14 g, 190 mmol) in water (180 mL) was added dropwise over 20 min under ice-cooling while maintaining the inside temperature at 11° C. or below and the mixture was stirred for 20 min, whereby diazonium salt solution was prepared. The obtained diazonium salt solution was added dropwise over 20 min to a solution of copper(I) chloride (18.0 g, 182 mmol) in concentrated hydrochloric acid (153 mL) at room temperature, and the mixture was stirred at room temperature for 2.5 hr. To the reaction solution was added water, and the mixture was extracted with ethyl acetate. The organic layer was washed with water and saturated brine, dried over anhydrous sodium sulfate, filtered, and concentrated. The obtained residue was recrystallized from n-hexane (250 mL) to give compound 4 (35.1 g, 72.7%).

$^1$H-NMR (400 MHz, CDCl$_3$) δ: 3.93 (6H, s), 7.16 (1H, d, J=2.0 Hz), 7.49 (1H, d, J=2.0 Hz).

[Step d]

To a solution of compound 4 (41.4 g, 148 mmol) in dichloromethane (210 mL) was added dropwise 1 M dichloromethane solution (385 mL, 385 mmol) of boron tribromide over 40 min under ice-cooling, and the mixture was stirred for 2 hr while raising the temperature to room temperature. To the reaction solution was added water (400 mL) under ice-cooling, and the mixture was filtered through celite, and the obtained filtrate was extracted with ethyl acetate. The organic layer was washed with water, saturated brine, dried over anhydrous sodium sulfate, filtered, and concentrated to give compound 5 (37.5 g).

$^1$H-NMR (400 MHz, CDCl$_3$) δ: 7.23 (1H, d, J=2.4 Hz), 7.28 (1H, d, J=2.0 Hz), 11.0 (1H, s), 13.5 (1H, brs).

[Step e]

To a solution of compound 5 (37.5 g, 148 mmol) in methanol (560 mL) was added concentrated sulfuric acid (30.2 g, 296 mmol), and the mixture was stirred with heating under reflux for 15 hr. The reaction solution was concentrated, water was added, and the mixture was extracted with ethyl acetate. The organic layer was washed with water and saturated brine, dried over anhydrous sodium sulfate, filtered, and concentrated. The residue was purified by silica gel chromatography to give compound 6 (36.0 g, 92.2%).

MS(ESI)m/z: 265, 267(M+1)+.

$^1$H-NMR (400 MHz, CDCl$_3$) δ: 3.94 (3H, s), 6.00 (1H, s), 7.35 (1H, d, J=2.4 Hz), 7.60 (1H, d, J=2.4 Hz).

[Step f]

To a solution of compound 6 (10.0 g, 37.7 mmol) in N,N-dimethylformamide (100 mL) were added potassium carbonate (10.4 g, 75.3 mmol), benzyl bromide (5.37 mL, 45.2 mmol), and the mixture was stirred at room temperature for 3 days. To the reaction solution was added water, and the mixture was extracted with ethyl acetate. The organic layer was washed with water and saturated brine, dried over anhydrous sodium sulfate, filtered, and concentrated. The residue was purified by silica gel chromatography to give compound 7 (12.4 g, 92.7%).

MS(ESI)m/z: 355, 357(M+1)+.

Reference Example 38

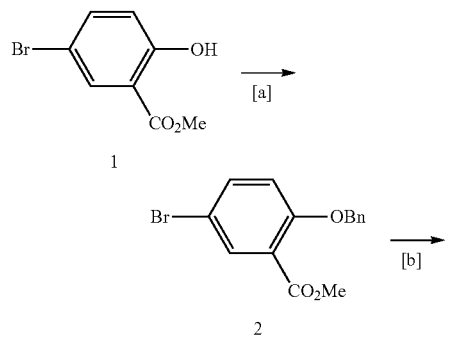

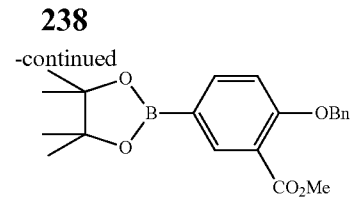

[Step a]

To a solution of compound 1 (15.0 g, 61.7 mmol) in N,N-dimethylformamide (61.7 mL) were added potassium carbonate (9.38 g, 67.8 mmol), benzyl bromide (11.8 g, 67.8 mmol) under ice-cooling, and the mixture was stirred for 6 hr while raising the temperature to room temperature. To the reaction solution was added water, and the mixture was extracted with ethyl acetate. The organic layer was washed with water and saturated brine, dried over anhydrous sodium sulfate, filtered, and concentrated. The residue was purified by silica gel chromatography to give compound 2 (20.7 g).

$^1$H-NMR (400 MHz, CDCl$_3$) δ: 3.81 (3H, s), 5.22 (2H, s), 7.22 (1H, d, J=8.7 Hz), 7.33 (1H, d, J=7.7 Hz), 7.40 (2H, t, J=7.7 Hz), 7.47 (2H, d, J=7.2 Hz), 7.7 (1H, dd, J=2.8, 9.0 Hz), 7.80 (1H, d, J=2.6 Hz).

[Step b]

To a solution of compound 2 (20.7 g, 64.6 mmol) in dimethyl sulfoxide (215 mL) were added bis(pinacolate)diborane (18.0 g, 71.0 mmol), potassium acetate (19.0 g, 194 mmol) and [1,1'-bis(diphenylphosphino)ferrocene]palladium(II) dichloride (5.27 g, 6.46 mmol), and the mixture was stirred with heating at 80° C. for 5 hr. The reaction solution was allowed to cool to room temperature, diluted with water and ethyl acetate, filtered through celite, and the filtrate was extracted with ethyl acetate. The organic layer was washed with water and saturated brine, dried over anhydrous magnesium sulfate, filtered, and concentrated. The residue was purified by silica gel chromatography to give compound 3 (17.7 g, 74.4%).

MS(SEI)m/z: 369(M+1)+.

Reference Example 39

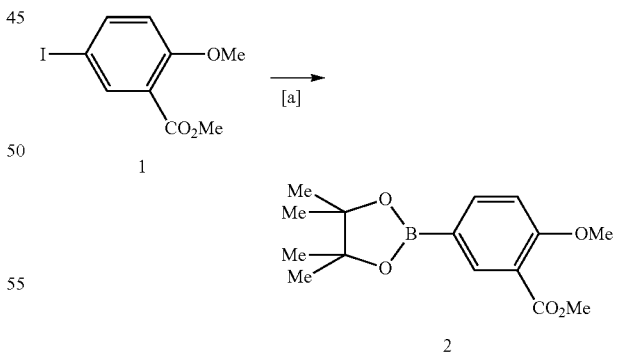

[Step a]

To a solution of compound 1 (29.3 g, 100 mmol) and bis(pinacolate)diborane (38.2 g, 150 mmol) and potassium acetate (29.4 g, 300 mmol) in dimethylformamide (250 mL) was added [1,1'-bis(diphenylphosphino)ferrocene]palladium(II) dichloride (2.92 g, 4.00 mmol), and the mixture was stirred in a nitrogen atmosphere with heating at 80° C. for 17 hr. The reaction solution was concentrated under reduced pressure, the solvent was evaporated, and the residue was diluted with water and ethyl acetate, and extracted with ethyl acetate. The organic layer was washed with water and saturated brine, dried over anhydrous sodium sulfate, filtered and concentrated under reduced pressure, and the residue was purified by silica gel chromatography. The obtained solid was suspended and washed in diisopropyl ether-hexane mixed solution (1:1) to give compound 2 (23.1 g, 79.1%).

MS(ESI)m/z: 293(M+1)+.

Reference Example 40

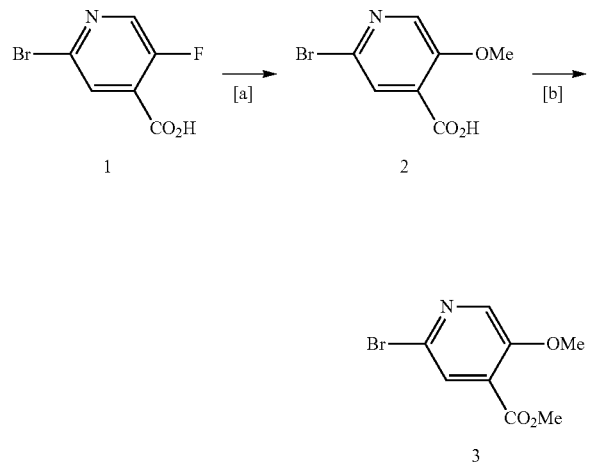

[Step a]

To a solution of compound 1 (8.00 g, 36.4 mmol) in methanol (120 mL) was added 5 M methanol solution (72.8 mL, 364 mmol) of sodium methoxide, and the mixture was stirred with heating under reflux for 1 day. The reaction solution was concentrated, and water was added to the residue. Under ice-cooling, concentrated hydrochloric acid was added to adjust to pH 3-4, and the mixture was extracted with ethyl acetate. The organic layer was washed with saturated brine, dried over anhydrous sodium sulfate, filtered, and concentrated under reduced pressure to give compound 2 (627 mg, 7.46%). The is aqueous layer obtained by extraction was concentrated, diluted with methanol, and filtered. The obtained filtrate was dried over sodium sulfate, and concentrated to give compound 2 (674 mg, 8.02%).

MS(ESI)m/z: 232,234(M+1)+.

[Step b]

To a solution of compound 2 (300 mg, 1.29 mmol) in methanol (3.00 mL) was added sulfuric acid (500 µL), and the mixture was stirred with heating under reflux for 2.5 hr. The reaction solution was allowed to cool to room temperature, neutralized with saturated aqueous sodium hydrogen carbonate solution, and extracted with ethyl acetate. The organic layer was washed with saturated brine, dried over anhydrous sodium sulfate, filtered, and concentrated under reduced pressure to give compound 3 (301 mg, 95.0%).

MS(ESI)m/z: 246, 248(M+1)+.

Reference Example 41

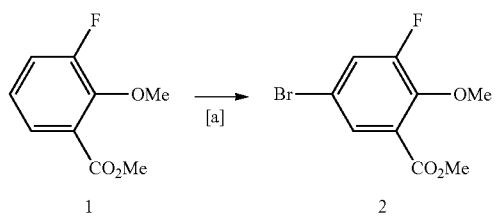 [SMILES: COC(=O)c1cccc(F)c1OC ; COC(=O)c1cc(Br)cc(F)c1OC]

[Step a]

To a solution of compound 1 (1.00 g, 5.43 mmol) in N,N-dimethylformamide (10.0 mL) was added bromine (836 µL, 16.2 mmol), and the mixture was stirred with heating at 60° C. for 1 day. The reaction solution was allowed to cool to room temperature, bromine (836 µL, 16.2 mmol) was added, and the mixture was further stirred with heating at 60° C. for 6 hr. To the reaction solution were added saturated aqueous sodium thiosulfate solution, saturated aqueous sodium hydrogen carbonate solution, ethyl acetate, and the mixture was extracted with ethyl acetate. The organic layer was washed with saturated brine, dried over anhydrous sodium sulfate, filtered and concentrated under reduced pressure, and the residue was purified by silica gel chromatography to give compound 2 (1.09 g, 76.6%).

MS(ESI)m/z: 263, 265(M+1)+.

Reference Example 42

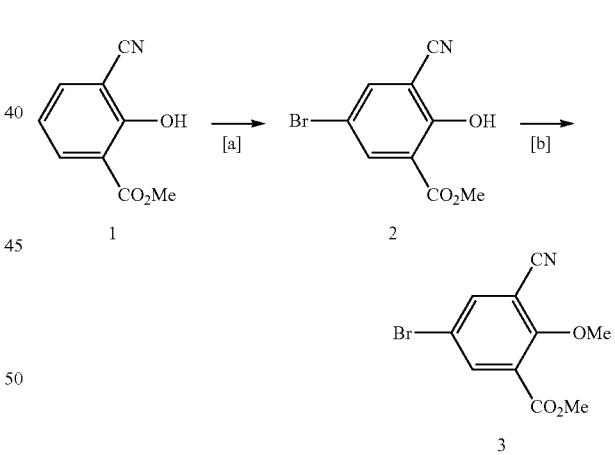

[Step a]

To a solution of compound 1 (350 mg, 1.98 mmol) in acetic acid (8.00 mL) was added dropwise a solution of bromine (130 µL, 2.54 mmol) in acetic acid (1.20 mL) at room temperature, and the mixture was stirred for 3 hr. To the reaction solution was further added dropwise a solution of bromine (120 µL, 2.34 mmol) in acetic acid (800 µL), and the mixture was stirred for 6.5 hr. To the reaction solution was added water, and the precipitated solid was collected by filtration. The obtained solid was washed with water, hexane to give compound 2 (480 mg, 94.7%).

MS(ESI)m/z: 254, 256(M−1)−.

[Step b]

To a solution of compound 2 (475 mg, 1.85 mmol) in N,N-dimethylformamide (7.50 mL) were added potassium carbonate (385 mg, 2.79 mmol) and methyl iodide (175 μL, 2.81 mmol), and the mixture was stirred at room temperature overnight. To the reaction solution were further added potassium carbonate (255 mg, 1.84 mmol) and methyl iodide (115 μL, 1.85 mmol), and the mixture was stirred at room temperature for 9.5 hr. To the reaction solution was added water (40.0 mL), and the precipitated solid was collected by filtration. The obtained solid was washed with water to give compound 3 (475 mg, 95.1%).

MS(ESI)m/z: 270, 272(M+1)+.

The following compounds were produced according to Production Methods 1-28, Examples, and Reference Examples.

TABLE 19

| Reference Example 43 | 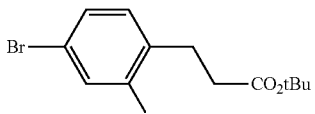 | MS (ESI) m/z: 259, 261 (M − tBu + 1)+. |
|---|---|---|
| Reference Example 44 | 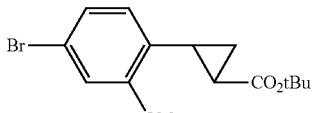 trans, racemate | MS (ESI) m/z: 271, 273 (M − tBu + 1)+. |
| Reference Example 45 | 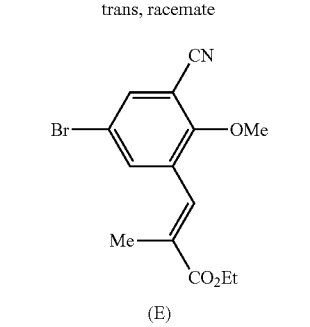 (E) | MS (ESI) m/z: 324, 326 (M + 1)+. |
| Reference Example 46 | 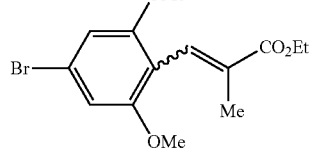 | MS (ESI) m/z: 329, 331 (M + 1)+. |
| Reference Example 47 | 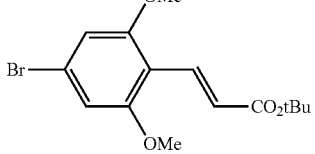 trans | MS (ESI) m/z: 287, 289 (M − tBu + 1)+. |
| Reference Example 48 | 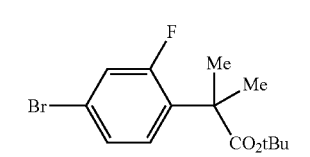 | MS (APCI) m/z: 317, 319 (M + 1)+. |

TABLE 19-continued

| Reference Example 49 | 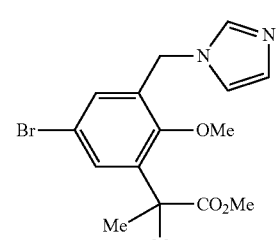 | MS (ESI) m/z: 367, 369 (M + 1)+ |
|---|---|---|
| Reference Example 50 | 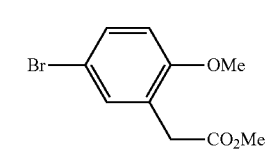 | MS (ESI) m/z: 259, 261 (M + 1)+ |

TABLE 20

| Reference Example 51 | 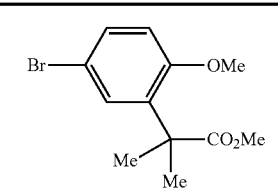 | MS (ESI) m/z: 287, 289 (M + 1)+ |
|---|---|---|
| Reference Example 52 | 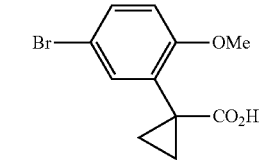 | MS (ESI) m/z: 271, 273 (M + 1)+ |
| Reference Example 53 | 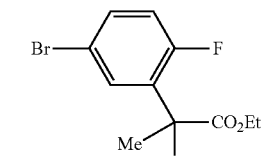 | MS (ESI) m/z: 289, 291 (M + 1)+ |
| Reference Example 54 | 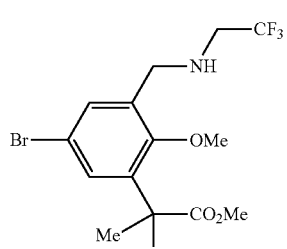 | MS (ESI) m/z: 398, 400 (M + 1)+ |

TABLE 20-continued

| Reference Example | Structure | MS |
|---|---|---|
| Reference Example 55 | 5-Bromo-2-methoxy-3-(2-methoxycarbonylpropan-2-yl)-N-methylbenzamide (Br, CONHMe, OMe, C(Me)₂CO₂Me) | MS (ESI) m/z: 344, 346 (M + 1)+ |
| Reference Example 56 | 5-Bromo-2-methoxy-3-(2-methoxycarbonylpropan-2-yl)-N,N-dimethylbenzamide (Br, CONHMe₂, OMe, C(Me)₂CO₂Me) | MS (ESI) m/z: 358, 360 (M + 1)+ |
| Reference Example 57 | (S)-Methyl 2-(6-(trifluoromethylsulfonyloxy)-2,3-dihydrobenzofuran-3-yl)acetate; chiral | MS (ESI) m/z: 341 (M + 1)+ |
| Reference Example 58 | Ethyl 5-bromobenzo[d]isoxazole-3-carboxylate | MS (ESI) m/z: 270, 272 (M + 1)+ |

TABLE 21

| Reference Example | Structure | MS |
|---|---|---|
| Reference Example 59 | Methyl 5-bromo-1-(2-methoxyethyl)-1H-indazole-3-carboxylate | MS (ESI) m/z: 313, 315 (M + 1)+ |
| Reference Example 60 | Methyl 5-bromo-1-(3-(methylsulfonyl)propyl)-1H-indazole-3-carboxylate | MS (ESI) m/z: 375, 377 (M + 1)+ |
| Reference Example 61 | Methyl 5-bromo-1-(3-cyanopropyl)-1H-indazole-3-carboxylate | MS (ESI) m/z: 322, 324 (M + 1)+ |
| Reference Example 62 | Ethyl (1S,2S)-2-(6-chloro-3-methoxypyridin-2-yl)cyclopropane-1-carboxylate; chiral | MS (APCI) m/z: 256, 258 (M + 1)+ |
| Reference Example 63 | Ethyl (1S,2S)-2-(6-chloro-3-(propan-2-yloxy)pyridin-2-yl)cyclopropane-1-carboxylate; chiral | MS (ESI) m/z: 284 (M + 1)+ |

TABLE 21-continued

| Reference Example 64 | [structure: 5-bromo-1-methyl-3-(2-methoxycarbonylpropan-2-yl)pyridin-2(1H)-one] | MS (ESI) m/z: 288, 290 (M + 1)+ |
|---|---|---|

Reference Example 65

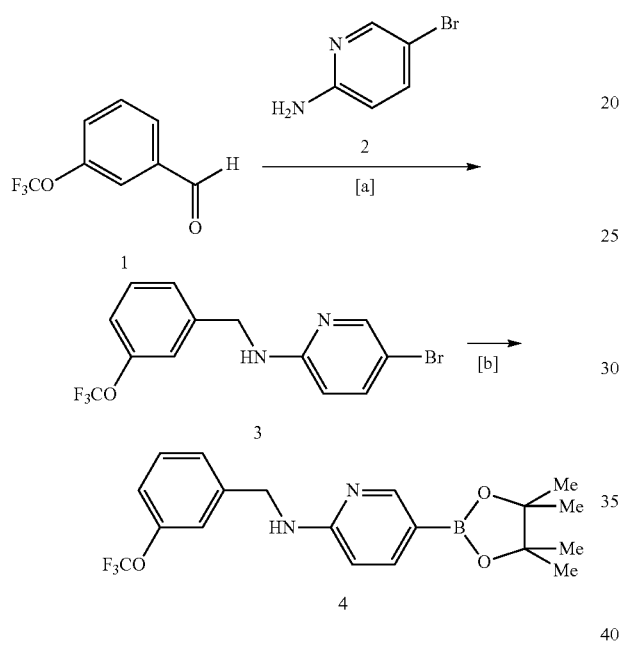

[Step a]

To a solution of compound 1 (25.0 g, 131 mmol) and compound 2 (25.0 g, 145 mmol) in N-methylpyrrolidone (NMP) (250 mL) was added trifluoroacetic acid (TFA) (100 mL, 1.31 µmol) under ice-cooling, and the mixture was stirred for 1 hr. To the reaction solution was added sodium triacetoxyborohydride (33.4 g, 158 mmol), and the mixture was stirred overnight while raising the temperature to room temperature. The reaction solution was ice-cooled, water (500 mL) was added, and the mixture was neutralized with 12N-aqueous sodium hydroxide solution (109 mL, 1.31 µmol). Water (1.00 µL) was further added, and the resulting solid was collected by filtration, and washed with water. The obtained solid was purified by silica gel chromatography to give compound 3 (41.5 g, 91.4%).

MS(APCI)m/z: 347, 349(M+1)+.

[Step b]

To a solution of compound 3 (50.0 g, 144 mmol) and bis(pinacolate)diborane (54.9 g, 216 mmol) in dioxane (1.00 µL) were added potassium acetate (42.4 g, 432 mmol) and [1,1'-bis(diphenylphosphino)ferrocene]palladium(II) dichloride (4.22 g, 5.77 mmol), and the mixture was stirred in a nitrogen atmosphere with heating at 80° C. overnight. The reaction solution was allowed to cool to room temperature, diluted with ethyl acetate, filtered through celite, and the obtained filtrate was concentrated. The residue was purified by silica gel chromatography to give compound 4 (42.3 g, 74.6%).

MS(APCI)m/z: 395(M+1)+.

Reference Example 66

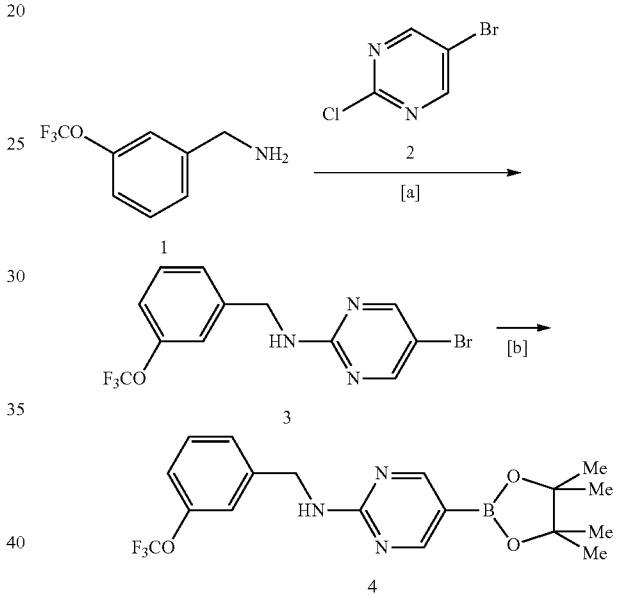

[Step a]

To a solution of compound 1 (69.0 g, 357 mmol) and compound 2 (75.0 g, 392 mmol) in N-methylpyrrolidone (NMP) (200 mL) was added diisopropylamine (55.3 g, 428 mmol), and the mixture was stirred at room temperature for 2 days. To the reaction solution was added water (1.00 µL), and the resulting solid was collected by filtration, and washed with water to give compound 3 (113 g, 99.6%).

MS(APCI)m/z: 348, 350(M+1)+.

[Step b]

To a solution of compound 3 (50.0 g, 144 mmol) and bis(pinacolate)diborane (54.7 g, 215 mmol) in dioxane (1.00 µL) were added potassium acetate (42.4 g, 432 mmol) and [1,1'-bis(diphenylphosphino)ferrocene]palladium(II) dichloride (4.20 g, 5.74 mmol), and the mixture was stirred in a nitrogen atmosphere with heating at 80° C. for 9 hr. The reaction solution was allowed to cool to room temperature, diluted with ethyl acetate, filtered through celite, and the filtrate was concentrated. The residue was purified by silica gel chromatography to give compound 4 (43.0 g, 75.7%).

MS(ESI)m/z: 396(M+1)+.

The following compounds were produced according to Production Methods 1-28, Examples, and Reference Examples.

TABLE 22

| | | |
|---|---|---|
| Reference Example 67 | [structure: 3-(trifluoromethoxy)benzyl-NH-pyridine with Br and F] | MS (ESI) m/z: 365, 367 (M + 1)+ |
| Reference Example 68 | [structure: 3-(trifluoromethoxy)benzyl-NH-pyridine with Br and Cl] | MS (ESI) m/z: 381, 383, 385 (M + 1)+ |
| Reference Example 69 | [structure: 3-(trifluoromethoxy)benzyl-NH-pyridine with Cl, and phenyl-OMe/CO2H substituent] | MS (ESI) m/z: 467, 469 (M + 1)+ |

Reference Example 70

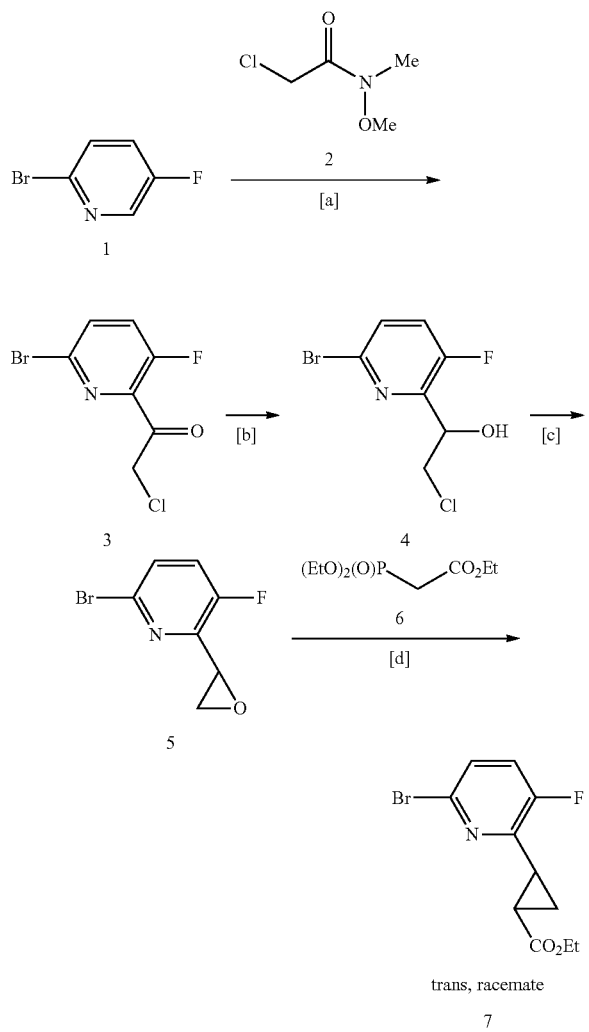

[Step a]

To a solution of compound 1 (5.00 g, 28.4 mmol) in diethyl ether (140 mL) was added dropwise 1.6 M hexane solution (18.0 mL, 28.4 mmol) of butyllithium in a nitrogen atmosphere at −78° C., and the mixture was stirred for 1 hr. To the reaction solution was further added dropwise a solution of compound 2 (4.30 g, 31.3 mmol) in diethyl ether (20 mL), and the mixture was stirred for 2 hr, and warmed to −20° C. by stirring for 3 hr. To the reaction solution was added saturated aqueous ammonium chloride solution (40 mL), and the mixture was extracted with ethyl acetate. The organic layer was washed with saturated brine, dried over anhydrous sodium sulfate, filtered, and concentrated. The residue was purified by silica gel chromatography to give compound 2 (2.30 g, 30.3%).

MS(ESI)m/z: 252, 254(M+1)+.

[Step b]

To a solution of compound 3 (1.00 g, 3.45 mmol) in methanol (27.3 mL) was added sodium borohydride (196 mg, 5.17 mmol) under an ice bath, and the mixture was stirred at room temperature for 30 min. To the reaction solution was added water (20 mL), and the mixture was extracted with ethyl acetate. The organic layer was washed with saturated brine, dried over anhydrous sodium sulfate, filtered, and concentrated. The residue was purified by silica gel chromatography to give compound 4 (0.80 g, 92%).

MS(ESI)m/z: 254, 256(M+1)+.

[Step c]

To a solution of compound 4 (500 mg, 1.96 mmol) in t-butyl methyl ether (5.0 mL) was added 2 M-aqueous potassium hydroxide solution (2.36 mL, 4.72 mmol), and the mixture was stirred at room temperature for 5 hr and half. To the reaction solution was added saturated aqueous ammonium chloride solution (4 mL), and the mixture was extracted with ethyl acetate. The organic layer was washed with saturated brine, dried over anhydrous sodium sulfate, filtered, and concentrated. The residue was purified by silica gel chromatography to give compound 5 (285 mg, 66.5%).

MS(ESI)m/z: 218, 220(M+1)+.

[Step d]

To a solution of compound 6 (370 mg, 1.65 mmol) in tetrahydrofuran (1.5 mL) was added dropwise 1 M solution (1.38 mL, 1.38 mmol) of potassium tert-butoxide in tetrahydrofuran, and the mixture was stirred for 1 hr. To the reaction solution was added compound 5 (150 mg, 0.688 mmol), and the mixture was stirred in a nitrogen atmosphere with heating under reflux for 6 hr and half. The reaction solution was allowed to cool to room temperature, water (30 mL) was added, and the mixture was extracted with ethyl acetate. The organic layer was washed with water (15 mL), saturated brine, dried over anhydrous sodium sulfate, filtered, and concentrated. The obtained residue was purified by silica gel chromatography to give compound 7 (0.11 g, 56%).

MS(ESI)m/z: 288, 290(M+1)+.

Reference Example 71

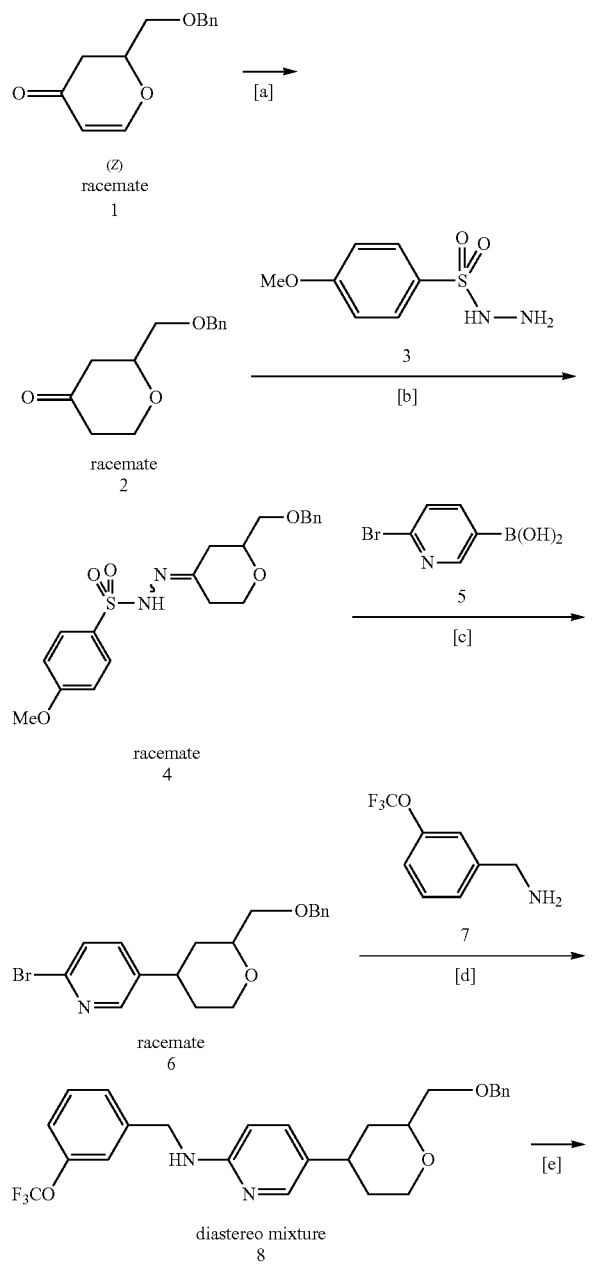

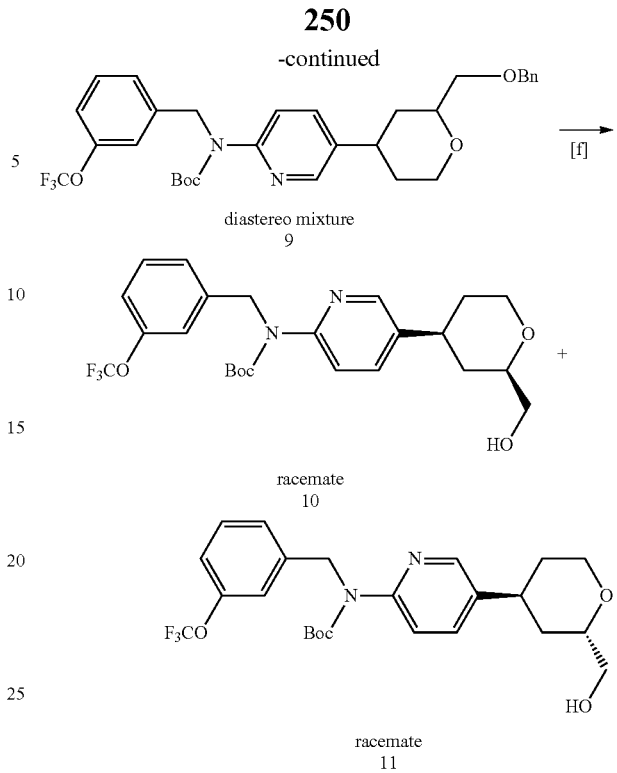

[Step a]

To a solution of compound 1 (CAS No. 80127-39-5, 1.90 g, 6.88 mmol) in ethyl acetate (35 mL) was added 10%-palladium/carbon (380 mg), and the mixture was stirred in a hydrogen atmosphere at room temperature for 3 hr. The reaction solution was filtered through celite, and concentrated to give compound 2 (1.04 g, 68.6%).

$^1$H-NMR (400 MHz, CDCl$_3$) δ: 2.34-2.37 (2H, m), 2.46-2.49 (1H, m), 2.53-2.62 (1H, m), 3.54-3.56 (2H, m), 3.70 (1H, m), 3.82-3.86 (1H, m), 4.33 (1H, m), 4.60 (1H, s), 7.33-7.36 (5H, m).

[Step b]

To a solution of compound 2 (1.04 g, 4.72 mmol) in methanol (20 mL) was added compound 3 (955 mg, 4.72 mmol), and the mixture was stirred at room temperature for 2 hr. The reaction solution was concentrated under reduced pressure to give compound 4 (1.9 g).

$^1$H-NMR (400 MHz, CDCl$_3$) δ: 2.00-2.45 (3H, m), 2.52-2.65 (1H, m), 3.40-3.70 (4H, m), 3.87 (3H, s), 4.10-4.20 (1H, m), 4.56 (2H, s), 6.95-7.00 (2H, m), 7.27-7.40 (5H, m), 7.82-7.90 (2H, m).

[Step c]

To a solution of compound 4 (1.9 g, 4.72 mmol) in 1,4-dioxane (15 mL) were added compound 5 (1.43 g, 7.09 mmol), cesium carbonate (2.31 g, 7.09 mmol), and the mixture was stirred in a nitrogen atmosphere with heating at 100° C. for 24 hr. The reaction solution was allowed to cool to room temperature, water was added, and the mixture was extracted with ethyl acetate. The organic layer was washed with saturated brine, dried over anhydrous sodium sulfate, filtered, and concentrated. The residue was purified by silica gel chromatography to give compound 6 (330 mg, 19.2%).

MS(ESI)m/z: 362, 364(M+1)+.

[Step d]

To a solution of compound 6 (330 mg, 1.13 mmol) in 1,4-dioxane (2.5 mL) were added compound 7 (325 mg, 1.70 mmol), t-butoxy sodium (163 mg, 1.70 mmol), palladium acetate (25 mg, 0.11 mmol), 2-(dicyclohexylphosphino)-3,6-dimethoxy-2',4',6'-triisopropyl-1,1'-biphenyl (122 mg, 0.226 mmol), and the mixture was stirred in a nitrogen atmosphere with heating at 100° C. for 5 hr. The reaction solution was allowed to cool to room temperature, saturated aqueous ammonium chloride solution and water were added, and the mixture was extracted with ethyl acetate. The organic layer was washed with saturated brine, dried over anhydrous sodium sulfate, filtered, and concentrated. The residue was purified by silica gel chromatography to give compound 8 (340 mg, 63.6%).

MS(ESI)m/z: 473(M+1)+.

[Step e]

To a solution of compound 8 (340 mg, 0.720 mmol) in tetrahydrofuran (7 mL) were added triethylamine (0.20 mL, 1.44 mmol), 4-dimethylaminopyridine (88 mg, 0.72 mmol), di-t-butyl dicarbonate (314 mg, 0.331 mmol), and the mixture was stirred at room temperature, 4 days. To the reaction solution was added water, and the mixture was extracted with ethyl acetate. The organic layer was washed with water and saturated brine, dried over anhydrous sodium sulfate, filtered, and concentrated. The residue was purified by silica gel chromatography to give compound 9 (385 mg, 93.4%).

MS(ESI)m/z: 573(M+1)+.

[Step f]

To a solution of compound 9 (370 mg, 0.646 mmol) in ethanol (15 mL) was added 20%-palladium hydroxide/carbon (75 mg), and the mixture was stirred in a hydrogen atmosphere at room temperature for 4 hr. The reaction solution was filtered through celite, and concentrated. The residue was purified by silica gel chromatography to give compound 10 (183 mg, 58.8%) and compound 11 (43 mg, 13.9%).

MS(ESI)m/z: 483(M+1)+, 483(M+1)+.

The following compounds were produced according to Production Methods 1-28, Examples, and Reference Examples.

TABLE 23

| Reference Example 72 | [structure: trans, racemate] | MS (ESI) m/z: 270, 272 (M + 1)+. |
|---|---|---|
| Reference Example 73 | [structure: cis, racemate] | MS (ESI) m/z: 270, 272 (M + 1)+. |
| Reference Example 74 | [structure] | MS (ESI) m/z: 301, 303 (M + 1)+. |
| Reference Example 75 | [structure] | MS (ESI) m/z: 298, 300 (M + 1)+. |

Experimental Example 1

Enzyme Inhibitory Test Method

A mixture (10 μL) of substrate and a set of choline quantification reagents (200 μM LPC (1-Oleoyl-sn-glycero-3-phosphocholine Sigma #L1881), 25 μM Amplex UltraRed reagent (Invitrogen), 0.1 U/mL Peroxidase (TOYOBO), 1 U/mL Choline oxidase (TOYOBO)), prepared with assay buffer (50 mM Tris (pH 8.0), 140 mM NaCl, 5 mM KCl, 1 mM CaCl$_2$, 1 mM MgCl$_2$, 0.1% BSA (Albumin from bovine serum, SIGMA), 0.0025% Triton X-100), enzyme (0.4 ng/μL human recombinant ATX) (10 μL), compound-containing solution (100 nL) were dispensed to a 384-well plate, incubated at room temperature for 1 hr and the fluorescence (Ex.525 nm/Em.598 nm) was measured. As the standard, choline chloride was used. With a blank free of enzyme was taken as inhibitory rate 100%, and a control free of inhibitor as inhibitory rate 0%, the inhibitory rate was calculated, and IC50 value was calculated from the inhibitory activity percentage at each concentration. The obtained results are shown in the following Table 24.

Experimental Example 2

Measurement of ATX Activity in Plasma (Ex Vivo)

A compound administration solution prepared by wet pulverization in a mixer mill (type: MM400) for 10 min and adjusting to a given concentration with 0.5% aqueous carboxymethylcellulose solution was orally administered to male Wistar rat (5-week-old when used) at 5 mL/kg. Blood samples were collected from the cervical vein over time at 8 to 24 hr after administration. The blood was heparin-treated using a micro blood collection tube Capiject (CJ-AL, TERUMO CORPORATION), and the plasma was separated by centrifugation (4° C., 12,000 rpm, 2 min), and preserved at −80° C. The rats after blood sampling were euthanized by exsanguination from the caudal vena cava under isoflurane inhalation anesthesia. The measurement of ATX activity in plasma was evaluated using the concentration of choline in the plasma, which was liberated from lysophosphatidylcholine (substrate of ATX) by the lysophospholipase D activity of ATX, as an index. An equal amount of 2× assay buffer (200 mM Tris-HCl pH9.0, 10 mM MgCl$_2$, 1 M NaCl, 0.1% Triton X-100) is added to plasma (12 μL) and reacted at 37° C. for 6 hr. The reaction mixture (10 μL) after reaction for 6 hr and 45 μL of reagent R1 solution (100 mM Tris-HCl pH 8.0, 0.5 mM TOOS, 10 U/mL peroxidase, 0.01% Triton X-100) were added and blended and absorbance at 550-700 nm was measured and used as a prevalue. As the standard, choline chloride was used. 1 mM choline chloride was diluted with 2× assay buffer up to 7 steps in 2-fold serial dilution, R1 solution was treated similarly and the absorbance was measured. Furthermore, 15 µL of reagent R2 solution (100 mM Tris-HCl pH 8.0, 1 mM 4-aminoantipyrine, 10 U/mL choline oxidase, 0.01% Triton X-100) was added, and the mixture was reacted at room temperature for 10 min, and absorbance at 550-700 nm was measured. The choline concentration per reaction time was calculated from the difference between the absorbance after R2 solution addition and prevalue measured before R2 addition and used as ATX activity value.

inhibitory activity (%)=100×{1-[choline concentration (µM) of test substance administration group/choline concentration (µM) of solvent control group]}     <calculating formula>

The obtained results are shown in the following Table 24.

TABLE 24

| Example | Experimental Example 1 human ATX IC50 (nM) | Experimental Example 2 rat single administration test (inhibitory activity (%) at 8 hr after 1 mg/kg oral administration) |
|---|---|---|
| 2 | 46 | |
| 3 | 35 | |
| 7 | 3 | |
| 10 | 17 | 84 |
| 11 | 13 | |
| 16 (compound 1a) | 2 | |
| 17 (compound 4a) | 2 | 88 |
| 21 | 37 | |
| 22 | 33 | |
| 26 | 15 | |
| 30 | 22 | |
| 33 | 10 | |
| 34 | 83 | |
| 44 | 75 | |
| 63 | 25 | |
| 69 | 10 | |
| 73 | 9 | |
| 74 | 3 | |
| 75 | 6 | |
| 85 | 7 | 88 |
| 88 | 20 | |
| 92 | 23 | |
| 98 | 7 | |
| 108 | 24 | |
| 109 | 12 | |
| 126 | 92 | |
| 129 | 43 | |
| 132 | 15 | |
| 133 | 10 | |
| 136 | 31 | |
| 140 | 31 | |
| 156 | 93 | 82 |
| 176 | 47 | |

INDUSTRIAL APPLICABILITY

The compound of the present invention has a superior autotaxin inhibitory action, and is useful as a prophylactic or therapeutic drug for diseases caused by autotaxin, for example, various diseases such as cancer or tumor such as malignant melanoma, brain tumor, neuroblastoma, glioblastoma multiforme, EBV positive Hodgkin lymphoma, glioblastoma, non-small cell lung cancer, lung tumor, breast tumor, ovary tumor, pancreas tumor, prostatic intraepithelial neoplasia, prostate tumor, thyroid tumor, follicular lymphoma, liver tumor, renal cell carcinoma and the like, fibrosis such as pulmonary fibrosis, hepatic fibrosis, renal fibrosis, atherosclerosis and the like, asthma, rheumatoid arthritis, type II diabetes-related obesity, acute coronary syndrome, cholestatic pruritus, or an inflammatory disease such as inflammatory bowel disease, Crohn's disease, ulcerative colitis, neuropathic pain and the like.

This application is based on patent application No. 2014-090759 filed in Japan, the contents of which are encompassed in full herein.

The invention claimed is:
1. A compound of formula (1) or a pharmacologically acceptable salt thereof:

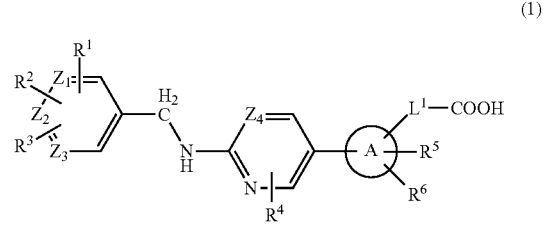

(1)

wherein
A is cycloalkyl, a heterocyclic group, aryl or heteroaryl;
$Z_1$, $Z_2$ and $Z_3$ are one of A)-D):
A) all of $Z_1$, $Z_2$ and $Z_3$ are carbons;
B) $Z_1$ is nitrogen, and $Z_2$ and $Z_3$ are carbons;
C) $Z_2$ is nitrogen, and $Z_1$ and $Z_3$ are carbons;
D) $Z_1$ and $Z_2$ are nitrogens, and $Z_3$ is carbon;
$Z_4$ is carbon or nitrogen;
$R^1$ is halogen, alkyl, haloalkyl, alkoxy, haloalkoxy, cyano, a heterocyclic group, aryl or heteroaryl where the heteroaryl optionally further has at least one substituent selected from alkyl;
$R^2$ and $R^3$ are the same or different and each is hydrogen, halogen, alkyl, haloalkyl, alkoxy, haloalkoxy or aryl;
$R^4$ is hydrogen, alkyl or halogen;
$R^5$ and $R^6$ are the same or different and each is —$X^1$—$R^{7a}$ where $X^1$ is a single bond, linear alkylene, cyclic alkylene, —O—, —O-alkylene- or —CO—, and the linear alkylene, cyclic alkylene or —O-alkylene- for $X^1$ optionally further has at least one substituent selected from hydroxy, halogen, alkyl, hydroxyalkyl and alkoxy;
$R^{7a}$ is hydrogen, hydroxy, halogen, alkyl, haloalkyl, hydroxyalkyl, alkoxy, carboxyl, —$NR^{7b}R^{7c}$, alkyleneoxide, cyano, dialkylcarbamoyl, alkylsulfonyl, a heterocyclic group or heteroaryl where $R^{7b}$ and $R^{7c}$ are the same or different and each is hydrogen, hydroxy, halogen, alkyl, haloalkyl, hydroxyalkyl, alkoxyalkyl or aminoalkyl, and the heterocyclic group or heteroaryl for $R^{7a}$ optionally further has at least one substituent selected from hydroxy, halogen, alkyl, haloalkyl, hydroxyalkyl, alkoxyalkyl and aminoalkyl; and
$L^1$ is a group selected from 1)-6):
1) —$X^2$—;
2) —$X^2$—$(CH_2)_n$—;
3) —O—$X^3$—,
4) —O—$(CH_2)_{n-X^3}$—;
5) —CO—$X^3$—; and
6) —CO—NH—$X^3$—
where $X^2$ is a single bond, linear alkylene, cyclic alkylene, alkenylene, alkynylene, heterocycloalkylene or heteroarylene, $X^3$ is linear alkylene, cyclic alkylene, alkenylene, alkynylene, heterocycloalkylene or heteroarylene, the linear alkylene, cyclic alkylene, alkenylene or alkynylene for $X^2$ or $X^3$ optionally further has at least one substituent selected from alkyl, cycloalkyl, hydroxyalkyl, haloalkyl and alkyleneoxide, the alkyl optionally has at least one substituent selected from aryl and heteroaryl, and n is an integer of 1-3.

2. The compound according to claim 1, wherein A is aryl or heteroaryl, or a pharmacologically acceptable salt thereof.

3. The compound according to claim 1, wherein A is a heterocyclic group, or a pharmacologically acceptable salt thereof.

4. The compound according to claim 1, wherein all of $Z_1$, $Z_2$ and $Z_3$ are carbons, or a pharmacologically acceptable salt thereof.

5. The compound according to claim 1, wherein $R^1$ is halogen, haloalkyl or haloalkoxy, or a pharmacologically acceptable salt thereof.

6. The compound according to claim 5, wherein $R^1$ is haloalkoxy, or a pharmacologically acceptable salt thereof.

7. The compound according to claim 1, wherein $R^1$ is substituted at the 3-position of the 6-membered ring, or a pharmacologically acceptable salt thereof.

8. The compound according to claim 1, wherein $R^5$ and $R^6$ are the same or different and each is one of
—$X^1$—$R^{7a}$ where $X^1$ is —O—, and $R^{7a}$ is alkyl,
—$X^1$—$R^{7a}$ where $X^1$ is linear alkylene or cyclic alkylene, and $R^{7a}$ is hydrogen, and
—$X^1$—$R^{7a}$ where $X^1$ is a single bond, and $R^{7a}$ is halogen or cyano, or a pharmacologically acceptable salt thereof.

9. The compound according to claim 1, wherein $L^1$ is —$X^2$— where $X^2$ is straight chain alkylene or cyclic alkylene, or a pharmacologically acceptable salt thereof.

10. The compound according to claim 9, wherein $L^1$ is —$X^2$— where $X^2$ is C1-2 straight chain alkylene or C3-6 cyclic alkylene, or a pharmacologically acceptable salt thereof.

11. The compound according to claim 1, wherein the cycloalkyl for A is a group selected from:

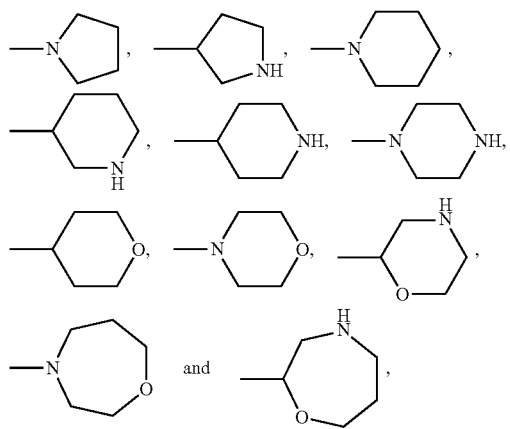

the heterocyclic group for A is a group selected from:

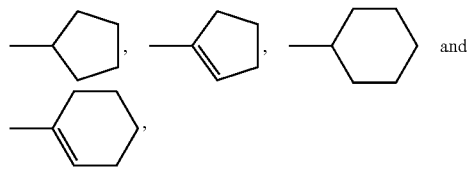

the aryl for A is:

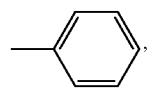

and the heteroaryl for A is a group selected from:

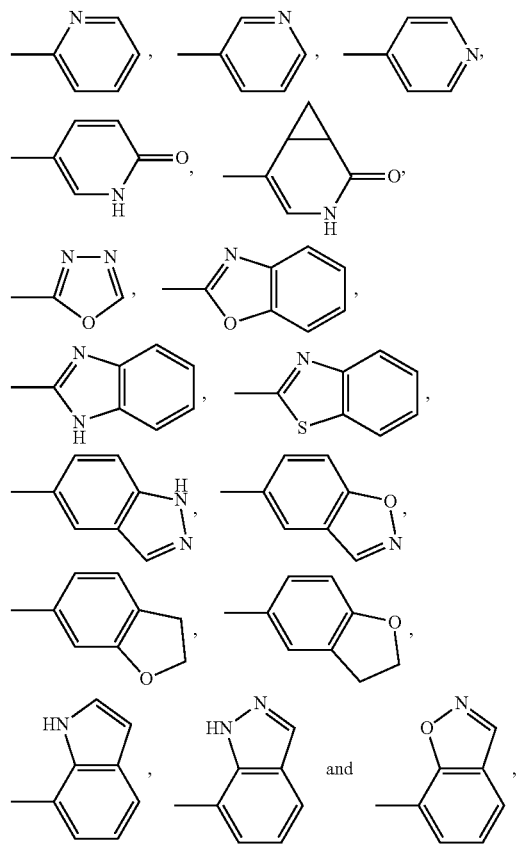

or a pharmacologically acceptable salt thereof.

12. The compound according to claim 2, wherein A is

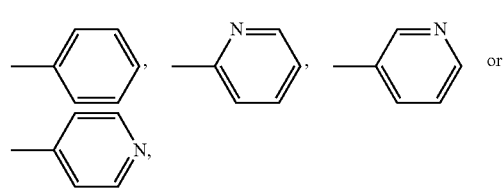

or a pharmacologically acceptable salt thereof.

13. The compound according to claim 3, wherein A is

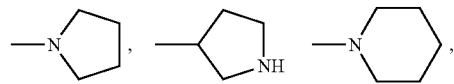

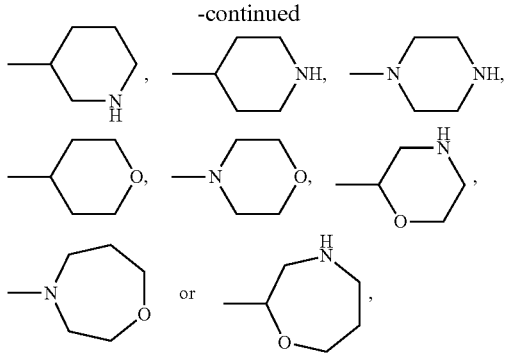

or a pharmacologically acceptable salt thereof.

14. A compound or a pharmacologically acceptable salt thereof, wherein the compound is one of
2-[6-(3 trifluoromethoxy-benzylamino)-pyridin-3-yl]-3H-benzimidazole-4-carboxylic acid,
2-[6-(3-trifluoromethoxy-benzylamino)-pyridin-3-yl]-benzoxazole-6-carboxylic acid,
1-methyl-5-[6-(3-trifluoromethoxy-benzylamino)-pyridin-3-yl]-1H-indazole-3-carboxylic acid,
5-[6-(3-trifluoromethoxy-benzylamino)-pyridin-3-yl]-1H-indazole-3-carboxylic acid,
3-{3-cyano-2-methoxy-5-[6-(3-trifluoromethoxy-benzylamino)-pyridin-3-yl]-phenyl}-propionic acid,
3-{2-chloro-5-[2-(3-trifluoromethoxy-benzylamino)-pyrimidin-5-yl]-phenyl}-propionic acid,
3-{3-cyano-2-methoxy-5-[6-(3-trifluoromethoxy-benzylamino)-pyridin-3-yl]-phenyl}-2-methyl-propionic acid,
2-{2-methoxy-5-[6-(3-trifluoromethoxy-benzylamino)-pyridin-3-yl]-phenyl}-cyclopropanecarboxylic acid,
(1S,2S)-2-{2-methoxy-5-[6-(3-trifluoromethoxy-benzylamino)-pyridin-3-yl]-phenyl}-cyclopropanecarboxylic acid,
2-[5-methoxy-6'-(3-trifluoromethoxy-benzylamino)-[2,3']bipyridinyl-6-yl]-cyclopropanecarboxylic acid,
(1S,2S)-2-[5-methoxy-6'-(3-trifluoromethoxy-benzylamino)-[2,3']bipyridinyl-6-yl]-cyclopropanecarboxylic acid,
(1S,2S)-2-{3-methoxy-6-[2-(3-trifluoromethoxy-benzylamino)-pyrimidin-5-yl]-pyridin-2-yl}-cyclopropanecarboxylic acid,
(1S,2S)-2-[5-chloro-6'-(3-trifluoromethoxy-benzylamino)-[2,3']bipyridinyl-6-yl]-cyclopropanecarboxylic acid,
(1S,2S)-2-[5-ethoxy-6'-(3-trifluoromethoxy-benzylamino)-[2,3']bipyridinyl-6-yl]-cyclopropanecarboxylic acid,
(1S,2S)-2-[5-methyl-6'-(3-trifluoromethoxy-benzylamino)-[2,3']bipyridinyl-6-yl]-cyclopropanecarboxylic acid,
3-{2-methoxy-5-[2-(3-trifluoromethoxy-benzylamino)-pyrimidin-5-yl]-phenyl}-propionic acid,
3-{2-methoxy-5-[6-(3-trifluoromethoxy-benzylamino)-pyridin-3-yl]-phenyl}-propionic acid,
2-{2-methoxy-5-[6-(3-trifluoromethoxy-benzylamino)-pyridin-3-yl]-phenyl}-2-methyl-propionic acid,
2-{3-cyano-2-methoxy-5-[6-(3-trifluoromethoxy-benzylamino)-pyridin-3-yl]-phenyl}-2-methyl-propionic acid,
2-chloro-3-(1-methyl-pyrrolidin-3-yloxy)-5-[2-(3-trifluoromethoxy-benzylamino)-pyrimidin-5-yl]-benzoic acid,
2-chloro-3-(pyrrolidin-3-yloxy)-5-[2-(3-trifluoromethoxy-benzylamino)-pyrimidin-5-yl]-benzoic acid,
3-(azetidin-3-yloxy)-2-chloro-5-[2-(3-trifluoromethoxy-benzylamino)-pyrimidin-5-yl]-benzoic acid,
2-chloro-3-(1-methyl-azetidin-3-yloxy)-5-[2-(3-trifluoromethoxy-benzylamino)-pyrimidin-5-yl]-benzoic acid,
2-methoxy-3-pyridin-4-yl-5-[2-(3-trifluoromethoxy-benzylamino)-pyrimidin-5-yl]-benzoic acid,
2-methoxy-5-[6-(3-trifluoromethoxy-benzylamino)-pyridin-3-yl]-benzoic acid,
3-fluoro-2-methoxy-5-[6-(3-trifluoromethoxy-benzylamino)-pyridin-3-yl]-benzoic acid,
2,3-dimethoxy-5-[6-(3-trifluoromethoxy-benzylamino)-pyridin-3-yl]-benzoic acid,
2-chloro-3-methoxy-5-[6-(3-trifluoromethoxy-benzylamino)-pyridin-3-yl]-benzoic acid,
3-cyano-2-methoxy-5-[6-(3-trifluoromethoxy-benzylamino)-pyridin-3-yl]-benzoic acid,
7-[6-(3-trifluoromethoxy-benzylamino)-pyridin-3-yl]-1H-indazole-3-carboxylic acid,
4-methoxy-7-[6-(3-trifluoromethoxy-benzylamino)-pyridin-3-yl]-1H-indazole-3-carboxylic acid,
1-(2-methoxy-ethyl)-5-[6-(3-trifluoromethoxy-benzylamino)-pyridin-3-yl]-1H-indazole-3-carboxylic acid,
1-methyl-5-[2-(3-trifluoromethoxy-benzylamino)-pyrimidin-5-yl]-1H-indazole-3-carboxylic acid,
1-(3-methanesulfonyl-propyl)-5-[6-(3-trifluoromethoxy-benzylamino)-pyridin-3-yl]-1H-indazole-3-carboxylic acid,
1-(3-cyano-propyl)-5-[6-(3-trifluoromethoxy-benzylamino)-pyridin-3-yl]-1H-indazole-3-carboxylic acid,
(E)-3-{3-methyl-2-oxo-5-[6-(3-trifluoromethoxy-benzylamino)-pyridin-3-yl]-3-aza-bicyclo[4.1.0]hept-4-en-1-yl}-acrylic acid,
(E)-3-[1-methyl-6-oxo-6'-(3-trifluoromethoxy-benzylamino)-1,6-dihydro-[3,3']bipyridinyl-5-yl]-acrylic acid,
(1S,2S)-2-[5-isopropoxy-6'-(3-trifluoromethoxy-benzylamino)-[2,3']bipyridinyl-6-yl]-cyclopropanecarboxylic acid,
3-{3-cyano-2-methoxy-5-[2-(3-trifluoromethoxy-benzylamino)-pyrimidin-5-yl]-phenyl}-propionic acid,
(E)-3-{2-methoxy-5-[6-(3-trifluoromethoxy-benzylamino)-pyridin-3-yl]-phenyl}-acrylic acid,
3-{2-methoxy-4-[6-(3-trifluoromethoxy-benzylamino)-pyridin-3-yl]-phenyl}-propionic acid,
(trans)-2-{2-methoxy-4-[6-(3-trifluoromethoxy-benzylamino)-pyridin-3-yl]-phenyl}-cyclopropanecarboxylic acid,
(trans)-2-{2-methoxy-5-[2-(3-trifluoromethoxy-benzylamino)-pyrimidin-5-yl]-phenyl}-cyclopropanecarboxylic acid,
3-{2-methoxy-3-oxetan-3-yl-5-[6-(3-trifluoromethoxy-benzylamino)-pyridin-3-yl]-phenyl}-propionic acid,
3-{3-cyano-2-methoxy-5-[6-(3-trifluoromethoxy-benzylamino)-pyridin-3-yl]-phenyl}-3-methyl-butyric acid,
3-{3-cyano-2-methoxy-5-[2-(3-trifluoromethoxy-benzylamino)-pyrimidin-5-yl]-phenyl}-3-methyl-butyric acid,
(3-{2-methoxy-5-[6-(3-trifluoromethoxy-benzylamino)-pyridin-3-yl]-phenyl}-oxetan-3-yl)-acetic acid,
3-{2-methoxy-5-[6-(3-trifluoromethoxy-benzylamino)-pyridin-3-yl]-phenyl}-3-methyl-butyric acid,
3-{2,6-dimethoxy-4-[6-(3-trifluoromethoxy-benzylamino)-pyridin-3-yl]-phenyl}-propionic acid, 3-{2,6-dimethoxy-4-[6-(3-trifluoromethoxy-benzylamino)-pyridin-3-yl]-phenyl}-2-methyl-propionic acid,
1-[1-methyl-6-oxo-6'-(3-trifluoromethoxy-benzylamino)-1,6-dihydro-[3,3']bipyridinyl-5-yl]-cyclopropanecarboxylic acid,
2-{3-imidazol-1-ylmethyl-2-methoxy-5-[6-(3-trifluoromethoxy-benzylamino) -pyridin-3-yl]-phenyl}-2-methyl-propionic acid,
{2-methoxy-5-[6-(3-trifluoromethoxy-benzylamino)-pyridin-3-yl]-phenyl}-acetic acid,
1-{2-methoxy-5-[6-(3-trifluoromethoxy-benzylamino)-pyridin-3-yl]-phenyl}-cyclopropanecarboxylic acid,
2-{2-methoxy-5-[2-(3-trifluoromethoxy-benzylamino)-pyrimidin-5-yl]-phenyl}-2-methyl-propionic acid,
2-[6-methoxy-6'-(3-trifluoromethoxy-benzylamino)-[3,3']bipyridinyl-5-yl]-2-methyl -propionic acid,
2-[5-methoxy-6'-(3-trifluoromethoxy-benzylamino)-[2,3']bipyridinyl-6-yl]-2-methyl -propionic acid,
2-{3-hydroxymethyl-2-methoxy-5-[6-(3-trifluoromethoxy-benzylamino)-pyridin-3-yl]-phenyl}-2-methyl-propionic acid,
2-{2-methoxy-3-methoxymethyl-5-[6-(3-trifluoromethoxy-benzylamino)-pyridin-3-yl]-phenyl}-2-methyl-propionic acid,
2-{2-methoxy-3-[(2,2,2-trifluoro-ethylamino)-methyl]-5-[6-(3-trifluoromethoxy -benzylamino)-pyridin-3-yl]-phenyl}-2-methyl-propionic acid,
2-{3-fluoromethyl-2-methoxy-5-[6-(3-trifluoromethoxy-benzylamino)-pyridin-3-yl]-phenyl}-2-methyl-propionic acid,
{2-methoxy-5-[6-(3-trifluoromethoxy-benzylamino)-pyridin-3-yl]-phenoxy}-acetic acid,
2-{2-methoxy-5-[6-(3-trifluoromethoxy-benzylamino)-pyridin-3-yl]-phenoxy}-propionic acid,
2-chloro-3-(2-methoxy-ethoxy)-5-[2-(3-trifluoromethoxy-benzylamino)-pyrimidin-5-yl]-benzoic acid,
2-chloro-3-(tetrahydro-pyran-4-yloxy)-5-[2-(3-trifluoromethoxy-benzylamino) -pyrimidin-5-yl]-benzoic acid,
2-chloro-3-[2-(2-oxo-pyrrolidin-1-yl)-ethoxy]-5-[2-(3-trifluoromethoxy -benzylamino)-pyrimidin-5-yl]-benzoic acid,
2-chloro-3-(2-oxo-pyrrolidin-3-yloxy)-5-[2-(3-trifluoromethoxy-benzylamino)-pyrimidin-5-yl]-benzoic acid,
2-chloro-3-(oxetan-3-yloxy)-5-[2-(3-trifluoromethoxy-benzylamino)-pyrimidin-5-yl]-benzoic acid,
2-chloro-3-dimethylcarbamoylmethoxy-5-[2-(3-trifluoromethoxy-benzylamino) -pyrimidin-5-yl]-benzoic acid,
2-chloro-3-(2-dimethylamino-ethoxy)-5-[2-(3-trifluoromethoxy-benzylamino) -pyrimidin-5-yl]-benzoic acid,
2-chloro-3-(2-morpholin-4-yl-ethoxy)-5-[2-(3-trifluoromethoxy-benzylamino) -pyrimidin-5-yl]-benzoic acid,
3-furan-3-yl-2-methoxy-5-[2-(3-trifluoromethoxy-benzylamino)-pyrimidin-5-yl]-benzoic acid,
2-methoxy-5-[2-(3-trifluoromethoxy-benzylamino)-pyrimidin-5-yl]-benzoic acid, and
5-[6-(3-isopropyl-benzylamino)-pyridin-3-yl]-2-methoxy-benzoic acid.

15. A pharmaceutical composition, comprising:
the compound according to claim 1, or a pharmacologically acceptable salt thereof; and
a pharmaceutically acceptable carrier.

16. The pharmaceutical composition according to claim 15, wherein the pharmaceutical composition is an ATX inhibitor.

17. A method for treating a disease involving ATX, wherein the disease involving ATX is cancer or tumor including malignant melanoma, brain tumor, neuroblastoma, glioblastoma multiforme, EBV positive Hodgkin lymphoma, glioblastoma, non-small cell lung cancer, lung tumor, breast tumor, ovary tumor, pancreas tumor, prostatic intraepithelial neoplasia, prostate tumor, thyroid tumor, follicular lymphoma, liver tumor, and renal cell carcinoma, fibrosis as including pulmonary fibrosis, hepatic fibrosis, renal fibrosis, and atherosclerosis, asthma, rheumatoid arthritis, type II diabetes-related obesity, acute coronary syndrome, cholestatic pruritus, or an inflammatory disease including inflammatory bowel disease, Crohn's disease, ulcerative colitis, and neuropathic pain, comprising: administering the pharmaceutical composition according to claim 15, to a patient in need thereof.

18. A pharmaceutical composition, comprising:
the compound according to claim 14, or a pharmacologically acceptable salt thereof; and
a pharmaceutically acceptable carrier.

19. A method for treating cancer or tumor including malignant melanoma, brain tumor, neuroblastoma, glioblastoma multiforme, EBV positive Hodgkin lymphoma, glioblastoma, non-small cell lung cancer, lung tumor, breast tumor, ovary tumor, pancreas tumor, prostatic intraepithelial neoplasia, prostate tumor, thyroid tumor, follicular lymphoma, liver tumor, and renal cell carcinoma, fibrosis including pulmonary fibrosis, hepatic fibrosis, renal fibrosis, and atherosclerosis, asthma, rheumatoid arthritis, type II diabetes-related obesity, acute coronary syndrome, cholestatic pruritus, or an inflammatory disease including inflammatory bowel disease, Crohn's disease, ulcerative colitis, and neuropathic pain, comprising:
administering the pharmaceutical composition according to claim 18 to a patient in need thereof.

* * * * *